US009102731B2

(12) United States Patent
Boone et al.

(10) Patent No.: US 9,102,731 B2
(45) Date of Patent: Aug. 11, 2015

(54) HUMAN CGRP RECEPTOR BINDING PROTEINS

(75) Inventors: Thomas C. Boone, Newbury Park, CA (US); David W. Brankow, Northridge, CA (US); Colin V. Gegg, Jr., Camarillo, CA (US); Shaw-Fen Sylvia Hu, Thousand Oaks, CA (US); Chadwick T. King, North Vancouver (CA); Hsieng Sen Lu, Westlake Village, CA (US); Licheng Shi, Newbury Park, CA (US); Cen Xu, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 349 days.

(21) Appl. No.: 12/642,711

(22) Filed: Dec. 18, 2009

(65) Prior Publication Data

US 2010/0172895 A1 Jul. 8, 2010

Related U.S. Application Data

(60) Provisional application No. 61/203,569, filed on Dec. 23, 2008, provisional application No. 61/264,622, filed on Nov. 25, 2009.

(51) Int. Cl.
*C07K 16/00* (2006.01)
*C12P 21/08* (2006.01)
*C07K 16/28* (2006.01)

(52) U.S. Cl.
CPC ......... *C07K 16/2869* (2013.01); *C07K 2317/21* (2013.01); *C07K 2317/32* (2013.01); *C07K 2317/56* (2013.01); *C07K 2317/565* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 5,866,124 | A * | 2/1999 | Hardman et al. | 424/131.1 |
| 7,193,070 | B2 | 3/2007 | Kane et al. | |
| 7,288,251 | B2 | 10/2007 | Bedian et al. | |
| 7,423,128 | B2 | 9/2008 | Gazit-Bornstein et al. | |
| 7,658,924 | B2 * | 2/2010 | Oliner et al. | 424/155.1 |
| 2002/0164707 | A1 | 11/2002 | Adamou et al. | |
| 2004/0110170 | A1 | 6/2004 | Pisegna et al. | |
| 2004/0176577 | A1 * | 9/2004 | Rojer et al. | 530/388.8 |
| 2005/0282252 | A1 | 12/2005 | Siegel et al. | |
| 2006/0018909 | A1 | 1/2006 | Oliner et al. | |
| 2006/0246071 | A1 | 11/2006 | Green et al. | |
| 2008/0057063 | A1 | 3/2008 | Rinkenberger et al. | |

FOREIGN PATENT DOCUMENTS

| | | |
|---|---|---|
| JP | 2005-503809 | 2/2005 |
| WO | WO 2004/097421 A2 | 11/2004 |
| WO | WO 2006/068953 A2 | 6/2006 |
| WO | WO 2007/045927 A2 | 4/2007 |
| WO | WO 2007/048026 A2 | 4/2007 |
| WO | WO 2007/054809 A2 | 5/2007 |
| WO | WO 2007/076336 A1 | 7/2007 |
| WO | WO 2008/132453 A1 | 11/2008 |
| WO | WO 2009/109908 A1 | 9/2009 |
| WO | WO 2010/012911 A1 | 2/2010 |
| WO | WO 2011/024113 A1 | 3/2011 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Taylor et al, "Pharmacological characterization of novel alpha-calcitonin gene-related peptide (CGRP) receptor peptide antagonists that are selective for human CGRP receptors", Journal of Pharmacology and Experimental Therapeutics, American Society for Pharmacology and Experimental Therapeutics.; vol. 319, No. 2, 749-757 (2006).
Davis et al., "The tortuous road to an ideal CGRP function blocker for the treatment of migraine", Current Topics in Medicial Chemistry; vol. 8, No. 16, (2008).
Durham et al., "CGRP—receptor antagonists—a fresh approach to migraine therapy?", New England Journal of Medicine, vol. 350, No. 11, 1073-1075 (2004).
Chauhan et al., "Studies on the effects of the N-terminal domain antibodies of calcitonin receptor-like receptor and receptor activity-modifying protein 1 on calcitonin gene-related peptide-induced vasorelaxation in rat uterine artery," Biology of Reproduction, vol. 70, Nr. 6, 1658-1663, (2004).
Lennerz et al., "Calcitonin receptor-like receptor (CLR), receptor activity-modifying protein 1 (Ramp1), and calcitonin gene-related peptide (CGRP) immunoreactivity in the rat trigeminovascular system: differences between peripheral and central CGRP receptor distribution", Journal of Comparative Neurology 507(3): 1277-1299, 2008.
Kuwasako et al., "Visualization of the calcitonin receptor-like receptor and its receptor activity-modifying proteins during internalization and recycling", Journal of Biological Chemistry, vol. 275, No. 28, 29602-29609, 2000.
Mach et al., "Origins of skeletal pain: sensory and sympathetic innervation for the mouse femur", Neuroscience, vol. 113, No. 1, pp. 155-166, 2002.
Poyner et al., "Intertnational union of pharmacology, XXXII. The mammalian calcitonin gene-related peptides, adrenomedulin, amylin and calcitonin receptors", Pharmacological Reviews, vol. 54, No. 2, 2002.

(Continued)

*Primary Examiner* — Hong Sang
(74) *Attorney, Agent, or Firm* — Angela L. Purcell

(57) ABSTRACT

Antigen binding proteins that bind to human CGRP receptor (CGRP R) are provided. Nucleic acids encoding the antigen binding protein, vectors, and cells encoding the same are also provided. The antigen binding proteins can inhibit binding of CGRP R to CGRP, and are useful in a number of CGRP R related disorders, including the treatment and/or prevention of migraine headaches.

15 Claims, 17 Drawing Sheets

(56) References Cited

OTHER PUBLICATIONS

Cottrell et al., "Localization of calcitonin receptor-like receptor and receptor acivity modifying protein 1 in enteric neuron, dorsal root ganglia, and the spinal cord of the rat," Journal of Comparative Neurology, 490:239-255, 2005.

Evans et al., "CGRP-RCP, a novel protein required for signal transduction at calcitonin gene-related peptide and adrenomedulin receptors", vol. 275. No. 40, pp. 31438-31443, 2000.

Wimalawansa et al., "Isolation, purification and raising of monoclonal antibodies for calcitonin gene-related. peptide (CGRP) receptor", Regulatory Peptides, 26(1), 1989.

http://www.labome.com/gene/10267/RAMP1/antibody, May 21, 2010.

http://www.labvome.com/gene/10203/CALCRL, May 21, 2010.

Written Opinion, PCT Searching Authority, issued Mar. 16, 2010, 14 pgs.

Office action Search Report dated Sep. 19, 2012, issued in corresponding Taiwanese Patent Application No. 098144377 (translation).

Office action dated Sep. 12, 2012, issued in corresponding European Patent Application No. 09775072.3.

Chauhan, M. et al.; "Studies on the Effects of the N-Terminal Domain Antibodies of Calcitonin Receptor-Like Receptor and Receptor Activity-Modifying Protein 1 on Calcitonin Gene-Related Peptide-Induced Vasorelaxation in Rat Uterine Artery" Biology of Reproduction, Feb. 11, 2004, vol. 70, pp. 1658-1663.

Taylor, Christopher K. et al.; "Pharmacological Characterization of Novel a-Calcitonin GeneRelated Peptide (CGRP) Receptor Peptide Antagonists That are Selective for Human CGRP Receptors" The Journal of Pharmacology and Experimental Therapeutics, vol. 319, No. 2, pp. 749-757, 2006.

Yuan-Lin Dong et al.; "Involvement of calcitonin gene-related peptide in control of human fetoplacental vascular tone" American Journal of Physiology Heart Circulation Physiology, Jan. 2004, vol. 286, pp. H230-H239.

J Zeller et al.; "CGRP function-blocking antibodies inhibit neurogenic vasodilatation without affecting heart rate or arterial blood pressure in the rat" British Journal of Pharmacology, Dec. 2008, published online Sep. 8, 2008, vol. 155, No. 7, pp. 1093-1103.

Austrian Search Report and Written Opinion mailed Sep. 7, 2012.

Office action of Feb. 20, 2014 in corresponding Japanese Patent Application No. 2011-543606.

Database Biosis [Online] Biosciences Information Service, Philadelphia, PA, US 2005 Corvera Carlos U et al: 'Localization of calcitonin receptor-like receptor (CLR) and calcitonin gene-related peptide (CGRP) in human gut' Database accession No. PREV200600210814 & Gastroenterology, vol. 128, No. 4, Suppl. 2, Apr. 2005, p. A361, Annual Meeting of the American-Gastroenterological-Association/Digestive Disease-Week; Chicago, IL USA; May 14-19.

* cited by examiner

```
                      1         10        20        30        40        50
SEQ ID NO:215(1)   MARALCRLPQRGLWLLLAHHLFMATACQEANYGALLQELCLTQFQVDMEAVGET
SEQ ID NO:4  (1)   MARALCRLPRRGLWLLLAHHLFMTTACQEANYGALLRELCLTQFQVDMEAVGET
SEQ ID NO:214(1)   MAPGLRGLPRRGLWLLLAHHLFMVTACRDPDYGTLIQELCLSRFKEDMETIGKT 60        70        80        90       100
SEQ ID NO:215(55)  LWCDWGRTIGSYRELADCTWHMAEKLGCFWPNAEVDRFFLAVHGHYFRACPISG
SEQ ID NO:4  (55)  LWCDWGRTIRSYRELADCTWHMAEKLGCFWPNAEVDRFFLAVHGRYFRSCPISG
SEQ ID NO:214(55)  LWCDWGKTIGSYGELTHCTKLVANKIGCFWPNPEVDKFIAVHHRYFSKCPVSG 110       120       130       140
SEQ ID NO:215(109) RAVRDPPGSVLYPFIVVPITVTLLVTALVVWQSKHTEGIV
SEQ ID NO:4  (109) RAVRDPPGSILYPFIVVPITVTLLVTALVVWQSKRTEGIV
SEQ ID NO:214(109) RALRDPPNSILCPFIVLPITVTLLMTALVVWRSKRTEGIV
```

Fig. 1

```
                  1         10        20        30        40        50
SEQ ID NO:221  -MEKKCTLYFLVLLPFFMIFVTAELEESPEDSIQLGVTRNKIMTAQYECYQKIMQDP
SEQ ID NO:2    -MEKKCTLYFLVLLPFFMILVTAELEESPEDSIQLGVTRNKIMTAQYECYQKIMQDP
SEQ ID NO:220  MMDKKCTLCFLFLLLNMALIAAESEEGANQT-DLGVTRNKIMTAQYECYQKIMQDP 60        70        80        90       100       110
SEQ ID NO:221  IQQAEGVYCNRTWDGWLCWNNVAAGTESMQLCPDYFQDFDPSEKVTKICDQDGNWFR
SEQ ID NO:2    IQQAEGVYCNRTWDGWLCWNDVAAGTESMQLCPDYFQDFDPSEKVTKICDQDGNWFR
SEQ ID NO:220  IQQGEGLYCNRTWDGWLCWNDVAAGTESMQYCPDYFQDFDPSEKVTKICDQDGNWFR 120       130       140       150       160       170
SEQ ID NO:221  HPASNRTWTNYTQCNVNTHEKVKTALNLFYLTIIGHGLSIASLLISLGIFFYFKSLS
SEQ ID NO:2    HPASNRTWTNYTQCNVNTHEKVKTALNLFYLTIIGHGLSIASLLISLGIFFYFKSLS
SEQ ID NO:220  HPDSNRTWTNYTLCNNSTHEKVKTALNLFYLTIIGHGLSIASLIISLIIFFYFKSLS 180       190       200       210       220
SEQ ID NO:221  CQRITLHKNLFFSFVCNSVVTIIHLTAVANNQALVATNPVSCKVSQFIHLYLMGCNY
SEQ ID NO:2    CQRITLHKNLFFSFVCNSVVTIIHLTAVANNQALVATNPVSCKVSQFIHLYLMGCNY
SEQ ID NO:220  CQRITLHKNLFFSFVCNSIVTIIHLTAVANNQALVATNPVSCKVSQFIHLYLMGCNY 230       240       250       260       270       280
SEQ ID NO:221  FWMLCEGIYLHTLIVVAVFAEKQHLMWYYFLGWGFPLIPACIHAIARSLYYNDNCWI
SEQ ID NO:2    FWMLCEGIYLHTLIVVAVFAEKQHLMWYYFLGWGFPLIPACIHAIARSLYYNDNCWI
SEQ ID NO:220  FWMLCEGIYLHTLIVVAVFAEKQHLMWYYFLGWGFPLLPACIHAIARSLYYNDNCWI 290       300       310       320       330       340
SEQ ID NO:221  SSDTHLLYIIHGPICAALLVNLFFLLNIVRVLITKLKVTHQAESNLYMKAVRATLIL
SEQ ID NO:2    SSDTHLLYIIHGPICAALLVNLFFLLNIVRVLITKLKVTHQAESNLYMKAVRATLIL
SEQ ID NO:220  SSDTHLLYIIHGPICAALLVNLFFLLNIVRVLITKLKVTHQAESNLYMKAVRATLIL 350       360       370       380       390
SEQ ID NO:221  VPLLGIEFVLIPWRPEGKIAEEVYDYIMHILMHFQGLLVSTIFCFFNGEVQAILRRN
SEQ ID NO:2    VPLLGIEFVLIPWRPEGKIAEEVYDYIMHILMHFQGLLVSTIFCFFNGEVQAILRRN
SEQ ID NO:220  VPLLGIEFVLFPWRPEGKVAEEVYDYVMHILMHYQGLLVSTIFCFFNGEVQAILRRN 400       410       420       430       440       450
SEQ ID NO:221  WNQYKIQFGNSFSNSEALRSASYTVSTISDGPGYSHDCPSEHLNGKSIHDIENVVLK
SEQ ID NO:2    WNQYKIQFGNSFSNSEALRSASYTVSTISDGPGYSHDCPSEHLNGKSIHDIENVLLK
SEQ ID NO:220  WNQYKIQFGNGFSHSDALRSASYTVSTISDVQGYSHDCPTEHLNGKSIQDIENVALK

460
SEQ ID NO:221  PENLYN----
SEQ ID NO:2    PENLYN----
SEQ ID NO:220  PEKMYDLVM
```

Fig. 2

| Kappa K1 | CDR1 | SEQ ID NO: | CDR2 | SEQ ID NO: | CDR3 | SEQ ID NO: |
|---|---|---|---|---|---|---|
| 2E7 | R A S Q G I R N D L G | 48 | A A S S L Q S | 49 | L Q Y N I Y P W T | 50 |
| 13H2 | R A S Q G I R K D L G | 66 | G A S S L Q S | 67 | L Q Y N S F P W T | 68 |
| K1 Consensus | R A S Q G I R N D L G<br>              K | 103 | A A S S L Q S<br>G | 104 | L Q Y N I Y P W T<br>         S F | 105 |

| Kappa K4 | CDR1 | SEQ ID NO: | CDR2 | SEQ ID NO: | CDR3 | SEQ ID NO: |
|---|---|---|---|---|---|---|
| 32H7 | R A S Q S V S S G Y L T | 69 | G A S S R A T | 70 | Q Q Y G N S L C R | 71 |
| 32H7a | R A S Q S V S S G Y L T | 69 | G A S S R A T | 70 | Q Q Y G N S L S R | 72 |
| K4 Consensus | R A S Q S V S S G Y L T | 69 | G A S S R A T | 70 | Q Q Y G N S L S R<br>          C | 106 |

| | CDR1 | SEQ ID NO: | CDR2 | SEQ ID NO: | CDR3 | SEQ ID NO: |
|---|---|---|---|---|---|---|
| Kappa K1,4 Cons | R A S Q S V S S G Y L T<br>      G I R N   D   G<br>          K | 107 | G A S S R A T<br>A      L Q S | 108 | Q Q Y G N S L C R<br>L    N T Y P W T<br>        F   S | 109 |

Fig 3A

| Kappa K2 | CDR1 | SEQ ID NO: | CDR2 | SEQ ID NO: | CDR3 | SEQ ID NO: |
|---|---|---|---|---|---|---|
| 4H6 | R S S Q S L L H S F G Y N Y L D | 57 | L G S N R A S | 58 | M Q A L Q T P F T | 59 |

| Kappa K3 | CDR1 | SEQ ID NO: | CDR2 | SEQ ID NO: | CDR3 | SEQ ID NO: |
|---|---|---|---|---|---|---|
| 3C8 | K S S Q S L L H S A G K T Y L Y | 54 | E V S N R F S | 55 | M Q S F P L P L T | 56 |
| 5F5 | K S S Q S L L H S D G K T Y L Y | 60 | E V S N R F S | 55 | M Q S F P L P L T | 56 |
| 12E8 | K S S Q S L L H S D G R N Y L Y | 65 | E V S N R F S | 55 | M Q S F P L P L T | 56 |
| K3 Consensus | K S S Q S L L H S D G R N Y L Y<br>          A  K T | 110 | E V S N R F S | 55 | M Q S F P L P L T | 56 |

| | CDR1 | SEQ ID NO: | CDR2 | SEQ ID NO: | CDR3 | SEQ ID NO: |
|---|---|---|---|---|---|---|
| Kappa K2,3 Cons | R S S Q S L L H S F G Y N Y L D<br>K            D  R T   Y<br>            A  K | 111 | L G S N R A S<br>E V     F | 112 | M Q A L Q T P F T<br>     S F P L   L | 113 |

Fig 3B

| Lambda L1 | CDR1 | SEQ ID NO: | CDR2 | SEQ ID NO: | CDR3 | SEQ ID NO: |
|---|---|---|---|---|---|---|
| 1E11 | SGSSSNIGNNYVS | 42 | DNNKRPS | 43 | GTWDSRLSAVV | 44 |
| 4E4 | SGSSSNIGNNYVS | 42 | DNNKRPS | 43 | GTWDSRLSAVV | 44 |
| 9D4 | SGSSSNIGNNYVS | 42 | DNNKRPS | 43 | GTWDSRLSAVV | 44 |
| 12G8 | SGSSSNIGNNYVS | 42 | DNNKRPS | 43 | GTWDSRLSAVV | 44 |
| L1 Consensus | SGSSSNIGNNYVS | 42 | DNNKRPS | 43 | GTWDSRLSAVV | 44 |

| Lambda L2 | CDR1 | SEQ ID NO: | CDR2 | SEQ ID NO: | CDR3 | SEQ ID NO: |
|---|---|---|---|---|---|---|
| 10E4 | SGSSSNIGSNTVN | 62 | TNNQRPS | 63 | AARDESLNGVV | 64 |

| Lambda L3 | CDR1 | SEQ ID NO: | CDR2 | SEQ ID NO: | CDR3 | SEQ ID NO: |
|---|---|---|---|---|---|---|
| 11D11 | SGSSSNIGSNYVY | 45 | RNNQRPS | 61 | AAWDDSLSGWV | 47 |
| 11H9 | SGSSSNIGSNYVY | 45 | RNNQRPS | 61 | AAWDDSLSGWV | 47 |
| 1H7 | SGSSSNIGSNYVY | 45 | RSNQRPS | 46 | AAWDDSLSGWV | 47 |
| 9F5 | SGSSSNIGSNYVY | 45 | RNNQRPS | 61 | AAWDDSLSGWV | 47 |
| L3 Consensus | SGSSSNIGSNYVY | 45 | RNNQRPS<br>S | 114 | AAWDDSLSGWV | 47 |

| Lambda L4 | CDR1 | SEQ ID NO: | CDR2 | SEQ ID NO: | CDR3 | SEQ ID NO: |
|---|---|---|---|---|---|---|
| 3B6 | QG DS LRSFYAS | 51 | GKNNRPS | 52 | NSRDSSVYHLV | 53 |

| | CDR1 | SEQ ID NO: | CDR2 | SEQ ID NO: | CDR3 | SEQ ID NO: |
|---|---|---|---|---|---|---|
| Lam L1,2,3 Cons | SGSSSNIGNNYVS<br>       S T N<br>          Y | 115 | DNNKRPS<br>TS Q<br>R | 116 | GTWDSRLSAVV<br>AAR DS NG | 117 |

| | CDR1 | SEQ ID NO: | CDR2 | SEQ ID NO: | CDR3 | SEQ ID NO: |
|---|---|---|---|---|---|---|
| Lambda All Cons | SGSSSNIGNNYVS<br>Q -D -LRSFTAN<br>            Y | 118 | DNNKRPS<br>GK N<br>TS Q<br>R | 119 | GTWDSRLSAVV<br>NSR DSVYHL<br>AA       NG | 120 |

| | CDR1 | SEQ ID NO: | CDR2 | SEQ ID NO: | CDR3 | SEQ ID NO: |
|---|---|---|---|---|---|---|
| 3B6 | GYYMH | 82 | WINPNSGGGTNYAQKFQG | 83 | DQMSIIMLRGVFPPYYYGMDV | 84 |
| 10E4 | DYYMY | 92 | WISPNSGGGTNYAQKFQG | 93 | GGYSGYA--GLYSHYY-GMDV | 94 |
| HC1 Consensus | GYYMH | 121 | WINPNSGGGTNYAQKFQG | 122 | DQMSIIMLRGVFPPYYYGMDV | 123 |
| | D  Y | | S | | GGY GYA-- LYSH - | |

HC2

| | CDR1 | SEQ ID NO: | CDR2 | SEQ ID NO: | CDR3 | SEQ ID NO: |
|---|---|---|---|---|---|---|
| 11D11 | NAWMS | 76 | RIKSKTDGGTTDYAAPVKG | 95 | DRTGYSISWSSYYYYGMDV | 78 |
| 9F5 | NAWMS | 76 | RIKSKTDGGTTDYTAPVKG | 91 | DRTGYSISWSSYYYYYGMDV | 78 |
| 11H9 | NAWMS | 76 | RIKSKTDGGTTDYAAPVKG | 95 | DRTGYSISWSSYYYYYGMDV | 78 |
| 1H7 | NAWMS | 76 | RIKSTTDGGTTDYAAPVKG | 77 | DRTGYSISWSSYYYYYGMDV | 78 |
| HC2 Consensus | NAWMS | 76 | RIKSKTDGGTTDYTAPVKG | 124 | DRTGYSISWSSYYYYYGMDV | 78 |
| | | | T            A | | | |

| | CDR1 | SEQ ID NO: | CDR2 | SEQ ID NO: | CDR3 | SEQ ID NO: |
|---|---|---|---|---|---|---|
| 13H2 | TYSMN | 97 | SISSSSSYRYYADSVKG | 98 | EGVSGSSPYSISWYDYYYGMDV | 99 |
| 2E7 | SYAMS | 79 | AISGSGGRTYYYADSVKG | 80 | DQREVG-PYSSGWYDYYYGMDV | 81 |
| HC3 Consensus | TYSMN | 125 | SISSSSSYRYYADSVKG | 126 | EGVSGSSPYSISWYDYYYGMDV | 127 |
| | S A S | | A G GGRT | | DQREVG- SG | |

| | CDR1 | SEQ ID NO: | CDR2 | SEQ ID NO: | CDR3 | SEQ ID NO: |
|---|---|---|---|---|---|---|
| 3C8 | SYGMH | 85 | VISYDGSHESYADSVKG | 86 | ERKRVTMSTLYYY-FYYGMDV | 87 |
| 4E4 | SFGMH | 73 | VISFDGSIKYSVDSVKG | 74 | DRLNYYDSSGYYHYKYYGMAV | 75 |
| 9D4 | SFGMH | 73 | VISFDGSIKYSVDSVKG | 74 | DRLNYYDSSGYYHYKYYGMAV | 75 |
| 1E11 | SFGMH | 73 | VISFDGSIKYSVDSVKG | 74 | DRLNYYDSSGYYHYKYYGMAV | 75 |
| 12E8 | SYGMH | 85 | VISYDGSHESYADSVKG | 86 | ERKRVTMSTLYYY-FYYGMDV | 87 |
| 5F5 | SYGMH | 85 | VISYDGSHESYADSVKG | 86 | ERKRVTMSTLYYY-FYYGMDV | 87 |
| 12G8 | SFGMH | 73 | VISFDGSIKYSVDSVKG | 74 | DRLNYYDSSGYYHYKYYGLAV | 96 |
| HC4 Consensus | SFGMH | 128 | VISFDGSIKYSVDSVKG | 129 | DRLNYYDSSGYYHYKYYGMAV | 130 |
| | Y | | Y     H    YA | | E KRVTM TL    Y-F    LD | |

```
HC5     SEQ           SEQ                SEQ
        ID NO: CDR2   ID NO: CDR3        ID NO:
CDR1    88            89                 90
4H6 DYAMS  FIRSRAYGGTPEYAASVKG  GRGIAARWDY
```

Fig 5D

```
HC6       SEQ                  SEQ
          ID NO: CDR2          ID NO: CDR3
CDR1      100                  101         102
32H7 SYGMH  VIWYDGSNKYYADSVKG    AGGIAAAGLYYYYGMDV
```

Fig 5E

```
           SEQ                        SEQ
           ID NO: CDR2                ID NO: CDR3                         SEQ
CDR1       131                        132                                 ID NO: 133
HC Con A  NAWMS  RIKSKTDGGTTDYTAPVKG   DRTGYSISWSS-YYYYYGMDV
          SYA H   A SG - - S SRKYSADS   AQREVGPYSGGWHDK - - LAV
          FG      V WFT      I    V    EGLNAYD - - LYY - F
                     Y       N         GI    AA  T   L
                             H         KR       TM

SEQ                        SEQ
           ID NO: CDR2                ID NO: CDR3                         SEQ
CDR1       134                        135                                 ID NO: 136
HC Con B  NAWMS  RIKSKTDGGTTDYTAPVKG   DRTGYSISWSS-YYYYYGMDV
          GFYLH   W NP - - NSSGKNSAQKFQ  GGMSIIMLRGVFPPK - - LA
          DYA     A SGTAH   RRY VDS    AQYEGYA - - LLYSHF
          SG      V WFR S   IPE        E RNVGPYS  GWHD
          A       S RY Y   N           LIAAD T Y -
                  F        H           GR     T
                           Y           K
```

Fig 5F

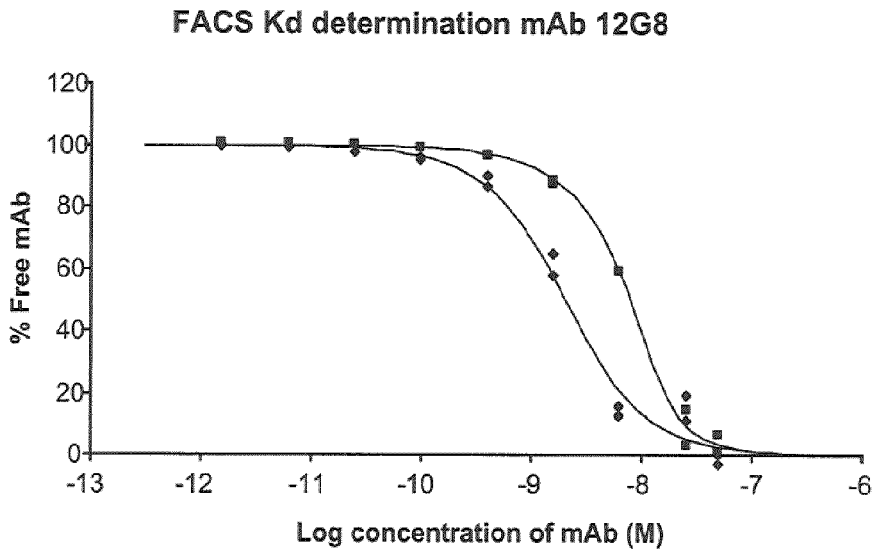
Fig 10
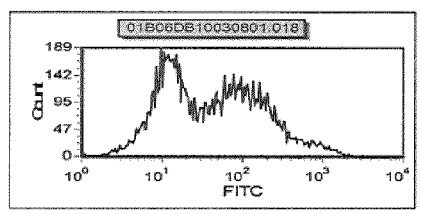
CRLR: RAMP1 Wild Type  Fig 13A
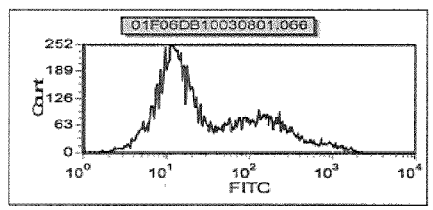
CRLR L24-Q33: RAMP1  Fig 13B
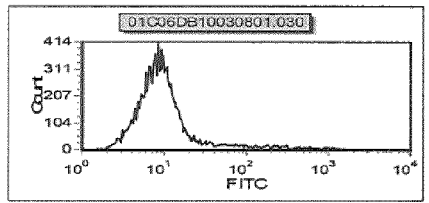
CRLR: RAMP1 Q28-A34  Fig 13C

```
                         1                                                                          50
SEQ ID NO:215    MARALCRLPQ  RGLWLLLAHH  LFMATACQEA  NYGALLQELC  LTQFQVDMEA
SEQ ID NO:4      MARALCRLPR  RGLWLLLAHH  LFMTTACQEA  NYGALLRELC  LTQFQVDMEA
SEQ ID NO:217    MARALCRLPR  RGLWLLLAHH  LFMTTACRDP  DYGTLLRELC  LTQFQVDMEA
SEQ ID NO:218    MARALCRLPR  RGLWLLLAHH  LFMTTACQEA  NYGALLRELC  LTRFKEDMET
SEQ ID NO:219    MARALCRLPR  RGLWLLLAHH  LFMTTACQEA  NYGALLRELC  LTQFQVDMEA
SEQ ID NO:214    MAPGLRGLPR  RGLWLLLAHH  LFMVTACRDP  DYGTLIQELC  LSRFKEDMET
SEQ ID NO:216    MARALCRLPQ  RGLWLLLAHH  LFMATACQEA  NYGALLQELC  LTQFQVDMEA 51                                                                         100
SEQ ID NO:215    VGETLWCDWG  RTIGSYRELA  DCTWHMAEKL  GCFWPNAEVD  RFFLAVHGRY
SEQ ID NO:4      VGETLWCDWG  RTIRSYRELA  DCTWHMAEKL  GCFWPNAEVD  RFFLAVHGRY
SEQ ID NO:217    VGETLWCDWG  RTIRSYRELA  DCTWHMAEKL  GCFWPNAEVD  RFFLAVHGRY
SEQ ID NO:218    IGKTLWCDWG  RTIRSYRELA  DCTWHMAEKL  GCFWPNAEVD  RFFLAVHGRY
SEQ ID NO:219    VGETLWCDWG  RTIRSYGELT  HCTKLVANKL  GCFWPNAEVD  RFFLAVHGRY
SEQ ID NO:214    IGKTLWCDWG  KTIGSYGELT  HCTKLVANKI  GCFWPNPEVD  KFFIAVHHRY
SEQ ID NO:216    VGETLWCDWG  RTIGSYRELA  DCTWHMAEKL  GCFWPNAEVD  RFFLAVHGHY 101                                                                        148
SEQ ID NO:215    FRACPISGRA  VRDPPGSVLY  PFIVVPITVT  LLVTALVVWQ  SKHTEGIV
SEQ ID NO:4      FRSCPISGRA  VRDPPGSILY  PFIVVPITVT  LLVTALVVWQ  SKRTEGIV
SEQ ID NO:217    FRSCPISGRA  VRDPPGSILY  PFIVVPITVT  LLVTALVVWQ  SKRTEGIV
SEQ ID NO:218    FRSCPISGRA  VRDPPGSILY  PFIVVPITVT  LLVTALVVWQ  SKRTEGIV
SEQ ID NO:219    FRSCPISGRA  VRDPPGSILY  PFIVVPITVT  LLVTALVVWQ  SKRTEGIV
SEQ ID NO:214    FSKCPVSGRA  LRDPPNSILC  PFIVLPITVT  LLMTALVVWR  SKRTEGIV
SEQ ID NO:216    FRACPISGRA  VRDPPGSVLY  PFIVVPITVT  LLVTALVVWQ  SKHTEGIV
```

Fig. 11

```
                                                                    50
SEQ ID NO:2    MEKKCTLYF LVLLPFFMIL VTAELEESPE DSIQLGVTRN KIMTAQYECY
SEQ ID NO:221  MEKKCTLYF LVLLPFFMIF VTAELEESPE DSIQLGVTRN KIMTAQYECY
SEQ ID NO:222  MEKKCTLYF LVLLPFFMIF VTAELEESPE DSIQLGVTRN KIMTAQYECY
SEQ ID NO:220  MMDKKCTLCF LFLLLLNMAL IAAESEEGAN QT-DLGVTRN KIMTAQYECY
SEQ ID NO:223  MEKKCTLYF LVLLPFFMIL VTAESEEGAN QT-DLGVTRN KIMTAQYECY 51                                                   100
SEQ ID NO:2    QKIMQDPIQQ AEGVYCNRTW DGWLCWNDVA AGTESMQLCP DYFQDFDPSE
SEQ ID NO:221  QKIMQDPIQQ AEGVYCNRTW DGWLCWNNVA AGTESMQLCP DYFQDFDPSE
SEQ ID NO:222  QKIMQDPIQQ AEGVYCNRTW DGWLCWNNVA AGTESMQLCP DYFQDFDPSE
SEQ ID NO:220  QKIMQDPIQQ GEGLYCNRTW DGWLCWNDVA AGTESMQYCP DYFQDFDPSE
SEQ ID NO:223  QKIMQDPIQQ AEGVYCNRTW DGWLCWNDVA AGTESMQLCP DYFQDFDPSE 101                                                  150
SEQ ID NO:2    KVTKICDQDG NWFRHPASNR TWTNYTQCNV NTHEKVKTAL NLFYLTIIGH
SEQ ID NO:221  KVTKICDQDG NWFRHPASNR TWTNYTQCNV NTHEKVKTAL NLFYLTIIGH
SEQ ID NO:222  KVTKICDQDG NWFRHPASNR TWTNYTQCNV NTHEKVKTAL NLFYLTIIGH
SEQ ID NO:220  KVTKICDQDG NWFRHPDSNR TWTNYTLCNN STHEKVKTAL NLFYLTIIGH
SEQ ID NO:223  KVTKICDQDG NWFRHPASNR TWTNYTQCNV NTHEKVKTAL NLFYLTIIGH 151                                                  200
SEQ ID NO:2    GLSIASLLIS LGIFFYFKSL SCQRITLHKN LFFSFVCNSV VTIIHLTAVA
SEQ ID NO:221  GLSIASLLIS LGIFFYFKSL SCQRITLHKN LFFSFVCNSV VTIIHLTAVA
SEQ ID NO:222  GLSIASLLIS LGIFFYFKSL SCQRITLHKN LFFSFVCNSV VTIIHLTAVA
SEQ ID NO:220  GLSIASLIIS LIIFFYFKSL SCQRITLHKN LFFSFVCNSI VTIIHLTAVA
SEQ ID NO:223  GLSIASLLIS LGIFFYFKSL SCQRITLHKN LFFSFVCNSV VTIIHLTAVA 201                                                  250
SEQ ID NO:2    NNQALVATNP VSCKVSQFIH LYLMGCNYFW MLCEGIYLHT LIVVAVFAEK
SEQ ID NO:221  NNQALVATNP VSCKVSQFIH LYLMGCNYFW MLCEGIYLHT LIVVAVFAEK
SEQ ID NO:222  NNQALVATNP VSCKVSQFIH LYLMGCNYFW MLCEGIYLHT LIVVAVFAEK
SEQ ID NO:220  NNQALVATNP VSCKVSQFIH LYLMGCNYFW MLCEGIYLHT LIVVAVFAEK
SEQ ID NO:223  NNQALVATNP VSCKVSQFIH LYLMGCNYFW MLCEGIYLHT LIVVAVFAEK 251                                                  300
SEQ ID NO:2    QHLMWYYFLG WGFPLIPACI HAIARSLYYN DNCWISSDTH LLYIIHGPIC
SEQ ID NO:221  QHLMWYYFLG WGFPLIPACI HAIARSLYYN DNCWISSDTH LLYIIHGPIC
SEQ ID NO:222  QHLMWYYFLG WGFPLIPACI HAIARSLYYN DNCWISSDTH LLYIIHGPIC
SEQ ID NO:220  QHLMWYYFLG WGFPLLPACI HAIARSLYYN DNCWISSDTH LLYIIHGPIC
SEQ ID NO:223  QHLMWYYFLG WGFPLIPACI HAIARSLYYN DNCWISSDTH LLYIIHGPIC
```

Fig. 12A

```
              301                                                    350
SEQ ID NO:2   AALLVNLFFL LNIVRVLITK LKVTHQAESN LYMKAVRATL ILVPLLGIEF
SEQ ID NO:221 AALLVNLFFL LNIVRVLITK LKVTHQAESN LYMKAVRATL ILVPLLGIEF
SEQ ID NO:222 AALLVNLFFL LNIVRVLITK LKVTHQAESN LYMKAVRATL ILVPLLGIEF
SEQ ID NO:220 AALLVNLFFL LNIVRVLITK LKVTHQAESN LYMKAVRATL ILVPLLGIEF
SEQ ID NO:223 AALLVNLFFL LNIVRVLITK LKVTHQAESN LYMKAVRATL ILVPLLGIEF

400
SEQ ID NO:2   VLIPWRPEGK IAEEVYDYIM HILMHFQGLL VSTIFCFFNG EVQAILRRNW
SEQ ID NO:221 VLIPWRPEGK IAEEVYDYIM HILMHFQGLL VSTIFCFFNG EVQAILRRNW
SEQ ID NO:222 VLIPWRPEGK IAEEVYDYIM HILMHFQGLL VSTIFCFFNG EVQAILRRNW
SEQ ID NO:220 VLFPWRPEGK VAEEVYDYVM HILMHYQGLL VSTIFCFFNG EVQAILRRNW
SEQ ID NO:223 VLIPWRPEGK IAEEVYDYIM HILMHFQGLL VSTIFCFFNG EVQAILRRNW 401                                                    450
SEQ ID NO:2   NQYKIQFGNS FSNSEALRSA SYTVSTISDG PGYSHDCPSE HLNGKSIHDI
SEQ ID NO:221 NQYKIQFGNS FSNSEALRSA SYTVSTISDG PGYSHDCPSE HLNGKSIHDI
SEQ ID NO:222 NQYKIQFGNS FSNSEALRSA SYTVSTISDG PGYSHDCPSE HLNGKSIHDI
SEQ ID NO:220 NQYKIQFGNG FSHSDALRSA SYTVSTISDV QGYSHDCPTE HLNGKSIQDI
SEQ ID NO:223 NQYKIQFGNS FSNSEALRSA SYTVSTISDG PGYSHDCPSE HLNGKSIHDI 451        465
SEQ ID NO:2   ENVLLKPENL YN----
SEQ ID NO:221 ENVVLKPENL YN----
SEQ ID NO:222 ENVVLKPENL YN----
SEQ ID NO:220 ENVALKPEKM YDLVM
SEQ ID NO:223 ENVLLKPENL YN----
```

Fig. 12B

SEQUENCE LISTING

<160> NUMBER OF SEQ ID NOS: 261

<210> SEQ ID NO 1
<211> LENGTH: 1419
<212> TYPE: DNA
<213> ORGANISM: Homo sapiens

<400> SEQUENCE: 1

| | | | | | |
|---|---|---|---|---|---|
| atgttataca | gcatatttca | ttttggctta | atgatggaga | aaaagtgtac | cctgtatttt | 60 |
| ctggttctct | tgccttttt | tatgattctt | gttacagcag | aattagaaga | gagtcctgag | 120 |

```
gactcaattc agttgggagt tactagaaat aaaatcatga cagctcaata tgaatgttac    180
caaaagatta tgcaagaccc cattcaacaa gcagaaggcg tttactgcaa cagaacctgg    240
gatggatggc tctgctggaa cgatgttgca gcaggaactg aatcaatgca gctctgccct    300
gattactttc aggactttga tccatcagaa aaagttacaa agatctgtga ccaagatgga    360
aactggttta gacatccagc aagcaacaga acatggacaa attatacccca gtgtaatgtt    420 aacacccacg agaaagtgaa gactgcacta aatttgtttt acctgaccat aattggacac    480
ggattgtcta ttgcatcact gcttatctcg cttggcatat tcttttattt caagagccta    540
agttgccaaa ggattacctt acacaaaaat ctgttcttct catttgtttg taactctgtt    600
gtaacaatca ttcacctcac tgcagtggcc aacaaccagg cttagtagc cacaaatcct    660 gttagttgca agtgtccca gttcattcat ctttacctga tgggctgtaa ttacttttgg    720
atgctctgtg aaggcattta cctacacaca ctcattgtgg tggccgtgtt tgcagagaag    780
caacatttaa tgtggtatta ttttcttggc tggggatttc cactgattcc tgcttgtata    840
catgccattg ctagaagctt atattacaat gacaattgct ggatcagttc tgatacccat    900
ctcctctaca ttatccatgg cccaatttgt gctgctttac tggtgaatct ttttttcttg    960
ttaaatattg tacgcgttct catcaccaag ttaaaagtta cacaccaagc ggaatccaat    1020
ctgtacatga agctgtgag agctactctt atcttggtgc cattgcttgg cattgaattt    1080
gtgctgattc catggcgacc tgaaggaaag attgcagagg aggtatatga ctacatcatg    1140
cacatcctta tgcacttcca gggtcttttg gtctctacca tttttctgctt ctttaatgga    1200 gaggttcaag caattctgag aagaaactgg aatcaataca aaatccaatt tggaaacagc    1260
ttttccaact cagaagctct tcgtagtgcg tcttacacag tgtcaacaat cagtgatggt    1320
ccaggttata gtcatgactg tcctagtgaa cacttaaatg gaaaaagcat ccatgatatt    1380
gaaaatgttc tcttaaaacc agaaaattta tataattga                          1419
```

<210> SEQ ID NO 2
<211> LENGTH: 472
<212> TYPE: PRT
<213> ORGANISM: Homo sapiens

<400> SEQUENCE: 2

```
Met Leu Tyr Ser Ile Phe His Phe Gly Leu Met Met Glu Lys Lys Cys
1               5                   10                  15

Thr Leu Tyr Phe Leu Val Leu Leu Pro Phe Phe Met Ile Leu Val Thr
            20                  25                  30

Ala Glu Leu Glu Glu Ser Pro Glu Asp Ser Ile Gln Leu Gly Val Thr
        35                  40                  45

Arg Asn Lys Ile Met Thr Ala Gln Tyr Glu Cys Tyr Gln Lys Ile Met
    50                  55                  60

Gln Asp Pro Ile Gln Gln Ala Glu Gly Val Tyr Cys Asn Arg Thr Trp
65                  70                  75                  80

Asp Gly Trp Leu Cys Trp Asn Asp Val Ala Ala Gly Thr Glu Ser Met
                85                  90                  95

Gln Leu Cys Pro Asp Tyr Phe Gln Asp Phe Asp Pro Ser Glu Lys Val
            100                 105                 110

Thr Lys Ile Cys Asp Gln Asp Gly Asn Trp Phe Arg His Pro Ala Ser
        115                 120                 125

Asn Arg Thr Trp Thr Asn Tyr Thr Gln Cys Asn Val Asn Thr His Glu
    130                 135                 140
```

Lys Val Lys Thr Ala Leu Asn Leu Phe Tyr Leu Thr Ile Ile Gly His
145                 150                 155                 160

Gly Leu Ser Ile Ala Ser Leu Leu Ile Ser Leu Gly Ile Phe Phe Tyr
            165                 170                 175

Phe Lys Ser Leu Ser Cys Gln Arg Ile Thr Leu His Lys Asn Leu Phe
        180                 185                 190

Phe Ser Phe Val Cys Asn Ser Val Thr Ile Ile His Leu Thr Ala
    195                 200                 205

Val Ala Asn Asn Gln Ala Leu Val Ala Thr Asn Pro Val Ser Cys Lys
    210                 215                 220

Val Ser Gln Phe Ile His Leu Tyr Leu Met Gly Cys Asn Tyr Phe Trp
225                 230                 235                 240

Met Leu Cys Glu Gly Ile Tyr Leu His Thr Leu Ile Val Val Ala Val
            245                 250                 255

Phe Ala Glu Lys Gln His Leu Met Trp Tyr Tyr Phe Leu Gly Trp Gly
            260                 265                 270

Phe Pro Leu Ile Pro Ala Cys Ile His Ala Ile Ala Arg Ser Leu Tyr
    275                 280                 285

Tyr Asn Asp Asn Cys Trp Ile Ser Ser Asp Thr His Leu Leu Tyr Ile
290                 295                 300

Ile His Gly Pro Ile Cys Ala Ala Leu Leu Val Asn Leu Phe Phe Leu
305                 310                 315                 320

Leu Asn Ile Val Arg Val Leu Ile Thr Lys Leu Lys Val Thr His Gln
            325                 330                 335

Ala Glu Ser Asn Leu Tyr Met Lys Ala Val Arg Ala Thr Leu Ile Leu
            340                 345                 350

Val Pro Leu Leu Gly Ile Glu Phe Val Leu Ile Pro Trp Arg Pro Glu
            355                 360                 365

Gly Lys Ile Ala Glu Glu Val Tyr Asp Tyr Ile Met His Ile Leu Met
        370                 375                 380

His Phe Gln Gly Leu Leu Val Ser Thr Ile Phe Cys Phe Phe Asn Gly
385                 390                 395                 400

Glu Val Gln Ala Ile Leu Arg Arg Asn Trp Asn Gln Tyr Lys Ile Gln
            405                 410                 415

Phe Gly Asn Ser Phe Ser Asn Ser Glu Ala Leu Arg Ser Ala Ser Tyr
        420                 425                 430

Thr Val Ser Thr Ile Ser Asp Gly Pro Gly Tyr Ser His Asp Cys Pro
        435                 440                 445

Ser Glu His Leu Asn Gly Lys Ser Ile His Asp Ile Glu Asn Val Leu
    450                 455                 460

Leu Lys Pro Glu Asn Leu Tyr Asn
465                 470

<210> SEQ ID NO 3
<211> LENGTH: 447
<212> TYPE: DNA
<213> ORGANISM: Homo sapiens

<400> SEQUENCE: 3
atggcccggg ccctgtgccg cctcccgcgg cgcggcctct ggctgctcct ggcccatcac    60
ctcttcatga ccactgcctg ccaggaggct aactacggtg ccctcctccg ggagctctgc    120
ctcacccagt ccaggtaga catggaggcc gtcggggaga cgctgtggtg tgactggggc    180
aggaccatca ggagctacag ggagctggcc gactgcacct ggcacatggc ggagaagctg    240

```
ggctgcttct ggcccaatgc agaggtggac aggttcttcc tggcagtgca tggccgctac      300
ttcaggagct gccccatctc aggcagggcc gtgcgggacc cgcccggcag catcctctac      360
cccttcatcg tggtccccat cacggtgacc ctgctggtga cggcactggt ggtctggcag      420
agcaagcgca ctgagggcat tgtgtag                                          447

<210> SEQ ID NO 4
<211> LENGTH: 148
<212> TYPE: PRT
<213> ORGANISM: Homo sapiens

<400> SEQUENCE: 4

Met Ala Arg Ala Leu Cys Arg Leu Pro Arg Arg Gly Leu Trp Leu Leu
1               5                   10                  15

Leu Ala His His Leu Phe Met Thr Thr Ala Cys Gln Glu Ala Asn Tyr
                20                  25                  30

Gly Ala Leu Leu Arg Glu Leu Cys Leu Thr Gln Phe Gln Val Asp Met
            35                  40                  45

Glu Ala Val Gly Glu Thr Leu Trp Cys Asp Trp Gly Arg Thr Ile Arg
        50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Leu Ala Val
                85                  90                  95

His Gly Arg Tyr Phe Arg Ser Cys Pro Ile Ser Gly Arg Ala Val Arg
            100                 105                 110

Asp Pro Pro Gly Ser Ile Leu Tyr Pro Phe Ile Val Pro Ile Thr
        115                 120                 125

Val Thr Leu Leu Val Thr Ala Leu Val Val Trp Gln Ser Lys Arg Thr
    130                 135                 140

Glu Gly Ile Val
145

<210> SEQ ID NO 5
<211> LENGTH: 414
<212> TYPE: DNA
<213> ORGANISM: Homo sapiens

<400> SEQUENCE: 5
atggagaaaa agtgtaccct gtattttctg gttctcttgc cttttttat gattcttgtt        60 acagcagaat tagaagagag tcctgaggac tcaattcagt gggagttac tagaaataaa      120 atcatgacag ctcaatatga atgttaccaa aagattatgc aagaccccat tcaacaagca      180
gaaggcgttt actgcaacag aacctgggat ggatggctct gctggaacga tgttgcagca      240
ggaactgaat caatgcagct ctgccctgat tactttcagg actttgatcc atcagaaaaa      300
gttacaaaga tctgtgacca agatggaaac tggtttagac atccagcaag caacagaaca      360
tggacaaatt atacccagtg taatgttaac acccacgaga aagtgaagac tgca           414

<210> SEQ ID NO 6
<211> LENGTH: 138
<212> TYPE: PRT
<213> ORGANISM: Homo sapiens

<400> SEQUENCE: 6

Met Glu Lys Lys Cys Thr Leu Tyr Phe Leu Val Leu Leu Pro Phe Phe
1               5                   10                  15
```

```
Met Ile Leu Val Thr Ala Glu Leu Glu Ser Pro Glu Asp Ser Ile
        20                  25                  30

Gln Leu Gly Val Thr Arg Asn Lys Ile Met Thr Ala Gln Tyr Glu Cys
    35                  40                  45

Tyr Gln Lys Ile Met Gln Asp Pro Ile Gln Gln Ala Glu Gly Val Tyr
50                  55                  60

Cys Asn Arg Thr Trp Asp Gly Trp Leu Cys Trp Asn Asp Val Ala Ala
65                  70                  75                  80

Gly Thr Glu Ser Met Gln Leu Cys Pro Asp Tyr Phe Gln Asp Phe Asp
                85                  90                  95

Pro Ser Glu Lys Val Thr Lys Ile Cys Asp Gln Asp Gly Asn Trp Phe
            100                 105                 110

Arg His Pro Ala Ser Asn Arg Thr Trp Thr Asn Tyr Thr Gln Cys Asn
        115                 120                 125

Val Asn Thr His Glu Lys Val Lys Thr Ala
    130                 135
```

```
<210> SEQ ID NO 7
<211> LENGTH: 351
<212> TYPE: DNA
<213> ORGANISM: Homo sapiens

<400> SEQUENCE: 7
atggcccggg ccctgtgccg cctcccgcgg cgcggcctct ggctgctcct ggcccatcac      60
ctcttcatga ccactgcctg ccaggaggct aactacggtg ccctcctccg ggagctctgc     120
ctcacccagt tccaggtaga catggaggcc gtcggggaga cgctgtggtg tgactggggc     180
aggaccatca ggagctacag ggagctggcc gactgcacct ggcacatggc ggagaagctg     240
ggctgcttct ggcccaatgc agaggtggac aggttcttcc tggcagtgca tggccgctac     300
ttcaggagct gccccatctc aggcagggcc gtgcgggacc cgcccggcag c              351
```

```
<210> SEQ ID NO 8
<211> LENGTH: 117
<212> TYPE: PRT
<213> ORGANISM: Homo sapiens

<400> SEQUENCE: 8

Met Ala Arg Ala Leu Cys Arg Leu Pro Arg Arg Gly Leu Trp Leu Leu
1               5                   10                  15

Leu Ala His His Leu Phe Met Thr Thr Ala Cys Gln Glu Ala Asn Tyr
            20                  25                  30

Gly Ala Leu Leu Arg Glu Leu Cys Leu Thr Gln Phe Gln Val Asp Met
        35                  40                  45

Glu Ala Val Gly Glu Thr Leu Trp Cys Asp Trp Gly Arg Thr Ile Arg
50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
                85                  90                  95

His Gly Arg Tyr Phe Arg Ser Cys Pro Ile Ser Gly Arg Ala Val Arg
            100                 105                 110

Asp Pro Pro Gly Ser
        115
```

```
<210> SEQ ID NO 9
<211> LENGTH: 31
```

<212> TYPE: PRT
<213> ORGANISM: Homo sapiens

<400> SEQUENCE: 9

```
Trp Val Thr His Arg Leu Ala Gly Leu Leu Ser Arg Ser Gly Gly Val
1               5                   10                  15

Val Arg Cys Asn Phe Val Pro Thr Asp Val Gly Pro Phe Ala Phe
            20                  25                  30
```

<210> SEQ ID NO 10
<211> LENGTH: 116
<212> TYPE: PRT
<213> ORGANISM: Homo sapiens

<400> SEQUENCE: 10

```
Glu Leu Glu Glu Ser Pro Glu Asp Ser Ile Gln Leu Gly Val Thr Arg
1               5                   10                  15

Asn Lys Ile Met Thr Ala Gln Tyr Glu Cys Tyr Gln Lys Ile Met Gln
            20                  25                  30

Asp Pro Ile Gln Gln Ala Glu Gly Val Tyr Cys Asn Arg Thr Trp Asp
        35                  40                  45

Gly Trp Leu Cys Trp Asn Asp Val Ala Ala Gly Thr Glu Ser Met Gln
50                  55                  60

Leu Cys Pro Asp Tyr Phe Gln Asp Phe Asp Pro Ser Glu Lys Val Thr
65                  70                  75                  80

Lys Ile Cys Asp Gln Asp Gly Asn Trp Phe Arg His Pro Ala Ser Asn
                85                  90                  95

Arg Thr Trp Thr Asn Tyr Thr Gln Cys Asn Val Asn Thr His Glu Lys
            100                 105                 110

Val Lys Thr Ala
        115
```

<210> SEQ ID NO 11
<211> LENGTH: 91
<212> TYPE: PRT
<213> ORGANISM: Homo sapiens

<400> SEQUENCE: 11

```
Cys Gln Glu Ala Asn Tyr Gly Ala Leu Leu Arg Glu Leu Cys Leu Thr
1               5                   10                  15

Gln Phe Gln Val Asp Met Glu Ala Val Gly Glu Thr Leu Trp Cys Asp
            20                  25                  30

Trp Gly Arg Thr Ile Arg Ser Tyr Arg Glu Leu Ala Asp Cys Thr Trp
        35                  40                  45

His Met Ala Glu Lys Leu Gly Cys Phe Trp Pro Asn Ala Glu Val Asp
    50                  55                  60

Arg Phe Phe Leu Ala Val His Gly Arg Tyr Phe Arg Ser Cys Pro Ile
65                  70                  75                  80

Ser Gly Arg Ala Val Arg Asp Pro Pro Gly Ser
                85                  90
```

<210> SEQ ID NO 12
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Met Asp Met Arg Val Pro Ala Gln Leu Leu Gly Leu Leu Leu Trp
1               5                   10                  15

Leu Arg Gly Ala Arg Cys Gln Ser Val Leu Thr Gln Pro Pro Ser Val
                20                  25                  30

Ser Glu Ala Pro Gly Gln Lys Val Thr Ile Ser Cys Ser Gly Ser Ser
            35                  40                  45

Ser Asn Ile Gly Asn Asn Tyr Val Ser Trp Tyr Gln Gln Leu Pro Gly
    50                  55                  60

Thr Ala Pro Lys Leu Leu Ile Tyr Asp Asn Asn Lys Arg Pro Ser Gly
65                  70                  75                  80

Ile Pro Asp Arg Phe Ser Gly Ser Lys Ser Gly Thr Ser Ala Thr Leu
                85                  90                  95

Gly Ile Thr Gly Leu Gln Thr Gly Asp Glu Ala Asp Tyr Tyr Cys Gly
            100                 105                 110

Thr Trp Asp Ser Arg Leu Ser Ala Val Val Phe Gly Gly Gly Thr Lys
    115                 120                 125

Leu Thr Val Leu Gly Gln Pro Lys Ala Asn Pro Thr Val Thr Leu Phe
130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 13
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asp Met Arg Val Pro Ala Gln Leu Leu Gly Leu Leu Leu Leu Trp
1               5                   10                  15

Leu Arg Gly Ala Arg Cys Gln Ser Val Leu Thr Gln Pro Pro Ser Ala
                20                  25                  30

Ser Gly Thr Pro Gly Gln Arg Val Thr Ile Ser Cys Ser Gly Ser Ser
            35                  40                  45

Ser Asn Ile Gly Ser Asn Tyr Val Tyr Trp Tyr Gln Gln Leu Pro Gly
    50                  55                  60

Ala Ala Pro Lys Leu Leu Ile Phe Arg Ser Asn Gln Arg Pro Ser Gly
65                  70                  75                  80

Val Pro Asp Arg Phe Ser Gly Ser Lys Ser Gly Thr Ser Ala Ser Leu
                85                  90                  95

Ala Ile Ser Gly Leu Arg Ser Glu Asp Glu Ala Asp Tyr Tyr Cys Ala
            100                 105                 110

Ala Trp Asp Asp Ser Leu Ser Gly Trp Val Phe Gly Gly Gly Thr Lys

```
                115                 120                 125
Leu Thr Val Leu Gly Gln Pro Lys Ala Asn Pro Thr Val Thr Leu Phe
130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Gly Ser Pro Val Lys Ala Gly Val Glu Thr Thr Lys Pro Ser Lys
                180                 185                 190

Gln Ser Asn Asn Lys Tyr Ala Ala Ser Ser Tyr Leu Ser Leu Thr Pro
                195                 200                 205

Glu Gln Trp Lys Ser His Arg Ser Tyr Ser Cys Gln Val Thr His Glu
210                 215                 220

Gly Ser Thr Val Glu Lys Thr Val Ala Pro Thr Glu Cys Ser
225                 230                 235

<210> SEQ ID NO 14
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Arg Asn Asp Leu Gly Trp Phe Gln Gln Lys Pro Gly Lys
        50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Leu Ala Thr Tyr Tyr Cys Leu Gln
                100                 105                 110

Tyr Asn Ile Tyr Pro Trp Thr Phe Gly Gln Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235
```

```
<210> SEQ ID NO 15
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Met Arg Val Pro Ala Gln Leu Leu Gly Leu Leu Leu Leu Trp
1               5                   10                  15

Leu Arg Gly Ala Arg Cys Ser Ser Glu Leu Thr Gln Asp Pro Thr Val
            20                  25                  30

Ser Val Ala Leu Gly Gln Thr Val Lys Ile Thr Cys Gln Gly Asp Ser
        35                  40                  45

Leu Arg Ser Phe Tyr Ala Ser Trp Tyr Gln Gln Lys Pro Gly Gln Ala
    50                  55                  60

Pro Val Leu Val Phe Tyr Gly Lys Asn Asn Arg Pro Ser Gly Ile Pro
65                  70                  75                  80

Asp Arg Phe Ser Gly Ser Ser Gly Asn Thr Ala Ser Leu Thr Ile
                85                  90                  95

Thr Gly Ala Gln Ala Glu Asp Glu Ala Asp Tyr Tyr Cys Asn Ser Arg
            100                 105                 110

Asp Ser Ser Val Tyr His Leu Val Leu Gly Gly Gly Thr Lys Leu Thr
            115                 120                 125

Val Leu Gly Gln Pro Lys Ala Asn Pro Thr Val Thr Leu Phe Pro Pro
        130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 16
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Asp Met Arg Val Pro Ala Gln Leu Leu Gly Leu Leu Leu Leu Trp
1               5                   10                  15

Leu Arg Gly Ala Arg Cys Asp Ile Ile Leu Ala Gln Thr Pro Leu Ser
            20                  25                  30

Leu Ser Val Thr Pro Gly Gln Pro Ala Ser Ile Ser Cys Lys Ser Ser
        35                  40                  45

Gln Ser Leu Leu His Ser Ala Gly Lys Thr Tyr Leu Tyr Trp Tyr Leu
    50                  55                  60
```

```
Gln Lys Pro Gly Gln Pro Gln Leu Leu Ile Tyr Glu Val Ser Asn
 65                 70                  75                  80

Arg Phe Ser Gly Val Pro Asp Arg Phe Ser Gly Ser Gly Ser Gly Thr
                 85                  90                  95

Asp Phe Thr Leu Lys Ile Ser Arg Val Glu Ala Glu Asp Val Gly Ile
            100                 105                 110

Tyr Tyr Cys Met Gln Ser Phe Pro Leu Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 17
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Met Arg Val Pro Ala Gln Leu Leu Gly Leu Leu Leu Leu Trp
 1               5                  10                  15

Leu Arg Gly Ala Arg Cys Gln Ser Val Leu Thr Gln Pro Pro Ser Val
                 20                  25                  30

Ser Ala Ala Pro Gly Gln Lys Val Thr Ile Ser Cys Ser Gly Ser Ser
            35                  40                  45

Ser Asn Ile Gly Asn Asn Tyr Val Ser Trp Tyr Gln Gln Leu Pro Gly
 50                  55                  60

Thr Ala Pro Lys Leu Leu Ile Tyr Asp Asn Asn Lys Arg Pro Ser Gly
 65                  70                  75                  80

Ile Pro Asp Arg Phe Ser Gly Ser Lys Ser Gly Thr Ser Thr Thr Leu
                 85                  90                  95

Gly Ile Thr Gly Leu Gln Thr Gly Asp Glu Ala Asp Tyr Tyr Cys Gly
            100                 105                 110

Thr Trp Asp Ser Arg Leu Ser Ala Val Val Phe Gly Gly Gly Thr Lys
        115                 120                 125

Leu Thr Val Leu Gly Gln Pro Lys Ala Asn Pro Thr Val Thr Leu Phe
    130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175
```

```
Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 18
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Phe Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Phe Thr Phe Gly Pro Gly
        115                 120                 125

Thr Lys Val Asp Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 19
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 19

Met Asp Met Arg Val Pro Ala Gln Leu Leu Gly Leu Leu Leu Trp
1               5                   10                  15

Leu Arg Gly Ala Arg Cys Asp Ile Ile Leu Thr Gln Thr Pro Leu Ser
            20                  25                  30

Leu Ser Val Thr Pro Gly Gln Pro Ala Ser Ile Ser Cys Lys Ser Ser
        35                  40                  45

Gln Ser Leu Leu His Ser Asp Gly Lys Thr Tyr Leu Tyr Trp Tyr Leu
    50                  55                  60

Gln Lys Pro Gly Gln Pro Pro Gln Leu Leu Ile Tyr Glu Val Ser Asn
65                  70                  75                  80

Arg Phe Ser Gly Glu Pro Asp Arg Phe Ser Gly Ser Gly Ser Gly Thr
                85                  90                  95

Asp Phe Thr Leu Lys Ile Ser Arg Val Glu Ala Glu Asp Val Gly Thr
            100                 105                 110

Tyr Tyr Cys Met Gln Ser Phe Pro Leu Pro Leu Thr Phe Gly Gly Gly
        115                 120                 125

Thr Lys Val Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys

<210> SEQ ID NO 20
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Asp Met Arg Val Pro Ala Gln Leu Leu Gly Leu Leu Leu Trp
1               5                   10                  15

Leu Arg Gly Ala Arg Cys Gln Ser Val Leu Thr Gln Pro Pro Ser Val
            20                  25                  30

Ser Ala Ala Pro Gly Gln Lys Val Thr Ile Ser Cys Ser Gly Ser Ser
        35                  40                  45

Ser Asn Ile Gly Asn Asn Tyr Val Ser Trp Tyr Gln Gln Phe Pro Gly
    50                  55                  60

Thr Ala Pro Lys Leu Leu Ile Tyr Asp Asn Asn Lys Arg Pro Ser Gly
65                  70                  75                  80

Ile Pro Asp Arg Phe Ser Gly Ser Lys Ser Gly Thr Ser Ala Thr Leu
                85                  90                  95

Gly Ile Thr Gly Leu Gln Thr Gly Asp Glu Ala Asp Tyr Tyr Cys Gly

```
            100                 105                 110
Thr Trp Asp Ser Arg Leu Ser Ala Val Val Phe Gly Gly Gly Thr Lys
            115                 120                 125

Leu Thr Val Leu Gly Gln Pro Lys Ala Asn Pro Thr Val Thr Leu Phe
            130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
            165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
            195                 200                 205

Glu Gln Trp Lys Ser His Arg Ser Tyr Ser Cys Gln Val Thr His Glu
            210                 215                 220

Gly Ser Thr Val Glu Lys Thr Val Ala Pro Thr Glu Cys Ser
225                 230                 235
```

<210> SEQ ID NO 21
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Asp Met Arg Val Pro Ala Gln Leu Leu Gly Leu Leu Leu Leu Trp
1               5                   10                  15

Leu Arg Gly Ala Arg Cys Gln Ser Val Leu Thr Gln Ser Pro Ser Ala
            20                  25                  30

Ser Gly Thr Pro Gly Gln Arg Val Thr Ile Ser Cys Ser Gly Ser Ser
            35                  40                  45

Ser Asn Ile Gly Ser Asn Tyr Val Tyr Trp Tyr Gln Gln Leu Pro Gly
        50                  55                  60

Ala Ala Pro Lys Leu Leu Ile Leu Arg Asn Asn Gln Arg Pro Ser Gly
65                  70                  75                  80

Val Pro Asp Arg Phe Ser Gly Ser Lys Ser Gly Thr Ser Ala Ser Leu
            85                  90                  95

Thr Ile Ser Gly Leu Arg Ser Glu Asp Glu Ala Asp Tyr Tyr Cys Ala
            100                 105                 110

Ala Trp Asp Asp Ser Leu Ser Gly Trp Val Phe Gly Gly Gly Thr Lys
            115                 120                 125

Leu Thr Val Leu Gly Gln Pro Lys Ala Asn Pro Thr Val Thr Leu Phe
            130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
            165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
            195                 200                 205

Glu Gln Trp Lys Ser His Arg Ser Tyr Ser Cys Gln Val Thr His Glu
            210                 215                 220
```

Gly Ser Thr Val Glu Lys Thr Val Ala Pro Thr Glu Cys Ser
225                 230                 235

<210> SEQ ID NO 22
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Asp Met Arg Val Pro Ala Gln Leu Leu Gly Leu Leu Leu Leu Trp
1               5                   10                  15

Leu Arg Gly Ala Arg Cys Gln Ser Val Leu Thr Gln Pro Pro Ser Ala
                20                  25                  30

Ser Gly Thr Pro Gly Gln Arg Val Thr Ile Ser Cys Ser Gly Ser Ser
            35                  40                  45

Ser Asn Ile Gly Ser Asn Thr Val Asn Trp Tyr Gln Gln Leu Pro Gly
    50                  55                  60

Thr Ala Pro Lys Leu Leu Ile Tyr Thr Asn Asn Gln Arg Pro Ser Gly
65                  70                  75                  80

Val Pro Asp Arg Phe Ser Gly Ser Lys Ser Gly Thr Ser Ala Ser Leu
                85                  90                  95

Ala Ile Ser Gly Leu Gln Ser Glu Asp Glu Ala Asp Phe Tyr Cys Ala
            100                 105                 110

Ala Arg Asp Glu Ser Leu Asn Gly Val Val Phe Gly Gly Gly Thr Lys
        115                 120                 125

Leu Thr Val Leu Gly Gln Pro Lys Ala Asn Pro Thr Val Thr Leu Phe
130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 23
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Asp Met Arg Val Pro Ala Gln Leu Leu Gly Leu Leu Leu Leu Trp
1               5                   10                  15

Leu Arg Gly Ala Arg Cys Gln Ser Val Leu Thr Gln Pro Pro Ser Ala
                20                  25                  30

Ser Gly Thr Pro Gly Gln Arg Val Thr Ile Ser Cys Ser Gly Ser Ser
            35                  40                  45

```
Ser Asn Ile Gly Ser Asn Tyr Val Tyr Trp Tyr Gln Gln Leu Pro Gly
 50                  55                  60

Ala Ala Pro Lys Leu Leu Ile Phe Arg Asn Asn Gln Arg Pro Ser Gly
 65                  70                  75                  80

Val Pro Asp Arg Phe Ser Gly Ser Lys Ser Gly Thr Ser Ala Ser Leu
                 85                  90                  95

Ala Ile Ser Gly Leu Arg Ser Glu Asp Glu Ala Asp Tyr Tyr Cys Ala
            100                 105                 110

Ala Trp Asp Asp Ser Leu Ser Gly Trp Val Phe Gly Gly Gly Thr Lys
            115                 120                 125

Leu Thr Val Leu Gly Gln Pro Lys Ala Asn Pro Thr Val Thr Leu Phe
130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
            195                 200                 205

Glu Gln Trp Lys Ser His Arg Ser Tyr Ser Cys Gln Val Thr His Glu
210                 215                 220

Gly Ser Thr Val Glu Lys Thr Val Ala Pro Thr Glu Cys Ser
225                 230                 235
```

<210> SEQ ID NO 24
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Asp Met Arg Val Pro Ala Gln Leu Leu Gly Leu Leu Leu Leu Trp
 1               5                  10                  15

Leu Arg Gly Ala Arg Cys Asp Ile Thr Leu Thr Gln Thr Pro Leu Ser
                 20                  25                  30

Leu Ser Val Ser Pro Gly Gln Pro Ala Ser Ile Ser Cys Lys Ser Ser
             35                  40                  45

Gln Ser Leu Leu His Ser Asp Gly Arg Asn Tyr Leu Tyr Trp Tyr Leu
 50                  55                  60

Gln Lys Pro Gly Gln Pro Pro Gln Leu Leu Ile Tyr Glu Val Ser Asn
 65                  70                  75                  80

Arg Phe Ser Gly Leu Pro Asp Arg Phe Ser Gly Ser Gly Ser Gly Thr
                 85                  90                  95

Asp Phe Thr Leu Lys Ile Ser Arg Val Glu Ala Glu Asp Val Gly Ile
            100                 105                 110

Tyr Tyr Cys Met Gln Ser Phe Pro Leu Pro Leu Thr Phe Gly Gly Gly
            115                 120                 125

Thr Lys Val Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175
```

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys

<210> SEQ ID NO 25
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Asp Met Arg Val Pro Ala Gln Leu Leu Gly Leu Leu Leu Leu Trp
1               5                   10                  15

Leu Arg Gly Ala Arg Cys Gln Ser Val Leu Thr Gln Pro Pro Ser Val
            20                  25                  30

Ser Ala Ala Pro Gly Gln Lys Val Thr Ile Ser Cys Ser Gly Ser Ser
        35                  40                  45

Ser Asn Ile Gly Asn Asn Tyr Val Ser Trp Tyr Gln Gln Leu Pro Gly
    50                  55                  60

Thr Ala Pro Lys Leu Leu Ile Tyr Asp Asn Asn Lys Arg Pro Ser Gly
65                  70                  75                  80

Ile Pro Asp Arg Phe Ser Gly Ser Lys Ser Gly Thr Ser Ala Thr Leu
                85                  90                  95

Gly Ile Thr Gly Leu Gln Thr Gly Asp Glu Ala Asp Tyr Tyr Cys Gly
            100                 105                 110

Thr Trp Asp Ser Arg Leu Ser Ala Val Val Phe Gly Gly Gly Thr Lys
        115                 120                 125

Leu Thr Val Leu Gly Gln Pro Lys Ala Asn Pro Thr Val Thr Leu Phe
130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 26
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 26

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Lys Asp Leu Gly Trp Tyr Gln Gln Lys Pro Gly Lys
    50                  55                  60

Ala Pro Lys Arg Leu Ile Tyr Gly Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

Tyr Asn Ser Phe Pro Trp Thr Phe Gly Gln Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 27
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Gly Tyr Leu Thr Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110
```

```
Gly Asn Ser Leu Cys Arg Phe Gly Gln Gly Thr Lys Leu Glu Ile Lys
            115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 28
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Gly Tyr Leu Thr Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Asn Ser Leu Ser Arg Phe Gly Gln Gly Thr Lys Leu Glu Ile Lys
            115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
```

```
225                 230                 235
```

<210> SEQ ID NO 29
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Phe Gly Met His Trp Val Arg Gln Ala Pro Gly
    50                  55                  60

Lys Gly Leu Glu Trp Val Ala Val Ile Ser Phe Asp Gly Ser Ile Lys
65                  70                  75                  80

Tyr Ser Val Asp Ser Val Lys Gly Arg Phe Thr Ile Ser Arg Asp Asn
                85                  90                  95

Ser Lys Asn Thr Leu Phe Leu Gln Met Asn Ser Leu Arg Ala Glu Asp
            100                 105                 110

Thr Ala Val Tyr Tyr Cys Ala Arg Asp Arg Leu Asn Tyr Tyr Asp Ser
        115                 120                 125

Ser Gly Tyr Tyr His Tyr Lys Tyr Tyr Gly Met Ala Val Trp Gly Gln
    130                 135                 140

Gly Thr Thr Val Thr Val Ser Ser Ala Ser Thr Lys Gly Pro Ser Val
145                 150                 155                 160

Phe Pro Leu Ala Pro Cys Ser Arg Ser Thr Ser Glu Ser Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Asn Phe Gly Thr Gln Thr Tyr Thr Cys Asn Val Asp His Lys
225                 230                 235                 240

Pro Ser Asn Thr Lys Val Asp Lys Thr Val Glu Arg Lys Cys Cys Val
                245                 250                 255

Glu Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Phe Arg Val Val Ser Val
                325                 330                 335

Leu Thr Val Val His Gln Asp Trp Leu Asn Gly Lys Glu Tyr Lys Cys
            340                 345                 350
```

```
Lys Val Ser Asn Lys Gly Leu Pro Ala Pro Ile Glu Lys Thr Ile Ser
            355                 360                 365

Lys Thr Lys Gly Gln Pro Arg Glu Pro Gln Val Tyr Thr Leu Pro Pro
    370                 375                 380

Ser Arg Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Met Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 30
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asn Ala Trp Met Ser Trp Val Arg Gln Ala Pro Gly
    50                  55                  60

Lys Gly Leu Glu Trp Val Gly Arg Ile Lys Ser Thr Thr Asp Gly Gly
65                  70                  75                  80

Thr Thr Asp Tyr Ala Ala Pro Val Lys Gly Arg Phe Thr Ile Ser Arg
                85                  90                  95

Asp Asp Ser Lys Asn Thr Leu Tyr Leu Gln Met Asn Ser Leu Lys Thr
            100                 105                 110

Glu Asp Thr Ala Val Tyr Tyr Cys Thr Thr Asp Arg Thr Gly Tyr Ser
        115                 120                 125

Ile Ser Trp Ser Ser Tyr Tyr Tyr Tyr Gly Met Asp Val Trp Gly
    130                 135                 140

Gln Gly Thr Thr Val Thr Val Ser Ser Ala Ser Thr Lys Gly Pro Ser
145                 150                 155                 160

Val Phe Pro Leu Ala Pro Cys Ser Arg Ser Thr Ser Glu Ser Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
    210                 215                 220

Pro Ser Ser Asn Phe Gly Thr Gln Thr Tyr Thr Cys Asn Val Asp His
225                 230                 235                 240
```

-continued

```
Lys Pro Ser Asn Thr Lys Val Asp Lys Thr Val Glu Arg Lys Cys Cys
                245                 250                 255

Val Glu Cys Pro Pro Cys Pro Ala Pro Val Ala Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Phe Arg Val Val Ser
                325                 330                 335

Val Leu Thr Val Val His Gln Asp Trp Leu Asn Gly Lys Glu Tyr Lys
            340                 345                 350

Cys Lys Val Ser Asn Lys Gly Leu Pro Ala Pro Ile Glu Lys Thr Ile
        355                 360                 365

Ser Lys Thr Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Met Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 31
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Asp Met Arg Val Pro Ala Gln Leu Leu Gly Leu Leu Leu Leu Trp
1               5                   10                  15

Leu Arg Gly Ala Arg Cys Glu Val Gln Leu Leu Glu Ser Gly Gly Gly
            20                  25                  30

Leu Val Gln Pro Gly Glu Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Arg Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Asp Gln Arg Glu Val Gly Pro Tyr
```

```
            115                 120                 125
Ser Ser Gly Trp Tyr Asp Tyr Tyr Gly Met Asp Val Trp Gly Gln
130                 135                 140

Gly Thr Thr Val Thr Val Ser Ser Ala Ser Thr Lys Gly Pro Ser Val
145                 150                 155                 160

Phe Pro Leu Ala Pro Cys Ser Arg Ser Thr Ser Glu Ser Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
210                 215                 220

Ser Ser Asn Phe Gly Thr Gln Thr Tyr Thr Cys Asn Val Asp His Lys
225                 230                 235                 240

Pro Ser Asn Thr Lys Val Asp Lys Thr Val Glu Arg Lys Cys Cys Val
                245                 250                 255

Glu Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Phe Arg Val Val Ser Val
                325                 330                 335

Leu Thr Val Val His Gln Asp Trp Leu Asn Gly Lys Glu Tyr Lys Cys
            340                 345                 350

Lys Val Ser Asn Lys Gly Leu Pro Ala Pro Ile Glu Lys Thr Ile Ser
        355                 360                 365

Lys Thr Lys Gly Gln Pro Arg Glu Pro Gln Val Tyr Thr Leu Pro Pro
370                 375                 380

Ser Arg Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Met Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Gly Lys
465                 470                 475
```

<210> SEQ ID NO 32
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Met Asp Met Arg Val Pro Ala Gln Leu Leu Gly Leu Leu Leu Leu Trp
 1               5                  10                  15
Leu Arg Gly Ala Arg Cys Gln Val Gln Leu Val Gln Ser Gly Ala Glu
             20                  25                  30
Val Lys Lys Pro Gly Ala Ser Val Lys Val Ser Cys Lys Ala Ser Gly
         35                  40                  45
Tyr Thr Phe Thr Gly Tyr Tyr Met His Trp Val Arg Gln Ala Pro Gly
     50                  55                  60
Gln Gly Leu Glu Trp Met Gly Trp Ile Asn Pro Asn Ser Gly Gly Thr
 65                  70                  75                  80
Asn Tyr Ala Gln Lys Phe Gln Gly Arg Val Thr Met Thr Arg Asp Thr
                 85                  90                  95
Ser Ile Ser Thr Ala Tyr Met Glu Leu Ser Arg Leu Arg Ser Asp Asp
             100                 105                 110
Thr Ala Val Tyr Phe Cys Ala Arg Asp Gln Met Ser Ile Ile Met Leu
         115                 120                 125
Arg Gly Val Phe Pro Pro Tyr Tyr Gly Met Asp Val Trp Gly Gln
     130                 135                 140
Gly Thr Thr Val Thr Val Ser Ser Ala Ser Thr Lys Gly Pro Ser Val
145                 150                 155                 160
Phe Pro Leu Ala Pro Cys Ser Arg Ser Thr Ser Glu Ser Thr Ala Ala
                 165                 170                 175
Leu Gly Cys Leu Val Lys Asp Tyr Phe Pro Glu Pro Val Thr Val Ser
             180                 185                 190
Trp Asn Ser Gly Ala Leu Thr Ser Gly Val His Thr Phe Pro Ala Val
         195                 200                 205
Leu Gln Ser Ser Gly Leu Tyr Ser Leu Ser Ser Val Val Thr Val Pro
     210                 215                 220
Ser Ser Asn Phe Gly Thr Gln Thr Tyr Thr Cys Asn Val Asp His Lys
225                 230                 235                 240
Pro Ser Asn Thr Lys Val Asp Lys Thr Val Glu Arg Lys Cys Cys Val
                 245                 250                 255
Glu Cys Pro Pro Cys Pro Ala Pro Pro Val Ala Gly Pro Ser Val Phe
             260                 265                 270
Leu Phe Pro Pro Lys Pro Lys Asp Thr Leu Met Ile Ser Arg Thr Pro
         275                 280                 285
Glu Val Thr Cys Val Val Val Asp Val Ser His Glu Asp Pro Glu Val
     290                 295                 300
Gln Phe Asn Trp Tyr Val Asp Gly Val Glu Val His Asn Ala Lys Thr
305                 310                 315                 320
Lys Pro Arg Glu Glu Gln Phe Asn Ser Thr Phe Arg Val Val Ser Val
                 325                 330                 335
Leu Thr Val Val His Gln Asp Trp Leu Asn Gly Lys Glu Tyr Lys Cys
             340                 345                 350
Lys Val Ser Asn Lys Gly Leu Pro Ala Pro Ile Glu Lys Thr Ile Ser
         355                 360                 365
Lys Thr Lys Gly Gln Pro Arg Glu Pro Gln Val Tyr Thr Leu Pro Pro
     370                 375                 380
Ser Arg Glu Glu Met Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
                 405                 410                 415
Gln Pro Glu Asn Asn Tyr Lys Thr Thr Pro Pro Met Leu Asp Ser Asp
```

```
                    420                 425                 430
Gly Ser Phe Phe Leu Tyr Ser Lys Leu Thr Val Asp Lys Ser Arg Trp
                435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475
```

<210> SEQ ID NO 33
<211> LENGTH: 477
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
                20                  25                  30

Val Val Gln Pro Gly Arg Ser Leu Arg Leu Ser Cys Ala Ala Ser Gly
            35                  40                  45

Phe Thr Phe Ser Ser Tyr Gly Met His Trp Val Arg Gln Ala Pro Gly
        50                  55                  60

Lys Gly Leu Glu Trp Val Ala Val Ile Ser Tyr Asp Gly Ser His Glu
65                  70                  75                  80

Ser Tyr Ala Asp Ser Val Lys Gly Arg Phe Thr Ile Ser Arg Asp Ile
                85                  90                  95

Ser Lys Asn Thr Leu Tyr Leu Gln Met Asn Ser Leu Arg Ala Glu Asp
            100                 105                 110

Thr Ala Val Tyr Phe Cys Ala Arg Glu Arg Lys Arg Val Thr Met Ser
        115                 120                 125

Thr Leu Tyr Tyr Tyr Phe Tyr Tyr Gly Met Asp Val Trp Gly Gln Gly
    130                 135                 140

Thr Thr Val Thr Val Ser Ser Ala Ser Thr Lys Gly Pro Ser Val Phe
145                 150                 155                 160

Pro Leu Ala Pro Cys Ser Arg Ser Thr Ser Glu Ser Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Asn Phe Gly Thr Gln Thr Tyr Thr Cys Asn Val Asp His Lys Pro
225                 230                 235                 240

Ser Asn Thr Lys Val Asp Lys Thr Val Glu Arg Lys Cys Cys Val Glu
                245                 250                 255

Cys Pro Pro Cys Pro Ala Pro Pro Val Ala Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Gln
    290                 295                 300
```

```
Phe Asn Trp Tyr Val Asp Gly Val Glu Val His Asn Ala Lys Thr Lys
305                 310                 315                 320

Pro Arg Glu Glu Gln Phe Asn Ser Thr Phe Arg Val Val Ser Val Leu
            325                 330                 335

Thr Val Val His Gln Asp Trp Leu Asn Gly Lys Glu Tyr Lys Cys Lys
        340                 345                 350

Val Ser Asn Lys Gly Leu Pro Ala Pro Ile Glu Lys Thr Ile Ser Lys
    355                 360                 365

Thr Lys Gly Gln Pro Arg Glu Pro Gln Val Tyr Thr Leu Pro Pro Ser
370                 375                 380

Arg Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Met Leu Asp Ser Asp Gly
        420                 425                 430

Ser Phe Phe Leu Tyr Ser Lys Leu Thr Val Asp Lys Ser Arg Trp Gln
    435                 440                 445

Gln Gly Asn Val Phe Ser Cys Ser Val Met His Glu Ala Leu His Asn
450                 455                 460

His Tyr Thr Gln Lys Ser Leu Ser Leu Ser Pro Gly Lys
465                 470                 475

<210> SEQ ID NO 34
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Lys Pro Gly Arg Ser Leu Arg Leu Ser Cys Thr Ala Ser Gly
        35                  40                  45

Phe Thr Phe Gly Asp Tyr Ala Met Ser Trp Phe Arg Gln Ala Pro Gly
    50                  55                  60

Lys Gly Leu Glu Trp Ile Gly Phe Ile Arg Ser Arg Ala Tyr Gly Gly
65                  70                  75                  80

Thr Pro Glu Tyr Ala Ala Ser Val Lys Gly Arg Phe Thr Ile Ser Arg
            85                  90                  95

Asp Asp Ser Lys Thr Ile Ala Tyr Leu Gln Met Asn Ser Leu Lys Thr
        100                 105                 110

Glu Asp Thr Ala Val Tyr Phe Cys Ala Arg Gly Arg Gly Ile Ala Ala
    115                 120                 125

Arg Trp Asp Tyr Trp Gly Gln Gly Thr Leu Val Thr Val Ser Ser Ala
130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
        180                 185                 190
```

Val His Thr Phe Pro Ala Val Leu Gln Ser Ser Gly Leu Tyr Ser Leu
            195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
            245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Gln Phe Asn Trp Tyr Val Asp Gly Val
            290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
            325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 35
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asn Ala Trp Met Ser Trp Val Arg Gln Ala Pro Gly
    50                  55                  60

Lys Gly Leu Glu Trp Val Gly Arg Ile Lys Ser Lys Thr Asp Gly Gly

```
                65                  70                  75                  80
        Thr Thr Asp Tyr Thr Ala Pro Val Lys Gly Arg Phe Thr Ile Ser Arg
                            85                  90                  95

Asp Asp Ser Lys Asn Thr Leu Tyr Leu Gln Met Asn Ser Leu Lys Ala
                            100                 105                 110

Glu Asp Thr Ala Val Tyr Tyr Cys Thr Thr Asp Arg Thr Gly Tyr Ser
                            115                 120                 125

Ile Ser Trp Ser Ser Tyr Tyr Tyr Tyr Gly Met Asp Val Trp Gly
                130                 135                 140

Gln Gly Thr Thr Val Thr Val Ser Ser Ala Ser Thr Lys Gly Pro Ser
        145                 150                 155                 160

Val Phe Pro Leu Ala Pro Cys Ser Arg Ser Thr Ser Glu Ser Thr Ala
                            165                 170                 175

Ala Leu Gly Cys Leu Val Lys Asp Tyr Phe Pro Glu Pro Val Thr Val
                            180                 185                 190

Ser Trp Asn Ser Gly Ala Leu Thr Ser Gly Val His Thr Phe Pro Ala
                            195                 200                 205

Val Leu Gln Ser Ser Gly Leu Tyr Ser Leu Ser Ser Val Val Thr Val
                            210                 215                 220

Pro Ser Ser Asn Phe Gly Thr Gln Thr Tyr Thr Cys Asn Val Asp His
        225                 230                 235                 240

Lys Pro Ser Asn Thr Lys Val Asp Lys Thr Val Glu Arg Lys Cys Cys
                            245                 250                 255

Val Glu Cys Pro Pro Cys Pro Ala Pro Pro Val Ala Gly Pro Ser Val
                            260                 265                 270

Phe Leu Phe Pro Pro Lys Pro Lys Asp Thr Leu Met Ile Ser Arg Thr
                            275                 280                 285

Pro Glu Val Thr Cys Val Val Val Asp Val Ser His Glu Asp Pro Glu
                            290                 295                 300

Val Gln Phe Asn Trp Tyr Val Asp Gly Val Glu Val His Asn Ala Lys
        305                 310                 315                 320

Thr Lys Pro Arg Glu Glu Gln Phe Asn Ser Thr Phe Arg Val Val Ser
                            325                 330                 335

Val Leu Thr Val Val His Gln Asp Trp Leu Asn Gly Lys Glu Tyr Lys
                            340                 345                 350

Cys Lys Val Ser Asn Lys Gly Leu Pro Ala Pro Ile Glu Lys Thr Ile
                            355                 360                 365

Ser Lys Thr Lys Gly Gln Pro Arg Glu Pro Gln Val Tyr Thr Leu Pro
                370                 375                 380

Pro Ser Arg Glu Glu Met Thr Lys Asn Gln Val Ser Leu Thr Cys Leu
        385                 390                 395                 400

Val Lys Gly Phe Tyr Pro Ser Asp Ile Ala Val Glu Trp Glu Ser Asn
                            405                 410                 415

Gly Gln Pro Glu Asn Asn Tyr Lys Thr Thr Pro Pro Met Leu Asp Ser
                            420                 425                 430

Asp Gly Ser Phe Phe Leu Tyr Ser Lys Leu Thr Val Asp Lys Ser Arg
                            435                 440                 445

Trp Gln Gln Gly Asn Val Phe Ser Cys Ser Val Met His Glu Ala Leu
                            450                 455                 460

His Asn His Tyr Thr Gln Lys Ser Leu Ser Leu Ser Pro Gly Lys
        465                 470                 475

<210> SEQ ID NO 36
```

```
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Asp Tyr Tyr Met Tyr Trp Val Arg Gln Ala Pro Gly
    50                  55                  60

Gln Gly Leu Glu Trp Met Gly Trp Ile Ser Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Val Arg Gly Gly Tyr Ser Gly Tyr Ala Gly
        115                 120                 125

Leu Tyr Ser His Tyr Tyr Gly Met Asp Val Trp Gly Gln Gly Thr Thr
    130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Gln Phe Asn
    290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
        355                 360                 365

Gly Gln Pro Arg Glu Pro Gln Val Tyr Thr Leu Pro Pro Ser Arg Glu
```

```
                    370                 375                 380
Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                    405                 410                 415

Asn Asn Tyr Lys Thr Thr Pro Pro Met Leu Asp Ser Asp Gly Ser Phe
                420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys
465                 470                 475

<210> SEQ ID NO 37
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
                20                  25                  30

Leu Val Lys Pro Gly Gly Ser Leu Arg Leu Ser Cys Ala Ala Ser Gly
            35                  40                  45

Phe Thr Phe Gly Asn Ala Trp Met Ser Trp Val Arg Gln Ala Pro Gly
        50                  55                  60

Lys Gly Leu Glu Trp Val Gly Arg Ile Lys Ser Lys Thr Asp Gly Gly
65                  70                  75                  80

Thr Thr Asp Tyr Ala Ala Pro Val Lys Gly Arg Phe Thr Ile Ser Arg
                85                  90                  95

Asp Asp Ser Lys Asn Thr Leu Tyr Leu Gln Met Asn Ser Leu Lys Thr
                100                 105                 110

Glu Asp Thr Ala Val Tyr Phe Cys Thr Thr Asp Arg Thr Gly Tyr Ser
            115                 120                 125

Ile Ser Trp Ser Ser Tyr Tyr Tyr Tyr Gly Met Asp Val Trp Gly
        130                 135                 140

Gln Gly Thr Thr Val Thr Val Ser Ser Ala Ser Thr Lys Gly Pro Ser
145                 150                 155                 160

Val Phe Pro Leu Ala Pro Cys Ser Arg Ser Thr Ser Glu Ser Thr Ala
                165                 170                 175

Ala Leu Gly Cys Leu Val Lys Asp Tyr Phe Pro Glu Pro Val Thr Val
                180                 185                 190

Ser Trp Asn Ser Gly Ala Leu Thr Ser Gly Val His Thr Phe Pro Ala
            195                 200                 205

Val Leu Gln Ser Ser Gly Leu Tyr Ser Leu Ser Ser Val Val Thr Val
        210                 215                 220

Pro Ser Ser Asn Phe Gly Thr Gln Thr Tyr Thr Cys Asn Val Asp His
225                 230                 235                 240

Lys Pro Ser Asn Thr Lys Val Asp Lys Thr Val Glu Arg Lys Cys Cys
                245                 250                 255
```

```
Val Glu Cys Pro Pro Cys Pro Ala Pro Pro Val Ala Gly Pro Ser Val
            260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
        290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Phe Arg Val Val Ser
                325                 330                 335

Val Leu Thr Val Val His Gln Asp Trp Leu Asn Gly Lys Glu Tyr Lys
            340                 345                 350

Cys Lys Val Ser Asn Lys Gly Leu Pro Ala Pro Ile Glu Lys Thr Ile
            355                 360                 365

Ser Lys Thr Lys Gly Gln Pro Arg Glu Pro Gln Val Tyr Thr Leu Pro
        370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Met Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys
465                 470                 475

<210> SEQ ID NO 38
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Gly Asn Ala Trp Met Ser Trp Val Arg Gln Ala Pro Gly
    50                  55                  60

Lys Gly Leu Glu Trp Val Gly Arg Ile Lys Ser Lys Thr Asp Gly Gly
65                  70                  75                  80

Thr Thr Asp Tyr Ala Ala Pro Val Lys Gly Arg Phe Thr Ile Ser Arg
                85                  90                  95

Asp Asp Ser Lys Asn Thr Leu Tyr Leu Gln Met Asn Ser Leu Lys Thr
            100                 105                 110

Glu Asp Thr Ala Val Tyr Tyr Cys Thr Thr Asp Arg Thr Gly Tyr Ser
        115                 120                 125

Ile Ser Trp Ser Ser Tyr Tyr Tyr Tyr Gly Met Asp Val Trp Gly
    130                 135                 140
```

```
Gln Gly Thr Thr Val Thr Val Ser Ser Ala Ser Thr Lys Gly Pro Ser
145                 150                 155                 160

Val Phe Pro Leu Ala Pro Cys Ser Arg Ser Thr Ser Glu Ser Thr Ala
            165                 170                 175

Ala Leu Gly Cys Leu Val Lys Asp Tyr Phe Pro Glu Pro Val Thr Val
        180                 185                 190

Ser Trp Asn Ser Gly Ala Leu Thr Ser Gly Val His Thr Phe Pro Ala
    195                 200                 205

Val Leu Gln Ser Ser Gly Leu Tyr Ser Leu Ser Ser Val Val Thr Val
210                 215                 220

Pro Ser Ser Asn Phe Gly Thr Gln Thr Tyr Thr Cys Asn Val Asp His
225                 230                 235                 240

Lys Pro Ser Asn Thr Lys Val Asp Lys Thr Val Glu Arg Lys Cys Cys
            245                 250                 255

Val Glu Cys Pro Pro Cys Pro Ala Pro Pro Val Ala Gly Pro Ser Val
        260                 265                 270

Phe Leu Phe Pro Pro Lys Pro Lys Asp Thr Leu Met Ile Ser Arg Thr
    275                 280                 285

Pro Glu Val Thr Cys Val Val Val Asp Val Ser His Glu Asp Pro Glu
        290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Phe Arg Val Val Ser
            325                 330                 335

Val Leu Thr Val Val His Gln Asp Trp Leu Asn Gly Lys Glu Tyr Lys
        340                 345                 350

Cys Lys Val Ser Asn Lys Gly Leu Pro Ala Pro Ile Glu Lys Thr Ile
    355                 360                 365

Ser Lys Thr Lys Gly Gln Pro Arg Glu Pro Gln Val Tyr Thr Leu Pro
370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Met Leu Asp Ser
        420                 425                 430

Asp Gly Ser Phe Phe Leu Tyr Ser Lys Leu Thr Val Asp Lys Ser Arg
    435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys
465                 470                 475

<210> SEQ ID NO 39
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
```

-continued

```
             20                  25                  30
Val Val Gln Pro Gly Arg Ser Leu Arg Leu Ser Cys Ala Ala Ser Gly
             35                  40                  45
Phe Thr Phe Ser Ser Phe Gly Met His Trp Val Arg Gln Ala Pro Gly
 50                  55                  60
Lys Gly Leu Glu Trp Val Ala Val Ile Ser Phe Asp Gly Ser Ile Lys
 65                  70                  75                  80
Tyr Ser Val Asp Ser Val Lys Gly Arg Phe Thr Ile Ser Arg Asp Asn
                     85                  90                  95
Ser Lys Asn Thr Leu Phe Leu Gln Met Asn Ser Leu Arg Ala Glu Asp
                100                 105                 110
Thr Ala Val Tyr Tyr Cys Ala Arg Asp Arg Leu Asn Tyr Tyr Asp Ser
                115                 120                 125
Ser Gly Tyr Tyr His Tyr Lys Tyr Tyr Gly Leu Ala Val Trp Gly Gln
                130                 135                 140
Gly Thr Thr Val Thr Val Ser Ser Ala Ser Thr Lys Gly Pro Ser Val
145                 150                 155                 160
Phe Pro Leu Ala Pro Cys Ser Arg Ser Thr Ser Glu Ser Thr Ala Ala
                165                 170                 175
Leu Gly Cys Leu Val Lys Asp Tyr Phe Pro Glu Pro Val Thr Val Ser
                180                 185                 190
Trp Asn Ser Gly Ala Leu Thr Ser Gly Val His Thr Phe Pro Ala Val
                195                 200                 205
Leu Gln Ser Ser Gly Leu Tyr Ser Leu Ser Ser Val Val Thr Val Pro
                210                 215                 220
Ser Ser Asn Phe Gly Thr Gln Thr Tyr Thr Cys Asn Val Asp His Lys
225                 230                 235                 240
Pro Ser Asn Thr Lys Val Asp Lys Thr Val Glu Arg Lys Cys Cys Val
                245                 250                 255
Glu Cys Pro Pro Cys Pro Ala Pro Pro Val Ala Gly Pro Ser Val Phe
                260                 265                 270
Leu Phe Pro Pro Lys Pro Lys Asp Thr Leu Met Ile Ser Arg Thr Pro
                275                 280                 285
Glu Val Thr Cys Val Val Val Asp Val Ser His Glu Asp Pro Glu Val
                290                 295                 300
Gln Phe Asn Trp Tyr Val Asp Gly Val Glu Val His Asn Ala Lys Thr
305                 310                 315                 320
Lys Pro Arg Glu Glu Gln Phe Asn Ser Thr Phe Arg Val Val Ser Val
                325                 330                 335
Leu Thr Val Val His Gln Asp Trp Leu Asn Gly Lys Glu Tyr Lys Cys
                340                 345                 350
Lys Val Ser Asn Lys Gly Leu Pro Ala Pro Ile Glu Lys Thr Ile Ser
                355                 360                 365
Lys Thr Lys Gly Gln Pro Arg Glu Pro Gln Val Tyr Thr Leu Pro Pro
                370                 375                 380
Ser Arg Glu Glu Met Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Met Leu Asp Ser Asp
                420                 425                 430
Gly Ser Phe Phe Leu Tyr Ser Lys Leu Thr Val Asp Lys Ser Arg Trp
                435                 440                 445
```

```
Gln Gln Gly Asn Val Phe Ser Cys Ser Val Met His Glu Ala Leu His
        450                 455                 460

Asn His Tyr Thr Gln Lys Ser Leu Ser Leu Ser Pro Gly Lys
465                 470                 475

<210> SEQ ID NO 40
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Tyr Thr Phe Ser Thr Tyr Ser Met Asn Trp Val Arg Gln Ala Pro Gly
    50                  55                  60

Lys Gly Leu Glu Trp Val Ser Ser Ile Ser Ser Ser Ser Tyr Arg
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Ser Ser Leu Arg Ala Glu Asp
            100                 105                 110

Thr Ala Val Tyr Tyr Cys Ala Arg Glu Gly Val Ser Gly Ser Ser Pro
        115                 120                 125

Tyr Ser Ile Ser Trp Tyr Asp Tyr Tyr Gly Met Asp Val Trp Gly
    130                 135                 140

Gln Gly Thr Thr Val Thr Val Ser Ser Ala Ser Thr Lys Gly Pro Ser
145                 150                 155                 160

Val Phe Pro Leu Ala Pro Cys Ser Arg Ser Thr Ser Glu Ser Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
    210                 215                 220

Pro Ser Ser Asn Phe Gly Thr Gln Thr Tyr Thr Cys Asn Val Asp His
225                 230                 235                 240

Lys Pro Ser Asn Thr Lys Val Asp Lys Thr Val Glu Arg Lys Cys Cys
                245                 250                 255

Val Glu Cys Pro Pro Cys Pro Ala Pro Pro Val Ala Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Phe Arg Val Val Ser
```

```
                    325                 330                 335
Val Leu Thr Val Val His Gln Asp Trp Leu Asn Gly Lys Glu Tyr Lys
                340                 345                 350

Cys Lys Val Ser Asn Lys Gly Leu Pro Ala Pro Ile Glu Lys Thr Ile
                355                 360                 365

Ser Lys Thr Lys Gly Gln Pro Arg Glu Pro Gln Val Tyr Thr Leu Pro
            370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Met Leu Asp Ser
                420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
        450                 455                 460

His Asn His Tyr Thr Gln Lys Ser Leu Ser Leu Ser Pro Gly Lys
465                 470                 475

<210> SEQ ID NO 41
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
                20                  25                  30

Val Val Gln Pro Gly Arg Ser Leu Arg Leu Ser Cys Ala Ala Ser Gly
            35                  40                  45

Phe Thr Phe Ser Ser Tyr Gly Met His Trp Val Arg Gln Ala Pro Gly
        50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Ile Ile Ser Arg Asp Lys
                85                  90                  95

Ser Lys Asn Thr Leu Tyr Leu Gln Met Asn Ser Leu Arg Ala Glu Asp
                100                 105                 110

Thr Ala Val Tyr Cys Ala Arg Ala Gly Gly Ile Ala Ala Ala Gly
            115                 120                 125

Leu Tyr Tyr Tyr Gly Met Asp Val Trp Gly Gln Gly Thr Thr Val
        130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205
```

```
Gly Leu Tyr Ser Leu Ser Ser Val Val Thr Val Pro Ser Ser Asn Phe
    210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Gln Phe Asn Trp
290                 295                 300

Tyr Val Asp Gly Val Glu Val His Asn Ala Lys Thr Lys Pro Arg Glu
305                 310                 315                 320

Glu Gln Phe Asn Ser Thr Phe Arg Val Val Ser Val Leu Thr Val Val
                325                 330                 335

His Gln Asp Trp Leu Asn Gly Lys Glu Tyr Lys Cys Lys Val Ser Asn
            340                 345                 350

Lys Gly Leu Pro Ala Pro Ile Glu Lys Thr Ile Ser Lys Thr Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Gly Ser Ser Ser Asn Ile Gly Asn Asn Tyr Val Ser
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Asn Asn Lys Arg Pro Ser
1               5
```

```
<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Thr Trp Asp Ser Arg Leu Ser Ala Val Val
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Gly Ser Ser Ser Asn Ile Gly Ser Asn Tyr Val Tyr
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Asn Gln Arg Pro Ser
1               5

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Ala Trp Asp Asp Ser Leu Ser Gly Trp Val
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Gln Gly Ile Arg Asn Asp Leu Gly
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 49

Ala Ala Ser Ser Leu Gln Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Gln Tyr Asn Ile Tyr Pro Trp Thr
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gly Asp Ser Leu Arg Ser Phe Tyr Ala Ser
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Lys Asn Asn Arg Pro Ser
1               5

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asn Ser Arg Asp Ser Ser Val Tyr His Leu Val
1               5                   10

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Ser Ser Gln Ser Leu Leu His Ser Ala Gly Lys Thr Tyr Leu Tyr
1               5                   10                  15

<210> SEQ ID NO 55
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 55

Glu Val Ser Asn Arg Phe Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Met Gln Ser Phe Pro Leu Pro Leu Thr
1               5

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Ser Gln Ser Leu Leu His Ser Phe Gly Tyr Asn Tyr Leu Asp
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Gly Ser Asn Arg Ala Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Gln Ala Leu Gln Thr Pro Phe Thr
1               5

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Ser Ser Gln Ser Leu Leu His Ser Asp Gly Lys Thr Tyr Leu Tyr
1               5                   10                  15
```

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Asn Asn Gln Arg Pro Ser
1               5

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Gly Ser Ser Ser Asn Ile Gly Ser Asn Thr Val Asn
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Asn Asn Gln Arg Pro Ser
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Ala Arg Asp Glu Ser Leu Asn Gly Val Val
1               5                   10

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Ser Ser Gln Ser Leu Leu His Ser Asp Gly Arg Asn Tyr Leu Tyr
1               5                   10                  15

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Ala Ser Gln Gly Ile Arg Lys Asp Leu Gly
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ala Ser Ser Leu Gln Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Gln Tyr Asn Ser Phe Pro Trp Thr
1               5

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ala Ser Gln Ser Val Ser Ser Gly Tyr Leu Thr
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ala Ser Ser Arg Ala Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gln Tyr Gly Asn Ser Leu Cys Arg
1               5

<210> SEQ ID NO 72
<211> LENGTH: 9

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Gln Tyr Gly Asn Ser Leu Ser Arg
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Phe Gly Met His
1               5

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Val Ile Ser Phe Asp Gly Ser Ile Lys Tyr Ser Val Asp Ser Val Lys
1               5                   10                  15

Gly

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Arg Leu Asn Tyr Tyr Asp Ser Ser Gly Tyr Tyr His Tyr Lys Tyr
1               5                   10                  15

Tyr Gly Met Ala Val
            20

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asn Ala Trp Met Ser
1               5

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Arg Ile Lys Ser Thr Thr Asp Gly Gly Thr Thr Asp Tyr Ala Ala Pro
1               5                   10                  15

Val Lys Gly

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Arg Thr Gly Tyr Ser Ile Ser Trp Ser Tyr Tyr Tyr Tyr
1               5                   10                  15

Gly Met Asp Val
            20

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Tyr Ala Met Ser
1               5

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Ile Ser Gly Ser Gly Gly Arg Thr Tyr Tyr Ala Asp Ser Val Lys
1               5                   10                  15

Gly

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Gln Arg Glu Val Gly Pro Tyr Ser Ser Gly Trp Tyr Asp Tyr Tyr
1               5                   10                  15

Tyr Gly Met Asp Val
            20

<210> SEQ ID NO 82
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 82

Gly Tyr Tyr Met His
1               5

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Trp Ile Asn Pro Asn Ser Gly Gly Thr Asn Tyr Ala Gln Lys Phe Gln
1               5                   10                  15

Gly

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Gln Met Ser Ile Ile Met Leu Arg Gly Val Phe Pro Pro Tyr Tyr
1               5                   10                  15

Tyr Gly Met Asp Val
            20

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Tyr Gly Met His
1               5

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Ile Ser Tyr Asp Gly Ser His Glu Ser Tyr Ala Asp Ser Val Lys
1               5                   10                  15

Gly

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Arg Lys Arg Val Thr Met Ser Thr Leu Tyr Tyr Tyr Phe Tyr Tyr
1               5                   10                  15

Gly Met Asp Val
            20

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Tyr Ala Met Ser
1               5

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Phe Ile Arg Ser Arg Ala Tyr Gly Gly Thr Pro Glu Tyr Ala Ala Ser
1               5                   10                  15

Val Lys Gly

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Arg Gly Ile Ala Ala Arg Trp Asp Tyr
1               5                   10

<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ile Lys Ser Lys Thr Asp Gly Gly Thr Thr Asp Tyr Thr Ala Pro
1               5                   10                  15

Val Lys Gly

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Asp Tyr Tyr Met Tyr
1               5

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Ile Ser Pro Asn Ser Gly Gly Thr Asn Tyr Ala Gln Lys Phe Gln
1               5                   10                  15

Gly

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Gly Tyr Ser Gly Tyr Ala Gly Leu Tyr Ser His Tyr Tyr Gly Met
1               5                   10                  15

Asp Val

<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Ile Lys Ser Lys Thr Asp Gly Gly Thr Thr Asp Tyr Ala Ala Pro
1               5                   10                  15

Val Lys Gly

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Arg Leu Asn Tyr Tyr Asp Ser Ser Gly Tyr Tyr His Tyr Lys Tyr
1               5                   10                  15

Tyr Gly Leu Ala Val
            20

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97
```

Thr Tyr Ser Met Asn
1               5

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Ile Ser Ser Ser Ser Ser Tyr Arg Tyr Tyr Ala Asp Ser Val Lys
1               5                   10                  15

Gly

<210> SEQ ID NO 99
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu Gly Val Ser Gly Ser Ser Pro Tyr Ser Ile Ser Trp Tyr Asp Tyr
1               5                   10                  15

Tyr Tyr Gly Met Asp Val
            20

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Tyr Gly Met His
1               5

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Val Ile Trp Tyr Asp Gly Ser Asn Lys Tyr Tyr Ala Asp Ser Val Lys
1               5                   10                  15

Gly

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Gly Gly Ile Ala Ala Ala Gly Leu Tyr Tyr Tyr Tyr Gly Met Asp

```
1               5                   10                  15
Val

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn or Lys

<400> SEQUENCE: 103

Arg Ala Ser Gln Gly Ile Arg Xaa Asp Leu Gly
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala or Gly

<400> SEQUENCE: 104

Xaa Ala Ser Ser Leu Gln Ser
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ile or Ser
<220> FEATURE:
<221> NAME/KEY: MOD_RES
<222> LOCATION: (6)..(6)
<223> OTHER INFORMATION: Tyr or Phe

<400> SEQUENCE: 105

Leu Gln Tyr Asn Xaa Xaa Pro Trp Thr
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ser or Cys

<400> SEQUENCE: 106

Gln Gln Tyr Gly Asn Ser Leu Xaa Arg
1               5
```

```
<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser or Gly
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (7)..(7)
<223> OTHER INFORMATION: Ser or Arg
<220> FEATURE:
<221> NAME/KEY: MOD_RES
<222> LOCATION: (8)..(8)
<223> OTHER INFORMATION: Ser, Asn, or Lys
<220> FEATURE:
<221> NAME/KEY: MOD_RES
<222> LOCATION: (10)..(10)
<223> OTHER INFORMATION: Tyr or Asp
<220> FEATURE:
<221> NAME/KEY: MOD_RES
<222> LOCATION: (12)..(12)
<223> OTHER INFORMATION: Thr or Gly

<400> SEQUENCE: 107

Arg Ala Ser Gln Xaa Xaa Xaa Xaa Gly Xaa Leu Xaa
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ala
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (6)..(6)
<223> OTHER INFORMATION: Ala or Gln
<220> FEATURE:
<221> NAME/KEY: MOD_RES
<222> LOCATION: (7)..(7)
<223> OTHER INFORMATION: Thr or Ser

<400> SEQUENCE: 108

Xaa Ala Ser Ser Xaa Xaa Xaa
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Gln or Leu
<220> FEATURE:
<221> NAME/KEY: MOD_RES
<222> LOCATION: (4)..(4)
<223> OTHER INFORMATION: Gly or Asn
<220> FEATURE:
<221> NAME/KEY: MOD_RES
<222> LOCATION: (5)..(5)
<223> OTHER INFORMATION: Asn or Thr
<220> FEATURE:
<221> NAME/KEY: MOD_RES
<222> LOCATION: (6)..(6)
<223> OTHER INFORMATION: Ser, Tyr, or Phe
<220> FEATURE:
<221> NAME/KEY: MOD_RES
<222> LOCATION: (7)..(7)
<223> OTHER INFORMATION: Leu or Pro
<220> FEATURE:
<221> NAME/KEY: MOD_RES
<222> LOCATION: (8)..(8)
<223> OTHER INFORMATION: Cys, Trp or Ser
<220> FEATURE:
<221> NAME/KEY: MOD_RES
<222> LOCATION: (9)..(9)
<223> OTHER INFORMATION: Arg or Thr

<400> SEQUENCE: 109

Xaa Gln Tyr Xaa Xaa Xaa Xaa Xaa Xaa
1               5

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Asp or Ala
<220> FEATURE:
<221> NAME/KEY: MOD_RES
<222> LOCATION: (12)..(12)
<223> OTHER INFORMATION: Arg or Lys
<220> FEATURE:
<221> NAME/KEY: MOD_RES
<222> LOCATION: (13)..(13)
<223> OTHER INFORMATION: Asn or Thr

<400> SEQUENCE: 110

Lys Ser Ser Gln Ser Leu Leu His Ser Xaa Gly Xaa Xaa Tyr Leu Tyr
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (10)..(10)
<223> OTHER INFORMATION: Phe, Asp or Ala
<220> FEATURE:
<221> NAME/KEY: MOD_RES
<222> LOCATION: (12)..(12)
<223> OTHER INFORMATION: Tyr, Arg or Lys
<220> FEATURE:
```

```
<221> NAME/KEY: MOD_RES
<222> LOCATION: (13)..(13)
<223> OTHER INFORMATION: Asn or Thr
<220> FEATURE:
<221> NAME/KEY: MOD_RES
<222> LOCATION: (16)..(16)
<223> OTHER INFORMATION: Asp or Tyr

<400> SEQUENCE: 111

Xaa Ser Ser Gln Ser Leu Leu His Ser Xaa Gly Xaa Xaa Tyr Leu Xaa
1               5                   10                  15

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Glu
<220> FEATURE:
<221> NAME/KEY: MOD_RES
<222> LOCATION: (2)..(2)
<223> OTHER INFORMATION: Gly or Val
<220> FEATURE:
<221> NAME/KEY: MOD_RES
<222> LOCATION: (6)..(6)
<223> OTHER INFORMATION: Ala or Phe

<400> SEQUENCE: 112

Xaa Xaa Ser Asn Arg Xaa Ser
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Ser
<220> FEATURE:
<221> NAME/KEY: MOD_RES
<222> LOCATION: (4)..(4)
<223> OTHER INFORMATION: Leu or Phe
<220> FEATURE:
<221> NAME/KEY: MOD_RES
<222> LOCATION: (5)..(5)
<223> OTHER INFORMATION: Gln or Pro
<220> FEATURE:
<221> NAME/KEY: MOD_RES
<222> LOCATION: (6)..(6)
<223> OTHER INFORMATION: Thr or Leu
<220> FEATURE:
<221> NAME/KEY: MOD_RES
<222> LOCATION: (8)..(8)
<223> OTHER INFORMATION: Phe or Leu

<400> SEQUENCE: 113

Met Gln Xaa Xaa Xaa Xaa Pro Xaa Thr
1               5

<210> SEQ ID NO 114
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn or Ser

<400> SEQUENCE: 114

Arg Xaa Asn Gln Arg Pro Ser
1               5

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Asn or Ser
<220> FEATURE:
<221> NAME/KEY: MOD_RES
<222> LOCATION: (11)..(11)
<223> OTHER INFORMATION: Tyr or Thr
<220> FEATURE:
<221> NAME/KEY: MOD_RES
<222> LOCATION: (13)..(13)
<223> OTHER INFORMATION: Ser, Asn or Tyr

<400> SEQUENCE: 115

Ser Gly Ser Ser Ser Asn Ile Gly Xaa Asn Xaa Val Xaa
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Thr or Arg
<220> FEATURE:
<221> NAME/KEY: MOD_RES
<222> LOCATION: (2)..(2)
<223> OTHER INFORMATION: Asn or Ser
<220> FEATURE:
<221> NAME/KEY: MOD_RES
<222> LOCATION: (4)..(4)
<223> OTHER INFORMATION: Lys or Gln

<400> SEQUENCE: 116

Xaa Xaa Asn Xaa Arg Pro Ser
1               5

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ala
<220> FEATURE:
<221> NAME/KEY: MOD_RES
<222> LOCATION: (2)..(2)
```

```
<223> OTHER INFORMATION: Thr or Ala
<220> FEATURE:
<221> NAME/KEY: MOD_RES
<222> LOCATION: (3)..(3)
<223> OTHER INFORMATION: Trp or Arg
<220> FEATURE:
<221> NAME/KEY: MOD_RES
<222> LOCATION: (5)..(5)
<223> OTHER INFORMATION: Ser or Asp
<220> FEATURE:
<221> NAME/KEY: MOD_RES
<222> LOCATION: (6)..(6)
<223> OTHER INFORMATION: Arg or Ser
<220> FEATURE:
<221> NAME/KEY: MOD_RES
<222> LOCATION: (8)..(8)
<223> OTHER INFORMATION: Ser or Asn
<220> FEATURE:
<221> NAME/KEY: MOD_RES
<222> LOCATION: (9)..(9)
<223> OTHER INFORMATION: Ala or Gly

<400> SEQUENCE: 117

Xaa Xaa Xaa Asp Xaa Xaa Leu Xaa Xaa Val Val
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Gln
<220> FEATURE:
<221> NAME/KEY: MOD_RES
<222> LOCATION: (3)..(3)
<223> OTHER INFORMATION: Ser or not present
<220> FEATURE:
<221> NAME/KEY: MOD_RES
<222> LOCATION: (4)..(4)
<223> OTHER INFORMATION: Ser or Asp
<220> FEATURE:
<221> NAME/KEY: MOD_RES
<222> LOCATION: (6)..(6)
<223> OTHER INFORMATION: Asn or not present
<220> FEATURE:
<221> NAME/KEY: MOD_RES
<222> LOCATION: (7)..(7)
<223> OTHER INFORMATION: Ile or Leu
<220> FEATURE:
<221> NAME/KEY: MOD_RES
<222> LOCATION: (8)..(8)
<223> OTHER INFORMATION: Gly or Arg
<220> FEATURE:
<221> NAME/KEY: MOD_RES
<222> LOCATION: (9)..(9)
<223> OTHER INFORMATION: Asn or Ser
<220> FEATURE:
<221> NAME/KEY: MOD_RES
<222> LOCATION: (10)..(10)
<223> OTHER INFORMATION: Asn or Phe
<220> FEATURE:
<221> NAME/KEY: MOD_RES
<222> LOCATION: (11)..(11)
<223> OTHER INFORMATION: Tyr or Thr
<220> FEATURE:
<221> NAME/KEY: MOD_RES
<222> LOCATION: (12)..(12)
<223> OTHER INFORMATION: Val or Ala
<220> FEATURE:
<221> NAME/KEY: MOD_RES
<222> LOCATION: (13)..(13)
<223> OTHER INFORMATION: Ser, Asn or Tyr
```

<400> SEQUENCE: 118

Xaa Gly Xaa Xaa Ser Xaa Xaa Xaa Xaa Xaa Xaa
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gly, Thr or Arg
<220> FEATURE:
<221> NAME/KEY: MOD_RES
<222> LOCATION: (2)..(2)
<223> OTHER INFORMATION: Asn, Lys or Ser
<220> FEATURE:
<221> NAME/KEY: MOD_RES
<222> LOCATION: (4)..(4)
<223> OTHER INFORMATION: Lys, Asn or Gln

<400> SEQUENCE: 119

Xaa Xaa Asn Xaa Arg Pro Ser
1               5

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly, Asn or Ala
<220> FEATURE:
<221> NAME/KEY: MOD_RES
<222> LOCATION: (2)..(2)
<223> OTHER INFORMATION: Thr, Ser or Ala
<220> FEATURE:
<221> NAME/KEY: MOD_RES
<222> LOCATION: (3)..(3)
<223> OTHER INFORMATION: Trp or Arg
<220> FEATURE:
<221> NAME/KEY: MOD_RES
<222> LOCATION: (5)..(5)
<223> OTHER INFORMATION: Ser or Asp
<220> FEATURE:
<221> NAME/KEY: MOD_RES
<222> LOCATION: (6)..(6)
<223> OTHER INFORMATION: Arg or Ser
<220> FEATURE:
<221> NAME/KEY: MOD_RES
<222> LOCATION: (7)..(7)
<223> OTHER INFORMATION: Leu or Val
<220> FEATURE:
<221> NAME/KEY: MOD_RES
<222> LOCATION: (8)..(8)
<223> OTHER INFORMATION: Ser, Tyr or Asn
<220> FEATURE:
<221> NAME/KEY: MOD_RES
<222> LOCATION: (9)..(9)
<223> OTHER INFORMATION: Ala, His or Gly
<220> FEATURE:
<221> NAME/KEY: MOD_RES
<222> LOCATION: (10)..(10)
<223> OTHER INFORMATION: Val or Leu

<400> SEQUENCE: 120

```
Xaa Xaa Xaa Asp Xaa Xaa Xaa Xaa Xaa Xaa Val
1               5                   10
```

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Asp
<220> FEATURE:
<221> NAME/KEY: MOD_RES
<222> LOCATION: (5)..(5)
<223> OTHER INFORMATION: His or Tyr

<400> SEQUENCE: 121

```
Xaa Tyr Tyr Met Xaa
1               5
```

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn or Ser

<400> SEQUENCE: 122

```
Trp Ile Xaa Pro Asn Ser Gly Gly Thr Asn Tyr Ala Gln Lys Phe Gln
1               5                   10                  15
Gly
```

<210> SEQ ID NO 123
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Gly
<220> FEATURE:
<221> NAME/KEY: MOD_RES
<222> LOCATION: (2)..(2)
<223> OTHER INFORMATION: Gln or Gly
<220> FEATURE:
<221> NAME/KEY: MOD_RES
<222> LOCATION: (3)..(3)
<223> OTHER INFORMATION: Met or Tyr
<220> FEATURE:
<221> NAME/KEY: MOD_RES
<222> LOCATION: (5)..(5)
<223> OTHER INFORMATION: Ile or Gly
<220> FEATURE:
<221> NAME/KEY: MOD_RES
<222> LOCATION: (6)..(6)
<223> OTHER INFORMATION: Ile or Tyr
<220> FEATURE:
<221> NAME/KEY: MOD_RES
<222> LOCATION: (7)..(7)
<223> OTHER INFORMATION: Met or Ala
<220> FEATURE:
<221> NAME/KEY: MOD_RES

```
<222> LOCATION: (8)..(8)
<223> OTHER INFORMATION: Leu or not present
<220> FEATURE:
<221> NAME/KEY: MOD_RES
<222> LOCATION: (9)..(9)
<223> OTHER INFORMATION: Arg or not present
<220> FEATURE:
<221> NAME/KEY: MOD_RES
<222> LOCATION: (11)..(11)
<223> OTHER INFORMATION: Val or Leu
<220> FEATURE:
<221> NAME/KEY: MOD_RES
<222> LOCATION: (12)..(12)
<223> OTHER INFORMATION: Phe or Tyr
<220> FEATURE:
<221> NAME/KEY: MOD_RES
<222> LOCATION: (13)..(13)
<223> OTHER INFORMATION: Pro or Ser
<220> FEATURE:
<221> NAME/KEY: MOD_RES
<222> LOCATION: (14)..(14)
<223> OTHER INFORMATION: Pro or His
<220> FEATURE:
<221> NAME/KEY: MOD_RES
<222> LOCATION: (17)..(17)
<223> OTHER INFORMATION: Tyr or not present

<400> SEQUENCE: 123

Xaa Xaa Xaa Ser Xaa Xaa Xaa Xaa Xaa Gly Xaa Xaa Xaa Xaa Tyr Tyr
1               5                   10                  15

Xaa Gly Met Asp Val
            20

<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys or Thr
<220> FEATURE:
<221> NAME/KEY: MOD_RES
<222> LOCATION: (14)..(14)
<223> OTHER INFORMATION: Thr or Ala

<400> SEQUENCE: 124

Arg Ile Lys Ser Xaa Thr Asp Gly Gly Thr Thr Asp Tyr Xaa Ala Pro
1               5                   10                  15

Val Lys Gly

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr or Ser
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (5)..(5)
<223> OTHER INFORMATION: Asn or Ser
```

```
<400> SEQUENCE: 125

Xaa Tyr Xaa Met Xaa
1               5

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Ala
<220> FEATURE:
<221> NAME/KEY: MOD_RES
<222> LOCATION: (4)..(4)
<223> OTHER INFORMATION: Ser or Gly
<220> FEATURE:
<221> NAME/KEY: MOD_RES
<222> LOCATION: (6)..(7)
<223> OTHER INFORMATION: Ser or Gly
<220> FEATURE:
<221> NAME/KEY: MOD_RES
<222> LOCATION: (8)..(8)
<223> OTHER INFORMATION: Tyr or Arg
<220> FEATURE:
<221> NAME/KEY: MOD_RES
<222> LOCATION: (9)..(9)
<223> OTHER INFORMATION: Arg or Thr

<400> SEQUENCE: 126

Xaa Ile Ser Xaa Ser Xaa Xaa Xaa Xaa Tyr Tyr Ala Asp Ser Val Lys
1               5                   10                  15
Gly

<210> SEQ ID NO 127
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(2)
<223> OTHER INFORMATION: Gly or Gln
<220> FEATURE:
<221> NAME/KEY: MOD_RES
<222> LOCATION: (3)..(3)
<223> OTHER INFORMATION: Val or Arg
<220> FEATURE:
<221> NAME/KEY: MOD_RES
<222> LOCATION: (4)..(4)
<223> OTHER INFORMATION: Ser or Glu
<220> FEATURE:
<221> NAME/KEY: MOD_RES
<222> LOCATION: (5)..(5)
<223> OTHER INFORMATION: Gly or Val
<220> FEATURE:
<221> NAME/KEY: MOD_RES
<222> LOCATION: (6)..(6)
<223> OTHER INFORMATION: Ser or Gly
<220> FEATURE:
<221> NAME/KEY: MOD_RES
<222> LOCATION: (7)..(7)
<223> OTHER INFORMATION: Ser or not present
<220> FEATURE:
```

```
<221> NAME/KEY: MOD_RES
<222> LOCATION: (11)..(11)
<223> OTHER INFORMATION: Ile or Ser
<220> FEATURE:
<221> NAME/KEY: MOD_RES
<222> LOCATION: (12)..(12)
<223> OTHER INFORMATION: Ser or Gly

<400> SEQUENCE: 127

Xaa Xaa Xaa Xaa Xaa Xaa Xaa Pro Tyr Ser Xaa Xaa Trp Tyr Asp Tyr
1               5                   10                  15

Tyr Tyr Gly Met Asp Val
            20

<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe or Tyr

<400> SEQUENCE: 128

Ser Xaa Gly Met His
1               5

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe or Tyr
<220> FEATURE:
<221> NAME/KEY: MOD_RES
<222> LOCATION: (8)..(8)
<223> OTHER INFORMATION: Ile or His
<220> FEATURE:
<221> NAME/KEY: MOD_RES
<222> LOCATION: (11)..(11)
<223> OTHER INFORMATION: Ser or Tyr
<220> FEATURE:
<221> NAME/KEY: MOD_RES
<222> LOCATION: (12)..(12)
<223> OTHER INFORMATION: Val or Ala

<400> SEQUENCE: 129

Val Ile Ser Xaa Asp Gly Ser Xaa Lys Tyr Xaa Xaa Asp Ser Val Lys
1               5                   10                  15

Gly

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Glu
<220> FEATURE:
```

```
<221> NAME/KEY: MOD_RES
<222> LOCATION: (3)..(3)
<223> OTHER INFORMATION: Leu or Lys
<220> FEATURE:
<221> NAME/KEY: MOD_RES
<222> LOCATION: (4)..(4)
<223> OTHER INFORMATION: Asn or Arg
<220> FEATURE:
<221> NAME/KEY: MOD_RES
<222> LOCATION: (5)..(5)
<223> OTHER INFORMATION: Tyr or Val
<220> FEATURE:
<221> NAME/KEY: MOD_RES
<222> LOCATION: (6)..(6)
<223> OTHER INFORMATION: Tyr or Thr
<220> FEATURE:
<221> NAME/KEY: MOD_RES
<222> LOCATION: (7)..(7)
<223> OTHER INFORMATION: Asp or Met
<220> FEATURE:
<221> NAME/KEY: MOD_RES
<222> LOCATION: (9)..(9)
<223> OTHER INFORMATION: Ser or Thr
<220> FEATURE:
<221> NAME/KEY: MOD_RES
<222> LOCATION: (10)..(10)
<223> OTHER INFORMATION: Gly or Leu
<220> FEATURE:
<221> NAME/KEY: MOD_RES
<222> LOCATION: (13)..(13)
<223> OTHER INFORMATION: His or Tyr
<220> FEATURE:
<221> NAME/KEY: MOD_RES
<222> LOCATION: (14)..(14)
<223> OTHER INFORMATION: Tyr or not present
<220> FEATURE:
<221> NAME/KEY: MOD_RES
<222> LOCATION: (15)..(15)
<223> OTHER INFORMATION: Lys or Phe
<220> FEATURE:
<221> NAME/KEY: MOD_RES
<222> LOCATION: (19)..(19)
<223> OTHER INFORMATION: Met or Leu
<220> FEATURE:
<221> NAME/KEY: MOD_RES
<222> LOCATION: (20)..(20)
<223> OTHER INFORMATION: Ala or Asp

<400> SEQUENCE: 130

Xaa Arg Xaa Xaa Xaa Xaa Xaa Ser Xaa Xaa Tyr Tyr Xaa Xaa Xaa Tyr
1               5                   10                  15

Tyr Gly Xaa Xaa Val
            20

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn or Ser
<220> FEATURE:
<221> NAME/KEY: MOD_RES
<222> LOCATION: (2)..(2)
<223> OTHER INFORMATION: Ala, Tyr or Phe
<220> FEATURE:
<221> NAME/KEY: MOD_RES
<222> LOCATION: (3)..(3)
<223> OTHER INFORMATION: Trp, Ala or Gly
<220> FEATURE:
<221> NAME/KEY: MOD_RES
<222> LOCATION: (5)..(5)
```

<223> OTHER INFORMATION: Ser or His

<400> SEQUENCE: 131

Xaa Xaa Xaa Met Xaa
1               5

<210> SEQ ID NO 132
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, Ala or Val
<220> FEATURE:
<221> NAME/KEY: MOD_RES
<222> LOCATION: (3)..(3)
<223> OTHER INFORMATION: Lys, Ser or Trp
<220> FEATURE:
<221> NAME/KEY: MOD_RES
<222> LOCATION: (4)..(4)
<223> OTHER INFORMATION: Ser, Gly, Phe or Tyr
<220> FEATURE:
<221> NAME/KEY: MOD_RES
<222> LOCATION: (5)..(5)
<223> OTHER INFORMATION: Lyr, Thr or not present
<220> FEATURE:
<221> NAME/KEY: MOD_RES
<222> LOCATION: (6)..(6)
<223> OTHER INFORMATION: Thr or not present
<220> FEATURE:
<221> NAME/KEY: MOD_RES
<222> LOCATION: (7)..(7)
<223> OTHER INFORMATION: Asp or Ser
<220> FEATURE:
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (10)..(10)
<223> OTHER INFORMATION: Thr, Arg, Ile, Asn or His
<220> FEATURE:
<221> NAME/KEY: MOD_RES
<222> LOCATION: (11)..(11)
<223> OTHER INFORMATION: Thr or Lys
<220> FEATURE:
<221> NAME/KEY: MOD_RES
<222> LOCATION: (12)..(12)
<223> OTHER INFORMATION: Asp or Tyr
<220> FEATURE:
<221> NAME/KEY: MOD_RES
<222> LOCATION: (13)..(13)
<223> OTHER INFORMATION: Tyr or Ser
<220> FEATURE:
<221> NAME/KEY: MOD_RES
<222> LOCATION: (14)..(14)
<223> OTHER INFORMATION: Thr, Ala or Val
<220> FEATURE:
<221> NAME/KEY: MOD_RES
<222> LOCATION: (15)..(15)
<223> OTHER INFORMATION: Ala or Asp
<220> FEATURE:
<221> NAME/KEY: MOD_RES
<222> LOCATION: (16)..(16)
<223> OTHER INFORMATION: Pro or Ser

<400> SEQUENCE: 132

Xaa Ile Xaa Xaa Xaa Xaa Xaa Gly Xaa Xaa Xaa Xaa Xaa Xaa Xaa
1               5                   10                  15

Val Lys Gly

-continued

```
<210> SEQ ID NO 133
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Ala or Glu
<220> FEATURE:
<221> NAME/KEY: MOD_RES
<222> LOCATION: (2)..(2)
<223> OTHER INFORMATION: Arg, Gln or Gly
<220> FEATURE:
<221> NAME/KEY: MOD_RES
<222> LOCATION: (3)..(3)
<223> OTHER INFORMATION: Thr, Arg, Leu, Gly or Lys
<220> FEATURE:
<221> NAME/KEY: MOD_RES
<222> LOCATION: (4)..(4)
<223> OTHER INFORMATION: Gly, Glu, Asn, Ile or Arg
<220> FEATURE:
<221> NAME/KEY: MOD_RES
<222> LOCATION: (5)..(5)
<223> OTHER INFORMATION: Tyr, Val or Ala
<220> FEATURE:
<221> NAME/KEY: MOD_RES
<222> LOCATION: (6)..(6)
<223> OTHER INFORMATION: Ser, Gly, Tyr, Ala or Thr
<220> FEATURE:
<221> NAME/KEY: MOD_RES
<222> LOCATION: (7)..(7)
<223> OTHER INFORMATION: Ile, Pro, Asp, Ala or Met
<220> FEATURE:
<221> NAME/KEY: MOD_RES
<222> LOCATION: (8)..(8)
<223> OTHER INFORMATION: Ser, Tyr or not present
<220> FEATURE:
<221> NAME/KEY: MOD_RES
<222> LOCATION: (9)..(9)
<223> OTHER INFORMATION: Trp, Ser, Thr or not present
<220> FEATURE:
<221> NAME/KEY: MOD_RES
<222> LOCATION: (10)..(10)
<223> OTHER INFORMATION: Ser, Gly or Leu
<220> FEATURE:
<221> NAME/KEY: MOD_RES
<222> LOCATION: (11)..(11)
<223> OTHER INFORMATION: Ser, Gly, Leu or Tyr
<220> FEATURE:
<221> NAME/KEY: MOD_RES
<222> LOCATION: (12)..(12)
<223> OTHER INFORMATION: Trp, Tyr or not present
<220> FEATURE:
<221> NAME/KEY: MOD_RES
<222> LOCATION: (13)..(13)
<223> OTHER INFORMATION: Tyr or His
<220> FEATURE:
<221> NAME/KEY: MOD_RES
<222> LOCATION: (14)..(14)
<223> OTHER INFORMATION: Tyr, Asp or not present
<220> FEATURE:
<221> NAME/KEY: MOD_RES
<222> LOCATION: (15)..(15)
<223> OTHER INFORMATION: Tyr, Lys or Phe
<220> FEATURE:
<221> NAME/KEY: MOD_RES
<222> LOCATION: (16)..(17)
<223> OTHER INFORMATION: Tyr or not present
<220> FEATURE:
<221> NAME/KEY: MOD_RES
<222> LOCATION: (19)..(19)
<223> OTHER INFORMATION: Met or Leu
<220> FEATURE:
<221> NAME/KEY: MOD_RES
<222> LOCATION: (20)..(20)
```

```
<223> OTHER INFORMATION: Asp or Ala

<400> SEQUENCE: 133

Xaa Xaa Xaa Xaa Xaa Xaa Xaa Xaa Xaa Xaa Xaa Xaa Xaa Xaa Xaa
1               5                   10                  15

Xaa Gly Xaa Xaa Val
            20

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Gly, Asp, Ser or Ala
<220> FEATURE:
<221> NAME/KEY: MOD_RES
<222> LOCATION: (2)..(2)
<223> OTHER INFORMATION: Ala, Phe or Tyr
<220> FEATURE:
<221> NAME/KEY: MOD_RES
<222> LOCATION: (3)..(3)
<223> OTHER INFORMATION: Trp, Tyr, Ala or Gly
<220> FEATURE:
<221> NAME/KEY: MOD_RES
<222> LOCATION: (4)..(4)
<223> OTHER INFORMATION: Met or Leu
<220> FEATURE:
<221> NAME/KEY: MOD_RES
<222> LOCATION: (5)..(5)
<223> OTHER INFORMATION: Ser or His

<400> SEQUENCE: 134

Xaa Xaa Xaa Xaa Xaa
1               5

<210> SEQ ID NO 135
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, Trp, Ala, Val, Ser or Phe
<220> FEATURE:
<221> NAME/KEY: MOD_RES
<222> LOCATION: (3)..(3)
<223> OTHER INFORMATION: Lys, Asn, Ser, Trp or Arg
<220> FEATURE:
<221> NAME/KEY: MOD_RES
<222> LOCATION: (4)..(4)
<223> OTHER INFORMATION: Ser, Pro, Gly, Phe or Tyr
<220> FEATURE:
<221> NAME/KEY: MOD_RES
<222> LOCATION: (5)..(5)
<223> OTHER INFORMATION: Lys, Thr, Arg or not present
<220> FEATURE:
<221> NAME/KEY: MOD_RES
<222> LOCATION: (6)..(6)
<223> OTHER INFORMATION: Thr, Ala or not present
<220> FEATURE:
<221> NAME/KEY: MOD_RES
<222> LOCATION: (7)..(7)
<223> OTHER INFORMATION: Asp, Asn, His, Ser or Tyr
<220> FEATURE:
<221> NAME/KEY: MOD_RES
<222> LOCATION: (8)..(9)
```

```
<223> OTHER INFORMATION: Gly or Ser
<220> FEATURE:
<221> NAME/KEY: MOD_RES
<222> LOCATION: (10)..(10)
<223> OTHER INFORMATION: Thr, Gly, Arg, Ile, Asn, His or Tyr
<220> FEATURE:
<221> NAME/KEY: MOD_RES
<222> LOCATION: (11)..(11)
<223> OTHER INFORMATION: Thr, Lys, Arg or Pro
<220> FEATURE:
<221> NAME/KEY: MOD_RES
<222> LOCATION: (12)..(12)
<223> OTHER INFORMATION: Asp, Asn, Tyr or Glu
<220> FEATURE:
<221> NAME/KEY: MOD_RES
<222> LOCATION: (13)..(13)
<223> OTHER INFORMATION: Tyr or Ser
<220> FEATURE:
<221> NAME/KEY: MOD_RES
<222> LOCATION: (14)..(14)
<223> OTHER INFORMATION: Thr, Ala or Val
<220> FEATURE:
<221> NAME/KEY: MOD_RES
<222> LOCATION: (15)..(15)
<223> OTHER INFORMATION: Ala, Gln or Asp
<220> FEATURE:
<221> NAME/KEY: MOD_RES
<222> LOCATION: (16)..(16)
<223> OTHER INFORMATION: Pro, Lys or Ser
<220> FEATURE:
<221> NAME/KEY: MOD_RES
<222> LOCATION: (17)..(17)
<223> OTHER INFORMATION: Val or Phe
<220> FEATURE:
<221> NAME/KEY: MOD_RES
<222> LOCATION: (18)..(18)
<223> OTHER INFORMATION: Lys or Gln

<400> SEQUENCE: 135

Xaa Ile Xaa Xaa Xaa Xaa Xaa Xaa Xaa Xaa Xaa Xaa Xaa Xaa Xaa Xaa
1               5                   10                  15

Xaa Xaa Gly

<210> SEQ ID NO 136
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gly, Ala or Glu
<220> FEATURE:
<221> NAME/KEY: MOD_RES
<222> LOCATION: (2)..(2)
<223> OTHER INFORMATION: Arg, Gly or Gln
<220> FEATURE:
<221> NAME/KEY: MOD_RES
<222> LOCATION: (3)..(3)
<223> OTHER INFORMATION: Thr, Met, Tyr, Arg, Leu, Gly or Lys
<220> FEATURE:
<221> NAME/KEY: MOD_RES
<222> LOCATION: (4)..(4)
<223> OTHER INFORMATION: Gly, Ser, Glu, Asn, Ile or Arg
<220> FEATURE:
<221> NAME/KEY: MOD_RES
<222> LOCATION: (5)..(5)
<223> OTHER INFORMATION: Tyr, Ile, Gly, Val or Ala
<220> FEATURE:
<221> NAME/KEY: MOD_RES
<222> LOCATION: (6)..(6)
<223> OTHER INFORMATION: Ser, Ile, Tyr, Gly, Ala or Thr
<220> FEATURE:
<221> NAME/KEY: MOD_RES
```

```
<222> LOCATION: (7)..(7)
<223> OTHER INFORMATION: Ile, Met, Ala, Pro or Asp
<220> FEATURE:
<221> NAME/KEY: MOD_RES
<222> LOCATION: (8)..(8)
<223> OTHER INFORMATION: Ser, Leu, Tyr or not present
<220> FEATURE:
<221> NAME/KEY: MOD_RES
<222> LOCATION: (9)..(9)
<223> OTHER INFORMATION: Trp, Arg, Ser, Thr or not present
<220> FEATURE:
<221> NAME/KEY: MOD_RES
<222> LOCATION: (10)..(10)
<223> OTHER INFORMATION: Ser, Gly or Leu
<220> FEATURE:
<221> NAME/KEY: MOD_RES
<222> LOCATION: (11)..(11)
<223> OTHER INFORMATION: Ser, Val, Leu, Gly or Tyr
<220> FEATURE:
<221> NAME/KEY: MOD_RES
<222> LOCATION: (12)..(12)
<223> OTHER INFORMATION: Phe, Tyr, Trp or not present
<220> FEATURE:
<221> NAME/KEY: MOD_RES
<222> LOCATION: (13)..(13)
<223> OTHER INFORMATION: Tyr, Pro, Ser or His
<220> FEATURE:
<221> NAME/KEY: MOD_RES
<222> LOCATION: (14)..(14)
<223> OTHER INFORMATION: Tyr, Pro, Asp, His or not present
<220> FEATURE:
<221> NAME/KEY: MOD_RES
<222> LOCATION: (15)..(15)
<223> OTHER INFORMATION: Tyr, Lys or Phe
<220> FEATURE:
<221> NAME/KEY: MOD_RES
<222> LOCATION: (16)..(17)
<223> OTHER INFORMATION: Tyr or not present
<220> FEATURE:
<221> NAME/KEY: MOD_RES
<222> LOCATION: (19)..(19)
<223> OTHER INFORMATION: Met or Leu
<220> FEATURE:
<221> NAME/KEY: MOD_RES
<222> LOCATION: (20)..(20)
<223> OTHER INFORMATION: Asp or Ala

<400> SEQUENCE: 136

Xaa Xaa Xaa Xaa Xaa Xaa Xaa Xaa Xaa Xaa Xaa Xaa Xaa Xaa Xaa Xaa
1               5                   10                  15

Xaa Gly Xaa Xaa Val
            20

<210> SEQ ID NO 137
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Ser Val Leu Thr Gln Pro Pro Ser Val Ser Glu Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
```

65                  70                  75                  80
Thr Gly Asp Glu Ala Asp Tyr Tyr Cys Gly Thr Trp Asp Ser Arg Leu
                    85                  90                  95

Ser Ala Val Val Phe Gly Gly Gly Thr Lys Leu Thr Val Leu
            100                 105                 110

<210> SEQ ID NO 138
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Ala Ala Pro Lys Leu Leu
            35                  40                  45

Ile Phe Arg Ser Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110

<210> SEQ ID NO 139
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Thr Tyr Tyr Cys Leu Gln Tyr Asn Ile Tyr Pro Trp
                85                  90                  95

Thr Phe Gly Gln Gly Thr Lys Val Glu Ile Lys
            100                 105

<210> SEQ ID NO 140
<211> LENGTH: 108
<212> TYPE: PRT
<213> ORGANISM: Artificial Sequence
<220> FEATURE:
<223> OTHER INFORMATION: Description of Artificial Sequence: Synthetic -continued

```
    polypeptide

<400> SEQUENCE: 140

Ser Ser Glu Leu Thr Gln Asp Pro Thr Val Ser Val Ala Leu Gly Gln
1               5                   10                  15

Thr Val Lys Ile Thr Cys Gln Gly Asp Ser Leu Arg Ser Phe Tyr Ala
            20                  25                  30

Ser Trp Tyr Gln Gln Lys Pro Gly Gln Ala Pro Val Leu Val Phe Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Val Tyr His
                85                  90                  95

Leu Val Leu Gly Gly Gly Thr Lys Leu Thr Val Leu
            100                 105

<210> SEQ ID NO 141
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Ile Leu Ala Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Ala Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Phe Pro Leu Pro Leu Thr Phe Gly Gly Gly Thr Lys Val Glu Ile Lys
            100                 105                 110

<210> SEQ ID NO 142
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60
```

Gly Ser Lys Ser Gly Thr Ser Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu
            100                 105                 110

<210> SEQ ID NO 143
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Phe Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 144
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Ile Leu Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Glu Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Met Gln Ser
                85                  90                  95

Phe Pro Leu Pro Leu Thr Phe Gly Gly Gly Thr Lys Val Glu Ile Lys
            100                 105                 110

<210> SEQ ID NO 145
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu
            100                 105                 110

<210> SEQ ID NO 146
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Ser Val Leu Thr Gln Ser Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Ala Ala Pro Lys Leu Leu
        35                  40                  45

Ile Leu Arg Asn Asn Gln Arg Pro Ser Gly Val Pro Asp Arg Phe Ser
50                  55                  60

Gly Ser Lys Ser Gly Thr Ser Ala Ser Leu Thr Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110

<210> SEQ ID NO 147
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

```
Ile Tyr Thr Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Phe Tyr Cys Ala Ala Arg Asp Glu Ser Leu
                85                  90                  95

Asn Gly Val Val Phe Gly Gly Gly Thr Lys Leu Thr Val Leu
                100                 105                 110
```

<210> SEQ ID NO 148
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Ala Ala Pro Lys Leu Leu
        35                  40                  45

Ile Phe Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
                100                 105                 110
```

<210> SEQ ID NO 149
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Asp Ile Thr Leu Thr Gln Thr Pro Leu Ser Leu Ser Val Ser Pro Gly
1               5                   10                  15

Gln Pro Ala Ser Ile Ser Cys Lys Ser Ser Gln Ser Leu Leu His Ser
            20                  25                  30

Asp Gly Arg Asn Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Leu Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Phe Pro Leu Pro Leu Thr Phe Gly Gly Gly Thr Lys Val Glu Ile Lys
                100                 105                 110
```

<210> SEQ ID NO 150
<211> LENGTH: 110

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu
            100                 105                 110

<210> SEQ ID NO 151
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Lys Asp
            20                  25                  30

Leu Gly Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Phe Pro Trp
                85                  90                  95

Thr Phe Gly Gln Gly Thr Lys Val Glu Ile Lys
            100                 105

<210> SEQ ID NO 152
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
            20                  25                  30

Tyr Leu Thr Trp Tyr Gln Gln Lys Pro Gly Gln Ala Pro Arg Leu Leu

```
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Asn Ser Leu
                 85                  90                  95

Cys Arg Phe Gly Gln Gly Thr Lys Leu Glu Ile Lys
                100                 105

<210> SEQ ID NO 153
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Gly
                20                  25                  30

Tyr Leu Thr Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Asn Ser Leu
                 85                  90                  95

Ser Arg Phe Gly Gln Gly Thr Lys Leu Glu Ile Lys
                100                 105

<210> SEQ ID NO 154
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Ile Leu Asp Ser
                20                  25                  30

Ser Asn Asn Asp Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Asn Thr Pro Phe Thr Phe Gly Pro Gly Thr Lys Val Asp Ile
                100                 105                 110

Lys
```

<210> SEQ ID NO 155
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Thr Tyr Pro Leu
                85                  90                  95

Thr Phe Gly Gly Gly Thr Lys Val Glu Ile Lys
            100                 105

<210> SEQ ID NO 156
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

His Asp Ala Ser Pro Arg Thr Ala Gly Ile Pro Ala Arg Phe Ser Gly
    50                  55                  60

Ser Gly Ser Gly Thr Glu Phe Thr Leu Thr Ile Asn Ser Leu Gln Ser
65                  70                  75                  80

Glu Asp Phe Ala Val Tyr Tyr Cys Gln Gln Tyr Asn Tyr Trp Thr Pro
                85                  90                  95

Ile Thr Phe Gly Gln Gly Thr Arg Leu Glu Ile Lys
            100                 105

<210> SEQ ID NO 157
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Ser Val Leu Thr Gln Pro Pro Ser Met Ser Ala Ala Pro Gly Gln
1               5                   10                  15

```
Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asn Tyr Cys Cys Gly Thr Trp Asp Ile Gly Leu
                85                  90                  95

Ser Val Trp Val Phe Gly Gly Gly Thr Lys Leu Thr Val Leu
                100                 105                 110

<210> SEQ ID NO 158
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Val Ile Ser Phe Asp Gly Ser Ile Lys Tyr Ser Val Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                85                  90                  95

Ala Arg Asp Arg Leu Asn Tyr Tyr Asp Ser Ser Gly Tyr Tyr His Tyr
                100                 105                 110

Lys Tyr Tyr Gly Met Ala Val Trp Gly Gln Gly Thr Thr Val Thr Val
            115                 120                 125

Ser Ser
130

<210> SEQ ID NO 159
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Thr Thr Asp Gly Gly Thr Thr Asp Tyr Ala Ala
 50                  55                  60
```

```
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
        115                 120                 125

Val Ser Ser
    130

<210> SEQ ID NO 160
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Val Gln Leu Leu Glu Ser Gly Gly Gly Leu Val Gln Pro Gly Glu
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gln Arg Glu Val Gly Pro Tyr Ser Ser Gly Trp Tyr Asp
            100                 105                 110

Tyr Tyr Tyr Gly Met Asp Val Trp Gly Gln Gly Thr Thr Val Thr Val
        115                 120                 125

Ser Ser
    130

<210> SEQ ID NO 161
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80
```

```
Met Glu Leu Ser Arg Leu Arg Ser Asp Asp Thr Ala Val Tyr Phe Cys
            85                  90                  95

Ala Arg Asp Gln Met Ser Ile Ile Met Leu Arg Gly Val Phe Pro Pro
            100                 105                 110

Tyr Tyr Tyr Gly Met Asp Val Trp Gly Gln Gly Thr Thr Val Thr Val
            115                 120                 125

Ser Ser
130

<210> SEQ ID NO 162
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser His Glu Ser Tyr Ala Asp Ser Val
50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Glu Asp Thr Ala Val Tyr Phe Cys
            85                  90                  95

Ala Arg Glu Arg Lys Arg Val Thr Met Ser Thr Leu Tyr Tyr Tyr Phe
            100                 105                 110

Tyr Tyr Gly Met Asp Val Trp Gly Gln Gly Thr Thr Val Thr Val Ser
            115                 120                 125

Ser

<210> SEQ ID NO 163
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Ile
            35                  40                  45

Gly Phe Ile Arg Ser Arg Ala Tyr Gly Gly Thr Pro Glu Tyr Ala Ala
        50                  55                  60

Ser Val Lys Gly Arg Phe Thr Ile Ser Arg Asp Asp Ser Lys Thr Ile
65                  70                  75                  80

Ala Tyr Leu Gln Met Asn Ser Leu Lys Thr Glu Asp Thr Ala Val Tyr
            85                  90                  95

Phe Cys Ala Arg Gly Arg Gly Ile Ala Ala Arg Trp Asp Tyr Trp Gly
```

Gln Gly Thr Leu Val Thr Val Ser Ser
            115                 120

<210> SEQ ID NO 164
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Thr Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Ala Glu Asp Thr Ala Val Tyr
                85                  90                  95

Tyr Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
        115                 120                 125

Val Ser Ser
    130

<210> SEQ ID NO 165
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Tyr Trp Val Arg Gln Ala Pro Gly Gln Gly Leu Glu Trp Met
        35                  40                  45

Gly Trp Ile Ser Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Gly Gly Tyr Ser Gly Tyr Ala Gly Leu Tyr Ser His Tyr Tyr
            100                 105                 110

Gly Met Asp Val Trp Gly Gln Gly Thr Thr Val Thr Val Ser Ser
        115                 120                 125

-continued

```
<210> SEQ ID NO 166
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Phe Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
        115                 120                 125

Val Ser Ser
        130

<210> SEQ ID NO 167
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
        115                 120                 125

Val Ser Ser
        130

<210> SEQ ID NO 168
<211> LENGTH: 130
<212> TYPE: PRT
```

<213> ORGANISM: Artificial Sequence
<220> FEATURE:
<223> OTHER INFORMATION: Description of Artificial Sequence: Synthetic
    polypeptide

<400> SEQUENCE: 168

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Phe
            20                  25                  30

Gly Met His Trp Val Arg Gln Ala Pro Gly Lys Gly Leu Glu Trp Val
        35                  40                  45

Ala Val Ile Ser Phe Asp Gly Ser Ile Lys Tyr Ser Val Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Arg Leu Asn Tyr Tyr Asp Ser Ser Gly Tyr Tyr His Tyr
            100                 105                 110

Lys Tyr Tyr Gly Leu Ala Val Trp Gly Gln Gly Thr Thr Val Thr Val
        115                 120                 125

Ser Ser
    130

<210> SEQ ID NO 169
<211> LENGTH: 131
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 169

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Arg Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Glu Gly Val Ser Gly Ser Pro Tyr Ser Ile Ser Trp Tyr
            100                 105                 110

Asp Tyr Tyr Gly Met Asp Val Trp Gly Gln Gly Thr Thr Val Thr
        115                 120                 125

Val Ser Ser
    130

<210> SEQ ID NO 170
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Ile Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Gly Ile Ala Ala Gly Leu Tyr Tyr Tyr Tyr Gly
            100                 105                 110

Met Asp Val Trp Gly Gln Gly Thr Thr Val Thr Val Ser Ser
        115                 120                 125

<210> SEQ ID NO 171
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Leu His Trp Val Arg Gln Ala Pro Gly Gln Gly Leu Glu Trp Met
        35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Phe Tyr Cys
                85                  90                  95

Ala Arg Gly Arg Gln Trp Leu Gly Phe Asp Tyr Trp Gly Gln Gly Thr
            100                 105                 110

Leu Val Thr Val Ser Ser
        115

<210> SEQ ID NO 172
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Val Gln Leu Gln Gln Trp Gly Ala Gly Leu Leu Lys Pro Ser Glu
1               5                   10                  15

Thr Leu Ser Leu Ser Cys Ala Val Tyr Gly Gly Ser Phe Gly Gly Tyr
            20                  25                  30

```
Tyr Trp Ser Trp Ile Arg Gln Pro Pro Gly Lys Gly Leu Glu Trp Ile
            35                  40                  45

Gly Glu Ile Asn His Ser Gly Thr Lys Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Phe Cys Ala
                 85                  90                  95

Arg Gly Asp Val Val Gly Phe Phe Asp Tyr Trp Gly Gln Gly Thr Leu
                100                 105                 110

Val Thr Val Ser Ser
            115
```

<210> SEQ ID NO 173
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

```
Gln Val Gln Leu Val Gln Ser Gly Ala Glu Val Lys Lys Ser Gly Ala
 1               5                  10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Val Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asn Glu Tyr Ser Ser Ala Trp Pro Leu Gly Tyr Trp Gly Gln
                100                 105                 110

Gly Thr Leu Val Thr Val Ser Ser
            115                 120
```

<210> SEQ ID NO 174
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

```
Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
                20                  25                  30

Gly Val Gly Val Ala Trp Ile Arg Gln Pro Pro Gly Lys Ala Leu Glu
            35                  40                  45

Trp Leu Ala Leu Ile Tyr Trp Thr Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80
```

```
Val Leu Arg Met Thr Asn Met Asp Pro Leu Asp Thr Ala Thr Tyr Phe
                85                  90                  95
Cys Ala His Arg Pro Gly Gly Trp Phe Asp Pro Trp Gly Gln Gly Thr
           100                 105                 110
Leu Val Thr Val Ser Ser
        115
```

<210> SEQ ID NO 175  
<211> LENGTH: 321  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 175

```
gacatccaga tgacccagtc tccatcctcc ctgtctgcat ctgtaggaga cagagtcacc      60
atcacttgcc gggcaagtca gggcattaga aatgatttag ctggtttca gcagaaacca     120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagatttag caacttatta ctgtctacag tataatattt acccgtggac gttcggccaa    300
gggaccaagg tggaaatcaa a                                              321
```

<210> SEQ ID NO 176  
<211> LENGTH: 321  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 176

```
gacatccaga tgacccagtc tccatcctcc ctgtctgcat ctgtaggaga cagagtcacc      60
atcacttgcc gggcaagtca gggcattaga aaggatttag ctggtatca gcagaaacca     120
gggaaagccc ctaagcgcct gatctatgga gcatccagtt tgcaaagtgg ggtcccatca    180
aggttcagcg gcagtggatc tgggacagaa ttcactctca caatcagcag cctgcagcct    240
gaagattttg caacttatta ctgtctacag tataatagtt tcccgtggac gttcggccaa    300
gggaccaagg tggaaatcaa a                                              321
```

<210> SEQ ID NO 177  
<211> LENGTH: 359  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 177

```
aggtgcagct ggtgcagtct ggggctgagg tgaagaagtc tggggcctca gtgaaggtct      60
cctgcaaggc ttctggatac accttcaccg gctactatat gcactgggtg cgacaggccc    120
ctggacaagg gcttgagtgg atgggatgga tcaaccctaa cagtggtggc acaaactatg    180
tacagaagtt tcagggcagg gtcaccatga ccagggacac gtccatcagc acagcctaca    240
tggagctgag caggctgaga tctgacgaca cggccgtgta ttactgtgcg agaaatgagt    300
atagcagtgc ctggcccttg ggtattgggg ccagggaac cctggtcacc gtctctagt     359
```

<210> SEQ ID NO 178
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 178

```
gatattgtga tgactcagtc tccactctcc ctgcccgtca cccctggaga gccggcctcc    60
atctcctgca ggtctagtca gagcctcctg catagttttg ggtacaacta tttggattgg   120
tacctgcaga agccagggca gtctccacag ctcctgatct atttgggttc taatcgggcc   180
tccggggtcc ctgacaggtt cagtggcagt ggatcaggca cagatttac actgaaaatc    240
agcagagtgg aggctgagga tgttggggtt tattactgca tgcaagctct acaaactcca   300
ttcactttcg gccctgggac caaagtggat atcaaa                             336
```

<210> SEQ ID NO 179
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 179

```
gatattatac tggcccagac tccactttct ctgtccgtca cccctggaca gccggcctcc    60
atctcctgca agtctagtca gagcctcctg cacagtgctg aaagaccta tttgtattgg   120
tacctgcaga agccaggcca gcctccacag ctcctgatct atgaagtttc aaccggttc    180
tctggagtgc cagataggtt cagtggcagc gggtcaggga cagatttcac actgaaaatc   240
agccgggtgg aggctgagga tgttgggatt tattactgca tgcaaagttt tccgcttccg   300
ctcactttcg gcggagggac caaggtggag atcaaa                             336
```

<210> SEQ ID NO 180
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 180

```
gatattattc tgacccagac tccactttct ctgtccgtca cccctggaca gccggcctcc    60
atctcctgca agtctagtca gagcctcctg cacagtgatg aaagaccta tttgtattgg   120
tacctgcaga agcccggcca gcctccacag ctcctgatct atgaagtttc aaccggttc    180
tctggagagc cagataggtt cagtggcagc gggtcaggga cagatttcac actgaaaatc   240
agccgggtgg aggctgagga tgttgggact tattattgca tgcaaagttt tccgcttccg   300
ctcactttcg gcggagggac caaggtggag atcaaa                             336
```

<210> SEQ ID NO 181
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 181

```
gatattacac tgacccagac tccactttct ctgtccgtct cccctggaca gccggcctcc    60
atctcctgca agtctagtca gagcctcctg cacagtgatg gaaggaacta tctgtattgg   120
tacctgcaga agccaggcca gcctccacag ctcctgatct atgaagtgtc caaccggttc   180
tctggactgc cagataggtt cagtggcagc gggtcaggga cagatttcac actgaaaatc   240
agccgggtgg aggctgagga tgttgggatt tattactgca tgcaaagttt tccgcttccg   300
ctcactttcg gcggagggac caaggtggag atcaaa                              336
```

<210> SEQ ID NO 182
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 182

```
gaaattgtgt tgacgcagtc tccaggcacc ctgtctttgt ctccagggga aagagccacc    60
ctctcctgca gggccagtca gagtgttagc agcggctact taacctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta actcactgtg caggtttggc   300
caggggacca agctggagat caaa                                           324
```

<210> SEQ ID NO 183
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 183

```
gaaattgtgt tgacgcagtc tccaggcacc ctgtctttgt ctccagggga aagagccacc    60
ctctcctgca gggccagtca gagtgttagc agcggctact taacctggta ccagcagaaa   120
cctggccagg ctcccagact cctcatctat ggtgcatcca gcagggccac tggcatccca   180
gacaggttca gtggcagtgg gtctgggacg gacttcactc tcaccatcag cagactggag   240
cctgaagatt ttgcagtgta ttactgtcag cagtatggta actcactgag caggtttggc   300
caggggacca agctggagat caaa                                           324
```

<210> SEQ ID NO 184
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 184

```
gaaatagtga tgacgcagtc tccagccacc ctgtctgtgt ctccagggga aagagccacc    60
ctctcctgta gggccagtca gagtgttcgc agcaatttag cctggtacca gcagaaacct   120
ggccaggctc ccaggctcct cattcatgat gcatccccca ggaccgctgg tatcccagcc   180
aggttcagtg gcagtggatc tgggacagaa ttcactctca ccatcaacag cctgcagtct   240
gaagattttg cagtttatta ctgtcagcag tataattact ggactccgat caccttcggc   300
```
caagggacac gactggagat taaa                                              324

<210> SEQ ID NO 185
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
gacatcgtga tgacccagtc tccagactcc ctggctgtgt ctctgggcga gagggccacc      60
atcaactgca agtccagcca gagtatttta gacagctcca acaatgataa ctacttagct     120
tggtaccagc agaaaccagg acagcctcct aaactgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttataatact     300
ccattcactt tcggccctgg gaccaaagtg gatatcaaa                            339

<210> SEQ ID NO 186
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
cagtctgtgt tgacgcagcc gccctcagtg tctgaggccc caggacagaa ggtcaccatc      60
tcctgctctg gaagcagctc caacattggg aataattatg tatcctggta ccagcagctc     120
ccaggaacag cccccaaact cctcatttat gacaataata agcgaccctc agggattcct     180
gaccgattct ctggctccaa gtctggcacg tcagccaccc tgggcatcac cggactccag     240
actggggacg aggccgatta ttactgcgga acatgggata ccgcctgag tgctgtggtt      300 ttcggcggag ggaccaagct gaccgtccta                                      330

<210> SEQ ID NO 187
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
cagtctgtgt tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata agcgaccctc agggattcct     180
gaccgattct ctggctccaa gtctggcacg tcaaccaccc tgggcatcac cggactccag     240
actggggacg aggccgatta ttactgcgga acatgggata ccgcctgag tgctgtggtt      300 ttcggcggag ggaccaagct gaccgtccta                                      330

<210> SEQ ID NO 188
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 188

| cagtctgtgt | tgacgcagcc | gccctcagtg | tctgcggccc | caggacagaa | ggtcaccatc | 60 |
| tcctgctctg | gaagcagctc | caacattggg | aataattatg | tatcctggta | ccagcagttc | 120 |
| ccaggaacag | cccccaaact | cctcatttat | gacaataata | agcgaccctc | agggattcct | 180 |
| gaccgattct | ctggctccaa | gtctggcacg | tcagccaccc | tgggcatcac | cggactccag | 240 |
| actggggacg | aggccgatta | ttactgcgga | acatgggata | gccgcctgag | tgctgtggtt | 300 |
| ttcggcggag | ggaccaagct | gaccgtccta | | | | 330 |

<210> SEQ ID NO 189
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 189

| cagtctgtgt | tgacgcagcc | gccctcagtg | tctgcggccc | caggacagaa | ggtcaccatc | 60 |
| tcctgctctg | gaagcagctc | caacattggg | aataattatg | tatcctggta | ccagcagctc | 120 |
| ccaggaacag | cccccaaact | cctcatttat | gacaataata | agcgaccctc | agggattcct | 180 |
| gaccgattct | ctggctccaa | gtctggcacg | tcagccaccc | tgggcatcac | cggactccag | 240 |
| actggggacg | aggccgatta | ttactgcgga | acatgggata | gccgcctgag | tgctgtggtt | 300 |
| ttcggcggag | ggaccaagct | gaccgtccta | | | | 330 |

<210> SEQ ID NO 190
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 190

| cagtctgtgt | tgacgcagcc | gccctcaatg | tctgcggccc | caggacagaa | ggtcaccatc | 60 |
| tcctgctctg | gaagcagctc | caacattggg | aataattatg | tatcctggta | ccagcagctc | 120 |
| ccaggaacag | cccccaaact | cctcatttat | gacaataata | agcgaccctc | agggattcct | 180 |
| gaccgattct | ctggctccaa | gtctggcacg | tcagccaccc | tgggcatcac | cggactccag | 240 |
| actggggacg | aggccaatta | ctgctgcgga | acatgggata | tcggcctgag | tgtttgggtg | 300 |
| ttcggcggag | ggaccaaact | gaccgtccta | | | | 330 |

<210> SEQ ID NO 191
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 191

| cagtctgtgc | tgactcagcc | accctcagcg | tctgggaccc | ccgggcagag | ggtcaccatc | 60 |
| tcttgttctg | gaagcagttc | caatatcgga | agtaatactg | tgaactggta | ccagcagctc | 120 |
| ccaggaacgg | cccccaaact | cctcatctat | actaataatc | agcggccctc | aggggtccct | 180 | gaccgattct ctggctccaa gtctggcacc tcagcctccc tggccatcag tggactccag    240 tctgaggatg aggctgattt ttactgtgca gcgcgggatg agagcctgaa tggtgtggta    300 ttcggcggag ggaccaagct gaccgtccta                                     330

<210> SEQ ID NO 192
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
cagtctgtgc tgactcagcc accctcagcg tctgggaccc ccgggcagag agtcaccatc    60
tcttgttctg gaagcagctc caacatcggc agtaattatg tatactggta ccagcagctc    120
ccaggagcgg ccccccaaact cctcatcttt aggaataatc agcggccctc aggggtccct    180
gaccgcttct ctggctccaa gtctggcacc tcagcctccc tggccatcag tgggctccgg    240
tccgaggatg aggctgatta ttactgtgca gcatgggatg acagcctgag tggttgggtg    300
ttcggcggag ggaccaagct gaccgtccta                                     330

<210> SEQ ID NO 193
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
cagtctgtgc tgactcagcc accctcagcg tctgggaccc ccgggcagag agtcaccatc    60
tcttgttctg gaagcagctc caacatcggc agtaattatg tatactggta ccagcagctc    120
ccaggagcgg ccccccaaact cctcatcttt aggagtaatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgag tggttgggtg    300
ttcggcggag ggaccaagct gaccgtccta                                     330

<210> SEQ ID NO 194
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
cagtctgtgc tgactcagtc accctcagcg tctgggaccc ccgggcagag agtcaccatc    60
tcttgttctg gaagcagctc caacatcggc agtaattatg tatactggta ccagcagctc    120
ccaggagcgg ccccccaaact cctcatcctt aggaataatc agcggccctc aggggtccct    180
gaccgattct ctggctccaa gtctggcacc tcagcctccc tgaccatcag tgggctccgg    240
tccgaggatg aggctgacta ttattgtgca gcatgggatg acagcctgag tggttgggtg    300
ttcggcggag ggaccaagct gaccgtccta                                     330

<210> SEQ ID NO 195
<211> LENGTH: 324
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 195

```
tcttctgagc tgactcagga ccctactgtg tctgtggcct tgggacagac agtcaaaatc    60
acatgccaag agacagcct cagaagtttt tatgcaagct ggtaccagca gaagccagga   120
caggcccctg tacttgtctt ctatggtaaa aacaaccggc cctcagggat cccagaccga   180
ttctctggct ccagctcagg aaacacagct tccttgacca tcactggggc tcaggcggaa   240
gatgaggctg actattattg taattcccgg gacagcagtg tttaccatct ggtactcggc   300
ggagggacca agctgaccgt ccta                                          324
```

<210> SEQ ID NO 196
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 196

```
caggtgcagt tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccct acagtggtgg cacaaactat   180
gcacagaagt tcagggcag gtcaccatg accaggaca cgtccatcag cacagcctac   240
atggagctga gcaggctgag atctgacgac acggccgtgt atttctgtgc gagagatcaa   300
atgagtatta ttatgcttcg gggagttttt cccccttact attacggtat ggacgtctgg   360
ggccaaggga ccacggtcac cgtctctagt                                    390
```

<210> SEQ ID NO 197
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 197

```
caggtgcagc tggtgcagtc tggggctgag gtgaagaagc ctggggcctc agtgaaggtc    60
tcctgcaagg cttctggata caccttcacc gactactata tgtactgggt gcgacaggcc   120
cctggacaag gcttgagtg gatgggatgg atcagcccta atagtggtgg cacaaactat   180
gcccagaagt tcagggcag gtcaccatg accaggaca cgtctatcag cacagcctac   240
atggagctga gtaggctgag atctgacgac acggccgtgt attactgtgt gagaggagga   300
tatagtggct acgctgggct ctactcccac tactacggta tggacgtctg ggggccaaggg   360
accacggtca ccgtctctag t                                             381
```

<210> SEQ ID NO 198
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 198

```
caggtgcagc tggtgcagtc tggggctgag gtgaagaagc ctggggcctc agtgaaggtc      60
tcctgcaagg cttctggata caccttcacc gcctactatt tacactgggt gcgacaggcc     120
cctggacaag ggcttgagtg gatgggatgg atcaaccctc acagtggtgg cacaaactat     180
gcacagaagt tcagggcag ggtcaccatg accaggaca cgtccatcag cacagcctac       240
atggagctga gcaggctgag atctgacgac acggccgtgt tctactgtgc gagaggaagg     300
cagtggctgg gctttgacta ctggggccag ggaaccctgg tcaccgtctc tagt           354
```

<210> SEQ ID NO 199
<211> LENGTH: 321
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 199

```
gacatccaga tgacccagtc tccatcctcc ctgtctgcat ctgtaggaga cagagttacc      60
attacttgcc gggcaagtca gggcattaga aatgatttag ctggtatca gcagaaacca     120 gggaaagccc ctaagcgcct gatctatgtt gcatccagtt tgcaaagtgg ggtcccatca     180
aggttcagcg gcagtggatc tgggacagaa ttcactctca caatcagcag cctgcagcct     240
gaagattttg caacttatta ctgtctacag tataacactt acccgctcac tttcggcgga     300
gggaccaagg tggagatcaa g                                               321
```

<210> SEQ ID NO 200
<211> LENGTH: 393
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 200

```
gaggtacagc tggtggagtc tgggggaggc ttggtaaagc ctgggggtc cctcagactc       60 tcctgtgcag cctctggatt cactttcggt aacgcctgga tgagctgggt ccgccaggct     120
ccagggaagg ggctggagtg ggttggccgt attaaaagca aaactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtattt ctgtaccaca     300
gatcggaccg ggtatagcat cagctggtct agttactact actactacgg tatggacgtc     360
tggggccaag ggaccacggt caccgtctct agt                                  393
```

<210> SEQ ID NO 201
<211> LENGTH: 393
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 201

```
gaggtgcagc tggtggagtc tgggggaggc ttggtaaagc ctgggggtc ccttagactc       60 tcctgtgcag cctctggatt cactttcagt aacgcctgga tgagctgggt ccgccaggct     120
ccagggaagg ggctggagtg ggttggccgt attaaaagca aaactgatgg tgggacaaca     180
gactacactg cacccgtgaa aggcagattc accatctcaa gagatgattc aaaaaacacg     240
```

```
ctgtatctgc aaatgaatag cctgaaagcc gaggacacag ccgtgtatta ctgtaccaca    300
gatcggaccg ggtatagcat cagctggtct agttactact actactacgg tatggacgtc    360
tggggccaag ggaccacggt caccgtctct agt                                 393
```

<210> SEQ ID NO 202
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202

```
gaggtacagc tggtggagtc tgggggaggc ttggtaaagc ctggggggtc ccttagactc     60
tcctgtgcag cctctggatt cactttcggt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gatcggaccg ggtatagcat cagctggtct agttactact actactacgg tatggacgtc    360
tggggccaag ggaccacggt caccgtctct agt                                 393
```

<210> SEQ ID NO 203
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203

```
gaggtgcagc tggtggagtc tgggggaggc ttggtaaagc ctggggggtc ccttagactc     60
tcctgtgcag cctctggatt cactttcagt aacgcctgga tgagctgggt ccgccaggct    120
ccagggaagg ggctggagtg ggttggccgt attaaaagca caactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gatcggaccg gatatagcat cagctggtct agttactact actactacgg tatggacgtc    360
tggggccaag ggaccacggt caccgtctct agt                                 393
```

<210> SEQ ID NO 204
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204

```
gaggtgcagc tggtggagtc tgggggaggc ctggtcaagc ctggggggtc cctgagactc     60
tcctgtgcag cctctggata caccttcagt acctatagca tgaactgggt ccgccaggct    120
ccagggaagg ggctggagtg ggtctcatcc attagtagta gtagtagtta cagatattac    180
gcagactcag tgaagggccg attcaccatc tccagagaca acgccaagaa ctcactgtat    240
ctgcaaatga gtagcctgag agccgaggac acggctgtgt attactgtgc gagagaaggg    300
gtgtctggca gttcgccgta tagcatcagc tggtacgact actattacgg tatggacgtc    360
```

```
tggggccaag ggaccacggt caccgtctct agt                                    393

<210> SEQ ID NO 205
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
gaggtgcagc tattggagtc tgggggaggc ttggtacagc ctggggagtc cctgagactc         60
tcctgtgcag cctctgggtt cacctttagc agctatgcca tgagctgggt ccgccaggct        120
ccagggaagg ggctggagtg ggtctcagct attagtggta gtggtggtcg cacatactac        180
gcagactccg tgaagggccg gttcaccatc tccagagaca attccaagaa cacgctgtat        240
ctgcaaatga atagcctgag agccgaggac acggccgtat attactgtgc gaaagatcaa        300
agggaggtag ggccgtatag cagtggctgg tacgactact actacggtat ggacgtctgg        360
ggccaaggga ccacggtcac cgtctctagt                                        390

<210> SEQ ID NO 206
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
caggtgcagc tggtggagtc tgggggaggc gtggtccagc ctgggaggtc cctgagactc         60
tcctgtgcag cctctggatt caccttcagt agctatgcca tgcactgggt ccgccaggct        120
ccaggcaagg ggctggagtg ggtggcagtt atttcatatg atggaagtca tgaatcctat        180
gcagactccg tgaagggccg attcaccatc tccagagaca tttccaagaa cacgctgtat        240
ctgcaaatga acagcctgag agctgaggac acggctgtgt atttctgtgc gagagagagg        300
aaacgggtta cgatgtctac cttatattac tacttctact acggtatgga cgtctggggc        360
caagggacca cggtcaccgt ctctagt                                           387

<210> SEQ ID NO 207
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207
caggtgcagc tggtggaatc tgggggaggc gtggtccagc ctgggaggtc cctgagactc         60
tcctgtgcag cctctggatt caccttcagt agctttggca tgcactgggt ccgccaggct        120
ccaggcaagg ggctggagtg ggtggcagtt atatcatttg atggaagtat taagtattct        180
gtagactccg tgaagggccg attcaccatc tccagagaca attcaaagaa cacgctgttt        240
ctgcaaatga acagcctgcg agccgaggac acggctgtgt attactgtgc gagagatcgg        300
ctcaattact atgatagtag tggttattat cactacaaat actacggtat ggccgtctgg        360
ggccaaggga ccacggtcac cgtctctagt                                        390
```

<210> SEQ ID NO 208
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 208

```
caggtgcagc tggtggaatc tgggggaggc gtggtccagc ctgggaggtc cctgagactc      60
tcctgtgcag cctctggatt caccttcagt agctttggca tgcattgggt ccgccaggct     120
ccaggcaagg ggctggagtg ggtggcagtt atatcatttg atggaagtat taagtactct     180
gtagactccg tgaagggccg attcaccatc tccagagaca attcaaagaa cacgctgttt     240
ctgcaaatga acagcctgcg agccgaggac acggctgtgt attactgtgc gagagatcgg     300
ctcaattact atgatagtag tggttattat cactacaaat actacggtct ggccgtctgg     360
ggccaaggga ccacggtcac cgtctctagt                                       390
```

<210> SEQ ID NO 209
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 209

```
gaggtgcagc tggtggagtc tgggggaggc ttggtaaagc cagggcggtc cctgagactc      60
tcctgtacag cttctggatt cacctttggt gattatgcta tgagctggtt ccgccaggct     120
ccagggaagg ggctggagtg gataggtttc attagaagca gagcttatgg tgggacacca     180
gaatacgccg cgtctgtgaa aggcagattc accatctcaa gagatgattc aaaaccatc      240
gcctatctgc aaatgaacag cctgaaaacc gaggacacag ccgtgtattt ctgtgctaga     300
ggacggggta ttgcagctcg ttgggactac tggggccagg gaaccctggt caccgtctct     360
agt                                                                    363
```

<210> SEQ ID NO 210
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 210

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcatcatc tccagagata atccaagaa cacgctgtat      240
ctgcaaatga acagcctgag agccgaggac acggctgtgt attactgtgc gagagcgggg     300
ggtatagcag cagctggcct ctactactac tacggtatgg acgtctgggg ccaagggacc     360
acggtcaccg tctctagt                                                    378
```

<210> SEQ ID NO 211
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
caggtgcagt tacagcagtg gggcgcagga ctgttgaagc cttcggagac cctgtccctc    60
agctgcgctg tctatggtgg gtccttcggt ggttactact ggagctggat ccgccagccc   120
ccagggaagg ggctggagtg gattggggaa atcaatcata gtggaggcac caagtacaac   180
ccgtccctca agagtcgagt caccatatca gtagacacgt ccaagaacca gttctccctg   240
aagctgagct ctgtgaccgc cgcggacacg gctgtgtatt tctgtgcgag aggcgatgta   300
gtaggtttct ttgactattg gggccaggga accctggtca ccgtctctag t            351

<210> SEQ ID NO 212
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
cagatcacct taaaggagtc tggtcctacg ctggtgaaac ccacacagac cctcacgctg    60
acctgcacct tctctgggtt ctcactcagc actagtggtg tgggtgtggc ctggatccgt   120
cagccccccg gaaaggccct ggagtggctt gcactcattt attggactga tgataagcgc   180
tacagtccat ctctgaagag caggctcacc atcaccaagg acacctccaa gaaccaggtg   240
gtccttagaa tgaccaacat ggacccttg gacacagcca cttatttctg tgcacacaga     300 ccaggggct ggttcgaccc ctggggccag ggaaccctgg tcaccgtctc tagt           354

<210> SEQ ID NO 213
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Gly Gly Gly Gly Val Asp Gly Gly Gly Gly Gly Val
1               5                   10

<210> SEQ ID NO 214
<211> LENGTH: 148
<212> TYPE: PRT
<213> ORGANISM: Rattus sp.

<400> SEQUENCE: 214

Met Ala Pro Gly Leu Arg Gly Leu Pro Arg Arg Gly Leu Trp Leu Leu
1               5                   10                  15

Leu Ala His His Leu Phe Met Val Thr Ala Cys Arg Asp Pro Asp Tyr
                20                  25                  30

Gly Thr Leu Ile Gln Glu Leu Cys Leu Ser Arg Phe Lys Glu Asp Met
            35                  40                  45

Glu Thr Ile Gly Lys Thr Leu Trp Cys Asp Trp Gly Lys Thr Ile Gly
        50                  55                  60

Ser Tyr Gly Glu Leu Thr His Cys Thr Lys Leu Val Ala Asn Lys Ile
65                  70                  75                  80

Gly Cys Phe Trp Pro Asn Pro Glu Val Asp Lys Phe Phe Ile Ala Val

```
                85                  90                  95

His His Arg Tyr Phe Ser Lys Cys Pro Val Ser Gly Arg Ala Leu Arg
            100                 105                 110

Asp Pro Pro Asn Ser Ile Leu Cys Pro Phe Ile Val Leu Pro Ile Thr
        115                 120                 125

Val Thr Leu Leu Met Thr Ala Leu Val Val Trp Arg Ser Lys Arg Thr
    130                 135                 140

Glu Gly Ile Val
145

<210> SEQ ID NO 215
<211> LENGTH: 148
<212> TYPE: PRT
<213> ORGANISM: Macaca fascicularis

<400> SEQUENCE: 215

Met Ala Arg Ala Leu Cys Arg Leu Pro Gln Arg Gly Leu Trp Leu Leu
1               5                   10                  15

Leu Ala His His Leu Phe Met Ala Thr Ala Cys Gln Glu Ala Asn Tyr
            20                  25                  30

Gly Ala Leu Leu Gln Glu Leu Cys Leu Thr Gln Phe Gln Val Asp Met
        35                  40                  45

Glu Ala Val Gly Glu Thr Leu Trp Cys Asp Trp Gly Arg Thr Ile Gly
    50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
                85                  90                  95

His Gly His Tyr Phe Arg Ala Cys Pro Ile Ser Gly Arg Ala Val Arg
            100                 105                 110

Asp Pro Pro Gly Ser Val Leu Tyr Pro Phe Ile Val Val Pro Ile Thr
        115                 120                 125

Val Thr Leu Leu Val Thr Ala Leu Val Val Trp Gln Ser Lys His Thr
    130                 135                 140

Glu Gly Ile Val
145

<210> SEQ ID NO 216
<211> LENGTH: 148
<212> TYPE: PRT
<213> ORGANISM: Macaca mulatta

<400> SEQUENCE: 216

Met Ala Arg Ala Leu Cys Arg Leu Pro Gln Arg Gly Leu Trp Leu Leu
1               5                   10                  15

Leu Ala His His Leu Phe Met Ala Thr Ala Cys Gln Glu Ala Asn Tyr
            20                  25                  30

Gly Ala Leu Leu Gln Glu Leu Cys Leu Thr Gln Phe Gln Val Asp Met
        35                  40                  45

Glu Ala Val Gly Glu Thr Leu Trp Cys Asp Trp Gly Arg Thr Ile Gly
    50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
                85                  90                  95

His Gly His Tyr Phe Arg Ala Cys Pro Ile Ser Gly Arg Ala Val Arg
```

```
                    100                 105                 110
Asp Pro Pro Gly Ser Val Leu Tyr Pro Phe Ile Val Val Pro Ile Thr
            115                 120                 125

Val Thr Leu Leu Val Thr Ala Leu Val Val Trp Gln Ser Lys His Thr
        130                 135                 140

Glu Gly Ile Val
145

<210> SEQ ID NO 217
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Met Ala Arg Ala Leu Cys Arg Leu Pro Arg Arg Gly Leu Trp Leu Leu
1               5                   10                  15

Leu Ala His His Leu Phe Met Thr Thr Ala Cys Arg Asp Pro Asp Tyr
            20                  25                  30

Gly Thr Leu Leu Arg Glu Leu Cys Leu Thr Gln Phe Gln Val Asp Met
        35                  40                  45

Glu Ala Val Gly Glu Thr Leu Trp Cys Asp Trp Gly Arg Thr Ile Arg
    50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
                85                  90                  95

His Gly Arg Tyr Phe Arg Ser Cys Pro Ile Ser Gly Arg Ala Val Arg
            100                 105                 110

Asp Pro Pro Gly Ser Ile Leu Tyr Pro Phe Ile Val Val Pro Ile Thr
        115                 120                 125

Val Thr Leu Leu Val Thr Ala Leu Val Val Trp Gln Ser Lys Arg Thr
    130                 135                 140

Glu Gly Ile Val
145

<210> SEQ ID NO 218
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Met Ala Arg Ala Leu Cys Arg Leu Pro Arg Arg Gly Leu Trp Leu Leu
1               5                   10                  15

Leu Ala His His Leu Phe Met Thr Thr Ala Cys Gln Glu Ala Asn Tyr
            20                  25                  30

Gly Ala Leu Leu Arg Glu Leu Cys Leu Thr Arg Phe Lys Glu Asp Met
        35                  40                  45

Glu Thr Ile Gly Lys Thr Leu Trp Cys Asp Trp Gly Arg Thr Ile Arg
    50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
```

```
                    85                  90                  95
His Gly Arg Tyr Phe Arg Ser Cys Pro Ile Ser Gly Arg Ala Val Arg
                100                 105                 110

Asp Pro Pro Gly Ser Ile Leu Tyr Pro Phe Ile Val Val Pro Ile Thr
            115                 120                 125

Val Thr Leu Leu Val Thr Ala Leu Val Val Trp Gln Ser Lys Arg Thr
        130                 135                 140

Glu Gly Ile Val
145

<210> SEQ ID NO 219
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Met Ala Arg Ala Leu Cys Arg Leu Pro Arg Arg Gly Leu Trp Leu Leu
1               5                   10                  15

Leu Ala His His Leu Phe Met Thr Thr Ala Cys Gln Glu Ala Asn Tyr
            20                  25                  30

Gly Ala Leu Leu Arg Glu Leu Cys Leu Thr Gln Phe Gln Val Asp Met
        35                  40                  45

Glu Ala Val Gly Glu Thr Leu Trp Cys Asp Trp Gly Arg Thr Ile Arg
    50                  55                  60

Ser Tyr Gly Glu Leu Thr His Cys Thr Lys Leu Val Ala Asn Lys Leu
65                  70                  75                  80

Gly Cys Phe Trp Pro Asn Ala Glu Val Asp Arg Phe Phe Leu Ala Val
                85                  90                  95

His Gly Arg Tyr Phe Arg Ser Cys Pro Ile Ser Gly Arg Ala Val Arg
                100                 105                 110

Asp Pro Pro Gly Ser Ile Leu Tyr Pro Phe Ile Val Val Pro Ile Thr
            115                 120                 125

Val Thr Leu Leu Val Thr Ala Leu Val Val Trp Gln Ser Lys Arg Thr
        130                 135                 140

Glu Gly Ile Val
145

<210> SEQ ID NO 220
<211> LENGTH: 464
<212> TYPE: PRT
<213> ORGANISM: Rattus sp.

<400> SEQUENCE: 220

Met Met Asp Lys Lys Cys Thr Leu Cys Phe Leu Phe Leu Leu Leu Leu
1               5                   10                  15

Asn Met Ala Leu Ile Ala Ala Glu Ser Glu Gly Ala Asn Gln Thr
            20                  25                  30

Asp Leu Gly Val Thr Arg Asn Lys Ile Met Thr Ala Gln Tyr Glu Cys
        35                  40                  45

Tyr Gln Lys Ile Met Gln Asp Pro Ile Gln Gly Glu Gly Leu Tyr
    50                  55                  60

Cys Asn Arg Thr Trp Asp Gly Trp Leu Cys Trp Asn Asp Val Ala Ala
65                  70                  75                  80

Gly Thr Glu Ser Met Gln Tyr Cys Pro Asp Tyr Phe Gln Asp Phe Asp
```

85                  90                  95
Pro Ser Glu Lys Val Thr Lys Ile Cys Asp Gln Asp Gly Asn Trp Phe
            100                 105                 110

Arg His Pro Asp Ser Asn Arg Thr Trp Thr Asn Tyr Thr Leu Cys Asn
            115                 120                 125

Asn Ser Thr His Glu Lys Val Lys Thr Ala Leu Asn Leu Phe Tyr Leu
130                 135                 140

Thr Ile Ile Gly His Gly Leu Ser Ile Ala Ser Leu Ile Ile Ser Leu
145                 150                 155                 160

Ile Ile Phe Phe Tyr Phe Lys Ser Leu Ser Cys Gln Arg Ile Thr Leu
                165                 170                 175

His Lys Asn Leu Phe Phe Ser Phe Val Cys Asn Ser Ile Val Thr Ile
            180                 185                 190

Ile His Leu Thr Ala Val Ala Asn Asn Gln Ala Leu Val Ala Thr Asn
            195                 200                 205

Pro Val Ser Cys Lys Val Ser Gln Phe Ile His Leu Tyr Leu Met Gly
210                 215                 220

Cys Asn Tyr Phe Trp Met Leu Cys Glu Gly Ile Tyr Leu His Thr Leu
225                 230                 235                 240

Ile Val Val Ala Val Phe Ala Glu Lys Gln His Leu Met Trp Tyr Tyr
                245                 250                 255

Phe Leu Gly Trp Gly Phe Pro Leu Leu Pro Ala Cys Ile His Ala Ile
            260                 265                 270

Ala Arg Ser Leu Tyr Tyr Asn Asp Asn Cys Trp Ile Ser Ser Asp Thr
            275                 280                 285

His Leu Leu Tyr Ile Ile His Gly Pro Ile Cys Ala Ala Leu Leu Val
290                 295                 300

Asn Leu Phe Phe Leu Leu Asn Ile Val Arg Val Leu Ile Thr Lys Leu
305                 310                 315                 320

Lys Val Thr His Gln Ala Glu Ser Asn Leu Tyr Met Lys Ala Val Arg
                325                 330                 335

Ala Thr Leu Ile Leu Val Pro Leu Leu Gly Ile Glu Phe Val Leu Phe
            340                 345                 350

Pro Trp Arg Pro Glu Gly Lys Val Ala Glu Val Tyr Asp Tyr Val
            355                 360                 365

Met His Ile Leu Met His Tyr Gln Gly Leu Leu Val Ser Thr Ile Phe
370                 375                 380

Cys Phe Phe Asn Gly Glu Val Gln Ala Ile Leu Arg Arg Asn Trp Asn
385                 390                 395                 400

Gln Tyr Lys Ile Gln Phe Gly Asn Gly Phe Ser His Ser Asp Ala Leu
                405                 410                 415

Arg Ser Ala Ser Tyr Thr Val Ser Thr Ile Ser Asp Val Gln Gly Tyr
            420                 425                 430

Ser His Asp Cys Pro Thr Glu His Leu Asn Gly Lys Ser Ile Gln Asp
            435                 440                 445

Ile Glu Asn Val Ala Leu Lys Pro Glu Lys Met Tyr Asp Leu Val Met
450                 455                 460

<210> SEQ ID NO 221
<211> LENGTH: 461
<212> TYPE: PRT
<213> ORGANISM: Macaca fascicularis

<400> SEQUENCE: 221

-continued

```
Met Glu Lys Lys Cys Thr Leu Tyr Phe Leu Val Leu Leu Pro Phe Phe
1               5                   10                  15

Met Ile Phe Val Thr Ala Glu Leu Glu Glu Ser Pro Glu Asp Ser Ile
            20                  25                  30

Gln Leu Gly Val Thr Arg Asn Lys Ile Met Thr Ala Gln Tyr Glu Cys
        35                  40                  45

Tyr Gln Lys Ile Met Gln Asp Pro Ile Gln Gln Ala Glu Gly Val Tyr
    50                  55                  60

Cys Asn Arg Thr Trp Asp Gly Trp Leu Cys Trp Asn Asn Val Ala Ala
65                  70                  75                  80

Gly Thr Glu Ser Met Gln Leu Cys Pro Asp Tyr Phe Gln Asp Phe Asp
                85                  90                  95

Pro Ser Glu Lys Val Thr Lys Ile Cys Asp Gln Asp Gly Asn Trp Phe
            100                 105                 110

Arg His Pro Ala Ser Asn Arg Thr Trp Thr Asn Tyr Thr Gln Cys Asn
            115                 120                 125

Val Asn Thr His Glu Lys Val Lys Thr Ala Leu Asn Leu Phe Tyr Leu
        130                 135                 140

Thr Ile Ile Gly His Gly Leu Ser Ile Ala Ser Leu Leu Ile Ser Leu
145                 150                 155                 160

Gly Ile Phe Phe Tyr Phe Lys Ser Leu Ser Cys Gln Arg Ile Thr Leu
                165                 170                 175

His Lys Asn Leu Phe Phe Ser Phe Val Cys Asn Ser Val Val Thr Ile
            180                 185                 190

Ile His Leu Thr Ala Val Ala Asn Asn Gln Ala Leu Val Ala Thr Asn
        195                 200                 205

Pro Val Ser Cys Lys Val Ser Gln Phe Ile His Leu Tyr Leu Met Gly
            210                 215                 220

Cys Asn Tyr Phe Trp Met Leu Cys Glu Gly Ile Tyr Leu His Thr Leu
225                 230                 235                 240

Ile Val Val Ala Val Phe Ala Glu Lys Gln His Leu Met Trp Tyr Tyr
                245                 250                 255

Phe Leu Gly Trp Gly Phe Pro Leu Ile Pro Ala Cys Ile His Ala Ile
            260                 265                 270

Ala Arg Ser Leu Tyr Tyr Asn Asp Asn Cys Trp Ile Ser Ser Asp Thr
        275                 280                 285

His Leu Leu Tyr Ile Ile His Gly Pro Ile Cys Ala Ala Leu Leu Val
    290                 295                 300

Asn Leu Phe Phe Leu Leu Asn Ile Val Arg Val Leu Ile Thr Lys Leu
305                 310                 315                 320

Lys Val Thr His Gln Ala Glu Ser Asn Leu Tyr Met Lys Ala Val Arg
                325                 330                 335

Ala Thr Leu Ile Leu Val Pro Leu Leu Gly Ile Glu Phe Val Leu Ile
            340                 345                 350

Pro Trp Arg Pro Glu Gly Lys Ile Ala Glu Val Tyr Asp Tyr Ile
        355                 360                 365

Met His Ile Leu Met His Phe Gln Gly Leu Leu Val Ser Thr Ile Phe
    370                 375                 380

Cys Phe Phe Asn Gly Glu Val Gln Ala Ile Leu Arg Arg Asn Trp Asn
385                 390                 395                 400

Gln Tyr Lys Ile Gln Phe Gly Asn Ser Phe Ser Asn Ser Glu Ala Leu
                405                 410                 415

Arg Ser Ala Ser Tyr Thr Val Ser Thr Ile Ser Asp Gly Pro Gly Tyr
```

```
                420                 425                 430
Ser His Asp Cys Pro Ser Glu His Leu Asn Gly Lys Ser Ile His Asp
                435                 440                 445

Ile Glu Asn Val Val Leu Lys Pro Glu Asn Leu Tyr Asn
        450                 455                 460

<210> SEQ ID NO 222
<211> LENGTH: 461
<212> TYPE: PRT
<213> ORGANISM: Macaca mulatta

<400> SEQUENCE: 222

Met Glu Lys Lys Cys Thr Leu Tyr Phe Leu Val Leu Leu Pro Phe Phe
1               5                   10                  15

Met Ile Phe Val Thr Ala Glu Leu Glu Glu Ser Pro Glu Asp Ser Ile
            20                  25                  30

Gln Leu Gly Val Thr Arg Asn Lys Ile Met Thr Ala Gln Tyr Glu Cys
        35                  40                  45

Tyr Gln Lys Ile Met Gln Asp Pro Ile Gln Gln Ala Glu Gly Val Tyr
    50                  55                  60

Cys Asn Arg Thr Trp Asp Gly Trp Leu Cys Trp Asn Asn Val Ala Ala
65                  70                  75                  80

Gly Thr Glu Ser Met Gln Leu Cys Pro Asp Tyr Phe Gln Asp Phe Asp
                85                  90                  95

Pro Ser Glu Lys Val Thr Lys Ile Cys Asp Gln Asp Gly Asn Trp Phe
            100                 105                 110

Arg His Pro Ala Ser Asn Arg Thr Trp Thr Asn Tyr Thr Gln Cys Asn
        115                 120                 125

Val Asn Thr His Glu Lys Val Lys Thr Ala Leu Asn Leu Phe Tyr Leu
    130                 135                 140

Thr Ile Ile Gly His Gly Leu Ser Ile Ala Ser Leu Leu Ile Ser Leu
145                 150                 155                 160

Gly Ile Phe Phe Tyr Phe Lys Ser Leu Ser Cys Gln Arg Ile Thr Leu
                165                 170                 175

His Lys Asn Leu Phe Phe Ser Phe Val Cys Asn Ser Val Val Thr Ile
            180                 185                 190

Ile His Leu Thr Ala Val Ala Asn Asn Gln Ala Leu Val Ala Thr Asn
        195                 200                 205

Pro Val Ser Cys Lys Val Ser Gln Phe Ile His Leu Tyr Leu Met Gly
    210                 215                 220

Cys Asn Tyr Phe Trp Met Leu Cys Glu Gly Ile Tyr Leu His Thr Leu
225                 230                 235                 240

Ile Val Val Ala Val Phe Ala Glu Lys Gln His Leu Met Trp Tyr Tyr
                245                 250                 255

Phe Leu Gly Trp Gly Phe Pro Leu Ile Pro Ala Cys Ile His Ala Ile
            260                 265                 270

Ala Arg Ser Leu Tyr Tyr Asn Asp Asn Cys Trp Ile Ser Ser Asp Thr
        275                 280                 285

His Leu Leu Tyr Ile Ile His Gly Pro Ile Cys Ala Ala Leu Leu Val
    290                 295                 300

Asn Leu Phe Phe Leu Leu Asn Ile Val Arg Val Leu Ile Thr Lys Leu
305                 310                 315                 320

Lys Val Thr His Gln Ala Glu Ser Asn Leu Tyr Met Lys Ala Val Arg
                325                 330                 335
```

```
Ala Thr Leu Ile Leu Val Pro Leu Leu Gly Ile Glu Phe Val Leu Ile
            340                 345                 350

Pro Trp Arg Pro Glu Gly Lys Ile Ala Glu Glu Val Tyr Asp Tyr Ile
        355                 360                 365

Met His Ile Leu Met His Phe Gln Gly Leu Leu Val Ser Thr Ile Phe
    370                 375                 380

Cys Phe Phe Asn Gly Glu Val Gln Ala Ile Leu Arg Arg Asn Trp Asn
385                 390                 395                 400

Gln Tyr Lys Ile Gln Phe Gly Asn Ser Phe Ser Asn Ser Glu Ala Leu
                405                 410                 415

Arg Ser Ala Ser Tyr Thr Val Ser Thr Ile Ser Asp Gly Pro Gly Tyr
            420                 425                 430

Ser His Asp Cys Pro Ser Glu His Leu Asn Gly Lys Ser Ile His Asp
        435                 440                 445

Ile Glu Asn Val Val Leu Lys Pro Glu Asn Leu Tyr Asn
    450                 455                 460

<210> SEQ ID NO 223
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Met Glu Lys Lys Cys Thr Leu Tyr Phe Leu Val Leu Pro Phe Phe
1               5                   10                  15

Met Ile Leu Val Thr Ala Glu Ser Glu Glu Gly Ala Asn Gln Thr Asp
            20                  25                  30

Leu Gly Val Thr Arg Asn Lys Ile Met Thr Ala Gln Tyr Glu Cys Tyr
        35                  40                  45

Gln Lys Ile Met Gln Asp Pro Ile Gln Gln Ala Glu Gly Val Tyr Cys
    50                  55                  60

Asn Arg Thr Trp Asp Gly Trp Leu Cys Trp Asn Asp Val Ala Ala Gly
65                  70                  75                  80

Thr Glu Ser Met Gln Leu Cys Pro Asp Tyr Phe Gln Asp Phe Asp Pro
            85                  90                  95

Ser Glu Lys Val Thr Lys Ile Cys Asp Gln Asp Gly Asn Trp Phe Arg
        100                 105                 110

His Pro Ala Ser Asn Arg Thr Trp Thr Asn Tyr Thr Gln Cys Asn Val
    115                 120                 125

Asn Thr His Glu Lys Val Lys Thr Ala Leu Asn Leu Phe Tyr Leu Thr
130                 135                 140

Ile Ile Gly His Gly Leu Ser Ile Ala Ser Leu Leu Ile Ser Leu Gly
145                 150                 155                 160

Ile Phe Phe Tyr Phe Lys Ser Leu Ser Cys Gln Arg Ile Thr Leu His
            165                 170                 175

Lys Asn Leu Phe Phe Ser Phe Val Cys Asn Ser Val Val Thr Ile Ile
        180                 185                 190

His Leu Thr Ala Val Ala Asn Asn Gln Ala Leu Val Ala Thr Asn Pro
    195                 200                 205

Val Ser Cys Lys Val Ser Gln Phe Ile His Leu Tyr Leu Met Gly Cys
210                 215                 220

Asn Tyr Phe Trp Met Leu Cys Glu Gly Ile Tyr Leu His Thr Leu Ile
225                 230                 235                 240
```

Val Val Ala Val Phe Ala Glu Lys Gln His Leu Met Trp Tyr Tyr Phe
            245                 250                 255

Leu Gly Trp Gly Phe Pro Leu Ile Pro Ala Cys Ile His Ala Ile Ala
        260                 265                 270

Arg Ser Leu Tyr Tyr Asn Asp Asn Cys Trp Ile Ser Ser Asp Thr His
        275                 280                 285

Leu Leu Tyr Ile Ile His Gly Pro Ile Cys Ala Ala Leu Leu Val Asn
        290                 295                 300

Leu Phe Phe Leu Leu Asn Ile Val Arg Val Leu Ile Thr Lys Leu Lys
305                 310                 315                 320

Val Thr His Gln Ala Glu Ser Asn Leu Tyr Met Lys Ala Val Arg Ala
            325                 330                 335

Thr Leu Ile Leu Val Pro Leu Leu Gly Ile Glu Phe Val Leu Ile Pro
            340                 345                 350

Trp Arg Pro Glu Gly Lys Ile Ala Glu Glu Val Tyr Asp Tyr Ile Met
        355                 360                 365

His Ile Leu Met His Phe Gln Gly Leu Leu Val Ser Thr Ile Phe Cys
        370                 375                 380

Phe Phe Asn Gly Glu Val Gln Ala Ile Leu Arg Arg Asn Trp Asn Gln
385                 390                 395                 400

Tyr Lys Ile Gln Phe Gly Asn Ser Phe Ser Asn Ser Glu Ala Leu Arg
            405                 410                 415

Ser Ala Ser Tyr Thr Val Ser Thr Ile Ser Asp Gly Pro Gly Tyr Ser
            420                 425                 430

His Asp Cys Pro Ser Glu His Leu Asn Gly Lys Ser Ile His Asp Ile
            435                 440                 445

Glu Asn Val Leu Leu Lys Pro Glu Asn Leu Tyr Asn
450                 455                 460

<210> SEQ ID NO 224
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224
atggacatga gggtgcccgc tcagctcctg gggctcctgc tgctgtggct gagaggtgcg    60
cgctgtcagt ctgtgttgac gcagccgccc tcagtgtctg aggccccagg acagaaggtc   120
accatctcct gctctggaag cagctccaac attgggaata attatgtatc ctggtaccag   180
cagctcccag gaacagcccc caaactcctc atttatgaca ataataagcg accctcaggg   240
attcctgacc gattctctgg ctccaagtct ggcacgtcag ccaccctggg catcaccgga   300
ctccagactg gggacgaggc cgattattac tgcggaacat gggatagccg cctgagtgct   360
gtggttttcg gcggagggac caagctgacc gtcctaggtc agcccaaggc caaccccact   420
gtcactctgt tcccgccctc ctctgaggag ctccaagcca caaggccac actagtgtgt   480 ctgatcagtg acttctaccc gggagctgtg acagtggcct ggaaggcaga tggcagcccc   540
gtcaaggcgg gagtggagac caccaaaccc tccaaacaga gcaacaacaa gtacgcggcc   600
agcagctacc tgagcctgac gcccgagcag tggaagtccc acagaagcta cagctgccag   660
gtcacgcatg aagggagcac cgtggagaag acagtggccc ctacagaatg ttca         714

```
<210> SEQ ID NO 225
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225
atggacatga gggtgcccgc tcagctcctg gggctcctgc tgctgtggct gagaggtgcg      60
cgctgtcagt ctgtgctgac tcagccaccc tcagcgtctg gaccccccgg gcagagagtc     120
accatctctt gttctggaag cagctccaac atcggcagta attatgtata ctggtaccag     180
cagctcccag gagcggcccc caaactcctc atctttagga gtaatcagcg gccctcaggg     240
gtccctgacc gattctctgg ctccaagtct ggcacctcag cctccctggc catcagtggg     300
ctccggtccg aggatgaggc tgattattac tgtgcagcat gggatgacag cctgagtggt     360
tgggtgttcg gcggagggac caagctgacc gtcctaggtc agcccaaggc caacccccact    420 gtcactctgt tcccgccctc ctctgaggag ctccaagcca caaggccac actagtgtgt      480 ctgatcagtg acttctaccc gggagctgtg acagtggcct ggaaggcaga tggcagcccc    540
gtcaaggcgg gagtggagac caccaaaccc tccaaacaga gcaacaacaa gtacgcggcc    600
agcagctacc tgagcctgac gcccgagcag tggaagtccc acagaagcta cagctgccag    660
gtcacgcatg aagggagcac cgtggagaag acagtggccc ctacagaatg ttca          714

<210> SEQ ID NO 226
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226
atggacatga gggtgcccgc tcagctcctg gggctcctgc tgctgtggct gagaggtgcg      60
cgctgtgaca tccagatgac ccagtctcca tcctccctgt ctgcatctgt aggagacaga    120
gtcaccatca cttgccgggc aagtcagggc attagaaatg atttaggctg gtttcagcag    180
aaaccaggga aagcccctaa gcgcctgatc tatgctgcat ccagtttgca aagtggggtc    240
ccatcaaggt tcagcggcag tggatctggg acagaattca ctctcacaat cagcagcctg    300
cagcctgaag attttagcaac ttattactgt ctacagtata atatttaccc gtggacgttc    360
ggccaaggga ccaaggtgga aatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                 708

<210> SEQ ID NO 227
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
```

```
atggacatga gggtgcccgc tcagctcctg gggctcctgc tgctgtggct gagaggtgcg    60
cgctgttctt ctgagctgac tcaggaccct actgtgtctg tggccttggg acagacagtc   120
aaaatcacat gccaaggaga cagcctcaga agtttttatg caagctggta ccagcagaag   180
ccaggacagg cccctgtact tgtcttctat ggtaaaaaca accggccctc agggatccca   240
gaccgattct ctggctccag ctcaggaaac acagcttcct tgaccatcac tgggctcag    300 gcggaagatg aggctgacta ttattgtaat tcccgggaca gcagtgttta ccatctggta   360
ctcggcggag ggaccaagct gaccgtccta ggtcagccca aggccaaccc cactgtcact   420
ctgttcccgc cctcctctga ggagctcaa gccaacaagg ccacactagt gtgtctgatc    480
agtgacttct acccgggagc tgtgacagtg gcctggaagg cagatggcag ccccgtcaag   540
gcgggagtgg agaccaccaa accctccaaa cagagcaaca caagtacgc ggccagcagc    600 tacctgagcc tgacgcccga gcagtggaag tcccacagaa gctacagctg ccaggtcacg   660
catgaaggga gcaccgtgga gaagacagtg gcccctacag aatgttca               708
```

<210> SEQ ID NO 228
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 228

```
atggacatga gggtgcccgc tcagctcctg gggctcctgc tgctgtggct gagaggtgcg    60
cgctgtgata ttatactggc ccagactcca ctttctctgt ccgtcacccc tggacagccg   120
gcctccatct cctgcaagtc tagtcagagc ctcctgcaca gtgctggaaa gacctatttg   180
tattggtacc tgcagaagcc aggccagcct ccacagctcc tgatctatga gtttccaac    240 cggttctctg gagtgccaga taggttcagt ggcagcgggt cagggacaga tttcacactg   300
aaaatcagcc gggtggaggc tgaggatgtt gggatttatt actgcatgca agtttttccg   360
cttccgctca ctttcggcgg agggaccaag gtggagatca aacgtacggt ggctgcacca   420
tctgtcttca tcttcccgcc atctgatgag cagttgaaat ctggaactgc ctctgttgtg   480
tgcctgctga ataacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgt                                                                 723
```

<210> SEQ ID NO 229
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 229

```
atggacatga gggtgcccgc tcagctcctg gggctcctgc tgctgtggct gagaggtgcg    60
cgctgtcagt ctgtgttgac gcagccgccc tcagtgtctg cggccccagg acagaaggtc   120
accatctcct gctctggaag cagctccaac attgggaata attatgtatc ctggtaccag   180
```

| | |
|---|---|
| cagctcccag gaacagcccc caaactcctc atttatgaca ataataagcg accctcaggg | 240 |
| attcctgacc gattctctgg ctccaagtct ggcacgtcaa ccaccctggg catcaccgga | 300 |
| ctccagactg gggacgaggc cgattattac tgcggaacat gggatagccg cctgagtgct | 360 |
| gtggttttcg gcggagggac caagctgacc gtcctaggtc agcccaaggc caacccccact | 420 |
| gtcactctgt tcccgccctc ctctgaggag ctccaagcca acaaggccac actagtgtgt | 480 |
| ctgatcagtg acttctaccc gggagctgtg acagtggcct ggaaggcaga tggcagcccc | 540 |
| gtcaaggcgg gagtggagac caccaaaccc tccaaacaga gcaacaacaa gtacgcggcc | 600 |
| agcagctacc tgagcctgac gcccgagcag tggaagtccc acagaagcta cagctgccag | 660 |
| gtcacgcatg aagggagcac cgtggagaag acagtggccc ctacagaatg ttca | 714 |

<210> SEQ ID NO 230
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230

| | |
|---|---|
| atggacatga gggtgcccgc tcagctcctg ggctcctgc tgctgtggct gagaggtgcg | 60 |
| cgctgtgata ttgtgatgac tcagtctcca ctctccctgc ccgtcacccc tggagagccg | 120 |
| gcctccatct cctgcaggtc tagtcagagc ctcctgcata gttttgggta caactatttg | 180 |
| gattggtacc tgcagaagcc agggcagtct ccacagctcc tgatctattt gggttctaat | 240 |
| cgggcctccg ggtccctga caggttcagt ggcagtggat caggcacaga ttttacactg | 300 |
| aaaatcagca gagtggaggc tgaggatgtt ggggtttatt actgcatgca agctctacaa | 360 |
| actccattca ctttcggccc tgggaccaaa gtggatatca aacgtacggt ggctgcacca | 420 |
| tctgtcttca tcttcccgcc atctgatgag cagttgaaat ctggaactgc ctctgttgtg | 480 |
| tgcctgctga ataacttcta tcccagagag gccaaagtac agtggaaggt ggataacgcc | 540 |
| ctccaatcgg gtaactccca ggagagtgtc acagagcagg acagcaagga cagcacctac | 600 |
| agcctcagca gcaccctgac gctgagcaaa gcagactacg agaaacacaa agtctacgcc | 660 |
| tgcgaagtca cccatcaggg cctgagctcg cccgtcacaa agagcttcaa caggggagag | 720 |
| tgt | 723 |

<210> SEQ ID NO 231
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231

| | |
|---|---|
| atggacatga gggtgcccgc tcagctcctg ggctcctgc tgctgtggct gagaggtgcg | 60 |
| cgctgtgata ttattctgac ccagactcca ctttctctgt ccgtcacccc tggacagccg | 120 |
| gcctccatct cctgcaagtc tagtcagagc ctcctgcaca gtgatggaaa gacctatttg | 180 |
| tattggtacc tgcagaagcc cggccagcct ccacagctcc tgatctatga agtttccaac | 240 |
| cggttctctg gagagccaga taggttcagt ggcagcgggt cagggacaga tttcacactg | 300 |
| aaaatcagcc gggtggaggc tgaggatgtt ggactttatt attgcatgca aagttttccg | 360 |
| cttccgctca ctttcggcgg agggaccaag gtggagatca aacgtacggt ggctgcacca | 420 |

```
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgt                                                                  723
```

<210> SEQ ID NO 232
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232

```
atggacatga gggtgcccgc tcagctcctg gggctcctgc tgctgtggct gagaggtgcg     60
cgctgtcagt ctgtgttgac gcagccgccc tcagtgtctg cggccccagg acagaaggtc    120
accatctcct gctctggaag cagctccaac attgggaata attatgtatc ctggtaccag    180
cagttcccag gaacagcccc caaactcctc atttatgaca ataataagcg ccctcaggg    240 attcctgacc gattctctgg ctccaagtct ggcacgtcag ccaccctggg catcaccgga    300
ctccagactg gggacgaggc cgattattac tgcggaacat gggatagccg cctgagtgct    360
gtggttttcg gcggagggac caagctgacc gtcctaggtc agcccaaggc caacccact    420 gtcactctgt tcccgccctc ctctgaggag ctccaagcca caaggccac actagtgtgt    480 ctgatcagtg acttctaccc gggagctgtg acagtggcct ggaaggcaga tggcagcccc    540
gtcaaggcgg gagtggagac caccaaaccc tccaaacaga gcaacaacaa gtacgcggcc    600
agcagctacc tgagcctgac gcccgagcag tggaagtccc acagaagcta cagctgccag    660
gtcacgcatg aagggagcac cgtggagaag acagtggccc ctacagaatg ttca         714
```

<210> SEQ ID NO 233
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233

```
atggacatga gggtgcccgc tcagctcctg gggctcctgc tgctgtggct gagaggtgcg     60
cgctgtcagt ctgtgctgac tcagtcaccc tcagcgtctg gaccccccgg gcagagagtc    120
accatctctt gttctggaag cagctccaac atcggcagta attatgtata ctggtaccag    180
cagctcccag gagcggcccc caaactcctc atccttagga ataatcagcg gccctcaggg    240
gtccctgacc gattctctgg ctccaagtct ggcacctcag cctccctgac catcagtggg    300
ctccggtccg aggatgaggc tgactattat tgtgcagcat gggatgacag cctgagtggt    360
tgggtgttcg gcggagggac caagctgacc gtcctaggtc agcccaaggc caacccact    420 gtcactctgt tcccgccctc ctctgaggag ctccaagcca caaggccac actagtgtgt    480 ctgatcagtg acttctaccc gggagctgtg acagtggcct ggaaggcaga tggcagcccc    540
gtcaaggcgg gagtggagac caccaaaccc tccaaacaga gcaacaacaa gtacgcggcc    600
```

```
agcagctacc tgagcctgac gcccgagcag tggaagtccc acagaagcta cagctgccag      660
gtcacgcatg aagggagcac cgtggagaag acagtggccc ctacagaatg ttca            714
```

<210> SEQ ID NO 234
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 234

```
atggacatga gggtgcccgc tcagctcctg gggctcctgc tgctgtggct gagaggtgcg      60
cgctgtcagt ctgtgctgac tcagccaccc tcagcgtctg gaccccccgg cagagggtc      120 accatctctt gttctggaag cagttccaat atcggaagta atactgtgaa ctggtaccag     180
cagctcccag gaacggcccc caaactcctc atctatacta ataatcagcg gccctcaggg     240
gtccctgacc gattctctgg ctccaagtct ggcacctcag cctccctggc catcagtgga     300
ctccagtctg aggatgaggc tgattttac tgtgcagcgc gggatgagag cctgaatggt     360
gtggtattcg gcggagggac caagctgacc gtcctaggtc agcccaaggc caacccccact    420 gtcactctgt tcccgccctc ctctgaggag ctccaagcca acaaggccac actagtgtgt    480
ctgatcagtg acttctaccc gggagctgtg acagtggcct ggaaggcaga tggcagcccc    540
gtcaaggcgg gagtggagac caccaaaccc tccaaacaga gcaacaacaa gtacgcggcc   600
agcagctacc tgagcctgac gcccgagcag tggaagtccc acagaagcta cagctgccag    660
gtcacgcatg aagggagcac cgtggagaag acagtggccc ctacagaatg ttca          714
```

<210> SEQ ID NO 235
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 235

```
atggacatga gggtgcccgc tcagctcctg gggctcctgc tgctgtggct gagaggtgcg      60
cgctgtcagt ctgtgctgac tcagccaccc tcagcgtctg gaccccccgg cagagagtc     120 accatctctt gttctggaag cagctccaac atcggcagta attatgtata ctggtaccag     180
cagctcccag gagcggcccc caaactcctc atctttagga ataatcagcg gccctcaggg    240
gtccctgacc gcttctctgg ctccaagtct ggcacctcag cctccctggc catcagtggg    300
ctccggtccg aggatgaggc tgattattac tgtgcagcat gggatgacag cctgagtggt   360
tgggtgttcg gcggagggac caagctgacc gtcctaggtc agcccaaggc caacccccact   420 gtcactctgt tcccgccctc ctctgaggag ctccaagcca acaaggccac actagtgtgt   480
ctgatcagtg acttctaccc gggagctgtg acagtggcct ggaaggcaga tggcagcccc   540
gtcaaggcgg gagtggagac caccaaaccc tccaaacaga gcaacaacaa gtacgcggcc   600
agcagctacc tgagcctgac gcccgagcag tggaagtccc acagaagcta cagctgccag    660
gtcacgcatg aagggagcac cgtggagaag acagtggccc ctacagaatg ttca          714
```

<210> SEQ ID NO 236
<211> LENGTH: 714
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 236

| | | | | | |
|---|---|---|---|---|---|
| atggacatga | gggtgcccgc | tcagctcctg | gggctcctgc | tgctgtggct gagaggtgcg | 60 |
| cgctgtcagt | ctgtgctgac | tcagccaccc | tcagcgtctg | ggaccccgg gcagagagtc | 120 |
| accatctctt | gttctggaag | cagctccaac | atcggcagta | attatgtata ctggtaccag | 180 |
| cagctcccag | gagcggcccc | caaactcctc | atctttagga | ataatcagcg gccctcaggg | 240 |
| gtccctgacc | gcttctctgg | ctccaagtct | ggcacctcag | cctccctggc catcagtggg | 300 |
| ctccggtccg | aggatgaggc | tgattattac | tgtgcagcat | gggatgacag cctgagtggt | 360 |
| tgggtgttcg | gcggagggac | caagctgacc | gtcctaggtc | agcccaaggc caacccccact | 420 |
| gtcactctgt | tcccgccctc | ctctgaggag | ctccaagcca | caaggccac actagtgtgt | 480 |
| ctgatcagtg | acttctaccc | gggagctgtg | acagtggcct | ggaaggcaga tggcagcccc | 540 |
| gtcaaggcgg | gagtggagac | caccaaaccc | tccaaacaga | gcaacaacaa gtacgcggcc | 600 |
| agcagctacc | tgagcctgac | gcccgagcag | tggaagtccc | acagaagcta cagctgccag | 660 |
| gtcacgcatg | aagggagcac | cgtggagaag | acagtggccc | ctacagaatg ttca | 714 |

<210> SEQ ID NO 237
<211> LENGTH: 723
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 237

| | | | | | |
|---|---|---|---|---|---|
| atggacatga | gggtgcccgc | tcagctcctg | gggctcctgc | tgctgtggct gagaggtgcg | 60 |
| cgctgtgata | ttacactgac | ccagactcca | ctttctctgt | ccgtctcccc tggacagccg | 120 |
| gcctccatct | cctgcaagtc | tagtcagagc | ctcctgcaca | gtgatggaag gaactatctg | 180 |
| tattggtacc | tgcagaagcc | aggccagcct | ccacagctcc | tgatctatga agtgtccaac | 240 |
| cggttctctg | gactgccaga | taggttcagt | ggcagcgggt | cagggacaga tttcacactg | 300 |
| aaaatcagcc | gggtggaggc | tgaggatgtt | gggatttatt | actgcatgca aagttttccg | 360 |
| cttccgctca | ctttcggcgg | agggaccaag | gtggagatca | aacgtacggt ggctgcacca | 420 |
| tctgtcttca | tcttcccgcc | atctgatgag | cagttgaaat | ctggaactgc ctctgttgtg | 480 |
| tgcctgctga | ataacttcta | tcccagagag | gccaaagtac | agtggaaggt ggataacgcc | 540 |
| ctccaatcgg | gtaactccca | ggagagtgtc | acagagcagg | acagcaagga cagcacctac | 600 |
| agcctcagca | gcaccctgac | gctgagcaaa | gcagactacg | agaaacacaa agtctacgcc | 660 |
| tgcgaagtca | cccatcaggg | cctgagctcg | cccgtcacaa | agagcttcaa caggggagag | 720 |
| tgt | | | | | 723 |

<210> SEQ ID NO 238
<211> LENGTH: 714
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 238

| | | | | | |
|---|---|---|---|---|---|
| atggacatga | gggtgcccgc | tcagctcctg | gggctcctgc | tgctgtggct gagaggtgcg | 60 |

```
cgctgtcagt ctgtgttgac gcagccgccc tcagtgtctg cggccccagg acagaaggtc    120
accatctcct gctctggaag cagctccaac attgggaata attatgtatc ctggtaccag    180
cagctcccag gaacagcccc caaactcctc atttatgaca ataataagcg accctcaggg    240
attcctgacc gattctctgg ctccaagtct ggcacgtcag ccaccctggg catcaccgga    300
ctccagactg gggacgaggc cgattattac tgcggaacat gggatagccg cctgagtgct    360
gtggttttcg gcggagggac caagctgacc gtcctaggtc agcccaaggc caaccccact    420
gtcactctgt tcccgccctc ctctgaggag ctccaagcca acaaggccac actagtgtgt    480
ctgatcagtg acttctaccc gggagctgtg acagtggcct ggaaggcaga tggcagcccc    540
gtcaaggcgg gagtggagac caccaaaccc tccaaacaga gcaacaacaa gtacgcggcc    600
agcagctacc tgagcctgac gcccgagcag tggaagtccc acagaagcta cagctgccag    660
gtcacgcatg aagggagcac cgtggagaag acagtggccc ctacagaatg ttca          714

<210> SEQ ID NO 239
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239
atggacatga gggtgcccgc tcagctcctg gggctcctgc tgctgtggct gagaggtgcg     60
cgctgtgaca tccagatgac ccagtctcca tcctccctgt ctgcatctgt aggagacaga    120
gtcaccatca cttgccgggc aagtcagggc attagaaagg atttaggctg gtatcagcag    180
aaaccaggga aagcccctaa gcgcctgatc tatggagcat ccagtttgca aagtggggtc    240
ccatcaaggt tcagcggcag tggatctggg acagaattca ctctcacaat cagcagcctg    300
cagcctgaag attttgcaac ttattactgt ctacagtata tagtttttcccc gtggacgttc    360 ggccaaggga ccaaggtgga aatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                  708

<210> SEQ ID NO 240
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 240
atggaaaccc cagctcagct tctcttcctc ctgctactct ggctcccaga taccaccgga     60
gaaattgtgt tgacgcagtc tccaggcacc ctgtctttgt ctccagggga aagagccacc    120
ctctcctgca gggccagtca gagtgttagc agcggctact taacctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
```

```
cctgaagatt ttgcagtgta ttactgtcag cagtatggta actcactgtg caggtttggc    360
caggggacca agctggagat caaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgt                    705
```

<210> SEQ ID NO 241
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241

```
atggaaaccc cagctcagct tctcttcctc ctgctactct ggctcccaga taccaccgga     60
gaaattgtgt tgacgcagtc tccaggcacc ctgtctttgt ctccagggga aagagccacc    120
ctctcctgca gggccagtca gagtgttagc agcggctact aacctggta ccagcagaaa    180 cctggccagg ctcccagact cctcatctat ggtgcatcca gcagggccac tggcatccca    240
gacaggttca gtggcagtgg gtctgggacg gacttcactc tcaccatcag cagactggag    300
cctgaagatt ttgcagtgta ttactgtcag cagtatggta actcactgag caggtttggc    360
caggggacca agctggagat caaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgt                    705
```

<210> SEQ ID NO 242
<211> LENGTH: 1434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 242

```
atggacatga gggtgcccgc tcagctcctg gggctcctgc tgctgtggct gagaggtgcg     60
cgctgtcagg tgcagctggt ggaatctggg ggaggcgtgg tccagcctgg gaggtccctg    120
agactctcct gtgcagcctc tggattcacc ttcagtagct ttggcatgca ctgggtccgc    180
caggctccag gcaaggggct ggagtgggtg gcagttatat catttgatgg aagtattaag    240
tattctgtag actccgtgaa gggccgattc accatctcca gagacaattc aaagaacacg    300
ctgtttctgc aaatgaacag cctgcgagcc gaggacacgg ctgtgtatta ctgtgcgaga    360
gatcggctca attactatga tagtagtggt tattatcact acaaatacta cggtatggcc    420
gtctggggcc aagggaccac ggtcaccgtc tctagtgcct ccaccaaggg cccatcggtc    480
ttccccctgg cgccctgctc caggagcacc tccgagagca gcggccct gggctgcctg    540 gtcaaggact acttccccga accggtgacg gtgtcgtgga actcaggcgc tctgaccagc    600
```

```
ggcgtgcaca ccttcccagc tgtcctacag tcctcaggac tctactccct cagcagcgtg      660
gtgaccgtgc cctccagcaa cttcggcacc cagacctaca cctgcaacgt agatcacaag      720
cccagcaaca ccaaggtgga caagacagtt gagcgcaaat gttgtgtcga gtgcccaccg      780
tgcccagcac cacctgtggc aggaccgtca gtcttcctct tccccccaaa acccaaggac      840
accctcatga tctcccggac ccctgaggtc acgtgcgtgg tggtggacgt gagccacgaa      900
gaccccgagg tccagttcaa ctggtacgtg gacggcgtgg aggtgcataa tgccaagaca      960
aagccacggg aggagcagtt caacagcacg ttccgtgtgg tcagcgtcct caccgttgtg     1020
caccaggact ggctgaacgg caaggagtac aagtgcaagg tctccaacaa aggcctccca     1080
gcccccatcg agaaaaccat ctccaaaacc aaagggcagc ccgagaacc acaggtgtac      1140 accctgcccc catcccggga ggagatgacc aagaaccagg tcagcctgac ctgcctggtc     1200
aaaggcttct accccagcga catcgccgtg gagtgggaga gcaatgggca gccggagaac     1260
aactacaaga ccacacctcc catgctggac tccgacggct ccttcttcct ctacagcaag     1320
ctcaccgtgg acaagagcag gtggcagcag gggaacgtct tctcatgctc cgtgatgcat     1380
gaggctctgc acaaccacta cacgcagaag agcctctccc tgtctccggg taaa           1434
```

<210> SEQ ID NO 243
<211> LENGTH: 1437
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 243

```
atggacatga gggtgcccgc tcagctcctg gggctcctgc tgctgtggct gagaggtgcg       60
cgctgtgagg tgcagctggt ggagtctggg ggaggcttgg taaagcctgg ggggtccctt      120
agactctcct gtgcagcctc tggattcact ttcagtaacg cctggatgag ctgggtccgc      180
caggctccag ggaaggggct ggagtgggtt ggccgtatta aagcacaac tgatggtggg       240 acaacagact acgctgcacc cgtgaaaggc agattcacca tctcaagaga tgattcaaaa      300
aacacgctgt atctgcaaat gaacagcctg aaaaccgagg acacagccgt gtattactgt      360
accacagatc ggaccggata tagcatcagc tggtctagtt actactacta ctacggtatg      420
gacgtctggg gccaagggac cacggtcacc gtctctagtg cctccaccaa gggcccatcg      480
gtcttccccc tggcgccctg ctccaggagc acctccgaga gcacagcggc cctgggctgc      540
ctggtcaagg actacttccc cgaaccggtg acggtgtcgt ggaactcagg cgctctgacc      600
agcggcgtgc acaccttccc agctgtccta cagtcctcag gactctactc cctcagcagc      660
gtggtgaccg tgccctccag caacttcggc acccagacct acacctgcaa cgtagatcac      720
aagcccagca caccaaggt ggacaagaca gttgagcgca atgttgtgt cgagtgccca        780 ccgtgcccag caccacctgt ggcaggaccg tcagtcttcc tcttcccccc aaaacccaag      840
gacaccctca tgatctcccg gacccctgag gtcacgtgcg tggtggtgga cgtgagccac      900
gaagaccccg aggtccagtt caactggtac gtggacggcg tggaggtgca taatgccaag      960
acaaagccac gggaggagca gttcaacagc acgttccgtg tggtcagcgt cctcaccgtt     1020
gtgcaccagg actggctgaa cggcaaggag tacaagtgca aggtctccaa caaaggcctc     1080
ccagccccca tcgagaaaac catctccaaa accaaagggc agcccgaga ccacaggtgt      1140 acaccctgc ccccatcccg ggaggagatg accaagaacc aggtcagcct gacctgcctg      1200
```

```
gtcaaaggct tctaccccag cgacatcgcc gtggagtggg agagcaatgg gcagccggag    1260
aacaactaca agaccacacc tcccatgctg gactccgacg gctccttctt cctctacagc    1320
aagctcaccg tggacaagag caggtggcag caggggaacg tcttctcatg ctccgtgatg    1380
catgaggctc tgcacaacca ctacacgcag aagagcctct ccctgtctcc gggtaaa      1437
```

<210> SEQ ID NO 244
<211> LENGTH: 1434
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 244

```
atggacatga gggtgcccgc tcagctcctg gggctcctgc tgctgtggct gagaggtgcg     60
cgctgtgagg tgcagctatt ggagtctggg ggaggcttgg tacagcctgg ggagtccctg    120
agactctcct gtgcagcctc tgggttcacc tttagcagct atgccatgag ctgggtccgc    180
caggctccag gaaggggct ggagtgggtc tcagctatta gtggtagtgg tggtcgcaca    240
tactacgcag actccgtgaa gggccggttc accatctcca gagacaattc caagaacacg    300
ctgtatctgc aaatgaatag cctgagagcc gaggacacgg ccgtatatta ctgtgcgaaa    360
gatcaaaggg aggtagggcc gtatagcagt ggctggtacg actactacta cggtatggac    420
gtctggggcc aagggaccac ggtcaccgtc tctagtgcct ccaccaaggg cccatcggtc    480
ttccccctgg cgccctgctc caggagcacc tccgagagca cagcggccct gggctgcctg    540
gtcaaggact acttccccga accggtgacg gtgtcgtgga actcaggcgc tctgaccagc    600
ggcgtgcaca ccttcccagc tgtcctacag tcctcaggac tctactccct cagcagcgtg    660
gtgaccgtgc cctccagcaa cttcggcacc cagacctaca cctgcaacgt agatcacaag    720
cccagcaaca ccaaggtgga caagacagtt gagcgcaaat gttgtgtcga gtgcccaccg    780
tgcccagcac cacctgtggc aggaccgtca gtcttcctct tccccccaaa acccaaggac    840
accctcatga tctcccggac ccctgaggtc acgtgcgtgg tggtggacgt gagccacgaa    900
gaccccgagg tccagttcaa ctggtacgtg gacggcgtgg aggtgcataa tgccaagaca    960
aagccacggg aggagcagtt caacagcacg ttccgtgtgg tcagcgtcct caccgttgtg   1020
caccaggact ggctgaacgg caaggagtac aagtgcaagg tctccaacaa aggcctccca   1080
gcccccatcg agaaaaccat ctccaaaacc aaagggcagc cccgagaacc acaggtgtac   1140
accctgcccc catcccggga ggagatgacc aagaaccagg tcagcctgac ctgcctggtc   1200
aaaggcttct accccagcga catcgccgtg gagtgggaga gcaatgggca gccggagaac   1260
aactacaaga ccacacctcc catgctggac tccgacggct ccttcttcct ctacagcaag   1320
ctcaccgtgg acaagagcag gtggcagcag gggaacgtct tctcatgctc cgtgatgcat   1380
gaggctctgc acaaccacta cacgcagaag agcctctccc tgtctccggg taaa         1434
```

<210> SEQ ID NO 245
<211> LENGTH: 1434
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 245

```
atggacatga gggtgcccgc tcagctcctg gggctcctgc tgctgtggct gagaggtgcg      60
cgctgtcagg tgcagttggt gcagtctggg gctgaggtga agaagcctgg ggcctcagtg     120
aaggtctcct gcaaggcttc tggatacacc ttcaccggct actatatgca ctgggtgcga     180
caggcccctg gacaagggct tgagtggatg ggatggatca accctaacag tggtggcaca     240
aactatgcac agaagtttca gggcagggtc accatgacca gggacacgtc catcagcaca     300
gcctacatgg agctgagcag gctgagatct gacgacacgg ccgtgtattt ctgtgcgaga     360
gatcaaatga gtattattat gcttcgggga gttttttccc cttactatta cggtatggac     420
gtctggggcc aagggaccac ggtcaccgtc tctagtgcct ccaccaaggg cccatcggtc     480
ttccccctgg cgccctgctc caggagcacc tccgagagca gcggccctg  ggctgcctg     540 gtcaaggact acttccccga accggtgacg gtgtcgtgga actcaggcgc tctgaccagc     600
ggcgtgcaca ccttcccagc tgtcctacag tcctcaggac tctactccct cagcagcgtg     660
gtgaccgtgc cctccagcaa cttcggcacc cagacctaca cctgcaacgt agatcacaag     720
cccagcaaca ccaaggtgga caagacagtt gagcgcaaat gttgtgtcga gtgcccaccg     780
tgcccagcac cacctgtggc aggaccgtca gtcttcctct tccccccaaa acccaaggac     840
accctcatga tctcccggac ccctgaggtc acgtgcgtgg tggtggacgt gagccacgaa     900
gaccccgagg tccagttcaa ctggtacgtg gacggcgtgg aggtgcataa tgccaagaca     960
aagccacggg aggagcagtt caacagcacg ttccgtgtgg tcagcgtcct caccgttgtg    1020
caccaggact ggctgaacgg caaggagtac aagtgcaagg tctccaacaa aggcctccca    1080
gcccccatcg agaaaaccat ctccaaaacc aaagggcagc cccgagaacc acaggtgtac    1140
accctgcccc catcccggga ggagatgacc aagaaccagg tcagcctgac ctgcctggtc    1200
aaaggcttct accccagcga catcgccgtg gagtgggaga gcaatgggca gccggagaac    1260
aactacaaga ccacacctcc catgctggac tccgacggct ccttcttcct ctacagcaag    1320
ctcaccgtgg acaagagcag gtggcagcag gggaacgtct tctcatgctc cgtgatgcat    1380
gaggctctgc acaaccacta cacgcagaag agcctctccc tgtctccggg taaa          1434
```

<210> SEQ ID NO 246
<211> LENGTH: 1431
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 246

```
atggacatga gggtgcccgc tcagctcctg gggctcctgc tgctgtggct gagaggtgcg      60
cgctgtcagg tgcagctggt ggagtctggg ggaggcgtgg tccagcctgg gaggtccctg     120
agactctcct gtgcagcctc tggattcacc ttcagtagct atggcatgca ctgggtccgc     180
caggctccag gcaaggggct ggagtgggtg gcagttattt catatgatgg aagtcatgaa     240
tcctatgcag actccgtgaa gggccgattc accatctcca gagacatttc caagaacacg     300
ctgtatctgc aaatgaacag cctgagagct gaggacacgg ctgtgtattt ctgtgcgaga     360
gagaggaaac gggttacgat gtctaccttg tattactact tctactacgg tatggacgtc     420
tggggccaag ggaccacggt caccgtctct agtgcctcca ccaagggccc atcggtcttc     480
cccctggcgc cctgctccag gagcacctcc gagagcacag cggccctggg ctgcctggtc     540
aaggactact tccccgaacc ggtgacggtg tcgtggaact caggcgctct gaccagcggc     600
```

```
gtgcacacct tcccagctgt cctacagtcc tcaggactct actccctcag cagcgtggtg      660
accgtgccct ccagcaactt cggcacccag acctacacct gcaacgtaga tcacaagccc      720
agcaacacca aggtggacaa gacagttgag cgcaaatgtt gtgtcgagtg cccaccgtgc      780
ccagcaccac ctgtggcagg accgtcagtc ttcctcttcc ccccaaaacc caaggacacc      840
ctcatgatct cccggacccc tgaggtcacg tgcgtggtgg tggacgtgag ccacgaagac      900
cccgaggtcc agttcaactg gtacgtggac ggcgtggagg tgcataatgc caagacaaag      960
ccacgggagg agcagttcaa cagcacgttc cgtgtggtca gcgtcctcac cgttgtgcac     1020
caggactggc tgaacggcaa ggagtacaag tgcaaggtct ccaacaaagg cctcccagcc     1080
cccatcgaga aaaccatctc caaaaccaaa gggcagcccc gagaaccaca ggtgtacacc     1140
ctgcccccat cccgggagga gatgaccaag aaccaggtca gcctgacctg cctggtcaaa     1200
ggcttctacc ccagcgacat cgccgtggag tgggagagca atgggcagcc ggagaacaac     1260
tacaagacca cacctcccat gctggactcc gacggctcct tcttcctcta cagcaagctc     1320
accgtggaca gagcaggtg gcagcagggg aacgtcttct catgctccgt gatgcatgag     1380
gctctgcaca accactacac gcagaagagc ctctccctgt ctccgggtaa a              1431
```

<210> SEQ ID NO 247
<211> LENGTH: 1434
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 247

```
atggacatga gggtgcccgc tcagctcctg gggctcctgc tgctgtggct gagaggtgcg       60
cgctgtcagg tgcagctggt ggaatctggg ggaggcgtgg tccagcctgg aggtccctg      120 agactctcct gtgcagcctc tggattcacc ttcagtagct ttggcatgca ctgggtccgc      180
caggctccag gcaaggggct ggagtgggtg gcagttatat catttgatgg aagtattaag      240
tattctgtag actccgtgaa gggccgattc accatctcca gagacaattc aaagaacacg      300
ctgtttctgc aaatgaacag cctgcgagcc gaggacacgg ctgtgtatta ctgtgcgaga      360
gatcggctca attactatga tagtagtggt tattatcact acaaatacta cggtatggcc      420
gtctggggcc aagggaccac ggtcaccgtc tctagtgcct ccaccaaggg cccatcggtc      480
ttccccctgg cgccctgctc caggagcacc tccgagagca gcggccct gggctgcctg       540 gtcaaggact acttccccga accggtgacg gtgtcgtgga actcaggcgc tctgaccagc      600
ggcgtgcaca ccttcccagc tgtcctacag tcctcaggac tctactccct cagcagcgtg      660
gtgaccgtgc cctccagcaa cttcggcacc cagacctaca cctgcaacgt agatcacaag      720
cccagcaaca ccaaggtgga caagacagtt gagcgcaaat gttgtgtcga gtgcccaccg      780
tgcccagcac cacctgtggc aggaccgtca gtcttcctct tccccccaaa acccaaggac      840
accctcatga tctcccggac ccctgaggtc acgtgcgtgg tggtggacgt gagccacgaa      900
gaccccgagg tccagttcaa ctggtacgtg gacggcgtgg aggtgcataa tgccaagaca      960
aagccacggg aggagcagtt caacagcacg ttccgtgtgg tcagcgtcct caccgttgtg     1020
caccaggact ggctgaacgg caaggagtac aagtgcaagg tctccaacaa aggcctccca     1080
gcccccatcg agaaaaccat ctccaaaacc aaagggcagc cccgagaacc acaggtgtac     1140
accctgcccc catcccggga ggagatgacc aagaaccagg tcagcctgac ctgcctggtc     1200
```

```
aaaggcttct accccagcga catcgccgtg gagtgggaga gcaatgggca gccggagaac    1260
aactacaaga ccacacctcc catgctggac tccgacggct ccttcttcct ctacagcaag    1320
ctcaccgtgg acaagagcag gtggcagcag gggaacgtct tctcatgctc cgtgatgcat    1380
gaggctctgc acaaccacta cacgcagaag agcctctccc tgtctccggg taaa          1434

<210> SEQ ID NO 248
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248
atggacatga gggtgcccgc tcagctcctg gggctcctgc tgctgtggct gagaggtgcg      60
cgctgtgagg tgcagctggt ggagtctggg ggaggcttgg taaagccagg cggtccctg     120 agactctcct gtacagcttc tggattcacc tttggtgatt atgctatgag ctggttccgc    180
caggctccag ggaaggggct ggagtggata ggtttcatta agcagagc ttatggtggg      240 acaccagaat acgccgcgtc tgtgaaaggc agattcacca tctcaagaga tgattccaaa    300
accatcgcct atctgcaaat gaacagcctg aaaaccgagg acacagccgt gtatttctgt    360
gctagaggac ggggtattgc agctcgttgg gactactggg gccagggaac cctggtcacc    420
gtctctagtg cctccaccaa gggcccatcg gtcttccccc tggcgccctg ctccaggagc    480
acctccgaga gcacagcggc cctgggctgc ctggtcaagg actacttccc cgaaccggtg    540
acggtgtcgt ggaactcagg cgctctgacc agcggcgtgc acaccttccc agctgtccta    600
cagtcctcag gactctactc cctcagcagc gtggtgaccg tgccctccag caacttcggc    660
acccagacct acacctgcaa cgtagatcac aagcccagca caccaaggt ggacaagaca     720 gttgagcgca aatgttgtgt cgagtgccca ccgtgcccag caccacctgt ggcaggaccg    780
tcagtcttcc tcttcccccc aaaacccaag gacaccctca tgatctcccg gacccctgag    840
gtcacgtgcg tggtggtgga cgtgagccac gaagacccccg aggtccagtt caactggtac    900
gtggacggcg tggaggtgca taatgccaag acaaagccac gggaggagca gttcaacagc    960
acgttccgtg tggtcagcgt cctcaccgtt gtgcaccagg actggctgaa cggcaaggag   1020
tacaagtgca aggtctccaa caaaggcctc ccagccccca tcgagaaaac catctccaaa   1080
accaaagggc agccccgaga accacaggtg tacaccctgc cccatcccg ggaggagatg    1140 accaagaacc aggtcagcct gacctgcctg gtcaaaggct tctacccag cgacatcgcc    1200 gtggagtggg agagcaatgg gcagccggag aacaactaca agaccacacc tcccatgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaa                                        1407

<210> SEQ ID NO 249
<211> LENGTH: 1431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
atggacatga gggtgcccgc tcagctcctg gggctcctgc tgctgtggct gagaggtgcg      60
```

```
cgctgtcagg tgcagctggt ggagtctggg ggaggcgtgg tccagcctgg gaggtccctg    120
agactctcct gtgcagcctc tggattcacc ttcagtagct atggcatgca ctgggtccgc    180
caggctccag gcaaggggct ggagtgggtg gcagttattt catatgatgg aagtcatgaa    240
tcctatgcag actccgtgaa gggccgattc accatctcca gagacatttc aagaacacg     300 ctgtatctgc aaatgaacag cctgagagct gaggacacgg ctgtgtattt ctgtgcgaga    360
gagaggaaac gggttacgat gtctaccttta tattactact tctactacgg tatggacgtc    420
tggggccaag ggaccacggt caccgtctct agtgcctcca ccaagggccc atcggtcttc    480
cccctggcgc cctgctccag gagcacctcc gagagcacag cggccctggg ctgcctggtc    540
aaggactact ccccgaacc ggtgacggtg tcgtggaact caggcgctct gaccagcggc     600
gtgcacacct tcccagctgt cctacagtcc tcaggactct actccctcag cagcgtggtg    660
accgtgccct ccagcaactt cggcacccag acctacacct gcaacgtaga tcacaagccc    720
agcaacacca aggtggacaa gacagttgag cgcaaatgtt gtgtcgagtg cccaccgtgc    780
ccagcaccac ctgtggcagg accgtcagtc ttcctcttcc ccccaaaacc caaggacacc    840
ctcatgatct cccggacccc tgaggtcacg tgcgtggtgg tggacgtgag ccacgaagac    900
cccgaggtcc agttcaactg gtacgtggac ggcgtggagg tgcataatgc caagacaaag    960
ccacgggagg agcagttcaa cagcacgttc cgtgtggtca gcgtcctcac cgttgtgcac   1020
caggactggc tgaacggcaa ggagtacaag tgcaaggtct ccaacaaagg cctcccagcc   1080
cccatcgaga aaaccatctc caaaaccaaa gggcagcccc gagaaccaca ggtgtacacc   1140
ctgcccccat cccgggagga gatgaccaag aaccaggtca gcctgacctg cctggtcaaa   1200
ggcttctacc ccagcgacat cgccgtggag tgggagagca atgggcagcc ggagaacaac   1260
tacaagacca cacctcccat gctggactcc gacggctcct tcttcctcta cagcaagctc   1320
accgtggaca gagcaggtg gcagcagggg aacgtcttct catgctccgt gatgcatgag   1380
gctctgcaca accactacac gcagaagagc ctctccctgt ctccgggtaa a            1431
```

<210> SEQ ID NO 250
<211> LENGTH: 1434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250

```
atggacatga gggtgcccgc tcagctcctg gggctcctgc tgctgtggct gagaggtgcg     60
cgctgtcagg tgcagctggt ggaatctggg ggaggcgtgg tccagcctgg gaggtccctg    120
agactctcct gtgcagcctc tggattcacc ttcagtagct ttggcatgca ctgggtccgc    180
caggctccag gcaaggggct ggagtgggtg gcagttatat catttgatgg aagtattaag    240
tattctgtag actccgtgaa gggccgattc accatctcca gagacaattc aaagaacacg    300
ctgtttctgc aaatgaacag cctgcgagcc gaggacacgg ctgtgtatta ctgtgcgaga    360
gatcggctca attactatga tagtagtggt tattatcact acaaatacta cggtatggcc    420
gtctggggcc aagggaccac ggtcaccgtc tctagtgcct ccaccaaggg cccatcggtc    480
ttccccctgg cgccctgctc caggagcacc tccgagagca cagcggccct gggctgcctg    540
gtcaaggact acttccccga accggtgacg gtgtcgtgga actcaggcgc tctgaccagc    600
ggcgtgcaca ccttcccagc tgtcctacag tcctcaggac tctactccct cagcagcgtg    660
```

```
gtgaccgtgc cctccagcaa cttcggcacc cagacctaca cctgcaacgt agatcacaag      720
cccagcaaca ccaaggtgga caagacagtt gagcgcaaat gttgtgtcga gtgcccaccg      780
tgcccagcac cacctgtggc aggaccgtca gtcttcctct tccccccaaa acccaaggac      840
accctcatga tctcccggac ccctgaggtc acgtgcgtgg tggtggacgt gagccacgaa      900
gaccccgagg tccagttcaa ctggtacgtg gacggcgtgg aggtgcataa tgccaagaca      960
aagccacggg aggagcagtt caacagcacg ttccgtgtgg tcagcgtcct caccgttgtg     1020
caccaggact ggctgaacgg caaggagtac aagtgcaagg tctccaacaa aggcctccca     1080
gcccccatcg agaaaaccat ctccaaaacc aagggcagc cccgagaacc acaggtgtac      1140
accctgcccc catcccggga ggagatgacc aagaaccagg tcagcctgac ctgcctggtc     1200
aaaggcttct accccagcga catcgccgtg gagtgggaga gcaatgggca gccggagaac     1260
aactacaaga ccacacctcc catgctggac tccgacggct ccttcttcct ctacagcaag     1320
ctcaccgtgg acaagagcag gtggcagcag gggaacgtct tctcatgctc cgtgatgcat     1380
gaggctctgc acaaccacta cacgcagaag agcctctccc tgtctccggg taaa            1434
```

<210> SEQ ID NO 251
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251

```
atggacatga gggtgcccgc tcagctcctg gggctcctgc tgctgtggct gagaggtgcg       60
cgctgtgagg tgcagctggt ggagtctggg ggaggcttgg taaagcctgg ggggtccctt      120
agactctcct gtgcagcctc tggattcact ttcagtaacg cctggatgag ctgggtccgc      180
caggctccag ggaaggggct ggagtgggtt ggccgtatta aagcaaaac tgatggtggg       240 acaacagact acactgcacc cgtgaaaggc agattcacca tctcaagaga tgattcaaaa      300
aacacgctgt atctgcaaat gaatagcctg aaagccgagg acacagccgt gtattactgt      360
accacagatc ggaccgggta tagcatcagc tggtctagtt actactacta ctacggtatg      420
gacgtctggg gccaagggac cacggtcacc gtctctagtg cctccaccaa gggcccatcg      480
gtcttccccc tggcgccctg ctccaggagc acctccgaga gcacagcggc cctgggctgc     540
ctggtcaagg actacttccc cgaaccggtg acggtgtcgt ggaactcagg cgctctgacc     600
agcggcgtgc acaccttccc agctgtccta cagtcctcag gactctactc cctcagcagc    660
gtggtgaccg tgccctccag caacttcggc acccagacct acacctgcaa cgtagatcac    720
aagcccagca caccaaggt ggacaagaca gttgagcgca atgttgtgt cgagtgccca       780 ccgtgcccag caccacctgt ggcaggaccg tcagtcttcc tcttcccccc aaaacccaag    840
gacaccctca tgatctcccg gacccctgag gtcacgtgcg tggtggtgga cgtgagccac    900
gaagaccccg aggtccagtt caactggtac gtggacggcg tggaggtgca taatgccaag    960
acaaagccac gggaggagca gttcaacagc acgttccgtg tggtcagcgt cctcaccgtt    1020
gtgcaccagg actggctgaa cggcaaggag tacaagtgca aggtctccaa caaaggcctc   1080
ccagccccca tcgagaaaac catctccaaa accaagggc agccccgaga accacaggtg    1140
tacaccctgc ccccatcccg ggaggagatg accaagaacc aggtcagcct gacctgcctg   1200
gtcaaaggct tctaccccag cgacatcgcc gtggagtggg agagcaatgg gcagccggag   1260
```

```
aacaactaca agaccacacc tcccatgctg gactccgacg gctccttctt cctctacagc    1320
aagctcaccg tggacaagag caggtggcag caggggaacg tcttctcatg ctccgtgatg    1380
catgaggctc tgcacaacca ctacacgcag aagagcctct ccctgtctcc gggtaaa      1437
```

<210> SEQ ID NO 252
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252

```
atggacatga gggtgcccgc tcagctcctg gggctcctgc tgctgtggct gagaggtgcg    60
cgctgtcagg tgcagctggt gcagtctggg gctgaggtga agaagcctgg ggcctcagtg    120
aaggtctcct gcaaggcttc tggatacacc ttcaccgact actatatgta ctgggtgcga    180
caggcccctg gacaagggct tgagtggatg ggatggatca gccctaatag tggtggcaca    240
aactatgccc agaagtttca gggcagggtc accatgacca ggacacgtc tatcagcaca    300 gcctacatgg agctgagtag gctgagatct gacgacacgg ccgtgtatta ctgtgtgaga    360
ggaggatata gtggctacgc tgggctctac tcccactact acggtatgga cgtctggggc    420
caagggacca cggtcaccgt ctctagtgcc tccaccaagg gcccatcggt cttccccctg    480
gcgccctgct ccaggagcac ctccgagagc acagcggccc tgggctgcct ggtcaaggac    540
tacttccccg aaccggtgac ggtgtcgtgg aactcaggcg ctctgaccag cggcgtgcac    600
accttcccag ctgtcctaca gtcctcagga ctctactccc tcagcagcgt ggtgaccgtg    660
ccctccagca cttcggcac ccagacctac acctgcaacg tagatcacaa gcccagcaac    720
accaaggtgg acaagacagt tgagcgcaaa tgttgtgtcg agtgcccacc gtgcccagca    780
ccacctgtgg caggaccgtc agtcttcctc ttccccccaa aacccaagga caccctcatg    840
atctcccgga cccctgaggt cacgtgcgtg gtggtggacg tgagccacga agaccccgag    900
gtccagttca actggtacgt ggacggcgtg gaggtgcata atgccaagac aaagccacgg    960
gaggagcagt tcaacagcac gttccgtgtg gtcagcgtcc tcaccgttgt gcaccaggac    1020
tggctgaacg gcaaggagta caagtgcaag gtctccaaca aaggcctccc agcccccatc    1080
gagaaaacca tctccaaaac caaagggcag ccccgagaac cacaggtgta caccctgccc    1140
ccatcccggg aggagatgac caagaaccag gtcagcctga cctgcctggt caaaggcttc    1200
taccccagcg acatcgccgt ggagtgggag agcaatgggc agccggagaa caactacaag    1260
accacacctc ccatgctgga ctccgacggc tccttcttcc tctacagcaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaa                   1425
```

<210> SEQ ID NO 253
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253

```
atggacatga gggtgcccgc tcagctcctg gggctcctgc tgctgtggct gagaggtgcg    60
```

```
cgctgtgagg tacagctggt ggagtctggg ggaggcttgg taaagcctgg ggggtccctc    120
agactctcct gtgcagcctc tggattcact ttcggtaacg cctggatgag ctgggtccgc    180
caggctccag ggaaggggct ggagtgggtt ggccgtatta aaagcaaaac tgatggtggg    240
acaacagact acgctgcacc cgtgaaaggc agattcacca tctcaagaga tgattcaaaa    300
aacacgctgt atctgcaaat gaacagcctg aaaaccgagg acacagccgt gtatttctgt    360
accacagatc ggaccgggta tagcatcagc tggtctagtt actactacta ctacggtatg    420
gacgtctggg gccaagggac cacggtcacc gtctctagtg cctccaccaa gggcccatcg    480
gtcttccccc tggcgccctg ctccaggagc acctccgaga gcacagcggc cctgggctgc    540
ctggtcaagg actacttccc cgaaccggtg acggtgtcgt ggaactcagg cgctctgacc    600
agcggcgtgc acaccttccc agctgtccta cagtcctcag gactctactc cctcagcagc    660
gtggtgaccg tgcctccag caacttcggc acccagacct acacctgcaa cgtagatcac    720
aagcccagca caccaaggt ggacaagaca gttgagcgca aatgttgtgt cgagtgccca    780
ccgtgcccag caccacctgt ggcaggaccg tcagtcttcc tcttcccccc aaaacccaag    840
gacaccctca tgatctcccg gacccctgag gtcacgtgcg tggtggtgga cgtgagccac    900
gaagaccccg aggtccagtt caactggtac gtggacggcg tggaggtgca taatgccaag    960
acaaagccac gggaggagca gttcaacagc acgttccgtg tggtcagcgt cctcaccgtt   1020
gtgcaccagg actggctgaa cggcaaggag tacaagtgca aggtctccaa caaaggcctc   1080
ccagccccca tcgagaaaac catctccaaa accaaagggc agccccgaga accacaggtg   1140
tacaccctgc ccccatcccg ggaggagatg accaagaacc aggtcagcct gacctgcctg   1200
gtcaaaggct tctaccccag cgacatcgcc gtggagtggg agagcaatgg gcagccggag   1260
aacaactaca agaccacacc tcccatgctg gactccgacg gctccttctt cctctacagc   1320
aagctcaccg tggacaagag caggtggcag caggggaacg tcttctcatg ctccgtgatg   1380
catgaggctc tgcacaacca ctacacgcag aagagcctct ccctgtctcc gggtaaa    1437
```

<210> SEQ ID NO 254
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254

```
atggacatga gggtgcccgc tcagctcctg gggctcctgc tgctgtggct gagaggtgcg     60
cgctgtgagg tacagctggt ggagtctggg ggaggcttgg taaagcctgg ggggtccctt    120
agactctcct gtgcagcctc tggattcact ttcggtaacg cctggatgag ctgggtccgc    180
caggctccag ggaaggggct ggagtgggtt ggccgtatta aaagcaaaac tgatggtggg    240
acaacagact acgctgcacc cgtgaaaggc agattcacca tctcaagaga tgattcaaaa    300
aacacgctgt atctgcaaat gaacagcctg aaaaccgagg acacagccgt gtattactgt    360
accacagatc ggaccgggta tagcatcagc tggtctagtt actactacta ctacggtatg    420
gacgtctggg gccaagggac cacggtcacc gtctctagtg cctccaccaa gggcccatcg    480
gtcttccccc tggcgccctg ctccaggagc acctccgaga gcacagcggc cctgggctgc    540
ctggtcaagg actacttccc cgaaccggtg acggtgtcgt ggaactcagg cgctctgacc    600
agcggcgtgc acaccttccc agctgtccta cagtcctcag gactctactc cctcagcagc    660
```

| | |
|---|---|
| gtggtgaccg tgccctccag caacttcggc acccagacct acacctgcaa cgtagatcac | 720 |
| aagcccagca acaccaaggt ggacaagaca gttgagcgca aatgttgtgt cgagtgccca | 780 |
| ccgtgcccag caccacctgt ggcaggaccg tcagtcttcc tcttcccccc aaaacccaag | 840 |
| gacaccctca tgatctcccg gacccctgag gtcacgtgcg tggtggtgga cgtgagccac | 900 |
| gaagacccccg aggtccagtt caactggtac gtggacggcg tggaggtgca taatgccaag | 960 |
| acaaagccac gggaggagca gttcaacagc acgttccgtg tggtcagcgt cctcaccgtt | 1020 |
| gtgcaccagg actggctgaa cggcaaggag tacaagtgca aggtctccaa caaaggcctc | 1080 |
| ccagccccca tcgagaaaac catctccaaa accaaagggc agccccgaga accacaggtg | 1140 |
| tacaccctgc cccatcccg ggaggagatg accaagaacc aggtcagcct gacctgcctg | 1200 |
| gtcaaaggct tctaccccag cgacatcgcc gtggagtggg agagcaatgg gcagccggag | 1260 |
| aacaactaca agaccacacc tcccatgctg gactccgacg gctccttctt cctctacagc | 1320 |
| aagctcaccg tggacaagag caggtggcag caggggaacg tcttctcatg ctccgtgatg | 1380 |
| catgaggctc tgcacaacca ctacacgcag aagagcctct ccctgtctcc gggtaaa | 1437 |

<210> SEQ ID NO 255
<211> LENGTH: 1431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255

| | |
|---|---|
| atggacatga gggtgcccgc tcagctcctg gggctcctgc tgctgtggct gagaggtgcg | 60 |
| cgctgtcagg tgcagctggt ggagtctggg ggaggcgtgg tccagcctgg gaggtccctg | 120 |
| agactctcct gtgcagcctc tggattcacc ttcagtagct atggcatgca ctgggtccgc | 180 |
| caggctccag gcaaggggct ggagtgggtg gcagttattt catatgatgg aagtcatgaa | 240 |
| tcctatgcag actccgtgaa gggccgattc accatctcca gagacatttc caagaacacg | 300 |
| ctgtatctgc aaatgaacag cctgagagct gaggacacgg ctgtgtattt ctgtgcgaga | 360 |
| gagaggaaac gggttacgat gtctacctta tattactact tctactacgg tatggacgtc | 420 |
| tggggccaag ggaccacggt caccgtctct agtgcctcca ccaagggccc atcggtcttc | 480 |
| cccctggcgc cctgctccag gagcacctcc gagagcacag cggccctggg ctgcctggtc | 540 |
| aaggactact tccccgaacc ggtgacggtg tcgtggaact caggcgctct gaccagcggc | 600 |
| gtgcacacct tcccagctgt cctacagtcc tcaggactct actccctcag cagcgtggtg | 660 |
| accgtgccct ccagcaactt cggcacccag acctacacct gcaacgtaga tcacaagccc | 720 |
| agcaacacca aggtggacaa gacagttgag cgcaaatgtt gtgtcgagtg cccaccgtgc | 780 |
| ccagcaccac tgtggcagg accgtcagtc ttcctcttcc cccaaaaccc aaggacacc | 840 |
| ctcatgatct cccggacccc tgaggtcacg tgcgtggtgg tggacgtgag ccacgaagac | 900 |
| cccgaggtcc agttcaactg gtacgtggac ggcgtggagg tgcataatgc caagacaaag | 960 |
| ccacgggagg agcagttcaa cagcacgttc cgtgtggtca gcgtcctcac cgttgtgcac | 1020 |
| caggactggc tgaacggcaa ggagtacaag tgcaaggtct ccaacaaagg cctcccagcc | 1080 |
| cccatcgaga aaccatctc caaaaccaaa gggcagcccc gagaaccaca ggtgtacacc | 1140 |
| ctgcccccat cccgggagga gatgaccaag aaccaggtca gcctgacctg cctggtcaaa | 1200 |
| ggcttctacc ccagcgacat cgccgtggag tgggagagca atgggcagcc ggagaacaac | 1260 |

```
tacaagacca cacctcccat gctggactcc gacggctcct tcttcctcta cagcaagctc    1320
accgtggaca agagcaggtg gcagcagggg aacgtcttct catgctccgt gatgcatgag    1380
gctctgcaca accactacac gcagaagagc ctctccctgt ctccgggtaa a             1431
```

<210> SEQ ID NO 256
<211> LENGTH: 1434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256

```
atggacatga gggtgcccgc tcagctcctg gggctcctgc tgctgtggct gagaggtgcg     60
cgctgtcagg tgcagctggt ggaatctggg ggaggcgtgg tccagcctgg gaggtccctg    120
agactctcct gtgcagcctc tggattcacc ttcagtagct ttggcatgca ttgggtccgc    180
caggctccag gcaaggggct ggagtgggtg gcagttatat catttgatgg aagtattaag    240
tactctgtag actccgtgaa gggccgattc accatctcca gagacaattc aaagaacacg    300
ctgtttctgc aaatgaacag cctgcgagcc gaggacacgg ctgtgtatta ctgtgcgaga    360
gatcggctca attactatga tagtagtggt tattatcact acaaatacta cggtctggcc    420
gtctggggcc aagggaccac ggtcaccgtc tctagtgcct ccaccaaggg cccatcggtc    480
ttccccctgg cgccctgctc caggagcacc tccgagagca gcggccct gggctgcctg     540 gtcaaggact acttccccga accggtgacg gtgtcgtgga actcaggcgc tctgaccagc    600
ggcgtgcaca ccttcccagc tgtcctacag tcctcaggac tctactccct cagcagcgtg    660
gtgaccgtgc cctccagcaa cttcggcacc cagacctaca cctgcaacgt agatcacaag    720
cccagcaaca ccaaggtgga agacagtt gagcgcaaat gttgtgtcga gtgcccaccg     780
tgcccagcac cacctgtggc aggaccgtca gtcttcctct tccccccaaa acccaaggac    840
accctcatga tctcccggac ccctgaggtc acgtgcgtgg tggtggacgt gagccacgaa    900
gaccccgagg tccagttcaa ctggtacgtg gacggcgtgg aggtgcataa tgccaagaca    960
aagccacggg aggagcagtt caacagcacg ttccgtgtgg tcagcgtcct caccgttgtg   1020
caccaggact ggctgaacgg caaggagtac aagtgcaagg tctccaacaa aggcctccca   1080
gcccccatcg agaaaaccat ctccaaaacc aaagggcagc ccgagaacc acaggtgtac    1140 accctgcccc catcccggga ggagatgacc aagaaccagg tcagcctgac ctgcctggtc   1200
aaaggcttct accccagcga catcgccgtg gagtgggaga gcaatgggca gccggagaac   1260
aactacaaga ccacacctcc catgctggac tccgacggct ccttcttcct ctacagcaag   1320
ctcaccgtgg acaagagcag gtggcagcag gggaacgtct tctcatgctc cgtgatgcat   1380
gaggctctgc acaaccacta cacgcagaag agcctctccc tgtctccggg taaa         1434
```

<210> SEQ ID NO 257
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257

```
atggacatga gggtgcccgc tcagctcctg gggctcctgc tgctgtggct gagaggtgcg     60
cgctgtgagg tgcagctggt ggagtctggg ggaggcctgg tcaagcctgg ggggtccctg    120
```

| | |
|---|---|
| agactctcct gtgcagcctc tggatacacc ttcagtacct atagcatgaa ctgggtccgc | 180 |
| caggctccag ggaaggggct ggagtgggtc tcatccatta gtagtagtag tagttacaga | 240 |
| tattacgcag actcagtgaa gggccgattc accatctcca gagacaacgc caagaactca | 300 |
| ctgtatctgc aaatgagtag cctgagagcc gaggacacgg ctgtgtatta ctgtgcgaga | 360 |
| gaagggtgt ctggcagttc gccgtatagc atcagctggt acgactacta ttacggtatg | 420 |
| gacgtctggg gccaagggac cacggtcacc gtctctagtg cctccaccaa gggcccatcg | 480 |
| gtcttccccc tggcgccctg ctccaggagc acctccgaga gcacagcggc cctgggctgc | 540 |
| ctggtcaagg actacttccc cgaaccggtg acggtgtcgt ggaactcagg cgctctgacc | 600 |
| agcggcgtgc acaccttccc agctgtccta cagtcctcag gactctactc cctcagcagc | 660 |
| gtggtgaccg tgccctccag caacttcggc acccagacct acacctgcaa cgtagatcac | 720 |
| aagcccagca acaccaaggt ggacaagaca gttgagcgca aatgttgtgt cgagtgccca | 780 |
| ccgtgcccag caccacctgt ggcaggaccg tcagtcttcc tcttcccccc aaaacccaag | 840 |
| gacaccctca tgatctcccg gacccctgag gtcacgtgcg tggtggtgga cgtgagccac | 900 |
| gaagacccg aggtccagtt caactggtac gtggacggcg tggaggtgca taatgccaag | 960 |
| acaaagccac gggaggagca gttcaacagc acgttccgtg tggtcagcgt cctcaccgtt | 1020 |
| gtgcaccagg actggctgaa cggcaaggag tacaagtgca aggtctccaa caaaggcctc | 1080 |
| ccagccccca tcgagaaaac catctccaaa accaaagggc agccccgaga accacaggtg | 1140 |
| tacaccctgc cccatcccg ggaggagatg accaagaacc aggtcagcct gacctgcctg | 1200 |
| gtcaaaggct tctaccccag cgacatcgcc gtggagtggg agagcaatgg gcagccggag | 1260 |
| aacaactaca agaccacacc tcccatgctg gactccgacg gctccttctt cctctacagc | 1320 |
| aagctcaccg tggacaagag caggtggcag caggggaacg tcttctcatg ctccgtgatg | 1380 |
| catgaggctc tgcacaacca ctacacgcag aagagcctct ccctgtctcc gggtaaa | 1437 |

<210> SEQ ID NO 258
<211> LENGTH: 1422
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 258

| | |
|---|---|
| atggacatga gggtgcccgc tcagctcctg gggctcctgc tgctgtggct gagaggtgcg | 60 |
| cgctgtcagg tgcagctggt ggagtctggg ggaggcgtgg tccagcctgg gaggtccctg | 120 |
| agactctcct gtgcagcgtc tggattcacc ttcagtagct atggcatgca ctgggtccgc | 180 |
| caggctccag gcaaggggct ggagtgggtg gcagttatat ggtatgatgg aagtaataaa | 240 |
| tactatgcag actccgtgaa gggccgattc atcatctcca gagataaatc caagaacacg | 300 |
| ctgtatctgc aaatgaacag cctgagagcc gaggacacgg ctgtgtatta ctgtgcgaga | 360 |
| gcgggggta tagcagcagc tggcctctac tactactacg gtatggacgt ctggggccaa | 420 |
| gggaccacgg tcaccgtctc tagtgcctcc accaagggcc catcggtctt ccccctggcg | 480 |
| ccctgctcca ggagcacctc cgagagcaca gcggccctgg gctgcctggt caaggactac | 540 |
| ttccccgaac cggtgacggt gtcgtggaac tcaggcgctc tgaccagcgg cgtgcacacc | 600 |
| ttcccagctg tcctacagtc ctcaggactc tactccctca gcagcgtggt gaccgtgccc | 660 |
| tccagcaact tcggcaccca gacctacacc tgcaacgtag atcacaagcc cagcaacacc | 720 |

```
aaggtggaca agacagttga gcgcaaatgt tgtgtcgagt gcccaccgtg cccagcacca      780
cctgtggcag gaccgtcagt cttcctcttc cccccaaaac ccaaggacac cctcatgatc      840
tcccggaccc ctgaggtcac gtgcgtggtg gtggacgtga gccacgaaga ccccgaggtc      900
cagttcaact ggtacgtgga cggcgtggag gtgcataatg ccaagacaaa gccacggggag     960 gagcagttca acagcacgtt ccgtgtggtc agcgtcctca ccgttgtgca ccaggactgg     1020
ctgaacggca aggagtacaa gtgcaaggtc tccaacaaag gcctcccagc ccccatcgag     1080
aaaaccatct ccaaaaccaa agggcagccc cgagaaccac aggtgtacac cctgccccca     1140
tcccgggagg agatgaccaa gaaccaggtc agcctgacct gcctggtcaa aggcttctac     1200
cccagcgaca tcgccgtgga gtgggagagc aatgggcagc cggagaacaa ctacaagacc     1260
acacctccca tgctggactc cgacggctcc ttcttcctct acagcaagct caccgtggac     1320
aagagcaggt ggcagcaggg gaacgtcttc tcatgctccg tgatgcatga ggctctgcac     1380
aaccactaca cgcagaagag cctctccctg tctccgggta aa                         1422
```

<210> SEQ ID NO 259
<211> LENGTH: 981
<212> TYPE: DNA
<213> ORGANISM: Homo sapiens

<400> SEQUENCE: 259

```
gctagcacca agggcccatc ggtcttcccc ctggcgccct gctccaggag cacctccgag       60
agcacagcgg ccctgggctg cctggtcaag gactacttcc ccgaaccggt gacggtgtcg      120
tggaactcag gcgctctgac cagcggcgtg cacaccttcc cagctgtcct acagtcctca      180
ggactctact ccctcagcag cgtggtgacc gtgccctcca gcaacttcgg cacccagacc      240
tacacctgca acgtagatca caagcccagc aacaccaagg tggacaagac agttgagcgc      300
aaatgttgtg tcgagtgccc accgtgccca gcaccacctg tggcaggacc gtcagtcttc      360
ctcttccccc caaaacccaa ggacaccctc atgatctccc ggacccctga ggtcacgtgc      420
gtggtggtgg acgtgagcca cgaagacccc gaggtccagt tcaactggta cgtggacggc      480
gtggaggtgc ataatgccaa gacaaagcca cgggaggagc agttcaacag cacgttccgt      540
gtggtcagcg tcctcaccgt tgtgcaccag gactggctga acggcaagga gtacaagtgc      600
aaggtctcca acaaaggcct cccagccccc atcgagaaaa ccatctccaa aaccaagggg      660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac tcccatgct ggactccgac       840 ggctccttct cctctacag caagctcacc gtggacaaga gcaggtggca gcaggggaac       900
gtcttctcat gctccgtgat gcatgaggct ctgcacaacc actacacgca gaagagcctc      960
tccctgtctc cgggtaaatg a                                                 981
```

<210> SEQ ID NO 260
<211> LENGTH: 324
<212> TYPE: DNA
<213> ORGANISM: Homo sapiens

<400> SEQUENCE: 260

```
cgtacggtgg ctgcaccatc tgtcttcatc ttcccgccat ctgatgagca gttgaaatct       60
ggaactgcct ctgttgtgtg cctgctgaat aacttctatc ccagagaggc caaagtacag      120
```

```
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg ttag                                             324

<210> SEQ ID NO 261
<211> LENGTH: 321
<212> TYPE: DNA
<213> ORGANISM: Homo sapiens

<400> SEQUENCE: 261
ggtcagccca aggccaaccc cactgtcact ctgttcccgc cctcctctga ggagctccaa       60
gccaacaagg ccacactagt gtgtctgatc agtgacttct acccgggagc tgtgacagtg      120
gcctggaagg cagatggcag ccccgtcaag gcgggagtgg agaccaccaa acctccaaa      180 cagagcaaca acaagtacgc ggccagcagc tacctgagcc tgacgcccga gcagtggaag      240
tcccacagaa gctacagctg ccaggtcacg catgaaggga gcaccgtgga gaagacagtg      300
gcccctacag aatgttcata g                                                321
```

HUMAN CGRP RECEPTOR BINDING PROTEINS

CROSS-REFERENCE TO RELATED APPLICATIONS

The present application claims benefit of priority to U.S. Ser. No. 61/203,569, filed 23 Dec. 2008 and U.S. Ser. No. 61/264,622, filed 25 Nov. 2009.

BACKGROUND

The instant application contains a Sequence Listing which has been submitted via EFS-Web and is hereby incorporated by reference in its entirety. Said ASCII copy, created on Dec. 14, 2009, is named A14720US.txt, and is 293,258 bytes in size The calcitonin superfamily of peptides includes at least five known members: calcitonin, amylin, adrenomedullin, and two calcitonin gene-related peptides ("CGRP"), CGRP1 (also known as ctCGRP, or CGRP) and CGRP2 (also known as βCGRP). CGRP is a 37 amino acid vasoactive neuropeptide expressed in both the central and peripheral nervous systems, and has been shown to be a potent vasodilator in the periphery, where CGRP-containing neurons are closely associated with blood vessels. CGRP-mediated vasodilatation is also associated with neurogenic inflammation, as part of a cascade of events that results in extravasation of plasma and vasodialation of the microvasculature and is present in migraine. Amy1 in also has specific binding sites in the CNS and is thought to regulate gastric emptying and have a role in carbohydrate metabolism. Adrenomedullin is a potent vasodilator. adrenomedullin has specific receptors on astrocytes and its messenger RNA is upregulated in CNS tissues that are subject to ischemia. (Zimmermann, et al., Identification of adrenomedullin receptors in cultured rat astrocytes and in neuroblastoma glioma hybrid cells (NG108-15), Brain Res., 724:238-245 (1996); Wang et al., Discovery of adrenomedullin in rat ischemic cortex and evidence for its role in exacerbating focal brain ischemic damage, Proc. Natl. Acad. Sci. USA, 92:11480-11484 (1995)).

Calcitonin is involved in the control of bone metabolism and is also active in the central nervous system (CNS). The biological activities of CGRP include the regulation of neuromuscular junctions, of antigen presentation within the immune system, of vascular tone and of sensory neurotransmission. (Poyner, D. R., Calcitonin gene-related peptide: multiple actions, multiple receptors, Pharmacol. Ther., 56:23-51 (1992); Muff et al., Calcitonin, calcitonin gene related peptide, adrenomedullin and amylin: homologous peptides, separate receptors and overlapping biological actions, Eur. J. Endocrinol., 133: 17-20 (1995)). Three calcitonin receptor stimulating peptides (CRSPs) have also been identified in a number of mammalian species; the CRSPs may form a new subfamily in the CGRP family. (Katafuchi, T and Minamino, N, Structure and biological properties of three calcitonin receptor-stimulating peptides, novel members of the calcitonin gene-related peptide family, Peptides, 25(11): 2039-2045 (2004)).

The calcitonin superfamily peptides act through seven-transmembrane-domain G-protein-coupled receptors (GPCRs). The calcitonin receptor ("CT", "CTR" or "CT receptor") and CGRP receptors are type II ("family B") GPCRs, which family includes other GPCRs that recognize regulatory peptides such as secretin, glucagon and vasoactive intestinal polypeptide (VIP). The best characterized splice variants of human calcitonin receptor differ depending on the presence (formerly $CTR_{II+}$ or CTR1, now known as $CT_{(b)}$) or absence (the major splice variant, formerly $CTR_{II-}$ or $CTR_2$, now known as $CT_{(a)}$) of 16 amino acids in the first intracellular loop. (Gorn et al., Expression of two human skeletal calcitonin receptor isoforms cloned from a giant cell tumor of bone: the first intracellular domain modulates ligand binding and signal transduction, J. Clin. Invest., 95:2680-2691 (1995); Hay et al., Amylin receptors: molecular composition and pharmacology, Biochem. Soc. Trans., 32:865-867 (2004); Poyner et al., 2002). The existence of at least two CGRP receptor subtypes had been proposed from differential antagonist affinities and agonist potencies in a variety of in vivo and in vitro bioassays. (Dennis et al., CGRP8-37, A calcitonin gene-related peptide antagonist revealing calcitonin gene-related peptide receptor heterogeneity in brain and periphery, J. Pharmacol. Exp. Ther., 254:123-128 (1990); Dennis et al., Structure-activity profile of calcitonin gene-related peptide in peripheral and brain tissues. Evidence for multiplicity, J. Pharmacol. Exp. Ther., 251:718-725 (1989); Dumont et al., A potent and selective CGRP2 agonist, [Cys(Et)2,7]hCGRP: comparison in prototypical $CGRP_1$ and CGRP2 in vitro assays, Can. J. Physiol. Pharmacol., 75:671-676 (1997)).

The $CGRP_1$ receptor subtype was found to be sensitive to the antagonist fragment CGRP(8-37). (Chiba et al., Calcitonin gene-related peptide receptor antagonist human CGRP-(8-37), Am. J. Physiol., 256:E331-E335 (1989); Dennis et al. (1990); Mimeault et al., Comparative affinities and antagonistic potencies of various human calcitonin gene-related peptide fragments on calcitonin gene-related peptide receptors in brain and periphery, J. Pharmacol. Exp. Ther., 258: 1084-1090 (1991)). By contrast, the $CGRP_2$ receptor was sensitive to linear human CGRP (hCGRP) analogs, in which the cysteine residues at positions 2 and 7 were derivatized (e.g., with acetoaminomethyl $[Cys(ACM)^{2,7}]$ or ethylamide $[Cys(Et)^{2,7}]$) but $CGRP_2$ receptor was insensitive to fragment CGRP(8-37). (Dennis et al. (1989); Dennis et al. (1990); Dumont et al. (1997)).

Ligand specificity of calcitonin receptor and calcitonin-like receptor ("CL", "CLR" or "CRLR") depend on the co-expression of members of a family of accessory proteins called the receptor activity modifying proteins (RAMPs). The RAMP family includes three polypeptides (RAMP1, RAMP2 and RAMP3) that act as receptor modulators that determine the ligand specificity of receptors for the calcitonin family members. RAMPs are type I transmembrane proteins that share about 30% amino acid sequence identity and a common predicted topology, with short cytoplasmic C-termini, one trans-membrane domain and large extracellular N-termini that are responsible for the specificity. (McLatchie et al., (1998) RAMPs regulate the transport and ligand specificity of the calcitonin-receptor-like receptor, Nature, 393: 333-339; Fraser et al., (1999) The amino terminus of receptor activity modifying proteins is a critical determinant of glycosylation state and ligand binding of calcitonin receptor-like receptor, Molecular Pharmacology, 55:1054-1059).

In 1998, the $CGRP_1$ receptor was identified as a heterodimer composed of a novel single transmembrane domain accessory protein, receptor activity-modifying protein 1 (RAMP1), and CRLR. (McLatchie et al., supra). Cross-linking experiments suggested the CGRP receptor consisted of a one-to-one stoichiometric arrangement of CRLR and RAMP1 (Hilairet et al. JBC 276, 42182-42190 (2001)), more recent studies using several methodologies such as BRET and BiFC revealed that the functional CGRP receptor complex may be composed of asymmetric homo-oligomer of CRLR and monomer of RAMP1 (Heroux et al. JBC 282, 31610-31620 (2007)).

A purified CRLR N-terminal domain has been shown to specifically bind $^{125}$I-CGRP (Chauhan et al. Biochemistry 44, 782 (2005)), confirming the important and direct interaction between the CRLR with CGRP ligand. In particular, Leu 24 and Leu 34 of CRLR are believed to constitute the docking site of the C-terminus Phe37 of CGRP (Banerjee et al. BMC Pharmacol. 6, 9 (2006)). Furthermore, Koller et al. (FEBS Lett. 531, 464-468 (2002)) obtained evidence that that the N-terminal 18 amino acid residues of CRLR contributes the selective interaction with CGRP or adrenomedullin, and Ittner et al (Biochemistry 44, 5749-5754 (2005)) suggested that the N-terminal amino acid residues 23-60 of CRLR mediate association with RAMP1.

A structure-function analysis of RAMP1 identified residues 91-103, which correlate to "helix 3" (Simms et al. Biophys. J. 91, 662-669 (2006)), as potentially significant in interaction with CRLR, and residues Trp74 and Phe92 as potentially interacting with the CGRP ligand in connection with its binding to the CGRP receptor complex. Ligand binding studies using a human/rat RAMP1 chimera suggest that the binding site for certain small molecule inhibitors of CGRP R (e.g., BIBN4096BS), is located within a region which includes amino acids 66-102 of RAMP1 (Mallee et al. JBC 277, 14294-14298 (2002)).

CRLR has 55% overall amino acid sequence identity with CTR, although the transmembrane domains are almost 80% identical. (McLatchie et al. (1998); Poyner et al., International union of pharmacology. XXXII. The mammalian calcitonin gene-related peptides, adrenomedullin, amylin and calcitonin receptors, Pharmacol. Rev., 54:233-246 (2002)).

CRLR has been shown to form a high affinity receptor for CGRP, when associated with RAMP1, or, to preferentially bind adrenomedullin when associated with RAMP2 or RAMP3. (McLatchie et al. (1998); Sexton et al., Receptor activity modifying proteins, Cellular Signaling, 13:73-83 (2001); Conner et al., Interaction of calcitonin-gene-related peptide with its receptors, Biochemical Society Transactions 30(Part 4): 451-454 (2002)). The glycosylation state of CRLR is associated with its pharmacology. RAMPs 1, 2, and 3 transport CRLR to the plasma membrane with similar efficiencies, however RAMP1 presents CRLR as a terminally glycosylated, mature glycoprotein and a CGRP receptor, whereas RAMPs 2 and 3 present CRLR as an immature, core glycosylated adrenomedullin receptor ("AM" or "AMR" or "AM receptor". (Fraser et al. (1999)). Characterization of the CRLR/RAMP2 and CRLR/RAMP3 receptors in HEK293T cells by radioligand binding ($^{125}$I-adrenomedullin as radioligand), functional assay (cAMP measurement), or biochemical analysis (SDS-polyacrylamide gel electrophoresis) revealed them to be indistinguishable, even though RAMPs 2 and 3 share only 30% amino acid sequence identity. (Fraser et al. 1999)). Differences have been observed, however, in the pharmacology for CRLR expressed with RAMP 2 versus RAMP 3. Both CGRP and CGRP8-37, as well as adrenomedullin and the adrenomedullin-derived peptide AM 22-52, are active at the RAMP 3 heterodimer, indicating that this complex may act as both a CGRP and an AM receptor. (Howitt et al., British Journal of Pharmacology, 140:477-486 (2003); Muff et al., Hypertens. Res., 26:S3-S8 (2003)). Co-expression of human CRLR with rat RAMP1, and vice versa, suggested that the RAMP1 species determined the pharmacological characteristics of the CRLR/RAMP1 complex with respect to several small molecule CGRP receptor antagonists tested. (Mallee et al., Receptor Activity-Modifying Protein 1 determines the species selectivity of non-peptide CGRP receptor antagonists, J. Biol. Chem., 277(16):14294-14298 (2002)). Unless associated with a RAMP, CRLR is not known to bind any endogenous ligand; it is currently the only GPCR thought to behave this way. (Conner et al., A key role for transmembrane prolines in calcitonin receptor-like agonist binding and signaling: implications for family B G-protein-coupled receptors, Molec. Pharmacol., 67(1):20-31 (2005)).

Calcitonin receptor (CT) has also been demonstrated to form heterodimeric complexes with RAMPs, which are known as amylin receptors ("AMY", "AMY R" or "AMY receptor"). Generally, CT/RAMP1 receptors (referred to as "AMY$_1$" or "AMY1") have high affinity for salmon calcitonin, amylin and CGRP and lower affinity for mammalian calcitonins. For CT/RAMP2 receptors ("AMY$_2$" or "AMY2") and CT/RAMP3 receptors ("AMY$_3$" or "AMY3"), a similar pattern is principally observed, although the affinity for CGRP is lower and may not be significant at physiologically relevant ligand concentrations. The precise receptor phenotype is dependent on cell type and CTR splice variant ($CT_{(a)}$ or $CT_{(b)}$), particularly for RAMP2-generated amylin receptors. For example, a pure population of osteoclast-like cells reportedly expressed RAMP2, CTR, and CRLR, but not RAMP1 or RAMP3. (Hay et al. (2004); Christopoulos et al., Multiple amylin receptors arise from receptor activity-modifying protein interaction with the calcitonin receptor gene product, Molecular Pharmacology, 56:235-242 (1999); Muff et al., An amylin receptor is revealed following co-transfection of a calcitonin receptor with receptor activity modifying proteins-1 or -3, Endocrinology, 140:2924-2927 (1999); Sexton et al. (2001); Leuthauser et al., Receptor-activity-modifying protein 1 forms heterodimers with two G-protein-coupled receptors to define ligand recognition, Biochem. J., 351:347-351 (2000); Tilakaratne et al., Amylin receptor phenotypes derived from human calcitonin receptor/RAMP co-expression exhibit pharmacological differences dependent on receptor isoform and host cell environment, J. Pharmacol. Exp. Ther., 294:61-72 (2000); Nakamura et al., Osteoclast-like cells express receptor activity modifying protein 2: application of laser capture microdissection, J. Molec. Endocrinol., 34:257-261 (2005)).

Table 1, below, summarizes the relationship of the receptor components discussed above.

TABLE 1

| Receptor Component | CRLR (CL) | CT (calcitonin receptor) |
|---|---|---|
| RAMP1 | CGRP receptor | AMY1 receptor |
| RAMP2 | AM1 receptor | AMY2 receptor |
| RAMP3 | AM2 receptor | AMY3 receptor |

Therapeutic uses of CGRP antagonists have been proposed. Noda et al. described the use of CGRP or CGRP derivatives for inhibiting platelet aggregation and for the treatment or prevention of arteriosclerosis or thrombosis. (EP 0385712 B1). Liu et al. disclosed therapeutic agents that modulate the activity of CTR, including vehicle-conjugated peptides such as calcitonin and human αCGRP. (WO 01/83526 A2; US 2002/0090646 A1). Vasoactive CGRP peptide antagonists and their use in a method for inhibiting CGRP binding to CGRP receptors were disclosed by Smith et al.; such CGRP peptide antagonists were shown to inhibit CGRP binding to coronary artery membranes and to relax capsaicin-treated pig coronary arteries. (U.S. Pat. No. 6,268,474 B1; and U.S. Pat. No. 6,756,205 B2). Rist et al. disclosed peptide analogs with CGRP receptor antagonist activity and their use in a drug for treatment and prophylaxis of a variety of disorders. (DE 19732944 A1).

CGRP is a potent vasodilator that has been implicated in the pathology of a number of vasomotor symptoms, such as all forms of vascular headache, including migraines (with or without aura) and cluster headache. Durham, N. Engl. J. Med. 350:1073-1 075, 2004. Migraine pathophysiology involves the activation of the trigeminal ganglia, where CGRP is localized, and CGRP levels significantly increase during a migraine attack. This in turn, promotes cranial blood vessel dilation and neurogenic inflammation and sensitization. (Doods, H., Curr. Opin. Investig. Drugs, 2:1261-1268 (2001)). Further, the serum levels of CGRP in the external jugular vein are elevated in patients during migraine headache. Goadsby et al., Ann. Neurol. 28:183-7, 1990. Intravenous administration of human ci-CGRP induced headache and migraine in patients suffering from migraine without aura, supporting the view that CGRP has a causative role in migraine (Lassen et al, Cephalalgia 22:54-61, 2002).

Migraine is a complex, common neurological condition that is characterized by severe, episodic attacks of headache and associated features, which may include nausea, vomiting, sensitivity to light, sound or movement. In some patients, the headache is preceded or accompanied by an aura. The headache pain may be severe and may also be unilateral in certain patients. Migraine attacks are disruptive to daily life. In US and Western Europe, the overall prevalence of migraine sufferers is 11% of the general population (6% males; 15-18% females). Furthermore, the median frequency of attacks in an individual is 1.5/month. While there are a number of treatments available to alleviate or reduce symptoms, preventive therapy is recommended for those patients having more than 3-4 attacks of migraine per month. Goadsby, et al. New Engl. J. Med. 346(4): 257-275, 2002. Some migraine patients have been treated with topiramate, an anticonvulsant that blocks voltage-dependent sodium channels and certain glutamate receptors (AMPA-kainate), potentiates GABA-A receptor activity, and blocks carbonic anhydrase. The relatively recent success of serotonin 5HT-I B/ID and/or 5HT-1 a receptor agonists, such as sumatriptan, in some patients has led researchers to propose a serotonergic etiology of the disorder. Unfortunately, while some patients respond well to this treatment, others are relatively resistant to its effects.

Possible CGRP involvement in migraine has been the basis for the development and testing of a number of compounds that inhibit release of CGRP (e.g., sumatriptan), antagonize at the CGRP receptor (e.g., dipeptide derivative BIBN4096BS (Boehringer Ingelheim); CGRP(8-37)), or interact with one or more of receptor-associated proteins, such as, RAMP1. Brain, S. et al., Trends in Pharmacological Sciences 23:51-53, 2002. Alpha-2 adrenoceptor subtypes and adenosine Al receptors also control (inhibit) CGRP release and trigeminal activation (Goadsby et al., Brain 125:1392-401, 2002). On the other hand, treatment with compounds that exclusively inhibit neurogenic inflammation (e.g., tachykinin NKI receptor antagonists) or trigeminal activation (e.g., 5HT10 receptor agonists) appears to be relatively ineffective as acute treatments for migraine, leading some to question whether inhibiting release of CGRP is the basis of effective anti-migraine treatments. Arulmani et al., Eur. J. Pharmacol. 500:315-330, 2004.

Although the precise pathophysiology of migraine is not yet well understood, the therapeutic use of CGRP antagonists and CGRP-targeting aptamers has been proposed for the treatment of migraine and other disorders. (E.g., Olesen et al., Calcitonin gene-related peptide receptor antagonist BIBN 4096 BS for the acute treatment of migraine, New Engl. J. Med., 350:1104-1110 (2004); Perspective: CGRP-receptor antagonists—a fresh approach to migraine, New Engl. J. Med., 350:1075 (2004); Vater et al., Short bioactive Spiegelmers to migraine-associated calcitonin gene-related peptide rapidly identified by a novel approach: tailored-SELEX, Nuc. Acids Res., 31(21 e130):1-7 (2003); WO 96/03993). Further, a potent small-molecule CGRP antagonist has been shown to relieve moderate-to-severe migraine attacks, including migraine pain and migraine-associated symptoms, in a recent Phase III clinical trial (Connor, et al. Efficacy and Safety of telcagepant (MK-0974), a Novel Oral CGRP Receptor Antagonist, for Acute Migraine Attacks. Poster, European Headache and Migraine Trust International Congress, London, England, September 2008).

CGRP may also be involved in chronic pain syndromes other than migraine. In rodents, intrathecally delivered CGRP induces severe pain, and CGRP levels are enhanced in a number of pain models. In addition, CGRP antagonists partially block nociception in acute pancreatitis in rodents (Wick, et al., (2006) Surgery, Volume 139, Issue 2, Pages 197-201). Together, these observations imply that a potent and selective CGRP receptor antagonist can be an effective therapeutic for treatment of chronic pain, including migraine.

SUMMARY

Isolated antibodies, antigen-binding fragments thereof and other isolated antigen-binding proteins that bind CGRP R, particularly primate CGRP R, e.g., human CGRP R, are described herein. Such isolated antigen-binding proteins may selectively inhibit primate CGRP R (as compared with primate AM1, AM2, CT or amylin receptors) and may bind both the CRLR and RAMP1 components of CGRP R. The CGRP R binding proteins were found to inhibit, interfere with, or modulate at least one of the biological responses related to CGRP R, and as such, are useful for ameliorating the effects of CGRP R-related diseases or disorders. Binding of certain antigen-binding proteins to CGRP R can, therefore, have one or more of the following activities: inhibiting, interfering with, or modulating CGRP R, inhibiting vasodialation, decreasing neurogenic inflammation, and alleviating, ameliorating, treating, preventing, or reducing symptoms of chronic pain or migraine.

In one exemplary aspect, the isolated antigen-binding proteins selectively inhibit human CGRP receptor (as compared with the human AM1, AM2 or amylin receptors). In some embodiments, the isolated antigen binding protein selectively inhibits the human CGRP receptor with a selectivity ratio of 50 or more, 75 or more, 100 or more, 150 or more, 200 or more, 250 or more, 300 or more, 400 or more, 500 or more, 750 or more or 1,000 or more. The degree of selective inhibition may be determined using any suitable method, e.g., using a cAMP assay as described in the Examples herein. In some embodiments, the isolated antigen binding protein specifically binds to both human CRLR and human RAMP1, and does not specifically bind to human AM1, human AM2 or a human amylin receptor (e.g., AMY1 or AMY2). For example, the isolated antigen binding protein may specifically bind human CGRP R with a $K_D \leq 1$ μM, $\leq 100$ nM, $\leq 10$ nM, or $\leq 5$ nM. In some embodiments, the isolated antigen binding protein specifically binds to human CGRP R with a $K_D \leq 100$ nM, $\leq 10$ nM, or $\leq 5$ nM as determined using a FACS binding assay and analyzed, for example, using methods described in Rathanaswami, et al., *Biochemical and Biophysical Research Communications* 334 (2005) 1004-1013. In some embodiments, the isolated antigen binding protein has a Ki of $\leq 100$ nM, ≤10 nM, ≤1 nM, ≤0.5 nM or ≤0.1 nM in a CGRP binding competition assay. In some embodiments, the isolated antigen binding protein has a Ki of ≤100 nM, ≤50 nM, ≤20 nM, ≤10 nM, ≤1 nM, ≤0.5 nM or ≤0.1 nM in a radiolabeled $^{125}$I-CGRP binding competition assay to membranes from cells expressing human CGRP R, for example, the assay described in Example 5 herein.

In another exemplary aspect, the isolated antigen-binding proteins compete for binding to human CGRP R, e.g., the extracellular portion of CGRP R, with a reference antibody comprising a heavy chain variable region comprising a sequence selected from the group consisting of SEQ ID NO:158-170 and a light chain variable region comprising a sequence selected from the group consisting of SEQ ID NO:137-153. In some embodiments, binding competition is assessed using a binning assays, e.g., using a Biacore analysis, for example, as described in Example 7 herein. In some embodiments, the isolated antigen binding protein competes for binding to human CGRP R with a reference antibody, the reference antibody comprising (i) a heavy chain variable region comprising a sequence selected from the group consisting of SEQ ID NOs:161, 163, 164, 166 and 168; and (ii) a light chain variable region comprising a sequence selected from the group consisting of SEQ ID NOs: 140, 143, 146, 148 and 150. In certain embodiments, the reference antibody comprises (i) a heavy chain defined by a sequence selected from the group consisting of SEQ ID NOs:32, 34, 35, 37 and 39; and (ii) a light chain defined by a sequence selected from the group consisting of SEQ ID NOs: 15, 18, 21, 23 and 25. In more specific embodiments, the reference antibody comprises a heavy chain and a light chain defined by one of the following pairs of sequences: (i) SEQ ID NO: 32 and SEQ ID NO: 15; (ii) SEQ ID NO: 34 and SEQ ID NO: 18; (iii) SEQ ID NO: 35 and SEQ ID NO: 21; (iv) SEQ ID NO: 37 and SEQ ID NO: 23; and (v) SEQ ID NO: 39 and SEQ ID NO: 25. In one such embodiment, the reference antibody comprises a heavy chain comprising SEQ ID NO: 32 and a light chain comprising SEQ ID NO: 15. In another such embodiment, the reference antibody comprises a heavy chain comprising SEQ ID NO: 34 and a light chain comprising SEQ ID NO: 18. In another such embodiment, the reference antibody comprises a heavy chain comprising SEQ ID NO: 35 and a light chain comprising SEQ ID NO: 21. In another such embodiment, the reference antibody comprises a heavy chain comprising SEQ ID NO: 37 and a light chain comprising SEQ ID NO: 23. In another such embodiment, the reference antibody comprises a heavy chain comprising SEQ ID NO: 39 and a light chain comprising SEQ ID NO: 25.

In certain embodiments, the isolated antigen-binding proteins that compete for binding to human CGRP R also selectively inhibit the human CGRP receptor, e.g., with a selectivity ratio of 100 or more, 250 or more, 500 or more, 750 or more, 1,000 or more, 2,500 or more, 5,000 or more or 10,000 or more, and such selectivity may be determined, e.g., using a cAMP assay as described in the Examples herein. In related embodiments, the isolated antigen-binding proteins that compete for binding to human CGRP R specifically binds to human CGRP R with a $K_D$≤1 µM, ≤100 nM, ≤10 nM, or ≤5 nM, e.g., as determined using a FACS binding assay and analyzed, for example, using methods described in Rathanaswami, et al., *Biochemical and Biophysical Research Communications* 334 (2005) 1004-1013. In related embodiments, the isolated antigen-binding proteins that compete for binding to human CGRP R have a Ki of ≤100 nM, ≤10 nM, ≤1 nM, ≤0.5 nM or ≤0.1 nM in a CGRP binding competition assay, e.g., in a radiolabeled $^{125}$I-CGRP binding competition assay to membranes from cells expressing human CGRP R, for example, the assay described in Example 5 herein.

In any of the above-mentioned embodiments, the isolated antigen-binding protein that competes for binding to human CGRP R may be, for example, a monoclonal antibody, a polyclonal antibody, a recombinant antibody, a human (e.g., fully human) antibody, a humanized antibody, a chimeric antibody, a multi-specific antibody, or an antigen binding fragment thereof. Further, the antibody fragment of the isolated antigen-binding protein that competes for binding to human CGRP R can be a Fab fragment, and Fab' fragment, an F(ab')$_2$ fragment, an Fv fragment, a diabody or a single chain antibody molecule; and may be, for example, a human monoclonal antibody, e.g., an IgG1-, IgG2-, IgG3-, or IgG4-type antibody. In certain embodiments, the isolated antigen binding proteins that compete for binding to human CGRP R may be neutralizing antigen binding proteins.

In certain exemplary aspects, the isolated antigen-binding proteins described, e.g., isolated antibodies or fragments thereof, comprise (A) one or more heavy chain complementary determining regions (CDRHs) selected from the group consisting of: (i) a CDRH1 having SEQ ID NO:134; (ii) a CDRH2 having SEQ ID NO:135; (iii) a CDRH3 having SEQ ID NO:136; and optionally (iv) a CDRH of (i), (ii) and (iii) that contains one or more amino acid substitutions (e.g., conservative amino acid substitutions), deletions or insertions that collectively total no more than four amino acids; (B) one or more light chain complementary determining regions (CDRLs) selected from the group consisting of: (i) a CDRL1 selected from the group consisting of SEQ ID NOs:107, 111 and 118; (ii) a CDRL2 selected from the group consisting of SEQ ID NOs: 108, 112 and 119; (iii) a CDRL3 selected from the group consisting of SEQ ID NOs: 109, 113 and 120; and optionally (iv) a CDRL of (i), (ii) and (iii) that contains one or more, e.g., one, two, three, four or more, amino acid substitutions (e.g., conservative amino acid substitutions), deletions or insertions that collectively total no more than four amino acids; or (C) one or more heavy chain CDRHs of (A) and one or more light chain CDRLs of (B).

In some embodiments, the CDRHs are further selected from the group consisting of: (i) a CDRH1 having SEQ ID NO:131; (ii) a CDRH2 having SEQ ID NO:132; (iii) a CDRH3 having SEQ ID NO:133; and optionally (iv) a CDRH of (i), (ii) and (iii) that contains one or more, e.g., one, two, three, four or more amino acid substitutions (e.g., conservative amino acid substitutions), deletions or insertions that collectively total no more than three amino acids. In related embodiments, the CDRHs are further selected from the group consisting of: (i) a CDRH1 selected from the group consisting of SEQ ID NO:76, 88, 100, 121, 125 and 128; (ii) a CDRH2 selected from the group consisting of SEQ ID NO: 89, 101, 122, 124, 126, and 129; (iii) a CDRH3 selected from the group consisting of SEQ ID NO: 78, 90, 102, 123, 127, and 130; and optionally (iv) a CDRH of (i), (ii) and (iii) that contains one or more, e.g., one, two, three, four or more amino acid substitutions (e.g., conservative amino acid substitutions), deletions or insertions that collectively total no more than two amino acids. In other related embodiments, the CDRHs are further selected from the group consisting of: (i) a CDRH1 selected from the group consisting of SEQ ID NO: 73, 76, 79, 82, 85, 88, 92, 97, and 100; (ii) a CDRH2 selected from the group consisting of SEQ ID NO: 74, 77, 80, 83, 86, 89, 91, 93, 95, 98, 101, and 129; (iii) a CDRH3 selected from the group consisting of SEQ ID NO: 75, 78, 81, 84, 87, 90, 96, 99, 102, and 123; and optionally (iv) a CDRH of (i), (ii) and (iii) that contains one or more, e.g., one, two, three, four or more amino acid substitutions (e.g., conservative amino acid substitutions), deletions or insertions that collectively total no more than two amino acids.

In some embodiments, the CDRLs are further selected from the group consisting of: (i) a CDRL1 selected from the group consisting of SEQ ID NOs:107, 111 and 115; (ii) a CDRL2 selected from the group consisting of SEQ ID NOs: 108, 112 and 116; (iii) a CDRL3 selected from the group consisting of SEQ ID NOs: 109, 113 and 117; and optionally (iv) a CDRL of (i), (ii) and (iii) that contains one or more, e.g., one, two, three, four or more amino acid substitutions (e.g., conservative amino acid substitutions), deletions or insertions. In some embodiments, the amino acid substitutions (e.g., conservative amino acid substitutions), deletions or insertions collectively total no more than three amino acids per CDRL. In some embodiments, the amino acid substitutions, deletions or insertions collectively total no more than two amino acids per CDRL. In related embodiments, the CDRLs are further selected from the group consisting of: (i) a CDRL1 selected from the group consisting of SEQ ID NOs: 42, 45, 51, 57, 62, 69, 103, and 110; (ii) a CDRL2 selected from the group consisting of SEQ ID NOs: 43, 52, 55, 58, 63, 70, 104, 108, and 114; (iii) a CDRL3 selected from the group consisting of SEQ ID NOs: 44, 47, 53, 56, 59, 64, 105, and 106; and optionally (iv) a CDRL of (i), (ii) and (iii) that contains one or more, e.g., one, two, three, four or more amino acid substitutions (e.g., conservative amino acid substitutions), deletions or insertions that collectively total no more than two amino acids. In additional related embodiments, the CDRLs are further selected from the group consisting of: (i) a CDRL1 selected from the group consisting of SEQ ID NOs: 42, 45, 48, 51, 54, 57, 62, 65, 66, and 69; (ii) a CDRL2 selected from the group consisting of SEQ ID NOs: 43, 46, 49, 52, 55, 58, 61, 63, 67, and 70; (iii) a CDRL3 selected from the group consisting of SEQ ID NOs: 44, 47, 50, 53, 56, 59, 64, 68, 71, and 72; and optionally (iv) a CDRL of (i), (ii) and (iii) that contains one or more, e.g., one, two, three, four or more amino acid substitutions (e.g., conservative amino acid substitutions), deletions or insertions. In one embodiment, the total number of amino acid substitutions, deletions or insertions is no more than two amino acids per CDR. In another embodiment, the amino acid substitutions are conservative substitutions.

In another embodiment, the isolated antigen-binding protein comprises at least one or two CDRH of any of the above-mentioned (A) and at least one or two CDRL of any of the above-mentioned (B). In yet another embodiment, the isolated antigen-binding protein comprises (i) at least three CDRH of any of the above-mentioned (A), where the three CDRHs include CDRH1, a CDRH2 and a CDRH3, and (ii) at least three CDRL of any of the above-mentioned (B), where the three CDRLs include CDRL1, a CDRL2 and a CDRL3. In additional embodiments, the isolated antigen binding proteins described above comprise a first amino acid sequence comprising at least one CDRH and a second amino acid sequence comprising at least one CDRL. In one embodiment, the first and the second amino acid sequences are covalently bonded to each other.

In another aspect, the isolated antigen-binding protein includes a CDRH1, a CDRH2 and a CDRH3. In one embodiment, CDRH1 comprises SEQ ID NO:73, CDRH2 comprises SEQ ID NO:74 and CDRH3 comprises SEQ ID NO:75. In another embodiment, CDRH1 comprises SEQ ID NO:76, CDRH2 comprises SEQ ID NO:77 and CDRH3 comprises SEQ ID NO:78. In another embodiment, CDRH1 comprises SEQ ID NO:79, CDRH2 comprises SEQ ID NO:80 and CDRH3 comprises SEQ ID NO:81. In another embodiment, CDRH1 comprises SEQ ID NO:82, CDRH2 comprises SEQ ID NO:83 and CDRH3 comprises SEQ ID NO:84. In another embodiment, CDRH1 comprises SEQ ID NO:85, CDRH2 comprises SEQ ID NO:86 and CDRH3 comprises SEQ ID NO:87. In another embodiment, CDRH1 comprises SEQ ID NO:88, CDRH2 comprises SEQ ID NO:89 and CDRH3 comprises SEQ ID NO:90. In another embodiment, CDRH1 comprises SEQ ID NO:76, CDRH2 comprises SEQ ID NO:91 and CDRH3 comprises SEQ ID NO:78. In another embodiment, CDRH1 comprises SEQ ID NO:92, CDRH2 comprises SEQ ID NO:93 and CDRH3 comprises SEQ ID NO:94. In another embodiment, CDRH1 comprises SEQ ID NO:76, CDRH2 comprises SEQ ID NO:95 and CDRH3 comprises SEQ ID NO:78. In another embodiment, CDRH1 comprises SEQ ID NO:73, CDRH2 comprises SEQ ID NO:74 and CDRH3 comprises SEQ ID NO:96. In another embodiment, CDRH1 comprises SEQ ID NO:97, CDRH2 comprises SEQ ID NO:98 and CDRH3 comprises SEQ ID NO:99. In another embodiment, CDRH1 comprises SEQ ID NO:100, CDRH2 comprises SEQ ID NO:101 and CDRH3 comprises SEQ ID NO:102.

In another aspect, the isolated antigen-binding protein includes a CDRL1 sequence, a CDRL2 sequence and a CDRL3 sequence. In one embodiment, CDRL1 comprises SEQ ID NO:42, CDRL2 comprises SEQ ID NO:43 and CDRL3 comprises SEQ ID NO:44. In another embodiment, CDRL1 comprises SEQ ID NO:45, CDRL2 comprises SEQ ID NO:46 and CDRL3 comprises SEQ ID NO:47. In another embodiment, CDRL1 comprises SEQ ID NO:48, CDRL2 comprises SEQ ID NO:49 and CDRL3 comprises SEQ ID NO:50. In another embodiment, CDRL1 comprises SEQ ID NO:51, CDRL2 comprises SEQ ID NO:52 and CDRL3 comprises SEQ ID NO:53. In another embodiment, CDRL1 comprises SEQ ID NO:54, CDRL2 comprises SEQ ID NO:55 and CDRL3 comprises SEQ ID NO:56. In another embodiment, CDRL1 comprises SEQ ID NO:57, CDRL2 comprises SEQ ID NO:58 and CDRL3 comprises SEQ ID NO:59. In another embodiment, CDRL1 comprises SEQ ID NO:60, CDRL2 comprises SEQ ID NO:55 and CDRL3 comprises SEQ ID NO:56. In another embodiment, CDRL1 comprises SEQ ID NO:45, CDRL2 comprises SEQ ID NO:61 and CDRL3 comprises SEQ ID NO:47. In another embodiment, CDRL1 comprises SEQ ID NO:62, CDRL2 comprises SEQ ID NO:63 and CDRL3 comprises SEQ ID NO:64. In another embodiment, CDRL1 comprises SEQ ID NO:65, CDRL2 comprises SEQ ID NO:55 and CDRL3 comprises SEQ ID NO:56. In another embodiment, CDRL1 comprises SEQ ID NO:66, CDRL2 comprises SEQ ID NO:67 and CDRL3 comprises SEQ ID NO:68. In another embodiment, CDRL1 comprises SEQ ID NO:69, CDRL2 comprises SEQ ID NO:70 and CDRL3 comprises SEQ ID NO:71. In another embodiment, CDRL1 comprises SEQ ID NO:69, CDRL2 comprises SEQ ID NO:70 and CDRL3 comprises SEQ ID NO:72.

In another aspect, the isolated antigen-binding protein includes a CDRL1 sequence, a CDRL2 sequence, a CDRL3 sequence, a CDRH1 sequence, a CDRH2 sequence and a CDRH3 sequence. In one embodiment, CDRL1 comprises SEQ ID NO:42, CDRL2 comprises SEQ ID NO:43, CDRL3 comprises SEQ ID NO:44, CDRH1 comprises SEQ ID NO:73, CDRH2 comprises SEQ ID NO:74 and CDRH3 comprises SEQ ID NO:75. In another embodiment, CDRL1 comprises SEQ ID NO:45, CDRL2 comprises SEQ ID NO:46, CDRL3 comprises SEQ ID NO:47, CDRH1 comprises SEQ ID NO:76, CDRH2 comprises SEQ ID NO:77 and CDRH3 comprises SEQ ID NO:78. In another embodiment, CDRL1 comprises SEQ ID NO:48, CDRL2 comprises SEQ ID NO:49, CDRL3 comprises SEQ ID NO:50, CDRH1 comprises SEQ ID NO:79, CDRH2 comprises SEQ ID NO:80 and CDRH3 comprises SEQ ID NO:81. In another embodiment, CDRL1 comprises SEQ ID NO:51, CDRL2 comprises SEQ ID NO:52, CDRL3 comprises SEQ ID NO:53, CDRH1 comprises SEQ ID NO:82, CDRH2 comprises SEQ ID NO:83 and CDRH3 comprises SEQ ID NO:84. In another embodiment, CDRL1 comprises SEQ ID NO:54, CDRL2 comprises SEQ ID NO:55, CDRL3 comprises SEQ ID NO:56, CDRH1 comprises SEQ ID NO:85, CDRH2 comprises SEQ ID NO:86 and CDRH3 comprises SEQ ID NO:87. In another embodiment, CDRL1 comprises SEQ ID NO:57, CDRL2 comprises SEQ ID NO:58, CDRL3 comprises SEQ ID NO:59, CDRH1 comprises SEQ ID NO:88, CDRH2 comprises SEQ ID NO:89 and CDRH3 comprises SEQ ID NO:90. In another embodiment, CDRL1 comprises SEQ ID NO:60, CDRL2 comprises SEQ ID NO:55, CDRL3 comprises SEQ ID NO:56, CDRH1 comprises SEQ ID NO:85, CDRH2 comprises SEQ ID NO:86 and CDRH3 comprises SEQ ID NO:87. In another embodiment, CDRL1 comprises SEQ ID NO:45, CDRL2 comprises SEQ ID NO:61, CDRL3 comprises SEQ ID NO:47, CDRH1 comprises SEQ ID NO:76, CDRH2 comprises SEQ ID NO:91 and CDRH3 comprises SEQ ID NO:78. In another embodiment, CDRL1 comprises SEQ ID NO:62, CDRL2 comprises SEQ ID NO:63, CDRL3 comprises SEQ ID NO:64, CDRH1 comprises SEQ ID NO:92, CDRH2 comprises SEQ ID NO:93 and CDRH3 comprises SEQ ID NO:94. In another embodiment, CDRL1 comprises SEQ ID NO:45, CDRL2 comprises SEQ ID NO:61, CDRL3 comprises SEQ ID NO:47, CDRH1 comprises SEQ ID NO:76, CDRH2 comprises SEQ ID NO:95 and CDRH3 comprises SEQ ID NO:78. In another embodiment, CDRL1 comprises SEQ ID NO:65, CDRL2 comprises SEQ ID NO:55, CDRL3 comprises SEQ ID NO:56, CDRH1 comprises SEQ ID NO:85, CDRH2 comprises SEQ ID NO:86 and CDRH3 comprises SEQ ID NO:87. In another embodiment, CDRL1 comprises SEQ ID NO:42, CDRL2 comprises SEQ ID NO:43, CDRL3 comprises SEQ ID NO:44, CDRH1 comprises SEQ ID NO:73, CDRH2 comprises SEQ ID NO:74 and CDRH3 comprises SEQ ID NO:96. In another embodiment, CDRL1 comprises SEQ ID NO:66, CDRL2 comprises SEQ ID NO:67, CDRL3 comprises SEQ ID NO:68, CDRH1 comprises SEQ ID NO:97, CDRH2 comprises SEQ ID NO:98 and CDRH3 comprises SEQ ID NO:99. In another embodiment, CDRL1 comprises SEQ ID NO:69, CDRL2 comprises SEQ ID NO:70, CDRL3 comprises SEQ ID NO:71, CDRH1 comprises SEQ ID NO:100, CDRH2 comprises SEQ ID NO:101 and CDRH3 comprises SEQ ID NO:102. In another embodiment, CDRL1 comprises SEQ ID NO:69, CDRL2 comprises SEQ ID NO:70, CDRL3 comprises SEQ ID NO:72, CDRH1 comprises SEQ ID NO:100, CDRH2 comprises SEQ ID NO:101 and CDRH3 comprises SEQ ID NO:102.

In any of the above-mentioned sequence-defined embodiments, the isolated antigen-binding protein may be, for example, a monoclonal antibody, a polyclonal antibody, a recombinant antibody, a human (e.g., fully human) antibody, a humanized antibody, a chimeric antibody, a multi-specific antibody, or an antigen binding fragment thereof. Further, the antibody fragment of the isolated antigen-binding proteins may be a Fab fragment, and Fab' fragment, an F(ab')$_2$ fragment, an Fv fragment, a diabody, or a single chain antibody molecule. For example, the isolated antigen binding protein may be a human monoclonal antibody, and may be, e.g., an IgG1-, IgG2-, IgG3-, or IgG4-type antibody. Further, the isolated antigen binding proteins may be neutralizing antigen binding proteins.

In any of the above-mentioned sequence-defined embodiments, the isolated antigen-binding protein may specifically bind to both human CRLR and human RAMP1 and not specifically bind to AM1, AM2 or a human amylin receptor (e.g., AMY1), for example, the isolated antigen binding protein may specifically bind to human CGRP R with a $K_D \leq 1$ µM, $\leq 100$ nM, $\leq 10$ nM, or $\leq 5$ nM, e.g., as determined using a FACS binding assay and analyzed, for example, using methods described in Rathanaswami, et al., *Biochemical and Biophysical Research Communications* 334 (2005) 1004-1013. In any of the above-mentioned sequence-defined embodiments, the isolated antigen-binding protein may selectively inhibit human CGRP R, relative to the human the AM1, AM2 or AMY1 receptors, e.g., with a selectivity ratio of 100 or more, 250 or more, 500 or more, 750 or more, 1,000 or more, 2,500 or more, 5,000 or more or 10,000 or more, where the degree of selective inhibition may be determined using any suitable method, e.g., using a cAMP assay as described in the Examples herein. In any of the above-mentioned sequence-defined embodiments, the isolated antigen-binding protein may have a Ki of $\leq 100$ nM, $\leq 10$ nM, $\leq 1$ nM, $\leq 0.5$ nM or $\leq 0.1$ nM in a CGRP binding competition assay, e.g., in a radiolabeled $^{125}$I-CGRP binding competition assay to membranes from cells expressing human CGRP R, e.g., the assay described in Example 5 herein.

Another set of embodiments includes isolated antigen-binding proteins that include one or a combination of CDRs having the consensus sequences described below, and optionally, bind human CGRP R. The consensus sequences are derived from phylogenetically related CDR sequences. In one aspect, the CDRs from the various groups may be mixed and matched in any particular isolated antigen-binding protein that binds human CGRP R. In another aspect, the antigen binding protein comprises heavy and light chain CDRs that are derived from the same phylogenetically-related group of antibody clones. Exemplary CDR consensus sequences are as follows:

K1 Consensus
CDR1 RASQGIRX$_1$DLG (SEQ ID NO:103), wherein X$_1$ is selected from the group consisting of N and K.
CDR2 X$_1$ASSLQS (SEQ ID NO:104), wherein X$_1$ is selected from the group consisting of A and G.
CDR3 LQYNX$_1$X$_2$PWT (SEQ ID NO:105), wherein X$_1$ is selected from the group consisting of I and S, and X$_2$ is selected from the group consisting of Y and F.

K4 Consensus
CDR3 QQYGNSLX$_1$R (SEQ ID NO:106), wherein X$_1$ is selected from the group consisting of S and C.

K1,4 Consensus
CDR1 RASQX$_1$X$_2$X$_3$X$_4$GX$_5$LX$_6$ (SEQ ID NO:107), wherein X$_1$ is selected from the group consisting of S and G, X$_2$ is selected from the group consisting of V and I, X$_3$ is selected from the group consisting of S and R, X$_4$ is selected from the group consisting of S, N and K, X$_5$ is selected from the group consisting of Y and D, and X$_6$ is selected from the group consisting of T and G.
CDR2 X$_1$ASSX$_2$X$_3$X$_4$ (SEQ ID NO:108), wherein X$_1$ is selected from the group consisting of G and A, X$_2$ is selected from the group consisting of R and L, X$_3$ is selected from the group consisting of A and Q, and X$_4$ is selected from the group consisting of T and S.
CDR3 X$_1$QYX$_2$X$_3$X$_4$X$_5$X$_6$X$_7$ (SEQ ID NO:109), wherein X$_1$ is selected from the group consisting of Q and L, X$_2$ is selected from the group consisting of G and N, X$_3$ is selected from the group consisting of N and T, X$_4$ is selected from the group consisting of S, Y and F, X$_5$ is selected from the group consisting of L and P, $X_6$ is selected from the group consisting of C, W and S, and $X_7$ is selected from the group consisting of R and T.

K3 Consensus

CDR1 KSSQSLLHS$X_1$G$X_2X_3$YLY (SEQ ID NO:110), wherein $X_1$ is selected from the group consisting of D and A, $X_2$ is selected from the group consisting of R and K, and $X_3$ is selected from the group consisting of N and T.

K2,3 Consensus

CDR1 $X_1$SSQSLLHS$X_2$G$X_3X_4$YL$X_5$ (SEQ ID NO:111), wherein $X_1$ is selected from the group consisting of R and K, $X_2$ is selected from the group consisting of F, D and A, $X_3$ is selected from the group consisting of Y, R and K, $X_4$ is selected from the group consisting of N and T, and $X_5$ is selected from the group consisting of D and Y.

CDR2 $X_1X_2$SNR$X_3$S (SEQ ID NO:112), wherein $X_1$ is selected from the group consisting of L and E, $X_2$ is selected from the group consisting of G and V, and $X_3$ is selected from the group consisting of A and F.

CDR3 MQ$X_1X_2X_3X_4$P$X_5$T (SEQ ID NO:113), wherein $X_1$ is selected from the group consisting of A and S, $X_2$ is selected from the group consisting of L and F, $X_3$ is selected from the group consisting of Q and P, $X_4$ is selected from the group consisting of T and L, and $X_5$ is selected from the group consisting of F and L.

Lm3 Consensus

CDR2 R$X_1$NQRPS (SEQ ID NO:114), wherein $X_1$ is selected from the group consisting of N and S.

Lm1,2,3 Consensus

CDR1 SGSSSNIG$X_1$N$X_2$V$X_3$ (SEQ ID NO:115), wherein $X_1$ is selected from the group consisting of N and S, $X_2$ is selected from the group consisting of Y and T, and $X_3$ is selected from the group consisting of S, N and Y.

CDR2 $X_1X_2$N$X_3$RPS (SEQ ID NO:116), wherein $X_1$ is selected from the group consisting of D, T and R, $X_2$ is selected from the group consisting of N and S, and $X_3$ is selected from the group consisting of K and Q.

CDR3 $X_1X_2X_3$D$X_4X_5$L$X_6X_7$VV (SEQ ID NO:117), wherein $X_1$ is selected from the group consisting of G and A, $X_2$ is selected from the group consisting of T and A, $X_3$ is selected from the group consisting of W and R, $X_4$ is selected from the group consisting of S and D, $X_5$ is selected from the group consisting of R and S, $X_6$ is selected from the group consisting of S and N, and $X_7$ is selected from the group consisting of A and G.

LmAll Consensus

CDR1 $X_1$G$X_2X_3$S$X_4X_5X_6X_7X_8X_9X_{10}X_{11}$ (SEQ ID NO:118), wherein $X_1$ is selected from the group consisting of S and Q, $X_2$ is present or absent, and if present, is S, $X_3$ is selected from the group consisting of S and D, $X_4$ is present or absent, and if present, is N, $X_5$ is selected from the group consisting of I and L, $X_6$ is selected from the group consisting of G and R, $X_7$ is selected from the group consisting of N and S, $X_8$ is selected from the group consisting of N and F, $X_9$ is selected from the group consisting of Y and T, $X_{10}$ is selected from the group consisting of V and A, and $X_{11}$ is selected from the group consisting of S, N and Y.

CDR2 $X_1X_2$N$X_3$RPS (SEQ ID NO:119), wherein $X_1$ is selected from the group consisting of D, G, T, and R, $X_2$ is selected from the group consisting of N, K and S, and $X_3$ is selected from the group consisting of K, N and Q.

CDR3 $X_1X_2X_3$D$X_4X_5X_6X_7X_8X_9$V (SEQ ID NO:120), wherein $X_1$ is selected from the group consisting of G, N and A, $X_2$ is selected from the group consisting of T, S and A, $X_3$ is selected from the group consisting of W and R, $X_4$ is selected from the group consisting of S and D, $X_5$ is selected from the group consisting of R and S, $X_6$ is selected from the group consisting of L and V, $X_7$ is selected from the group consisting of S, Y and N, $X_8$ is selected from the group consisting of A, H and G, and $X_9$ is selected from the group consisting of V and L.

HC1 Consensus

CDR1 $X_1$YYM$X_2$ (SEQ ID NO:121), wherein $X_1$ is selected from the group consisting of G and D, $X_2$ is selected from the group consisting of H and Y.

CDR2 WI$X_1$PNSGGTNYAQKFQG (SEQ ID NO:122), wherein $X_1$ is selected from the group consisting of N and S.

CDR3 $X_1X_2X_3$S$X_4X_5X_6X_7X_8$G$X_9X_{10}X_{11}X_{12}$YY$X_{13}$GMDV (SEQ ID NO:123), wherein $X_1$ is selected from the group consisting of D and G, $X_2$ is selected from the group consisting of Q and G, $X_3$ is selected from the group consisting of M and Y, $X_4$ is selected from the group consisting of I and G, $X_5$ is selected from the group consisting of I and Y, $X_6$ is selected from the group consisting of M and A, $X_7$ is present or absent, and if present, is L, $X_8$ is present or absent, and if present, is R, $X_9$ is selected from the group consisting of V and L, $X_{10}$ is selected from the group consisting of F and Y, $X_{11}$ is selected from the group consisting of P and S, $X_{12}$ is selected from the group consisting of P and H, and $X_{13}$ is present or absent, and if present, is Y.

HC2 Consensus

CDR2 RIKS$X_1$TDGGTTDY$X_2$APVKG (SEQ ID NO:124), wherein $X_1$ is selected from the group consisting of K and T, and $X_2$ is selected from the group consisting of T and A.

HC3 Consensus

CDR1 $X_1$Y$X_2$M$X_3$ (SEQ ID NO:125), wherein $X_1$ is selected from the group consisting of T and S, $X_2$ is selected from the group consisting of S and A, and $X_3$ is selected from the group consisting of N and S.

CDR2 $X_1$IS$X_2$S$X_3X_4X_5X_6$YYADSVKG (SEQ ID NO:126), wherein $X_1$ is selected from the group consisting of S and A, $X_2$ is selected from the group consisting of S and G, $X_3$ is selected from the group consisting of S and G, $X_4$ is selected from the group consisting of S and G, $X_5$ is selected from the group consisting of Y and R, and $X_6$ is selected from the group consisting of R and T.

CDR3 $X_1X_2X_3X_4X_5X_6X_7$PYS$X_8X_9$WYDYYYGMDV (SEQ ID NO:127), wherein $X_1$ is selected from the group consisting of E and D, $X_2$ is selected from the group consisting of G and Q, $X_3$ is selected from the group consisting of V and R, $X_4$ is selected from the group consisting of S and E, $X_5$ is selected from the group consisting of G and V, $X_6$ is selected from the group consisting of S and G, $X_7$ is present or absent, and if present, is S, $X_8$ is selected from the group consisting of I and S, and $X_9$ is selected from the group consisting of S and G.

HC4 Consensus

CDR1 S$X_1$GMH (SEQ ID NO:128), wherein $X_1$ is selected from the group consisting of F and Y.

CDR2 VIS$X_1$DGS$X_2$KY$X_3X_4$DSVKG (SEQ ID NO:129), wherein $X_1$ is selected from the group consisting of F and Y, $X_2$ is selected from the group consisting of I and H, $X_3$ is selected from the group consisting of S and Y, and $X_4$ is selected from the group consisting of V and A.

CDR3 $X_1$R$X_2X_3X_4X_5X_6$S$X_7X_8$YY$X_9X_{10}X_{11}$YYG$X_{12}X_{13}$V (SEQ ID NO:130), wherein $X_1$ is selected from the group consisting of D and E, $X_2$ is selected from the group consisting of L and K, $X_3$ is selected from the group consisting of N and R, $X_4$ is selected from the group consisting of Y and V, $X_5$ is selected from the group consisting of Y and T, $X_6$ is selected from the group consisting of D and M, $X_7$ is selected from the group consisting of S and T, $X_8$ is selected from the group consisting of G and L, $X_9$ is selected from the group consisting of H and Y, $X_{10}$ is present or absent, and if present, is Y, $X_{11}$ is selected from the group consisting of K and F, $X_{12}$ is selected from the group consisting of M and L, and $X_{13}$ is selected from the group consisting of A and D.

HCA Consensus

CDR1 $X_1X_2X_3MX_4$ (SEQ ID NO:131), wherein $X_1$ is selected from the group consisting of N and S, $X_2$ is selected from the group consisting of A, Y and F, $X_3$ is selected from the group consisting of W, A and G, and $X_4$ is selected from the group consisting of S and H.

CDR2

$X_1IX_2X_3X_4X_5X_6GX_7X_8X_9X_{10}X_{11}X_{12}X_{13}X_{14}VKG$ (SEQ ID NO:132), wherein $X_1$ is selected from the group consisting of R, A and V, $X_2$ is selected from the group consisting of K, S and W, $X_3$ is selected from the group consisting of S, G, F and Y, $X_4$ is present or absent, and if present, is selected from the group consisting of K and T, $X_5$ is present or absent, and if present, is T, $X_6$ is selected from the group consisting of D and S, $X_7$ is selected from the group consisting of G and S, $X_8$ is selected from the group consisting of T, R, I, N and H, $X_9$ is selected from the group consisting of T and K, $X_{10}$ is selected from the group consisting of D and Y, $X_{11}$ is selected from the group consisting of Y and S, $X_{12}$ is selected from the group consisting of T, A and V, $X_{13}$ is selected from the group consisting of A and D, and $X_{14}$ is selected from the group consisting of P and S.

CDR3

$X_1X_2X_3X_4X_5X_6X_7X_8X_9X_{10}X_{11}X_{12}X_{13}X_{14}X_{15}X_{16}X_{17}GX_{18}X_{19}V$ (SEQ ID NO:133), wherein $X_1$ is selected from the group consisting of D, A and E, $X_2$ is selected from the group consisting of R, Q and G, $X_3$ is selected from the group consisting of T, R, L, G and K, $X_4$ is selected from the group consisting of G, E, N, I and R, $X_5$ is selected from the group consisting of Y, V and A, $X_6$ is selected from the group consisting of S, G, Y, A and T, $X_7$ is selected from the group consisting of I, P, D, A and M, $X_8$ is present or absent, and if present, is selected from the group consisting of S and Y, $X_9$ is present or absent, and if present, is selected from the group consisting of W, S and T, $X_{10}$ is selected from the group consisting of S, G and L, $X_{11}$ is selected from the group consisting of S, G, L and Y, $X_{12}$ is present or absent, and if present, is selected from the group consisting of W and Y, $X_{13}$ is selected from the group consisting of Y and H, $X_{14}$ is present or absent, and if present, is selected from the group consisting of Y and D, $X_{15}$ is selected from the group consisting of Y, K and F, $X_{16}$ is present or absent, and if present, is Y, $X_{17}$ is present or absent, and if present, is Y, $X_{18}$ is selected from the group consisting of M and L, and $X_{19}$ is selected from the group consisting of D and A.

HCB Consensus

CDR1 $X_1X_2X_3X_4X_5$ (SEQ ID NO:134), wherein $X_1$ is selected from the group consisting of N, G, D, S and A, $X_2$ is selected from the group consisting of A, F and Y, $X_3$ is selected from the group consisting of W, Y, A and G, $X_4$ is selected from the group consisting of M and L, and $X_5$ is selected from the group consisting of S and H.

CDR2

$X_1IX_2X_3X_4X_5X_6X_7X_8X_9X_{10}X_{11}X_{12}X_{13}X_{14}X_{15}X_{16}X_{17}G$ (SEQ ID NO:135), wherein $X_1$ is selected from the group consisting of R, W, A, V, S and F, $X_2$ is selected from the group consisting of K, N, S, W and R, $X_3$ is selected from the group consisting of S, P, G, F and Y, $X_4$ is present or absent, and if present, is selected from the group consisting of K, T and R, $X_5$ is present or absent, and if present, is selected from the group consisting of T and A, $X_6$ is selected from the group consisting of D, N, H, S and Y, $X_7$ is selected from the group consisting of G and S, $X_8$ is selected from the group consisting of G and S, $X_9$ is selected from the group consisting of T, G, R, I, N, H and Y, $X_{10}$ is selected from the group consisting of T, K, R and P, $X_{11}$ is selected from the group consisting of D, N, Y and E, $X_{12}$ is selected from the group consisting of Y and S, $X_{13}$ is selected from the group consisting of T, A and V, $X_{14}$ is selected from the group consisting of A, Q and D, $X_{15}$ is selected from the group consisting of P, K and S, $X_{16}$ is selected from the group consisting of V and F, and $X_{17}$ is selected from the group consisting of K and Q.

CDR3

$X_1X_2X_3X_4X_5SX_6X_7X_8X_9X_{10}X_{11}X_{12}X_{13}X_{14}X_{15}X_{16}GX_{17}X_{18}V$ (SEQ ID NO:136), wherein $X_1$ is selected from the group consisting of D, G, A and E, $X_2$ is selected from the group consisting of R, G and Q, $X_3$ is selected from the group consisting of T, M, Y, R, L, G and K, $X_4$ is selected from the group consisting of G, S, E, N, I and R, $X_5$ is selected from the group consisting of Y, I, G, V and A, $X_6$ is selected from the group consisting of S, I, Y, G, A and T, $X_7$ is selected from the group consisting of I, M, A, P and D, $X_8$ is present or absent, and if present, is selected from the group consisting of S, L and Y, $X_9$ is present or absent, and if present, is selected from the group consisting of W, R, S and T, $X_{10}$ is selected from the group consisting of S, G and L, $X_{11}$ is selected from the group consisting of S, V, L, G and Y, $X_{12}$ is present or absent, and if present, is selected from the group consisting of F, Y and W, $X_{13}$ is selected from the group consisting of Y, P, S and H, $X_{14}$ is present or absent, and if present, is selected from the group consisting of Y, P, D and H, $X_{15}$ is selected from the group consisting of Y, K and F, $X_{16}$ is present or absent, and if present, is Y, $X_{17}$ is present or absent, and if present, is Y and $X_{18}$ is selected from the group consisting of M and L.

In any of the above-mentioned consensus sequence defined embodiments, the isolated antigen-binding protein may be, for example, an AVIMER polypeptide, a monoclonal antibody, a polyclonal antibody, a recombinant antibody, a human (e.g., fully human) antibody, a humanized antibody, a chimeric antibody, a multi-specific antibody, or an antigen binding fragment thereof. Further, the antibody fragment of the isolated antigen-binding proteins may be a Fab fragment, and Fab' fragment, an F(ab')$_2$ fragment, an Fv fragment, a diabody, or a single chain antibody molecule. For example, the isolated antigen binding protein may be a human monoclonal antibody, and may be, e.g., an IgG1-, IgG2-, IgG3-, or IgG4-type antibody. Further, the isolated antigen binding proteins may be neutralizing antigen binding proteins.

In any of the above-mentioned consensus sequence defined embodiments, the isolated antigen-binding protein may specifically bind to both human CRLR and human RAMP1 and not specifically bind to AM1, AM2 or a human amylin receptor (e.g., AMY1), for example, the isolated antigen binding protein may specifically bind to human CGRP R with a $K_D \leq 1$ µM, ≤100 nM, ≤10 nM, or ≤5 nM, e.g., as determined using a FACS binding assay and analyzed, for example, using methods described in Rathanaswami, et al., *Biochemical and Biophysical Research Communications* 334 (2005) 1004-1013. In any of the above-mentioned consensus sequence defined embodiments, the isolated antigen-binding protein may selectively inhibit human CGRP R, relative to the human the AM1, AM2 or AMY1 receptors, e.g., with a selectivity ratio of 100 or more, 250 or more, 500 or more, 750 or more, 1,000 or more, 2,500 or more, 5,000 or more or 10,000 or more, where the degree of selective inhibition may be determined using any suitable method, e.g., using a cAMP assay as described in the Examples herein. In any of the above-mentioned consensus sequence defined embodiments, the isolated antigen-binding protein may have a Ki of ≤100 nM, ≤10 nM, ≤1 nM, ≤0.5 nM or ≤0.1 nM in a CGRP binding competition assay, e.g., in a radiolabeled $^{125}$I-CGRP binding competition assay to membranes from cells expressing human CGRP R, e.g., the assay described in Example 5 herein.

Some of the isolated antigen-binding proteins described comprise a heavy chain variable region ($V_H$) sequence that has at least 80%, 85%, and 90% or 95% sequence identity with an amino acid sequence selected from the group consisting of SEQ ID NOs:158-170. Some of the isolated antigen-binding proteins described comprise a light chain variable region ($V_L$) sequence that has at least 80%, 85%, and 90% or 95% sequence identity with an amino acid sequence selected from the group consisting of SEQ ID NOs:137-153. Some of the isolated antigen-binding proteins described comprise a $V_H$ sequence that has at least 80%, 85%, 90% or 95% sequence identity with an amino acid sequence selected from the group consisting of SEQ ID NOs:158-170, and a $V_L$ that has at least 80%, 85%, 90% or 95% sequence identity with an amino acid sequence selected from the group consisting of SEQ ID NOs:137-153. In some embodiments, the isolated antigen-binding proteins comprise (A) a heavy chain variable region ($V_H$) comprising a sequence (i) selected from the group consisting of SEQ ID NOs:158-170, or (ii) as defined by (i) and containing one or more (e.g., five, ten, fifteen or twenty) amino acid substitutions (e.g., conservative amino acid substitutions), deletions or insertions; (B) a $V_L$ comprising a sequence (iii) selected from the group consisting of SEQ ID NOs:137-153, or (iv) as defined by (iii) containing one or more (e.g., five, ten, fifteen or twenty) amino acid substitutions (e.g., conservative amino acid substitutions), deletions or insertions; or (C) a $V_H$ of (A) and a $V_L$ of (B). In some embodiments, the isolated antigen-binding proteins comprise a heavy chain variable region ($V_H$) comprising a sequence selected from the group consisting of SEQ ID NOs:158-170 and a $V_L$ comprising a sequence selected from the group consisting of SEQ ID NOs:137-153.

In one embodiment, the isolated antigen-binding protein comprises a heavy chain variable region ($V_H$) comprising an amino acid sequence selected from the group consisting of (i) SEQ ID NO:158, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:159, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:160, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:161, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:162, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:163, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:164, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:165, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:166, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:167, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:168, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:169, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_H$ comprising an amino acid sequence selected from the group consisting of (i) SEQ ID NO:170, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In one embodiment, the isolated antigen-binding protein comprises a light chain variable region ($V_L$) comprising an amino acid sequence selected from the group consisting of (i) SEQ ID NO:137, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:138, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:139, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:140, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:141, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:142, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:143, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:144, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:145, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:146, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:147, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:148, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:149, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:150, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:151, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:152, (ii) a sequence that is at least 90% or 95% identical to the sequence defined by (i), and (iii) a sequence as defined by (i) containing up to ten amino acid substitutions (e.g., conservative amino acid substitutions), deletions or insertions. In another embodiment, the isolated antigen-binding protein comprises a $V_L$ comprising an amino acid sequence selected from the group consisting of (i) SEQ ID NO:153, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In any of the above-mentioned $V_L$ and $V_H$ sequence defined embodiments, the isolated antigen-binding protein may be, for example, a monoclonal antibody, a polyclonal antibody, a recombinant antibody, a human (e.g., fully human) antibody, a humanized antibody, a chimeric antibody, a multi-specific antibody, or an antigen binding fragment thereof. Further, the antibody fragment of the isolated antigen-binding proteins may be a Fab fragment, and Fab' fragment, an $F(ab')_2$ fragment, an Fv fragment, a diabody, or a single chain antibody molecule. For example, the isolated antigen binding protein may be a human monoclonal antibody, and may be, e.g., an IgG1-, IgG2-, IgG3-, or IgG4-type antibody. Further, the isolated antigen binding proteins may be neutralizing antigen binding proteins.

In any of the above-mentioned $V_L$ and $V_H$ sequence defined embodiments, the isolated antigen-binding protein may specifically bind to both human CRLR and human RAMP1 and not specifically bind to AM1, AM2 or a human amylin receptor (e.g., AMY1), for example, the isolated antigen binding protein may specifically bind to human CGRP R with a $K_D \leq 1$ µM, ≤100 nM, ≤10 nM, or ≤5 nM, e.g., as determined using a FACS binding assay and analyzed, for example, using methods described in Rathanaswami, et al., *Biochemical and Biophysical Research Communications* 334 (2005) 1004-1013.

In any of the above-mentioned $V_L$ and $V_H$ sequence defined embodiments, the isolated antigen-binding protein may selectively inhibit human CGRP R, relative to the human the AM1, AM2 or AMY1 receptors, e.g., with a selectivity ratio of 100 or more, 250 or more, 500 or more, 750 or more, 1,000 or more, 2,500 or more, 5,000 or more or 10,000 or more, where the degree of selective inhibition may be determined using any suitable method, e.g., using a cAMP assay as described in the Examples herein. In any of the above-mentioned $V_L$ and $V_H$ sequence-defined embodiments, the isolated antigen-binding protein may have a Ki of ≤100 nM, ≤10 nM, ≤1 nM, ≤0.5 nM or ≤0.1 nM in a CGRP binding competition assay, e.g., in a radiolabeled $^{125}$I-CGRP binding competition assay to membranes from cells expressing human CGRP R, e.g., the assay described in Example 5 herein.

In one aspect, the isolated antigen-binding proteins comprise a heavy chain sequence that has at least 80%, 85%, 90% or 95% sequence identity with an amino acid sequence selected from the group consisting of SEQ ID NOs:29-41. Some of the isolated antigen-binding proteins described comprise a light chain sequence that has at least 80%, 85%, 90% or 95% sequence identity with an amino acid sequence selected from the group consisting of SEQ ID NOs:12-28. Some of the isolated antigen-binding proteins comprise a heavy chain sequence that has at least 80%, 85%, 90% or 95% sequence identity with an amino acid sequence selected from the group consisting of SEQ ID NOs: 29-41, and a light chain sequence that has at least 80%, 85%, 90% or 95% sequence identity with an amino acid sequence selected from the group consisting of SEQ ID NOs: 12-28. In some embodiments, the isolated antigen-binding proteins comprise (A) a heavy chain comprising a sequence (i) selected from the group consisting of SEQ ID NOs: 29-41, or (ii) as defined by (i) and containing one or more (e.g., five, ten, fifteen or twenty) amino acid substitutions (e.g., conservative amino acid substitutions), deletions or insertions; (B) a light chain comprising a sequence (iii) selected from the group consisting of SEQ ID NOs: 12-28, or (iv) as defined by (iii) containing one or more (e.g., five, ten, fifteen or twenty) amino acid substitutions (e.g., conservative amino acid substitutions), deletions or insertions; or (C) a heavy chain of (A) and a light chain of (B). In some embodiments, the isolated antigen-binding proteins comprise a heavy chain comprising a sequence selected from the group consisting of SEQ ID NOs: 29-41 and a light chain comprising a sequence selected from the group consisting of SEQ ID NOs: 12-28.

In one embodiment, the isolated antigen-binding protein comprises (A) a heavy chain comprising an amino acid sequence selected from the group consisting of (i) SEQ ID NO:29, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:12, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:30, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:13, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:31, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:14, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:32, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:15, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:33, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:16, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:29, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:17, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:34, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:18, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:33, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:19, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:29, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:20, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:35, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:21, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:36, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:22, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:37, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:23, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:38, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:23, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:33, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:24, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:39, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:25, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:40, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:26, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:41, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:27, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In another embodiment, the isolated antigen-binding protein comprises (A) a heavy chain comprising an amino acid sequence selected from the group consisting of (i) SEQ ID NO:41, (ii) a sequence that is at least 90% or 95% identical to the sequence defined by (i), and (iii) a sequence as defined by (i) containing up to ten amino acid substitutions (e.g., conservative amino acid substitutions), deletions or insertions; and (B) a light chain comprising an amino acid sequence selected from the group consisting of (i) SEQ ID NO:28, (ii) a sequence that is at least 90% or 95% identical to the sequence defined by (i), and (iii) a sequence as defined by (i) containing up to ten amino acid substitutions (e.g., conservative amino acid substitutions), deletions or insertions.

In any of the above-mentioned light and heavy chain sequence defined embodiments, the isolated antigen-binding protein may comprise the specified heavy and/or light chain sequence, but with a different signal peptide or with no signal peptide. In any of the above-mentioned light and heavy chain sequence defined embodiments, the isolated antigen-binding protein may be, for example, a monoclonal antibody, a polyclonal antibody, a recombinant antibody, a human (e.g., fully human) antibody, a humanized antibody, a chimeric antibody, a multi-specific antibody, or an antigen binding fragment thereof. Further, the antibody fragment of the isolated antigen-binding proteins may be a Fab fragment, and Fab' fragment, an F(ab')$_2$ fragment, an Fv fragment, a diabody, or a single chain antibody molecule. For example, the isolated antigen binding protein may be a human monoclonal antibody, and may be, e.g., an IgG1-, IgG2-, IgG3-, or IgG4-type antibody. Further, the isolated antigen binding proteins may be neutralizing antigen binding proteins.

In any of the above-mentioned light and heavy chain sequence defined embodiments, the isolated antigen-binding protein may specifically bind to both human CRLR and human RAMP1 and not specifically bind to AM1, AM2 or a human amylin receptor (e.g., AMY1), for example, the isolated antigen binding protein may specifically bind to human CGRP R with a $K_D \leq 1$ µM, $\leq 100$ nM, $\leq 10$ nM, or $\leq 5$ nM, e.g., as determined using a FACS binding assay and analyzed, for example, using methods described in Rathanaswami, et al., *Biochemical and Biophysical Research Communications* 334 (2005) 1004-1013. In any of the above-mentioned light and heavy chain sequence defined embodiments, the isolated antigen-binding protein may selectively inhibit human CGRP R, relative to the human the AM1, AM2 or AMY1 receptors, e.g., with a selectivity ratio of 100 or more, 250 or more, 500 or more, 750 or more, 1,000 or more, 2,500 or more, 5,000 or more or 10,000 or more, where the degree of selective inhibition may be determined using any suitable method, e.g., using a cAMP assay as described in the Examples herein. In any of the above-mentioned light and heavy chain sequence-defined embodiments, the isolated antigen-binding protein may have a Ki of $\leq 100$ nM, $\leq 10$ nM, $\leq 1$ nM, $\leq 0.5$ nM or $\leq 0.1$ nM in a CGRP binding competition assay, e.g., in a radiolabeled $^{125}$I-CGRP binding competition assay to membranes from cells expressing human CGRP R, e.g., the assay described in Example 5 herein.

In a further aspect, also provided are isolated nucleic acid polynucleotides that encode any of the CGRP R antigen-binding proteins summarized above. In one embodiment, the isolated polynucleotide comprises a sequence selected from the group consisting of SEQ ID NOs:175, 176, 178, 179, 180, 181, 182, 183, 186, 187, 188, 189, 191, 192, 193, 194, 195, 196, 197, 200, 201, 202, 203, 204, 205, 206, 207, 208, 209 and 210. In another embodiment, the isolated polynucleotide comprises a sequence selected from the group consisting of SEQ ID NOs:224-258. In another embodiment, the isolated polynucleotide comprises a sequence capable of hybridizing under stringent hybridization conditions with a sequence selected from the group consisting of SEQ ID NOs:224-258. In another embodiment, the isolated polynucleotide comprises a sequence that is about 80%, 85%, 90% or 95% or more identical to a sequence selected from the group consisting of SEQ ID NOs:224-258. In some instances, the isolated nucleic acid molecules are operably-linked to a control sequence. In related embodiments, the isolated polynucleotides are incorporated into an expression vector.

Also included are cell lines transformed with expression vectors comprising isolated polynucleotides as described above. In a related aspect, also provided are expression vectors and host cells transformed or transfected with the expression vectors that comprise the aforementioned isolated nucleic acid molecules that encode CGRP R antigen-binding proteins described above In another aspect, also provided is a method of preparing the antigen-binding proteins that includes the step of preparing the antigen binding protein from a host cell that secretes the antigen-binding protein. In some embodiments, the antigen binding protein is generated using an immunogen comprising soluble CGRP receptor. In some embodiments, such soluble CGRP receptor is obtained by co-expressing and purifying an N-terminal extracellular domain (ECD) of human CRLR and an ECD of human RAMP1, e.g., an ECD of human CRLR comprising SEQ ID NO: 6 and an ECD of RAMP1 comprising SEQ ID NO: 8, for example, as described in Examples 1 and 2 herein.

In yet another aspect, a pharmaceutical composition is provided comprising at least one of the antigen-binding proteins summarized above and a pharmaceutically acceptable excipient. In one embodiment, the pharmaceutical composition may comprise an additional active agent that is selected from the group consisting of a radioisotope, radionuclide, a toxin, or a therapeutic and a chemotherapeutic group.

In one aspect, the isolated antigen binding protein is effective to inhibit vasodialation and/or decrease neurogenic inflammation when administered to a patient. In one embodiment, the isolated antigen binding protein is effective to reduce the frequency and/or severity of headaches, for example, migraine headaches. For example, the antigen binding protein may be used as an acute treatment of migraine, and/or as a prophylactic treatment to prevent or reduce the frequency and/or severity of symptoms, particularly pain symptoms, associated with a migraine attack.

Other aspects further provide methods for treating or preventing a condition associated with CGRP R in a patient, comprising administering to a patient an effective amount of at least one isolated antigen-binding protein summarized above. In one embodiment, the condition is a headache, for example, a migraine headache or a cluster headache or another type of pain, e.g., a chronic pain; in another embodiment it is diabetes mellitus (type II); in another embodiment it is inflammation, particularly neurogenic inflammation; in another embodiment it is a cardiovascular disorder; in another embodiment it is a hemodynamic derangement associated with endotoxemia and sepsis; in another embodiment it is vasodialation.

In another aspect, also provided is a method of inhibiting binding of CGRP to human CGRP R, e.g., the extracellular portion of CGRP R, in a patient comprising administering an effective amount of at least one antigen-binding protein provided herein and/or summarized above.

These and other aspects will be described in greater detail herein. Each of the aspects provided can encompass various embodiments provided herein. It is therefore anticipated that each of the embodiments involving one element or combinations of elements can be included in each aspect described, and all such combinations of the above aspects and embodiments are expressly considered. Other features, objects, and advantages of the invention are apparent in the detailed description that follows.

BRIEF DESCRIPTION OF THE DRAWINGS

FIG. 1 shows an alignment of RAMP-1 sequences from human (SEQ ID NO:4), cynomolgus monkey (SEQ ID NO:215) and rat (SEQ ID NO:214).

FIG. 2 shows an alignment of CRLR sequences from human (SEQ ID NO:2), cynomolgus monkey (SEQ ID NO221) and rat (SEQ ID NO.220).

FIGS. 3A and 3B show phylogenetically-based sequence alignments of light chain CDRs from the indicated anti-CGRP receptor antibody clones having kappa light chains, and certain corresponding consensus sequences.

FIG. 4 shows phylogenetically-based sequence alignments of light chain CDRs from the indicated anti-CGRP receptor antibody clones having lambda light chains, and certain corresponding consensus sequences.

FIGS. 5A, 5B, 5C, 5D and 5E show phylogenetically-based sequence alignments of heavy chain CDRs from the indicated anti-CGRP receptor antibody clones, and certain corresponding consensus sequences.

FIG. 5F shows consensus sequences of exemplary anti-CGRP receptor antibody heavy chain CDRs disclosed herein.

FIG. 10 shows a FACS Kd determination of mAb 12G8.

FIG. 11 shows an alignment of cynomolgus (SEQ ID NO:215), human (SEQ ID NO:4), human chimeras (SEQ ID NOs: 217, 218, and 219), rat (SEQ NO:214), and rhesus RAMP1(SEQ ID NO:216) sequences.

FIGS. 12A-B shows an alignment of human (SEQ ID NO:2), cynomolgus (SEQ ID NO:221), rhesus (SEQ ID NO: 222), rat )SEQ ID NO:220), and human chimera (SEQ ID NO:223) CRLR sequences.

FIGS. 13A-13C show representative FACS data of different chimeric CGRP receptors binding to anti-CGRP R antibodies.

DETAILED DESCRIPTION

Figure 6:
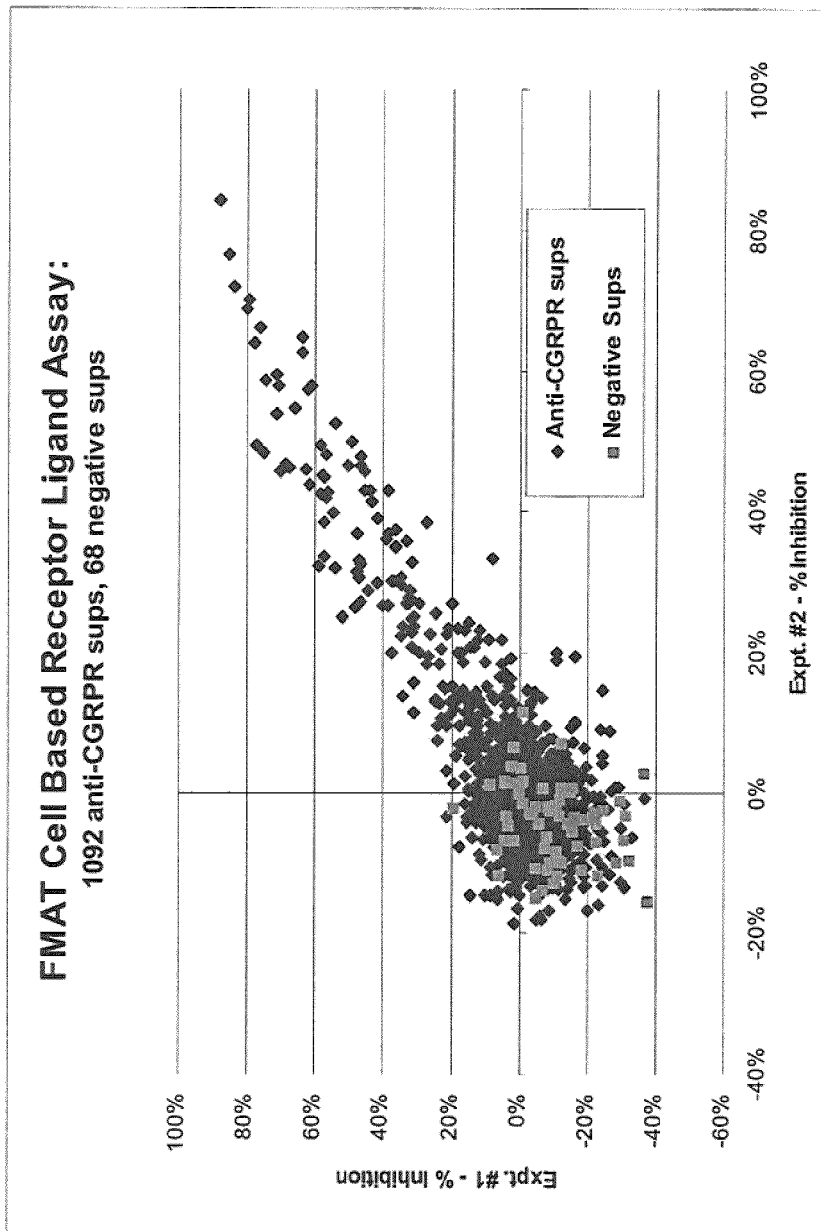
FIG. 6 is a plot of data from two experiments showing percent inhibition of labeled ligand binding to CGRP R by 1092 anti-CGRP R hybridoma supernatants (diamonds) and 68 negative control supernatants (squares).

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages means±1%.

Definitions

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transduction" means the transfer of genes from one bacterium to another, usually by bacteriophage. "Transduction" also refers to the acquisition and transfer of eukaryotic cellular sequences by replication defective retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, Molecular Cloning: A Laboratory Manual, supra; Davis et al., 1986, *Basic Methods in Molecular Biology*, Elsevier; Chu et al., 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The terms "polypeptide" or "protein" are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass antigen binding proteins, e.g., CGRP R antigen-binding proteins, CGRP R binding proteins, antibodies, or sequences that have deletions from, additions to, and/or substitutions of one or more amino acids of an antigen-binding protein. The term "polypeptide fragment" refers to a polypeptide that has an amino-terminal deletion, a carboxyl-terminal deletion, and/or an internal deletion as compared with the full-length protein. Such fragments may also contain modified amino acids as compared with the full-length protein. In certain embodiments, fragments are about five to 500 amino acids long. For example, fragments may be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a CGRP R-binding antibody, useful fragments include but are not limited to a CDR region, a variable domain of a heavy or light chain, a portion of an antibody chain or just its variable domain including two CDRs, and the like. The "CGRP receptor", or "CGRP R", is understood to comprise RAMP1 and CRLR.

The term "isolated protein" (e.g., isolated antigen binding protein), "isolated polypeptide" or "isolated antibody" means that a subject protein, polypeptide or antibody (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein", "isolated polypeptide" or "isolated antibody" constitutes at least about 5%, at least about 10%, at least about 25%, or at least about 50% of a given sample. Genomic DNA, cDNA, mRNA or other RNA, of synthetic origin, or any combination thereof may encode such an isolated protein. Preferably, the isolated protein polypeptide or antibody is substantially free from other proteins or other polypeptides or other contaminants that are found in its natural environment that would interfere with its therapeutic, diagnostic, prophylactic, research or other use.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

A "derivative" of a polypeptide is a polypeptide (e.g., an antigen binding protein, or an antibody) that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

An "antigen binding protein" as used herein means a protein that specifically binds a specified target antigen, such as CGRP R, particularly primate, e.g., human CGRP R. A CGRP R antigen binding protein specifically binds the human CGRP receptor.

An antigen binding protein is said to "specifically bind" its target when the dissociation constant ($K_D$) is $\leq 10^{-6}$ M. The antibody specifically binds the target antigen with "high affinity" when the $K_D$ is $\leq 1 \times 10^{-8}$ M. In one embodiment, the antibodies will bind to CGRP R, or human CGRP R with a $K_D \leq 5 \times 10^{-7}$; in another embodiment the antibodies will bind with a $K_D \leq 1 \times 10^{-7}$; in another embodiment the antibodies will bind with a $K_D \leq 5 \times 10^{-8}$; in another embodiment the antibodies will bind with a $K_D \leq 1 \times 10^{-8}$; in another embodiment the antibodies will bind with a $K_D \leq 5 \times 10^{-9}$; in another embodiment the antibodies will bind with a $K_D \leq 1 \times 10^{-9}$; in another embodiment the antibodies will bind with a $K_D \leq 5 \times 10^{-10}$; in another embodiment the antibodies will bind with a $K_D \leq 1 \times 10^{-10}$.

An antibody, antigen binding fragment thereof or antigen binding protein "selectively inhibits" a specific receptor relative to other receptors when the IC50 of the antibody, antigen binding fragment thereof or antigen binding protein in an inhibition assay of the specific receptor is at least 50-fold lower than the IC50 in an inhibition assay of another "reference" receptor. The "selectivity ratio" is the IC50 of the reference receptor divided by IC50 of the specific receptor.

An antibody, antigen binding fragment thereof or antigen binding protein selectively inhibits the human CGRP receptor if the IC50 of the antibody, antigen binding fragment thereof or antigen binding protein in a cAMP assay, e.g., the cAMP inhibition assay as described in Example 4 herein, is at least 50-fold lower than the IC50 of that same antibody, antigen binding fragment thereof or antigen binding protein in an inhibition assay of the human AM1, AM2 or an amylin receptor (e.g., AMY1). By way of non-limiting example, if the IC50 of a specific anti-CGRP R antibody in a cAMP assay of hCGRP R is, e.g., between 0.1 nM and 20 nM, and the IC50 of the same antibody in a cAMP assay of the hAM1, hAM2 or human AMY1 receptor is 1000 nM or more, that antibody selectively inhibits the hCGRP receptor. An antigen binding protein that selectively inhibits a specific receptor is also understood to be a neutralizing antigen binding protein with respect to that receptor.

"Antigen binding region" means a protein, or a portion of a protein, that specifically binds a specified antigen. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen.

In certain aspects, recombinant antigen binding proteins that bind CGRP R protein, or human CGRP R, are provided. In this context, a "recombinant protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or an antigen binding fragment thereof that can compete with the intact antibody for specific binding to the target antigen, and includes, for instance, chimeric, humanized, fully human, and bispecific antibodies. An "antibody" as such is a species of an antigen binding protein. An intact antibody generally will comprise at least two full-length heavy chains and two full-length light chains, but in some instances may include fewer chains such as antibodies naturally occurring in camelids which may comprise only heavy chains. Antibodies may be derived solely from a single source, or may be "chimeric," that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and mutations thereof, examples of which are described below.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains may be of any isotype, including IgG (including IgG1, IgG2, IgG3 and IgG4 subtypes), IgA (including IgA1 and IgA2 subtypes), IgM and IgE.

The term "signal sequence", "leader sequence" or "signal peptide" refers to a short (3-60 amino acids long) peptide chain that directs the transport of a protein. Signal peptides may also be called targeting signals, signal sequences, transit peptides, or localization signals. Some signal peptides are cleaved from the protein by signal peptidase after the proteins are transported, such that the biologically active form of the protein (e.g., an antigen binding protein as described herein) is the cleaved, shorter form. Accordingly, terms such as "antibody comprising a heavy chain . . . ", "antibody comprising a light chain . . . ", etc., where the antibody is characterized as having a heavy and/or light chain with a particular identified sequence, are understood to include antibodies having the specific identified sequences, antibodies having the specific identified sequences except that the signal sequences are replaced by different signal sequences, as well as antibodies having the identified sequences, minus any signal sequences.

The term "antigen binding fragment" (or simply "fragment") of an antibody or immunoglobulin chain (heavy or light chain), as used herein, comprises a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope. In one aspect, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of antigen binding proteins, including intact antibodies. Immunologically functional immunoglobulin fragments include, but are not limited to, Fab, Fab', F(ab')$_2$, Fv, domain antibodies and single-chain antibodies, and may be derived from any mammalian source, including but not limited to human, mouse, rat, camelid or rabbit. It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

An "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

An "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an F(ab')$_2$ molecule.

An "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antigen binding protein" or "bivalent antibody" comprises two antigen binding sites. In some instances, the two binding sites have the same antigen specificities. Bivalent antigen binding proteins and bivalent antibodies may be bispecific, see, infra.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein or multispecific antibody and may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553. The two binding sites of a bispecific antigen binding protein or antibody will bind to two different epitopes, which may reside on the same or different protein targets.

The term "neutralizing antigen binding protein" or "neutralizing antibody" refers to an antigen binding protein or antibody, respectively, that binds to a ligand, prevents binding of the ligand to its binding partner and interrupts the biological response that otherwise would result from the ligand binding to its binding partner. In assessing the binding and specificity of an antigen binding protein, e.g., an antibody or immunologically functional antigen binding fragment thereof, an antibody or fragment will substantially inhibit binding of a ligand to its binding partner when an excess of antibody reduces the quantity of binding partner bound to the ligand by at least about 20%, 30%, 40%, 50%, 60%, 70%, 80%, 85%, 90%, 95%, 97%, 99% or more (as measured in an in vitro competitive binding assay). In the case of a CGRP R binding protein, such a neutralizing molecule will diminish the ability of CGRP R to bind CGRP.

The term "compete", when used in the context of antigen binding proteins that may bind the same region on a target antigen, means competition between antigen binding proteins is determined by an assay in which the antigen binding protein (e.g., antibody or immunologically functional antigen binding fragment thereof) under test prevents or inhibits specific binding of a reference antigen binding protein (e.g., a ligand, or a reference antibody) to a common antigen (e.g., CGRP R or an antigen binding fragment thereof). Any of a number of competitive binding assays can be used, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using 1-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82). Such an assay may involve the use of purified antigen bound to a solid surface or cells bearing either of these, an unlabelled test antigen binding protein and a labeled reference antigen binding protein. Competitive inhibition may measured by determining the amount of label bound to the solid surface or cells in the presence of the test antigen binding protein. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for stearic hindrance to occur. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 95%, or 97% or more. Competitive inhibition may also be measured by immobilizing a reference antigen binding protein to a substrate, e.g., a "sensor chip", capturing antigen on the substrate via binding to the reference antibody, and assaying whether a different antigen binding protein (a competing antigen binding protein) can additionally bind to the antigen. An example of the latter competitive binding assay employs a Biacore analysis, and is described in Example 7 herein.

The term "antigen" or "immunogen" refers to a molecule or a portion of a molecule capable of being bound by a selective binding agent, such as an antigen binding protein (including, e.g., an antibody or immunological functional antigen binding fragment thereof), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, an antibody). The term includes any determinant capable of specifically binding to an antigen binding protein, such as an antibody or to a T-cell receptor. An epitope can be contiguous or non-contiguous (e.g., (i) in a single-chain polypeptide, amino acid residues that are not contiguous to one another in the polypeptide sequence but that within in context of the molecule are bound by the antigen binding protein, or (ii) in a multimeric receptor, e.g., CGRP R, comprising two or more individual components, e.g., RAMP1 and CRLR, amino acid residues present on two or more of the individual components, but that within the context of the multimeric receptor are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, *J. Mol. Biol.* 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods presented herein successfully treat migraine headaches either prophylactically or as an acute treatment, decreasing the frequency of migraine headaches, decreasing the severity of migraine headaches, and/or ameliorating a symptom associated with migraine headaches.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with migraine headache. In some embodiments, the effective amount is a therapeutically effective amount or a prophylactically effective amount. A "therapeutically effective amount" is an amount sufficient to remedy a disease state (e.g. migraine headache) or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount of a pharmaceutical composition that, when administered to a subject, will have the intended prophylactic effect, e.g., preventing or delaying the onset (or reoccurrence) of migraine headache, or reducing the likelihood of the onset (or reoccurrence) of migraine headache or migraine headache symptoms. The full therapeutic or prophylactic effect does not necessarily occur by administration of one dose, and may occur only after administration of a series of doses. Thus, a therapeutically or prophylactically effective amount may be administered in one or more administrations.

"Amino acid" includes its normal meaning in the art. The twenty naturally-occurring amino acids and their abbreviations follow conventional usage. See, Immunology-A Synthesis, 2nd Edition, (E. S. Golub and D. R. Green, eds.), Sinauer Associates: Sunderland, Mass. (1991), incorporated herein by reference for any purpose. Stereoisomers (e.g., D-amino acids) of the twenty conventional amino acids, unnatural amino acids such as α-,α-disubstituted amino acids, N-alkyl amino acids, and other unconventional amino acids may also be suitable components for polypeptides and are included in the phrase "amino acid." Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

General Overview

Antigen-binding proteins that bind CGRP R protein, including human CGRP R (hCGRP R) protein are provided herein. The antigen binding proteins provided are polypeptides into which one or more complementary determining regions (CDRs), as described herein, are embedded and/or joined. In some antigen binding proteins, the CDRs are embedded into a "framework" region, which orients the CDR(s) such that the proper antigen binding properties of the CDR(s) is achieved. In general, antigen binding proteins that are provided can interfere with, block, reduce or modulate the interaction between CGRP and CGRP R.

Certain antigen binding proteins described herein are antibodies or are derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof. The various structures are further described herein below.

The antigen binding proteins provided herein have been demonstrated to bind to CGRP R, in particular human CGRP R. As described further in the examples below, certain antigen binding proteins were tested and found to bind to epitopes different from those bound by a number of other antibodies directed against one or the other of the components of CGRP R. The antigen binding proteins that are provided compete with CGRP and thereby prevent CGRP from binding to its receptor. As a consequence, the antigen binding proteins provided herein are capable of inhibiting CGRP R activity. In particular, antigen binding proteins binding to these epitopes can have one or more of the following activities: inhibiting, inter alia, induction of CGRP R signal transduction pathways, inhibiting vasodialation, causing vasoconstriction, decreasing inflammation, e.g., neurogenic inflammation, and other physiological effects induced by CGRP R upon CGRP binding.

The antigen binding proteins that are disclosed herein have a variety of utilities. Some of the antigen binding proteins, for instance, are useful in specific binding assays, affinity purification of CGRP R, in particular hCGRP R or its ligands and in screening assays to identify other antagonists of CGRP R activity. Some of the antigen-binding proteins are useful for inhibiting binding of CGRP to CGRP R.

The antigen-binding proteins can be used in a variety of treatment applications, as explained herein. For example, certain CGRP R antigen-binding proteins are useful for treating conditions associated with CGRP R mediated signaling, such as reducing, alleviating, or treating the frequency and/or severity of migraine headache, reducing, alleviating, or treating cluster headache, reducing, alleviating, or treating chronic pain, alleviating or treating diabetes mellitus (type II), reducing, alleviating, or treating cardiovascular disorders, and reducing, alleviating, or treating hemodynamic derangements associated with endotoxemia and sepsis in a patient. Other uses for the antigen binding proteins include, for example, diagnosis of CGRP R-associated diseases or conditions and screening assays to determine the presence or absence of CGRP R. Some of the antigen binding proteins described herein are useful in treating consequences, symptoms, and/or the pathology associated with CGRP R activity. These include, but are not limited to, various types of migraine headaches.

CGRP Receptor

The antigen binding proteins disclosed herein bind to CGRP R, in particular human CGRP R. CGRP R is a multimer that includes both CRLR and RAMP1. The nucleotide sequence of human CRLR is provided herein as SEQ ID NO:1. The amino acid sequence of human CRLR is provided herein as SEQ ID NO:2. The nucleotide sequence of human RAMP1 is provided herein as SEQ ID NO:3. The amino acid sequence of human RAMP1 is provided herein as SEQ ID NO:4. The antigen binding proteins described herein bind the extracellular portion of CGRP R, which comprises the extracellular portions of CRLR and RAMP1. An exemplary extracellular domain ("ECD") of human CRLR is encoded by the nucleotide sequence presented as SEQ ID NO:5, and has the amino acid sequence presented as SEQ ID NO:6. This sequence includes a signal peptide; an exemplary mature (minus the signal peptide) CRLR ECD has the amino acid sequence presented as SEQ ID NO:10. An exemplary ECD of human RAMP1 is encoded by the nucleotide sequence presented as SEQ ID NO:7, and has the amino acid sequence presented as SEQ ID NO:8. This sequence includes a signal peptide; an exemplary mature (minus the signal peptide) RAMP1 ECD has the amino acid sequence presented as SEQ ID NO:11. As described below, CGRP R proteins may also include fragments. As used herein, the terms are used interchangeably to mean a receptor, in particular, unless otherwise specified, a human receptor that binds specifically to CGRP.

The term CGRP R also includes post-translational modifications of the CGRP R amino acid sequence, for example, possible N-linked glycosylation sites. Thus, the antigen binding proteins may bind to or be generated from proteins glycosylated at one or more of the positions.

CGRP Receptor Binding Proteins

A variety of selective binding agents useful for regulating the activity of CGRP R are provided. These agents include, for instance, antigen binding proteins that contain an antigen binding domain (e.g., single chain antibodies, domain antibodies, immunoadhesions, and polypeptides with an antigen binding region) and specifically bind to CGRP R, in particular human CGRP R. Some of the agents, for example, are useful in inhibiting the binding of CGRP to CGRP R, and can thus be used to inhibit, interfere with or modulate one or more activities associated with CGRP R signaling.

In general, the antigen binding proteins that are provided typically comprise one or more CDRs as described herein (e.g., 1, 2, 3, 4, 5 or 6). In some instances, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or may be completely synthetic in nature. Examples of various polypeptide structures are further described below.

In certain embodiments, the polypeptide structure of the antigen binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen binding protein is an immunological fragment of an antibody (e.g., a Fab, a Fab', a F(ab')$_2$, or a scFv). The various structures are further described and defined herein.

Certain of the antigen binding proteins as provided herein specifically bind to human CGRP R. In a specific embodiment, the antigen binding protein specifically binds to human CGRP R protein comprising human CRLR having the amino acid sequence of SEQ ID NO:2 and human RAMP1 having the amino acid sequence of SEQ ID NO:4.

In embodiments where the antigen binding protein is used for therapeutic applications, an antigen binding protein can inhibit, interfere with or modulate one or more biological activities of CGRP R. In this case, an antigen binding protein binds specifically and/or substantially inhibits binding of human CGRP R to CGRP when an excess of antibody reduces the quantity of human CGRP R bound to CGRP, or vice versa, by at least about 20%, 30%, 40%, 50%, 60%, 70%, 80%, 85%, 90%, 95%, 97%, 99% or more (for example by measuring binding in an in vitro competitive binding assay).

Naturally Occurring Antibody Structure

Some of the antigen binding proteins that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as $C_H1$, $C_H2$ and $C_H3$. The antibodies that are provided can have any of these isotypes and subtypes. In certain embodiments, the CGRP R antibody is of the IgG1, IgG2, or IgG4 subtype.

In full-length light and heavy chains, the variable and constant regions are joined by a "J" region of about twelve or more amino acids, with the heavy chain also including a "D" region of about ten more amino acids. See, e.g., Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

One example of an IgG2 heavy constant domain of an exemplary CGRP R monoclonal antibody has the amino acid sequence:

```
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK
```
(the last 326 residues of the sequence shown as SEQ. ID NO: 29).

One example of a kappa light Constant domain of an exemplary CGRP R monoclonal antibody has the amino acid sequence:

```
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```
(the last 107 residues of the sequence shown as SEQ ID NO: 14).

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., CGRP R). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; Chothia et al., 1989, *Nature* 342:878-883.

The various heavy chain and light chain variable regions provided herein are depicted in Table 3. Each of these variable regions may be attached to the above heavy and light chain constant regions to form a complete antibody heavy and light chain, respectively. Further, each of the so generated heavy and light chain sequences may be combined to form a complete antibody structure. It should be understood that the heavy chain and light chain variable regions provided herein can also be attached to other constant domains having different sequences than the exemplary sequences listed above.

Specific examples of some of the full length light and heavy chains of the antibodies that are provided and their corresponding amino acid sequences are summarized in Tables 2A and 2B. Table 2A shows exemplary light chain sequences, and Table 2B shows exemplary heavy chain sequences.

TABLE 2A

Exemplary Antibody Light Chain Amino Acid Sequences

| SEQ ID NO: | Designation | Contained in Clone | Sequence |
|---|---|---|---|
| 12 | L1 | 01E11 LC | MDMRVPAQLLGLLLLWLRGARCQSVLTQPPSVSEAPGQKVTISC SGSSSNIGNNYVSWYQQLPGTAPKLLIYDNNKRPSGIPDRFSGS KSGTSATLGITGLQTGDEADYYCGTWDSRLSAVVFGGGTKLTVL GQPKANPTVTLFPPSSEELQANKATLVCLISDFYPGAVTVAWKA DGSPVKAGVETTKPSKQSNNKYAASSYLSLTPEQWKSHRSYSCQ VTHEGSTVEKTVAPTECS |
| 13 | L2 | 01H7 LC | MDMRVPAQLLGLLLLWLRGARCQSVLTQPPSASGIPGQRVTISC SGSSSNIGSNYVYWYQQLPGAAPKLLIFRSNQRPSGVPDRFSGS KSGTSASLAISGLRSEDEADYYCAAWDDSLSGWVFGGGTKLTVL GQPKANPTVTLFPPSSEELQANKATLVCLISDFYPGAVTVAWKA DGSPVKAGVETTKPSKQSNNKYAASSYLSLTPEQWKSHRSYSCQ VTHEGSTVEKTVAPTECS |
| 14 | L3 | 02E7 LC | MDMRVPAQLLGLLLLWLRGARCDIQMTQSPSSLSASVGDRVTIT CRASQGIRNDLGWFQQKPGKAPKRLIYAASSLQSGVPSRFSGSG SGTEFTLTISSLQPEDLATYYCLQYNIYPWTFGQGTKVEIKRTV AAPSVFIFPPSDEQLKSGTASVVCLLNNFYPREAKVQWKVDNAL QSGNSQESVTEQDSKDSTYSLSSTLTLSKADYEKHKVYACEVTH QGLSSPVTKSFNRGEC |

TABLE 2A-continued

Exemplary Antibody Light Chain Amino Acid Sequences

| SEQ ID NO: | Designation | Contained in Clone | Sequence |
|---|---|---|---|
| 15 | L4 | 03B6 LC | MDMRVPAQLLGLLLLWLRGARCSSELTQDPTVSVALGQTVKITC QGDSLRSFYASWYQQKPGQAPVLVFYGKNNRPSGIPDRFSGSSS GNTASLTITGAQAEDEADYYCNSRDSSVYHLVLGGGTKLTVLGQ PKANPTVTLFPPSSEELQANKATLVCLISDFYPGAVTVAWKADG SPVKAGVETTKPSKQSNNKYAASSYLSLTPEQWKSHRSYSCQVT HEGSTVEKTVAPTECS |
| 16 | L5 | 03C8 LC | MDMRVPAQLLGLLLLWLRGARCDIILAQTPLSLSVTPGQPASISC KSSQSLLHSAGKTYLYWYLQKPGQPPQLLIYEVSNRFSGVPDRFS GSGSGTDFTLKISRVEAEDVGIYYCMQSFPLPLTFGGGIKVEIKR TVAAPSVFIFPPSDEQLKSGTASVVCLLNNFYPREAKVQWKVDNA LQSGNSQESVTEQDSKDSIYSLSSTLTLSKADYEKHKVYACEVTH QGLSSPVTKSFNRGEC |
| 17 | L6 | 04E4 LC | MDMRVPAQLLGLLLLWLRGARCQSVLTQPPSVSAAPGQKVTISCS GSSSNIGNNYVSWYQQLPGTAPKLLIYDNNKRPSGIPDRFSGSKS GTSTTLGITGLQTGDEADYYCGTWDSRLSAVVFGGGTKLTVLGQP KANPTVTLFPPSSEELQANKATLVCLISDFYPGAVTVAWKADGSP VKAGVETTKPSKQSNNKYAASSYLSLTPEQWKSHRSYSCQVTHEG STVEKTVAPTECS |
| 18 | L7 | 04H6 LC | MDMRVPAQLLGLLLLWLRGARCDIVMTQSPLSLPVTPGEPASISC RSSQSLLHSFGYNYLDWYLQKPGQSPQLLIYLGSNRASGVPDRFS GSGSGTDFTLKISRVEAEDVGVYYCMQALQTPFTFGPGTKVDIKR TVAAPSVFIFPPSDEQLKSGTASVVCLLNNFYPREAKVQWKVDNA LQSGNSQESVTEQDSKDSTYSLSSTLTLSKADYEKHKVYACEVTH QGLSSPVTKSFNRGEC |
| 19 | L8 | 05F5 LC | MDMRVPAQLLGLLLLWLRGARCDIILTQTPLSLSVTPGQPASISC KSSQSLLHSDGKTYLYWYLQKPGQPPQLLIYEVSNRFSGEPDRFS GSGSGTDFTLKISRVEAEDVGTYYCMQSFPLPLTFGGGTKVEIKR TVAAPSVFIFPPSDEQLKSGTASVVCLLNNFYPREAKVQWKVDNA LQSGNSQESVTEQDSKDSTYSLSSTLTLSKADYEKHKVYACEVTH QGLSSPVTKSFNRGEC |
| 20 | L9 | 09D4 LC | MDMRVPAQLLGLLLLWLRGARCQSVLTQPPSVSAAPGQKVTISCS GSSSNIGNNYVSWYQQFPGTAPKLLIYDNNKRPSGIPDRFSGSKS GTSATLGITGLQTGDEADYYCGTWDSRLSAVVFGGGTKLTVLGQP KANPTVTLFPPSSEELQANKATLVCLISDFYPGAVTVAWKADGSP VKAGVETTKPSKQSNNKYAASSYLSLTPEQWKSHRSYSCQVTHEG STVEKTVAPTECS |
| 21 | L10 | 09F5 LC | MDMRVPAQLLGLLLLWLRGARCQSVLTQPSASGTPGQRVTISCS GSSSNIGSNYVYWYQQLPGAAPKLLILRNNQRPSGVPDRFSGSKS GTSASLTISGLRSEDEADYYCAAWDDSLSGWVFGGGTKLTVLGQP KANPTVTLFPPSSEELQANKATLVCLISDFYPGAVTVAWKADGSP VKAGVETTKPSKQSNNKYAASSYLSLTPEQWKSHRSYSCQVTHEG STVEKTVAPTECS |
| 22 | L11 | 10E4 LC | MDMRVPAQLLGLLLLWLRGARCQSVLTQPPSASGTPGQRVTISCS GSSSNIGSNTVNWYQQLPGTAPKLLIYTNNQRPSGVPDRFSGSKS GTSASLAISGLQSEDEADFYCAARDESLNGVVFGGGTKLTVLGQP KANPTVTLFPPSSEELQANKATLVCLISDFYPGAVTVAWKADGSP VKAGVETTKPSKQSNNKYAASSYLSLTPEQWKSHRSYSCQVTHEG STVEKTVAPTECS |
| 23 | L12 | 11D11 HL 11H9 LC | MDMRVPAQLLGLLLLWLRGARCQSVLTQPPSASGIPGQRVTISCS GSSSNIGSNYVYWYQQLPGAAPKLLIFRNNQRPSGVPDRFSGSKS GTSASLAISGLRSEDEADYYCAAWDDSLSGWVFGGGIKLTVLGQP KANPTVTLFPPSSEELQANKATLVCLISDFYPGAVTVAWKADGSP VKAGVETTKPSKQSNNKYAASSYLSLTPEQWKSHRSYSCQVTHEG STVEKTVAPTECS |
| 24 | L13 | 12E8 LC | MDMRVPAQLLGLLLLWLRGARCDITLTQTPLSLSVSPGQPASISC KSSQSLLHSDGRNYLYWYLQKPGQPPQLLIYEVSNRFSGLPDRFS GSGSGTDFTLKISRVEAEDVGIYYCMQSFPLPLTFGGGTKVEIKR TVAAPSVFIFPPSDEQLKSGTASVVCLLNNFYPREAKVQWKVDNA LQSGNSQESVTEQDSKDSTYSLSSTLTLSKADYEKHKVYACEVTH QGLSSPVTKSFNRGEC |

TABLE 2A-continued

Exemplary Antibody Light Chain Amino Acid Sequences

| SEQ ID NO: | Designation | Contained in Clone | Sequence |
|---|---|---|---|
| 25 | L14 | 12G8 HL | MDMRVPAQLLGLLLLWLRGARCQSVLTQPPSVSAAPGQKVTISCS GSSSNIGNNYVSWYQQLPGTAPKLLIYDNNKRPSGIPDRFSGSKS GTSATLGITGLQTGDEADYYCGTWDSRLSAWFGGGTKLTVLGQPK ANPTVTLFPPSSEELQANKATLVCLISDFYPGAVTVAWKADGSPV KAGVETTKPSKQSNNKYAASSYLSLTPEQWKSHRSYSCQVTHEGS TVEKTVAPTECS |
| 26 | L15 | 13H2 LC | MDMRVPAQLLGLLLLWLRGARCDIQMTQSPSSLSASVGDRVTITC RASQGIRKDLGWYQQKPGKAPKRLIYGASSLQSGVPSRFSGSGSG TEFTLTISSLQPEDFATYYCLQYNSFPWTFGQGTKVEIKRTVAAP SVFIFPPSDEQLKSGTASVVCLLNNFYPREAKVQWKVDNALQSGN SQESVTEQDSKDSIYSLSSTLTLSKADYEKHKVYACEVTHQGLSS PVIKSFNRGEC |
| 27 | L16 | 32H7 LC | METPAQLLFLLLLWLPDTTGEIVLTQSPGTLSLSPGERATLSCRA SQSVSSGYLTWYQQKPGQAPRLLIYGASSRATGIPDRFSGSGSGT DFTLTISRLEPEDFAVYYCQQYGNSLCRFGQGTKLEIKRTVAAPS VFIFPPSDEQLKSGTASVVCLLNNFYPREAKVQWKVDNALQSGNS QESVTEQDSKDSTYSLSSTLTLSKADYEKHKVYACEVTHQGLSSP VTKSFNRGEC |
| 28 | L17 | 32H7 CS LC | METPAQLLFLLLLWLPDTTGEIVLTQSPGTLSLSPGERATLSCRA SQSVSSGYLTWYQQKPGQAPRLLIYGASSRATGIPDRFSGSGSGT DFTLTISRLEPEDFAVYYCQQYGNSLSRFGQGTKLEIKRTVAAPS VFIFPPSDEQLKSGTASVVCLLNNFYPREAKVQWKVDNALQSGNS QESVTEQDSKDSTYSLSSTLTLSKADYEKHKVYACEVTHQGLSSP VTKSFNRGEC |

TABLE 2B

Exemplary Antibody Heavy Chain Amino Acid Sequences

| SEQ ID NO: | Designation | Contained in Clone | Sequence |
|---|---|---|---|
| 29 | H1 | 01E11 HC<br>04E4 HC<br>09D4 HC | MDMRVPAQLLGLLLLWLRGARCQVQLVESGGGVVQPGRSLRLS CAASGFTFSSFGMHWVRQAPGKGLEWVAVISFDGSIKYSVDSV KGRFTISRDNSKNTLFLQMNSLRAEDTAVYYCARDRLNYYDSS GYYHYKYYGMAVWGQGTTVTVSSASTKGPSVFPLAPCSRSTSE STAALGCLVKDYFPEPVTVSWNSGALTSGVHTFPAVLQSSGLY SLSSVVTVPSSNFGTQTYTCNVDHKPSNTKVDKTVERKCCVEC PPCPAPPVAGPSVFLFPPKPKDTLMISRTPEVTCVVVDVSHED PEVQFNWYVDGVEVHNAKTKPREEQFNSTFRVVSVLTVVHQDW LNGKEYKCKVSNKGLPAPIEKTISKTKGQPREPQVYTLPPSRE EMTKNQVSLTCLVKGFYPSDIAVEWESNGQPENNYKTTPPMLD SDGSFFLYSKLTVDKSRWQQGNVFSCSVMHEALHNHYTQKSLS LSPGK |
| 30 | H2 | 01H7 HC | MDMRVPAQLLGLLLLWLRGARCEVQLVESGGGLVKPGGSLRLS CAASGFTFSNAWMSWVRQAPGKGLEWVGRIKSTTDGGTTDYAA PVKGRFTISRDDSKNTLYLQMNSLKTEDTAVYYCTTDRTGYSS WSSYYYYGMDVWGQGTTVTVSSASTKGPSVFPLAPCSRSTSE STAALGCLVKDYFPEPVTVSWNSGALTSGVHTFPAVLQSSGLY SLSSVVTVPSSNFGTQTYTCNVDHKPSNTKVDKTVERKCCVEC PPCPAPPVAGPSVFLFPPKPKDTLMISRTPEVTCVVVDVSHED PEVQFNWYVDGVEVHNAKTKPREEQFNSIFRWSVLTVVHQDWL NGKEYKCKVSNKGLPAPIEKTISKTKGQPREPQVYTLPPSREE MTKNQVSLTCLVKGFYPSDIAVEWESNGQPENNYKTTPPMLDS DGSFFLYSKLTVDKSRWQQGNVFSCSVMHEALHNHYTQKSLSL SPGK |
| 31 | H3 | 02E7 HC | MDMRVPAQLLGLLLLWLRGARCEVQLLESGGGLVQPGESLRLS CAASGFTFSSYAMSWVRQAPGKGLEWVSAISGSGGRTYYADSV KGRFTISRDNSKNTLYLQMNSLRAEDTAVYYCAKDQREVGPYS SGWYDYYYGMDVWGQGTTVTVSSASTKGPSVFPLAPCSRSTSE STAALGCLVKDYFPEPVTVSWNSGALTSGVHTFPAVLQSSGLY SLSSVVTVPSSNFGTQTYTCNVDHKPSNTKVDKTVERKCCVEC PPCPAPPVAGPSVFLFPPKPKDTLMISRTPEVTCVVVDVSHED PEVQFNWYVDGVEVHNAKTKPREEQFNSTFRVVSVLTVVHQDW LNGKEYKCKVSNKGLPAPIEKTISKTKGQPREPQVYTLPPSRE EMTKNQVSLTCLVKGFYPSDIAVEWESNGQPENNYKTTPPMLD |

TABLE 2B-continued

Exemplary Antibody Heavy Chain Amino Acid Sequences

| SEQ ID NO: | Designation | Contained in Clone | Sequence |
|---|---|---|---|
| | | | SDGSFFLYSKLTVDKSRWQQGNVFSCSVMHEALHNHYTQKSLS LSPGK |
| 32 | H4 | 03B6 HC | MDMRVPAQLLGLLLLWLRGARCQVQLVQSGAEVKKPGASVKVS CKASGYTFTGYYMHWVRQAPGQGLEWMGWINPNSGGTNYAQKF QGRVTMTRDTSISTAYMELSRLRSDDTAVYFCARDQMSIIMLR GVFPPYYYGMDVWGQGTTVTVSSASTKGPSVFPLAPCSRSTSE STAALGCLVKDYFPEPVTVSWNSGALTSGVHTFPAVLQSSGLY SLSSVVTVPSSNFGTQTYTCNVDHKPSNTKVDKTVERKCCVEC PPCPAPPVAGPSVFLFPPKPKDTLMISRTPEVTCVVVDVSHED PEVQFNWYVDGVEVHNAKTKPREEQFNSTFRVVSVLTVVHQDW LNGKEYKCKVSNKGLPAPIEKTISKTKGQPREPQVYTLPPSRE EMTKNQVSLTCLVKGFYPSDIAVEWESNGQPENNYKTTPPMLD SDGSFFLYSKLTVDKSRWQQGNVFSCSVMHEALHNHYTQKSLS LSPGK |
| 33 | H5 | 03C8 HC<br>05F5 HC<br>12E8 HC | MDMRVPAQLLGLLLLWLRGARCQVQLVESGGGWQPGRSLRLSC CAASGFTFSSYGMHWVRQAPGKGLEWVAVISYDGSHESYADSV KGRFTISRDISKNTLYLQMNSLRAEDTAVYFCARERKRVTMST LYYYFYYGMDVWGQGTTVTVSSASTKGPSVFPLAPCSRSTSES TAALGCLVKDYFPEPVTVSWNSGALTSGVHTFPAVLQSSGLYS LSSVVTVPSSNFGTQTYTCNVDHKPSNTKVDKTVERKCCVECP PCPAPPVAGPSVFLFPPKPKDTLMISRTPEVTCVVVDVSHEDP EVQFNWYVDGVEVHNAKTKPREEQFNSIFRWSVLTVVHQDWLN GKEYKCKVSNKGLPAPTEKTISKTKGQPREPQVYTLPPSREEM TKNQVSLTCLVKGFYPSDIAVEWESNGQPENNYKTTPPMLDSD GSFFLYSKLTVDKSRWQQGNVFSCSVMHEALHNHYTQKSLSLS PGK |
| 34 | H6 | 04H6 HC | MDMRVPAQLLGLLLLWLRGARCEVQLVESGGGLVKPGRSLRLS CTASGFTFGDYAMSWFRQAPGKGLEWIGFIRSRAYGGIPEYAA SVKGRFTISRDDSKTIAYLQMNSLKTEDTAVYFCARGRGIAAR WDYWGQGTLVTVSSASTKGPSVFPLAPCSRSTSESTAALGCLV KDYFPEPVTVSWNSGALTSGVHTFPAVLQSSGLYSLSSVVTVP SSNFGTQTYTCNVDHKPSNTKVDKTVERKCCVECPPCPAPPVA GPSVFLFPPKPKDTLMISRTPEVTCVVVDVSHEDPEVQFNWYV DGVEVHNAKTKPREEQFNSIFRVVSVLTVVHQDWLNGKEYKCK VSNKGLPAPIEKTISKTKGQPREPQVYTLPPSREEMTKNQVSL TCLVKGFYPSDIAVEWESNGQPENNYKTTPPMLDSDGSFFLYS KLTVDKSRWQQGNVFSCSVMHEALHNHYTQKSLSLSPGK |
| 35 | H7 | 09F5 HC | MDMRVPAQLLGLLLLWLRGARCEVQLVESGGGLVKPGGSLRLS CAASGFTFSNAWMSWVRQAPGKGLEWVGRIKSKTDGGTTDYTA PVKGRFTISRDDSKNTLYLQMNSLKAEDTAVYYCTTDRTGYSS WSSYYYYGMDVWGQGTTVTVSSASTKGPSVFPLAPCSRSTSE STAALGCLVKDYFPEPVTVSWNSGALTSGVHTFPAVLQSSGLY SLSSVVTVPSSNFGTQTYTCNVDHKPSNTKVDKTVERKCCVEC PPCPAPPVAGPSVFLFPPKPKDTLMISRTPEVTCVVVDVSHED PEVQFNWYVDGVEVHNAKTKPREEQFNSTFRVVSVLTVVHQDW LNGKEYKCKVSNKGLPAPIEKTISKTKGQPREPQVYTLPPSRE EMTKNQVSLTCLVKGFYPSDIAVEWESNGQPENNYKTTPPMLD SDGSFFLYSKLTVDKSRWQQGNVFSCSVMHEALHNHYTQKSLS LSPGK |
| 36 | H8 | 10E4 HC | MDMRVPAQLLGLLLLWLRGARCQVQLVQSGAEVKKPGASVKVS CKASGYTFTDYYMYWVRQAPGQGLEWMGWISPNSGGTNYAQKF QGRVTMTRDTSISTAYMELSRLRSDDTAVYYCVRGGYSGYAGL YSHYYGMDVWGQGTTVTVSSASIKGPSVFPLAPCSRSTSESTA ALGCLVKDYFPEPVTVSWNSGALTSGVHTFPAVLQSSGLYSLS SVVTVPSSNFGTQTYTCNVDHKPSNTKVDKTVERKCCVECPPC PAPPVAGPSVFLFPPKPKDTLMISRTPEVTCVVVDVSHEDPEV QFNWYVDGVEVHNAKTKPREEQFNSIFRWSVLTVVHQDWLNGK EYKCKVSNKGLPAPIEKTISKTKGQPREPQVYTLPPSREEMTK NQVSLTCLVKGFYPSDIAVEWESNGQPENNYKTTPPMLDSDGS FFLYSKLTVDKSRWQQGNVFSCSVMHEALHNHYTQKSLSLSPG K |
| 37 | H9 | 11D11 HC | MDMRVPAQLLGLLLLWLRGARCEVQLVESGGGLVKPGGSLRLS CAASGFTFGNAWMSWVRQAPGKGLEWVGRIKSKTDGGTTDYAA PVKGRFTISRDDSKNTLYLQMNSLKIEDTAVYFCTTDRIGYSI SWSSYYYYGMDVWGQGTTVTVSSASTKGPSVFPLAPCSRSTS ESTAALGCLVKDYFPEPVTVSWNSGALTSGVHTFPAVLQSSGL YSLSSVVTVPSSNFGTQTYTCNVDHKPSNTKVDKTVERKCCVE CPPCPAPPVAGPSVFLFPPKPKDTLMISRTPEVTCVVVDVSHE DPEVQFNWYVDGVEVHNAKIKPREEQFNSIFRWSVLIWHQDWL |

TABLE 2B-continued

Exemplary Antibody Heavy Chain Amino Acid Sequences

| SEQ ID NO: | Designation | Contained in Clone | Sequence |
|---|---|---|---|
| | | | NGKEYKCKVSNKGLPAPIEKYISKIKGQPREPQVYYLPPSREE<br>MKNQVSLTCLVKGFYPSDIAVEWESNGQPENNYKTTPPMLDSD<br>GSFFLYSKLTVDKSRWQQGNVFSCSVMHEALHNHYTQKSLSLS<br>PGK |
| 38 | H10 | 11H9 HC | MDMRVPAQLLGLLLLWLRGARCEVQLVESGGGLVKPGGSLRLS<br>CAASGFTFGNAWMSWVRQAPGKGLEWVGRIKSKTDGGTTDYAA<br>PVKGRFTISRDDSKNTLYLQMNSLKTEDTAVYYCTTDRTGYSI<br>SWSSYYYYGMDVWGQGTTVTVSSASTKGPSVFPLAPCSRSTS<br>ESTAALGCLVKDYFPEPVTVSWNSGALTSGVHTFPAVLQSSGL<br>YSLSSVVTVPSSNFGTQTYTCNVDHKPSNTKVDKTVERKCCVE<br>CPPCPAPPVAGPSVFLFPPKPKDTLMISRTPEVTCVVVDVSHE<br>DPEVQFNWYVDGVEVHNAKTKPREEQFNSTFRVVSVLTVVHQD<br>WLNGKEYKCKVSNKGLPAPIEKTISKTKGQPREPQVYTLPPSR<br>EEMTKNQVSLTCLVKGFYPSDIAVEWESNGQPENNYKTTPPML<br>DSDGSFFLYSKLTVDKSRWQQGNVFSCSVMHEALHNHYTQKSL<br>SLSPGK |
| 39 | H11 | 12G8 HC | MDMRVPAQLLGLLLLWLRGARCQVQLVESGGGWQPGRSLRLSC<br>AASGFTFSSFGMHWVRQAPGKGLEWVAVISFDGSIKYSVDSVK<br>GRFTISRDNSKNTLFLQMNSLRAEDTAVYYCARDRLNYYDSSG<br>YYHYKYYGLAVWGQGTTVTVSSASTKGPSVFPLAPCSRSTSES<br>TAALGCLVKDYFPEPVTVSWNSGALTSGVHTFPAVLQSSGLYS<br>LSSVVTVPSSNFGTQTYTCNVDHKPSNTKVDKTVERKCCVECP<br>PCPAPPVAGPSVFLFPPKPKDTLMISRTPEVTCVVVDVSHEDP<br>EVQFNWYVDGVEVHNAKTKPREEQFNSTFRVVSVLTVVHQDWL<br>NGKEYKCKVSNKGLPAPIEKTISKTKGQPREPQVYTLPPSREE<br>MTKNQVSLTCLVKGFYPSDIAVEWESNGQPENNYKTTPPMLDS<br>DGSFFLYSKLTVDKSRWQQGNVFSCSVMHEALHNHYTQKSLSL<br>SPGK |
| 40 | H12 | 13H2 HC | MDMRVPAQLLGLLLLWLRGARCEVQLVESGGGLVKPGGSLRLS<br>CAASGYTFSTYSMNWVRQAPGKGLEWVSSISSSSSYRYYADSV<br>KGRFTISRDNAKNSLYLQMSSLRAEDTAVYYCAREGVSGSSPY<br>SISWYDYYYGMDVWGQGTTVTVSSASTKGPSVFPLAPCSRSTS<br>ESTAALGCLVKDYFPEPVTVSWNSGALTSGVHTFPAVLQSSGL<br>YSLSSVVTVPSSNFGTQTYTCNVDHKPSNTKVDKTVERKCCVE<br>CPPCPAPPVAGPSVFLFPPKPKDTLMISRTPEVTCVVVDVSHE<br>DPEVQFNWYVDGVEVHNAKTKPREEQFNSTFRWSVLTVVHQDW<br>LNGKEYKCKVSNKGLPAPIEKTISKTKGQPREPQVYTLPPSRE<br>EMTKNQVSLTCLVKGFYPSDIAVEWESNGQPENNYKTTPPMLD<br>SDGSFFLYSKLTVDKSRWQQGNVFSCSVMHEALHNHYTQKSLS<br>LSPGK |
| 41 | H13 | 32H7 HC | MDMRVPAQLLGLLLLWLRGARCQVQLVESGGGVVQPGRSLRLS<br>CAASGFTFSSYGMHWVRQAPGKGLEWVAVIWYDGSNKYYADSV<br>KGRFIISRDKSKNTLYLQMNSLRAEDTAVYYCARAGGIAAAGL<br>YYYYGMDVWGQGTTVTVSSASTKGPSVFPLAPCSRSTSESTAA<br>LGCLVKDYFPEPVTVSWNSGALTSGVHTFPAVLQSSGLYSLSS<br>VVTVPSSNFGTQTYTCNVDHKPSNTKVDKTVERKCCVECPPCP<br>APPVAGPSVFLFPPKPKDTLMISRTPEVTCVWDVSHEDPEVQF<br>NWYVDGVEVHNAKTKPREEQFNSTFRVVSVLTVVHQDWLNGKE<br>YKCKVSNKGLPAPIEKTISKIKGQPREPQVYTLPPSREEMTKN<br>QVSLTCLVKGFYPSDIAVEWESNGQPENNYKTTPPMLDSDGSF<br>FLYSKLTVDKSRWQQGNVFSCSVMHEALHNHYTIQKSLSLSPG<br>K |

The first 22 amino acids of each of the light chain sequences in Table 2A, except 32H7 and 32H7CS, is a signal sequence. In the case of 32H7 and 32H7CS, the signal sequence is 20 amino acids. Similarly, the first 22 amino acids of each of the heavy chain sequences in Table 2B is a signal sequence. The signal peptides may be changed to signal peptides having different sequences, e.g., for more optimal expression in certain host cells. It will be therefore be understood that the invention also includes antibodies having the light and/or heavy chain sequences as specified in Tables 2A and 2B, but with different signal sequences.

Again, each of the exemplary heavy chains (H1, H2, H3 etc.) listed in Table 2B can be combined with any of the exemplary light chains shown in Table 2A to form an antibody. Examples of such combinations include H1 combined with any of L1 through L17; H2 combined with any of L1 through L17; H3 combined with any of L1 through L17, and so on. In some instances, the antibodies include at least one heavy chain and one light chain from those listed in Tables 2A and 2B. In some instances, the antibodies comprise two different heavy chains and two different light chains listed in Tables 2A and 2B. In other instances, the antibodies contain two identical light chains and two identical heavy chains. As an example, an antibody or immunologically functional fragment may include two H1 heavy chains and two L1 light chains, or two H2 heavy chains and two L2 light chains, or two H3 heavy chains and two L3 light chains and other similar combinations of pairs of light chains and pairs of heavy chains as listed in Tables 2A and 2B.

Other antigen binding proteins that are provided are variants of antibodies formed by combination of the heavy and light chains shown in Tables 2A and 2B and comprise light and/or heavy chains that each have at least 70%, 75%, 80%, 85%, 90%, 95%, 97% or 99% identity to the amino acid sequences of these chains. In some instances, such antibodies include at least one heavy chain and one light chain, whereas in other instances the variant forms contain two identical light chains and two identical heavy chains.

Variable Domains of Antibodies

Also provided are antigen binding proteins that contain an antibody heavy chain variable region selected from the group consisting of $V_H1$, $V_H2$, $V_H3$, $V_H4$, $V_H5$, $V_H6$, $V_H7$, $V_H8$, $V_H9$, $V_H10$, $V_H11$, $V_H12$, and $V_H13$, and/or an antibody light chain variable region selected from the group consisting of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, and $V_L17$, as shown in Table 3 below, and immunologically functional fragments, derivatives, muteins and variants of these light chain and heavy chain variable regions.

Sequence alignments of the various heavy and light chain variable regions, respectively, are provided in FIGS. 1A and 1B.

Antigen binding proteins of this type can generally be designated by the formula "$V_Hx/V_Ly$," where "x" corresponds to the number of heavy chain variable regions and "y" corresponds to the number of the light chain variable regions.

TABLE 3

Exemplary $V_H$ and $V_L$ Chain Amino Acid Sequences

| Contained in Clone | Designation | SEQ ID NO. | Amino Acid Sequence |
|---|---|---|---|
| 1E11 | $V_L1$ | 137 | QSVLTQPPSVSEAPGQKVTISCSGSSSNIGNNYVSWYQQLPGTAPKLLIYDNNKRPSGIPDRFSGSKSGTSATLGITGLQTGDEADYYCGTWDSRLSAWFGGGTKLTVL |
| 1H7 | $V_L2$ | 138 | QSVLTQPPSASGTPGQRVTISCSGSSSNIGSNYVYWYQQLPGAAPKLLIFRSNQRPSGVPDRFSGSKSGTSASLAISGLRSEDEADYYCAAWDDSLSGWVFGGGTKLTVL |
| 2E7 | $V_L3$ | 139 | DIQMTQSPSSLSASVGDRVTITCRASQGIRNDLGWFQQKPGKAPKRLIYAASSLQSGVPSRFSGSGSGTEFTLTISSLQPEDGLTYYCLQYNIYPWTFGQGTKVEIK |
| 3B6 | $V_L4$ | 140 | SSELTQDPTVSVALGQTVKITCQGDSLRSFYASWYQQKPGQAPVLVFYGKNNRPSGIPDRFSGSSSGNTASLTITGAQAEDEADYYCNSRDSSVYHLVLGGGTKLTVL |
| 3C8 | $V_L5$ | 141 | DIILAQTPLSLSVTPGQPASISCKSSQSLLHSAGKTYLYWYLQKPGQPPQLLIYEVSNRFSGVPDRFSGSGSGTDFTLKISRVEAEDVGIYYCMQSFPLPLTFGGGTKVEIK |
| 4E4 | $V_L6$ | 142 | QSVLTQPPSVSAAPGQKVTISCSGSSSNIGNNYVSWYQQLPGTAPKLLIYDNNKRPSGIPDRFSGSKSGTSTTLGITGLQTGDEADYYCGTWDSRLSAVVFGGGTKLTVL |
| 4H6 | $V_L7$ | 143 | DIVMTQSPLSLPVTPGEPASISCRSSQSLLHSFGYNYLDWYLQKPGQSPQLLIYLGSNRASGVPDRFSGSGSGTDFTLKISRVEAEDVGVYYCMQALQTPFFTFGPGTKVDIK |
| 5F5 | $V_L8$ | 144 | DIILTQTPLSLSVTPGQPASISCKSSQSLLHSDGKTYLYWYLQKPGQPPQLLIYEVSNRFSGEPDRFSGSGSGTDFTLKISRVEAEDVGTYYCMQSFPLPLTFGGGTKVEIK |
| 9D4 | $V_L9$ | 145 | QSVLTQPPSVSAAPGQKVTISCSGSSSNIGNNYVSWYQQFPGTAPKLLIYDNNKRPSGIPDRFSGSKSGTSATLGITGLQIGDEADYYCGTWDSRLSAVVFGGGTKLTVL |
| 9F5 | $V_L10$ | 146 | QSVLTQSPSASGTPGQRVTISCSGSSSNIGSNYVYWYQQLPGAAPKLLILRNNQRPSGVPDRFSGSKSGTSASLTISGLRSEDEADYYCAAWDDSLSGWVFGGGTKLTVL |
| 10E4 | $V_L11$ | 147 | QSVLTQPPSASGTPGQRVTISCSGSSSNIGSNTVNWYQQLPGTAPKLLIYTNNQRPSGVPDRFSGSKSGTSASLAISGLQSEDEADFYCAARDESLNGVVFGGGTKLTVL |
| 11D11 11H9 | $V_L12$ | 148 | QSVLTQPPSASGTPGQRVTISCSGSSSNIGSNYVYWYQQLPGAAPKLLIFRNNQRPSGVPDRFSGSKSGTSASLAISGLRSEDEADYYCAAWDDSLSGWVFGGGTKLTVL |
| 12E8 | $V_L13$ | 149 | DITLTQTPLSLSVSPGQPASISCKSSQSLLHSDGRNYLYWYLQKPGQPPQLLIYEVSNRFSGLPDRFSGSGSGTDFTLKISRVEAEDVGIYYCMQSFPLPLTFGGGIKVEIK |
| 12G8 | $V_L14$ | 150 | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSRLSAVVFGGGTKLTVL |

TABLE 3-continued

Exemplary V_H and V_L Chain Amino Acid Sequences

| Contained in Clone | Designation | SEQ ID NO. | Amino Acid Sequence |
|---|---|---|---|
| 13H2 | V_L15 | 151 | DIQMTQSPSSLSASVGDRVTITCRASQGIRKDLGWYQQKPG KAPKRLIYGASSLQSGVPSRFSGSGSGTEFTLTISSLQPED FATYYCLQYNSFPWTFGQGTKVEIK |
| 32H7 | V_L16 | 152 | EIVLTQSPGTLSLSPGERATLSCRASQSVSSGYLTWYQQKP GQAPRLLIYGASSRATGIPDRFSGSGSGTDFTLTISRLEPE DFAVYYCQQYGNSLCRFGQGTKLEIK |
| 32H7 CS | V_L17 | 153 | EIVLTQSPGTLSLSPGERATLSCRASQSVSSGYLTWYQQKP GQAPRLLIYGASSRATGIPDRFSGSGSGTDFTLTISRLEPE DFAVYYCQQYGNSLSRFGQGTKLEIK |
| 32H8 | V_L18 | 154 | DIVMTQSPDSLAVSLGERATINCKSSQSILDSSNNDNYLAW YQQKPGQPPKLLIYWASTRESGVPDRFSGSGSGTDFTLTIS SLQAEDVAVYYCQQYYNTPFTFGPGTKVDIK |
| 33B5 | V_L19 | 155 | DIQMTQSPSSLSASVGDRVTITCRASQGIRNDLGWYQQKPG KAPKRLIYVASSLQSGVPSRFSGSGSGTEFTLTISSLQPED FATYYCLQYNTYPLTFGGGTKVEIK |
| 33E4 | V_L20 | 156 | EIVMTQSPATLSVSPGERATLSCRASQSVRSNLAWYQQKPG QAPRLLIHDASPRIAGIPARFSGSGSGTEFTLTINSLQSED FAVYYCQQYNYWTPITFGQGTRLEIK |
| 34E3 | V_L21 | 157 | QSVLTQPPSMSAAPGQKVTISCSGSSSNIGNNYVSWYQQLP GTAPKLLIYDNNKRPSGIPDRFSGSKSGTSATLGITGLQTG DEANYCCGTWDIGLSVWVFGGGTKLTVL |
| 4E4 9D4 1E11 | V_H1 | 158 | QVQLVESGGGVVQPGRSLRLSCAASGFTFSSFGMHWVRQAP GKGLEWVAVISFDGSIKYSVDSVKGRFTISRDNSKNTLFLQ MNSLRAEDTAVYYCARDRLNYYDSSGYYHYKYYGMAVWGQG TTVTVSS |
| 1H7 | V_H2 | 159 | EVQLVESGGGLVKPGGSLRLSCAASGFTFSNAWMSWVRQAP GKGLEWVGRIKSTTDGGTTDYAAPVKGRFTISRDDSKNTLY LQMNSLKTEDTAVYYCTTDRTGYSISWSSYYYYGMDVWGQ GTTVTVSS |
| 2E7 | V_H3 | 160 | EVQLLESGGGLVQPGESLRLSCAASGFTFSSYAMSWVRQAP GKGLEWVSAISGSGGRTYYADSVKGRFTISRDNSKNTLYLQ MNSLRAEDTAVYYCAKDQREVGPYSSGWYDYYYGMDVWGQG TTVTVSS |
| 3B6 | V_H4 | 161 | QVQLVQSGAEVKKPGASVKVSCKASGYTFTGYYMHWVRQAP GQGLEWMGWINPNSGGTNYAQKFQGRVTMTRDTSISTAYME LSRLRSDDTAVYFCARDQMSIIMLRGVFPPYYYGMDVWGQG TTVTVSS |
| 3C8 12E8 5F5 | V_H5 | 162 | QVQLVESGGGVVQPGRSLRLSCAASGFTFSSYGMHWVRQAP GKGLEWVAVISYDGSHESYADSVKGRFTISRDISKNTLYLQ MNSLRAEDTAVYFCARERKRVTMSTLYYYFYYGMDVWGQGT TVTVSS |
| 4H6 | V_H6 | 163 | EVQLVESGGGLVKPGRSLRLSCTASGFTFGDYAMSWFRQAP GKGLEWIGFIRSRAYGGTPEYAASVKGRFTISRDDSKTIAY LQMNSLKTEDTAVYFCARGRGIAARWDYWGQGTLVTVSS |
| 9F5 | V_H7 | 164 | EVQLVESGGGLVKPGGSLRLSCAASGFTFSNAWMSWVRQAP GKGLEWVGRIKSKTDGGTTDYTAPVKGRFTISRDDSKNTLY LQMNSLKAEDTAVYYCTTDRTGYSISWSSYYYYGMDVWGQ GTTVTVSS |
| 10E4 | V_H8 | 165 | QVQLVQSGAEVKKPGASVKVSCKASGYTFTDYYMYWVRQAP GQGLEWMGWISPNSGGTNYAQKFQGRVTMTRDTSSTAYMEL SRLRSDDTAVYYCVRGGYSGYAGLYSHYYGMDVWGQGTTVT VSS |
| 11D11 | V_H9 | 166 | EVQLVESGGGLVKPGGSLRLSCAASGFTFGNAWMSWVRQAP GKGLEWVGRIKSKTDGGTTDYAAPVKGRFTISRDDSKNTLY LQMNSLKTEDTAVYFCTTDRTGYSISWSSYYYYGMDVWGQ GTTVTVSS |

TABLE 3-continued

Exemplary $V_H$ and $V_L$ Chain Amino Acid Sequences

| Contained in Clone | Designation | SEQ ID NO. | Amino Acid Sequence |
|---|---|---|---|
| 11H9 | $V_H$10 | 167 | EVQLVESGGGLVKPGGSLRLSCAASGFTFGNAWMSWVRQAP GKGLEWVGRIKSKTDGGTTDYAAPVKGRFTISRDDSKNTLY LQMNSLKTEDTAVYYCTTDRTGYSISWSSYYYYYGMDVWGQ GTTVTVSS |
| 12G8 | $V_H$11 | 168 | QVQLVESGGGVVQPGRSLRLSCAASGFTFSSFGMHWVRQAP GKGLEWVAVISFDGSIKYSVDSVKGRFTISRDNSKNTLFLQ MNSLRAEDTAVYYCARDRLNYYDSSGYYHYKYYGLAVWGQG TTVTVSS |
| 13H2 | $V_H$12 | 169 | EVQLVESGGGLVKPGGSLRLSCAASGYTFSTYSMNWVRQAP GKGLEWVSSISSSSSYRYYADSVKGRFTISRDNAKNSLYLQ MSSLRAEDTAVYYCAREGVSGSSPYSISWYDYYYGMDVWGQ GTTVTVSS |
| 32H7 | $V_H$13 | 170 | QVQLVESGGGGQPGRSLRLSCAASGFTFSSYGMHWVRQAP GKGLEWVAVIWYDGSNKYYADSVKGRFIISRDKSKNGLYLQ MNSLRAEDTAVYYCARAGGIAAAGLYYYYGMDVWGQGTTVT VSS |
| 32H8 | $V_H$14 | 171 | QVQLVQSGAEVKKPGASVKVSCKASGYTFTAYYLHWVRQAP GQGLEWMGWINPHSGGTNYAQKFQGRVTMTRDTSISTAYME LSRLRSDDTAVFYCARGRQWLGFDYWGQGTLVTVSS |
| 33E4 | $V_H$15 | 172 | QVQLQQWGAGLLKPSETLSLSCAVYGGSFGGYYWSWIRQPP GKGLEWIGEINHSGGTKYNPSLKSRVTISVDTSKNQFSLKL SSVTAADTAVYFCARGDVVGFFDYWGQGTLVTVSS |
| 33B5 | $V_H$16 | 173 | QVQLVQSGAEVKKSGASVKVSCKASGYTFTGYYMHWVRQAP GQGLEWMGWINPNSGGTNYVQKFQGRVTMTRDTSISTAYME LSRLRSDDTAVYYCARNEYSSAWPLGYWGQGTLVTVSS |
| 34E3 | $V_H$17 | 174 | QITLKESGPTLVKPTQTLTLTCTFSGFSLSTSGVGVAWTRQ PPGKALEWLALIYWTDDKRYSPSLKSRLTITKDTSKNQWLR MTNMDPLDTATYFCAHRPGGWFDPWGQGTLVTVSS |

Each of the heavy chain variable regions listed in Table 3 may be combined with any of the light chain variable regions shown in Table 3 to form an antigen binding protein. Examples of such combinations include $V_H$1 combined with any of $V_L$1, $V_L$2, $V_L$3, $V_L$4, $V_L$5, $V_L$6, $V_L$7, $V_L$8, $V_L$9, $V_L$10, $V_L$11, $V_L$12, $V_L$13, $V_L$14, $V_L$15, $V_L$16, or $V_L$17; $V_H$2 combined with any of $V_L$1, $V_L$2, $V_L$3, $V_L$4, $V_L$5, $V_L$6, $V_L$7, $V_L$8, $V_L$9, $V_L$10, $V_L$11, $V_L$12, $V_L$13, $V_L$14, $V_L$15, $V_L$16, or $V_L$17; $V_H$3 combined with any of $V_L$1, $V_L$2, $V_L$3, $V_L$4, $V_L$5, $V_L$6, $V_L$7, $V_L$8, $V_L$9, $V_L$10, $V_L$11, $V_L$12, $V_L$13, $V_L$14, $V_L$15, $V_L$16, or $V_L$17; and so on.

In some instances, the antigen binding protein includes at least one heavy chain variable region and/or one light chain variable region from those listed in Table 3. In some instances, the antigen binding protein includes at least two different heavy chain variable regions and/or light chain variable regions from those listed in Table 3. An example of such an antigen binding protein comprises (a) one $V_H$1, and (b) one of $V_H$2, $V_H$3, $V_H$4, $V_H$5, $V_H$6, $V_H$7, $V_H$8, $V_H$9, $V_H$10, $V_H$11, $V_H$12, or $V_H$13. Another example comprises (a) one $V_H$2, and (b) one of $V_H$1, $V_H$3, $V_H$4, $V_H$5, $V_H$6, $V_H$7, $V_H$8, $V_H$9, $V_H$10, $V_H$11, $V_H$12, or $V_H$13. Again another example comprises (a) one $V_H$3, and (b) one of $V_H$1, $V_H$2, $V_H$4, $V_H$5, $V_H$6, $V_H$7, $V_H$8, $V_H$9, $V_H$10, $V_H$11, $V_H$12, or $V_H$13, etc. Again another example of such an antigen binding protein comprises (a) one $V_L$1, and (b) one of $V_L$2, $V_L$3, $V_L$4, $V_L$5, $V_L$6, $V_L$7, $V_L$8, $V_L$9, $V_L$10, $V_L$11, $V_L$12, $V_L$13, $V_L$14, $V_L$15, $V_L$16, or $V_L$17, $V_L$18, $V_L$19, $V_L$20, or $V_L$21. Again another example of such an antigen binding protein comprises (a) one $V_L$2, and (b) one of $V_L$1, $V_L$3, $V_L$4, $V_L$5, $V_L$6, $V_L$7, $V_L$8, $V_L$9, $V_L$10, $V_L$11, $V_L$12, $V_L$13, $V_L$14, $V_L$15, $V_L$16, $V_L$17, $V_L$18, $V_L$19, $V_L$20, or $V_L$21. Again another example of such an antigen binding protein comprises (a) one $V_L$3, and (b) one of $V_L$1, $V_L$2, $V_L$4, $V_L$5, $V_L$6, $V_L$7, $V_L$8, $V_L$9, $V_L$10, $V_L$11, $V_L$12, $V_L$13, $V_L$14, $V_L$15, $V_L$16, $V_L$17, $V_L$18, $V_L$19, $V_L$20, or $V_L$21, etc.

The various combinations of heavy chain variable regions may be combined with any of the various combinations of light chain variable regions as is apparent to one of skill in the art.

In other instances, the antigen binding protein contains two identical light chain variable regions and/or two identical heavy chain variable regions. As an example, the antigen binding protein may be an antibody or immunologically functional fragment that includes two light chain variable regions and two heavy chain variable regions in combinations of pairs of light chain variable regions and pairs of heavy chain variable regions as listed in Table 3.

Some antigen binding proteins that are provided comprise a heavy chain variable domain comprising a sequence of amino acids that differs from the sequence of a heavy chain variable domain selected from $V_H$1, $V_H$2, $V_H$3, $V_H$4, $V_H$5, $V_H$6, $V_H$7, $V_H$8, $V_H$9, $V_H$10, $V_H$11, $V_H$12, and $V_H$13 at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The heavy chain variable region in some antigen binding proteins comprises a sequence of amino acids that has at least 70%, 75%, 80%, 85%, 90%, 95%, 97% or 99% sequence identity to the amino acid sequences of the heavy chain variable region of $V_H1$, $V_H2$, $V_H3$, $V_H4$, $V_H5$, $V_H6$, $V_H7$, $V_H8$, $V_H9$, $V_H10$, $V_H11$, $V_H12$, and $V_H13$.

Certain antigen binding proteins comprise a light chain variable domain comprising a sequence of amino acids that differs from the sequence of a light chain variable domain selected from $V_L1, V_L2, V_L3, V_L4, V_L5, V_L6, V_L7, V_L8, V_L9, V_L10, V_L11, V_L12, V_L13, V_L14, V_L15, V_L16,$ or $V_L17$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The light chain variable region in some antigen binding proteins comprises a sequence of amino acids that has at least 70%, 75%, 80%, 85%, 90%, 95%, 97% or 99% sequence identity to the amino acid sequences of the light chain variable region of $V_L1, V_L2, V_L3, V_L4, V_L5, V_L6, V_L7, V_L8, V_L9, V_L10, V_L11, V_L12, V_L13, V_L14, V_L15, V_L16,$ or $V_L17$.

In additional instances, antigen binding proteins comprise the following pairings of light chain and heavy chain variable domains: VL1 with VH1, VL2 with VH2, VL3 with VH3, VL4 with VH4, VL5 with VH5, VL6 with VH1, VL7 with VH6, VL8 with VH5, VL9 with VH1, VL10 with VH7, VL11 with, H8, VL12 with VH9, VL12 with VH10, VL13 with VH5, VL14 with VH11, VL15 with VH12, VL16 with VH13, and VL17 with VH13. In some instances, the antigen binding proteins in the above pairings may comprise amino acid sequences that have 70%, 75%, 80%, 85%, 90%, 95%, 97% or 99% sequence identity with the specified variable domains.

Still other antigen binding proteins, e.g., antibodies or immunologically functional fragments, include variant forms of a variant heavy chain and a variant light chain as just described.

CDRs

The antigen binding proteins disclosed herein are polypeptides into which one or more CDRs are grafted, inserted and/or joined. An antigen binding protein can have 1, 2, 3, 4, 5 or 6 CDRs. An antigen binding protein thus can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/ or one light chain CDR3 ("CDRL3"). Some antigen binding proteins include both a CDRH3 and a CDRL3. Specific heavy and light chain CDRs are identified in Tables 4A and 4B, respectively.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. Certain antibodies that are disclosed herein comprise one or more amino acid sequences that are identical or have substantial sequence identity to the amino acid sequences of one or more of the CDRs presented in Table 4A (CDRHs) and Table 4B (CDRLs).

TABLE 4A

Exemplary Heavy Chain CDR Amino Acid Sequences

| Alt Num | SEQ ID NO: | Contained in Reference | Designation | Sequence |
|---|---|---|---|---|
| 42 | 73 | 1E11HCDR1<br>4E4HCDR1<br>9D4HCDR1<br>12G8HCDR1 | CDRH 1-1 | SFGMH |
| 43 | 76 | 1H7HCDR1<br>9F5HCDR1<br>11D11HCDR1<br>11H9HCDR1 | CDRH 1-2 | NAWMS |
| 44 | 79 | 2E7HCDR1 | CDRH 1-3 | SYAMS |
| 45 | 82 | 3B6HCDR1 | CDRH 1-4 | GYYMH |
| 46 | 85 | 3C8HCDR1<br>5F5HCDR1<br>12E8HCDR1 | CDRH 1-5 | SYGMH |
| 47 | 88 | 4H6HCDR1 | CDRH 1-6 | DYAMS |
| 48 | 92 | 10E4HCDR1 | CDRH 1-7 | DYYMY |
| 49 | 97 | 13H2HCDR1 | CDRH 1-8 | TYSMN |
| 50 | 100 | 32H7HCDR1 | CDRH 1-9 | SYGMH |
| 51 | 74 | 1E11HCDR2<br>4E4HCDR2<br>9D4HCDR2<br>12G8HCDR2 | CDRH 2-1 | VISFDGSIKYSVDSVKG |
| 52 | 77 | 1H7HCDR2 | CDRH 2-2 | RIKSTTDGGTTDYAAPVKG |
| 53 | 80 | 2E7HCDR2 | CDRH 2-3 | AISGSGGRTYYADSVKG |
| 54 | 83 | 3B6HCDR2 | CDRH 2-4 | WINPNSGGTNYAQKFQG |

TABLE 4A-continued

Exemplary Heavy Chain CDR Amino Acid Sequences

| Alt Num | SEQ ID NO: | Contained in Reference | Designation | Sequence |
|---|---|---|---|---|
| 55 | 86 | 3C8HCDR2 5F5HCDR2 12E8HCDR2 | CDRH 2-5 | VISYDGSHESYADSVKG |
| 56 | 89 | 4H6HCDR2 | CDRH 2-6 | FIRSRAYGGIPEYAASVKG |
| 57 | 91 | 9F5HCDR2 | CDRH 2-7 | RIKSKIDGGIIDYIAPVKG |
| 58 | 93 | 10E4HCDR2 | CDRH 2-8 | WISPNSGGINYAQKFQG |
| 59 | 95 | 11D11HCDR2 11H9HCDR2 | CDRH 2-9 | RIKSKTDGGTTDYAAPVKG |
| 60 | 98 | 13H2HCDR2 | CDRH 2-10 | SISSSSSYRYYADSVKG |
| 61 | 101 | 32H7HCDR2 | CDRH 2-11 | VIWYDGSNKYYADSVKG |
| 62 | 75 | 1E11HCDR3 4E4HCDR3 9D4HCDR3 | CDRH 3-1 | DRLNYYDSSGYYHYKYYGMAV |
| 63 | 78 | 1H7HCDR3 9F5HCDR3 11D11HCDR3 11H9HCDR3 | CDRH 3-2 | DRTGYSISWSSYYYYYGMDV |
| 64 | 81 | 2E7HCDR3 | CDRH 3-3 | DQREVGPYSSGWYDYYYGMDV |
| 65 | 84 | 3B6HCDR3 | CDRH 3-4 | DQMSIIMLRGVFPPYYYGMDV |
| 66 | 87 | 3C8HCDR3 5F5HCDR3 12E8HCDR3 | CDRH 3-5 | ERKRVTMSTLYYYFYYGMDV |
| 67 | 90 | 4H6HCDR3 | CDRH 3-6 | GRGIAARWDY |
| 68 | 94 | 10E4HCDR3 | CDRH3-7 | GGYSGYAGLYSHYYGMDV |
| 69 | 96 | 12G8HCDR3 | CDRH 3-8 | DRLNYYDSSGYYHYKYYGLAV |
| 70 | 99 | 13H2HCDR3 | CDRH 3-9 | EGVSGSSPYSISWYDYYYGMDV |
| 71 | 102 | 32H7HCDR3 | CDRH 3-10 | AGGIAAAGLYYYYGMDV |

TABLE 4B

Exemplary Light Chain CDR Amino Acid Sequences

| Alt Num | SEQ ID NO: | Contained in Reference | Designation | Sequence |
|---|---|---|---|---|
| 72 | 42 | 1E11LCD1 4E4LCD1 9D4LCD1 12G8LCD1 | CDRL 1-1 | SGSSSNIGNNYVS |
| 73 | 45 | 1H7LCD1 9F5LCD1 11D11LC1 11H9LCD1 | CDRL 1-2 | SGSSSNIGSNYVY |
| 74 | 48 | 2E7LCD1 | CDRL 1-3 | RASQGIRNDLG |
| 75 | 51 | 3B6LCD1 | CDRL 1-4 | QGDSLRSFYAS |
| 76 | 54 | 3C8LCD1 | CDRL 1-5 | KSSQSLLHSAGKTYLY |
| 77 | 57 | 4H6LCD1 | CDRL 1-6 | RSSQSLLHSFGYNYLD |
| 78 | 60 | 5F5LCD1 | CDRL 1-7 | KSSQSLLHSDGKTYLY |
| 79 | 62 | 10E4LCD1 | CDRL 1-8 | SGSSSNIGSNTVN |

TABLE 4B-continued

Exemplary Light Chain CDR Amino Acid Sequences

| Alt Num | SEQ ID NO: | Contained in Reference | Designation | Sequence |
|---|---|---|---|---|
| 80 | 65 | 12E8LCD1 | CDRL 1-9 | KSSQSLLHSDGRNYLY |
| 81 | 66 | 13H2LCD1 | CDRL 1-10 | RASQGIRKDLG |
| 82 | 69 | 32H7 LCD1<br>32H7m LCD1 | CDRL 1-11 | RASQSVSSGYLT |
| 83 | 43 | 1E11LCD2<br>4E4LCD2<br>9D4LCD2<br>12G8LCD2 | CDRL 2-1 | DNNKRPS |
| 84 | 46 | 1H7LCD2 | CDRL 2-2 | RSNQRPS |
| 85 | 49 | 2E7LCD2 | CDRL 2-3 | AASSLQS |
| 86 | 52 | 3B6LCD2 | CDRL 2-4 | GKNNRPS |
| 87 | 55 | 3C8LCD2<br>5F5LCD2<br>12E8LCD2 | CDRL 2-5 | EVSNRFS |
| 88 | 58 | 4H6LCD2 | CDRL 2-6 | LGSNRAS |
| 89 | 61 | 9F5LCD2<br>11D11LC2<br>11H9LCD2 | CDRL 2-7 | RNNQRPS |
| 90 | 63 | 10E4LCD2 | CDRL 2-8 | INNQRPS |
| 91 | 67 | 13H2LCD2 | CDRL 2-9 | GASSLQS |
| 92 | 70 | 32H7 LCD2<br>32H7m LCD2 | CDRL 2-10 | GASSRAT |
| 93 | 44 | 1E11LCD3<br>4E4LCD3<br>9D4LCD3<br>12G8LCD3 | CDRL 3-1 | GTWDSRLSAVV |
| 94 | 47 | 1H7LCD3<br>9F5LCD3<br>11D11LC3<br>11H9LCD3 | CDRL 3-2 | AAWDDSLSGWV |
| 95 | 50 | 2E7LCD3 | CDRL 3-3 | LQYNIYPWT |
| 96 | 53 | 3B6LCD3 | CDRL 3-4 | NSRDSSVYHLV |
| 97 | 56 | 3C8LCD3<br>5F5LCD3<br>12E8LCD3 | CDRL 3-5 | MQSFPLPLT |
| 98 | 59 | 4H6LCD3 | CDRL 3-6 | MQALQTPFT |
| 99 | 64 | 10E4LCD3 | CDRL 3-7 | AARDESLNGW |
| 100 | 68 | 13H2LCD3 | CDRL 3-8 | LQYNSFPWT |
| 101 | 71 | 32H7 LCD3 | CDRL 3-9 | QQYGNSLCR |
| 102 | 72 | 32H7m LCD3 | CDRL 3-10 | QQYGNSLSR |

The structure and properties of CDRs within a naturally occurring antibody has been described, supra. Briefly, in a traditional antibody, the CDRs are embedded within a framework in the heavy and light chain variable region where they constitute the regions responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). The CDRs provided herein, however, may not only be used to define the antigen binding domain of a traditional antibody structure, but may be embedded in a variety of other polypeptide structures, as described herein.

In one aspect, the CDRs provided are (a) a CDRH selected from the group consisting of (i) a CDRH1 selected from the group consisting of SEQ ID NO:73, 76, 79, 82, 85, 88, 92, 97, and 100; (ii) a CDRH2 selected from the group consisting of SEQ ID NO:74, 77, 80, 83, 86, 89, 91, 93, 95, 98, 101, and 129; (iii) a CDRH3 selected from the group consisting of SEQ ID NO:75, 78, 81, 84, 87, 90, 96, 99, 102, and 123; and (iv) a CDRH of (i), (ii) and (iii) that contains one or more, e.g., one, two, three, four or more amino acid substitutions (e.g., conservative amino acid substitutions), deletions or insertions of no more than five, four, three, two, or one amino acids; (B) a CDRL selected from the group consisting of (i) a CDRL1 selected from the group consisting of SEQ ID NO:42, 45, 48, 51, 54, 57, 62, 65, 66, and 69; (ii) a CDRL2 selected from the group consisting of SEQ ID NO:43, 46, 49, 52, 55, 58, 61, 63, 67, and 70; (iii) a CDRL3 selected from the group consisting of SEQ ID NO:44, 47, 50, 53, 56, 59, 64, 68, 71, and 72; and (iv) a CDRL of (i), (ii) and (iii) that contains one or more, e.g., one, two, three, four or more amino acid substitutions (e.g., conservative amino acid substitutions), deletions or insertions of no more than five, four, three, two, or one amino acids amino acids.

In another aspect, an antigen binding protein includes 1, 2, 3, 4, 5, or 6 variant forms of the CDRs listed in Tables 4A and 4B, each having at least 80%, 85%, 90% or 95% sequence identity to a CDR sequence listed in Tables 4A and 4B. Some antigen binding proteins include 1, 2, 3, 4, 5, or 6 of the CDRs listed in Tables 4A and 4B, each differing by no more than 1, 2, 3, 4 or 5 amino acids from the CDRs listed in these tables.

In yet another aspect, the CDRs disclosed herein include consensus sequences derived from groups of related monoclonal antibodies. As described herein, a "consensus sequence" refers to amino acid sequences having conserved amino acids common among a number of sequences and variable amino acids that vary within a given amino acid sequences. The CDR consensus sequences provided include CDRs corresponding to each of CDRH1, CDRH2, CDRH3, CDRL1, CDRL2 and CDRL3.

In still another aspect, an antigen binding protein includes the following associations of CDRL1, CDRL2 and CDRL3: SEQ ID NOs: 42, 43, and 44; SEQ ID NOs: 45, 46, and 47; SEQ ID NOs: 48, 49, and 50; SEQ ID NOs: 51, 52, and 53; SEQ ID NOs: 54, 55, and 56; SEQ ID NOs: 57, 58, and 59; SEQ ID NOs: 60, 55, and 56; SEQ ID NOs: 45, 61, and 47; SEQ ID NOs: 62, 63, and 64; SEQ ID NOs: 65, 55, and 56; SEQ ID NOs: 66, 67, and 68; SEQ ID NOs: 69, 70, and 71; and SEQ ID NOs: 69, 70, and 72.

In an additional aspect, an antigen binding protein includes the following associations of CDRH1, CDRH2 and CDRH3: SEQ ID NOs: 73, 74, and 75; SEQ ID NOs: 76, 77, and 78; SEQ ID NOs: 79, 80, and 81; SEQ ID NOs: 82, 83, and 84; SEQ ID NOs: 85, 86, and 87; SEQ ID NOs: 88, 89, and 90; SEQ ID NOs: 76, 91, and 78; SEQ ID NOs: 92, 93, and 94; SEQ ID NOs: 76, 95, and 78; SEQ ID NOs: 73, 74, and 96; SEQ ID NOs: 97, 98, and 99; and SEQ ID NOs: 100, 101, and 102.

In another aspect, an antigen binding protein includes the following associations of CDRL1, CDRL2 and CDRL3 with CDRH1, CDRH2 and CDRH3: SEQ ID NOs: 42, 43, and 44 with SEQ ID NOs: 73, 74, and 75; SEQ ID NOs: 45, 46, and 47 with SEQ ID NOs: 76, 77, and 78; SEQ ID NOs: 48, 49, and 50 with SEQ ID NOs: 79, 80, and 81; SEQ ID NOs: 51, 52, and 53 with SEQ ID NOs: 82, 83, and 84; SEQ ID NOs: 54, 55, and 56 with SEQ ID NOs: 85, 86, and 87; SEQ ID NOs: 57, 58, and 59 with SEQ ID NOs: 88, 89, and 90; SEQ ID NOs: 60, 55, and 56 with SEQ ID NOs: 85, 86, and 87; SEQ ID NOs: 45, 61, and 47 with SEQ ID NOs: 76, 91, and 78; SEQ ID NOs: 62, 63, and 64 with SEQ ID NOs: 92, 93, and 94; SEQ ID NOs: 45, 61, and 47 with SEQ ID NOs: 76, 95, and 78; SEQ ID NOs: 65, 55, and 56 with SEQ ID NOs: 85, 86, and 87; SEQ ID NOs: 42, 43, and 44 with SEQ ID NOs: 73, 74, and 96; SEQ ID NOs: 66, 67, and 68 with SEQ ID NOs: 97, 98, and 99; SEQ ID NOs: 69, 70, and 71 with SEQ ID NOs: 100, 101, and 102; and SEQ ID NOs: 69, 70, and 72 with SEQ ID NOs: 100, 101, and 102.

Consensus sequences were determined using standard phylogenic analyses of the CDRs corresponding to the $V_H$ and $V_L$ of anti-CGRP R antibodies. The consensus sequences were determined by keeping the CDRs contiguous within the same sequence corresponding to a $V_H$ or $V_L$.

As illustrated in FIGS. 3A, 3B, 4, 5A, 5B, 5C, 5D and 5E, lineage analysis of a variety of the antigen binding proteins provided herein resulted in groups of related sequences, designated as light chain CDR groups K1, K2, K3, and K4 (FIGS. 3A and 3B), light chain CDR groups L1, L2, L3, and L4 (FIG. 4), and heavy chain CDR groups HC1 (FIG. 5A), HC2 (FIG. 5B), HC3 (FIG. 5C), HC4 (FIG. 5C), HC5 (FIG. 5D) and HC6 (FIG. 5E). Some of the above groups were used to generate additional consensus sequences, as illustrated in FIGS. 3A, 3B, 4, and 5F, to yield light chain CDR groups K1,4 (FIG. 3A), K2,3 (FIG. 3B), L1,2,3 (FIG. 4), and LAll (FIG. 4), and heavy chain CDR groups HCA and HCB (FIG. 5F).

The consensus sequences of the various CDR region groups are provided below:

K1 Consensus

CDR1 RASQGIRX$_1$DLG (SEQ ID NO:103), wherein X$_1$ is selected from the group consisting of N and K.

CDR2 X$_1$ASSLQS (SEQ ID NO:104), wherein X$_1$ is selected from the group consisting of A and G.

CDR3 LQYNX$_1$X$_2$PWT (SEQ ID NO:105), wherein X$_1$ is selected from the group consisting of I and S, and X$_2$ is selected from the group consisting of Y and F.

K4 Consensus

CDR3 QQYGNSLX$_1$R (SEQ ID NO:106), wherein X$_1$ is selected from the group consisting of S and C.

K1,4 Consensus

CDR1 RASQX$_1$X$_2$X$_3$X$_4$GX$_5$LX$_6$ (SEQ ID NO:107), wherein X$_1$ is selected from the group consisting of S and G, X$_2$ is selected from the group consisting of V and I, X$_3$ is selected from the group consisting of S and R, X$_4$ is selected from the group consisting of S, N and K, X$_5$ is selected from the group consisting of Y and D, and X$_6$ is selected from the group consisting of T and G.

CDR2 X$_1$ASSX$_2$X$_3$X$_4$ (SEQ ID NO:108), wherein X$_1$ is selected from the group consisting of G and A, X$_2$ is selected from the group consisting of R and L, X$_3$ is selected from the group consisting of A and Q, and X$_4$ is selected from the group consisting of T and S.

CDR3 X$_1$QYX$_2$X$_3$X$_4$X$_5$X$_6$X$_7$ (SEQ ID NO:109), wherein X$_1$ is selected from the group consisting of Q and L, X$_2$ is selected from the group consisting of G and N, X$_3$ is selected from the group consisting of N and T, X$_4$ is selected from the group consisting of S, Y and F, X$_5$ is selected from the group consisting of L and P, X$_6$ is selected from the group consisting of C, W and S, and X$_7$ is selected from the group consisting of R and T.

K3 Consensus

CDR1 KSSQSLLHSX$_1$GX$_2$X$_3$YLY (SEQ ID NO:110), wherein X$_1$ is selected from the group consisting of D and A, X$_2$ is selected from the group consisting of R and K, and X$_3$ is selected from the group consisting of N and T.

K2,3 Consensus

CDR1 $X_1$SSQSLLHS$X_2$G$X_3X_4$YL$X_5$ (SEQ ID NO:111), wherein $X_1$ is selected from the group consisting of R and K, $X_2$ is selected from the group consisting of F, D and A, $X_3$ is selected from the group consisting of Y, R and K, $X_4$ is selected from the group consisting of N and T, and $X_5$ is selected from the group consisting of D and Y.

CDR2 $X_1X_2$SNR$X_3$S (SEQ ID NO:112), wherein $X_1$ is selected from the group consisting of L and E, $X_2$ is selected from the group consisting of G and V, and $X_3$ is selected from the group consisting of A and F.

CDR3 MQ$X_1X_2X_3X_4$P$X_5$T (SEQ ID NO:113), wherein $X_1$ is selected from the group consisting of A and S, $X_2$ is selected from the group consisting of L and F, $X_3$ is selected from the group consisting of Q and P, $X_4$ is selected from the group consisting of T and L, and $X_5$ is selected from the group consisting of F and L.

Lm3 Consensus

CDR2 R$X_1$NQRPS (SEQ ID NO:114), wherein $X_1$ is selected from the group consisting of N and S.

Lm1,2,3 Consensus

CDR1 SGSSSNIG$X_1$N$X_2$V$X_3$ (SEQ ID NO:115), wherein $X_1$ is selected from the group consisting of N and S, $X_2$ is selected from the group consisting of Y and T, and $X_3$ is selected from the group consisting of S, N and Y.

CDR2 $X_1X_2$N$X_3$RPS (SEQ ID NO:116), wherein $X_1$ is selected from the group consisting of D, T and R, $X_2$ is selected from the group consisting of N and S, and $X_3$ is selected from the group consisting of K and Q.

CDR3 $X_1X_2X_3$D$X_4X_5$L$X_6X_7$VV (SEQ ID NO:117), wherein $X_1$ is selected from the group consisting of G and A, $X_2$ is selected from the group consisting of T and A, $X_3$ is selected from the group consisting of W and R, $X_4$ is selected from the group consisting of S and D, $X_5$ is selected from the group consisting of R and S, $X_6$ is selected from the group consisting of S and N, and $X_7$ is selected from the group consisting of A and G.

LAll Consensus

CDR1 $X_1$G$X_2X_3$S$X_4X_5X_6X_7X_8X_9X_{10}X_{11}$ (SEQ ID NO:118), wherein $X_1$ is selected from the group consisting of S and Q, $X_2$ is present or absent, and if present, is S, $X_3$ is selected from the group consisting of S and D, $X_4$ is present or absent, and if present, is N, $X_5$ is selected from the group consisting of I and L, $X_6$ is selected from the group consisting of G and R, $X_7$ is selected from the group consisting of N and S, $X_8$ is selected from the group consisting of N and F, $X_9$ is selected from the group consisting of Y and T, $X_{10}$ is selected from the group consisting of V and A, and $X_{11}$ is selected from the group consisting of S, N and Y.

CDR2 $X_1X_2$N$X_3$RPS (SEQ ID NO:119), wherein $X_1$ is selected from the group consisting of D, G, T, and R, $X_2$ is selected from the group consisting of N, K and S, and $X_3$ is selected from the group consisting of K, N and Q.

CDR3 $X_1X_2X_3$D$X_4X_5X_6X_7X_8X_9$V (SEQ ID NO:120), wherein $X_1$ is selected from the group consisting of G, N and A, $X_2$ is selected from the group consisting of T, S and A, $X_3$ is selected from the group consisting of W and R, $X_4$ is selected from the group consisting of S and D, $X_5$ is selected from the group consisting of R and S, $X_6$ is selected from the group consisting of L and V, $X_7$ is selected from the group consisting of S, Y and N, $X_8$ is selected from the group consisting of A, H and G, and $X_9$ is selected from the group consisting of V and L.

HC1 Consensus

CDR1 $X_1$YYM$X_2$ (SEQ ID NO:121), wherein $X_1$ is selected from the group consisting of G and D, $X_2$ is selected from the group consisting of H and Y.

CDR2 WI$X_1$PNSGGTNYAQKFQG (SEQ ID NO:122), wherein $X_1$ is selected from the group consisting of N and S.

CDR3 $X_1X_2X_3$S$X_4X_5X_6X_7X_8$G$X_9X_{10}X_{11}X_{12}$YY$X_{13}$GMDV (SEQ ID NO:123), wherein $X_1$ is selected from the group consisting of D and G, $X_2$ is selected from the group consisting of Q and G, $X_3$ is selected from the group consisting of M and Y, $X_4$ is selected from the group consisting of I and G, $X_5$ is selected from the group consisting of I and Y, $X_6$ is selected from the group consisting of M and A, $X_7$ is present or absent, and if present, is L, $X_8$ is present or absent, and if present, is R, $X_9$ is selected from the group consisting of V and L, $X_{10}$ is selected from the group consisting of F and Y, $X_{11}$ is selected from the group consisting of P and S, $X_{12}$ is selected from the group consisting of P and H, and $X_{13}$ is present or absent, and if present, is Y.

HC2 Consensus

CDR2 RIKS$X_1$TDGGTTDY$X_2$APVKG (SEQ ID NO:124), wherein $X_1$ is selected from the group consisting of K and T, and $X_2$ is selected from the group consisting of T and A.

HC3 Consensus

CDR1 $X_1$Y$X_2$M$X_3$ (SEQ ID NO:125), wherein $X_1$ is selected from the group consisting of T and S, $X_2$ is selected from the group consisting of S and A, and $X_3$ is selected from the group consisting of N and S.

CDR2 $X_1$IS$X_2$S$X_3X_4X_5X_6$YYADSVKG (SEQ ID NO:126), wherein $X_1$ is selected from the group consisting of S and A, $X_2$ is selected from the group consisting of S and G, $X_3$ is selected from the group consisting of S and G, $X_4$ is selected from the group consisting of S and G, $X_5$ is selected from the group consisting of Y and R, and $X_6$ is selected from the group consisting of R and T.

CDR3 $X_1X_2X_3X_4X_5X_6X_7$PYS$X_8X_9$WYDYYYGMDV (SEQ ID NO:127), wherein $X_1$ is selected from the group consisting of E and D, $X_2$ is selected from the group consisting of G and Q, $X_3$ is selected from the group consisting of V and R, $X_4$ is selected from the group consisting of S and E, $X_5$ is selected from the group consisting of G and V, $X_6$ is selected from the group consisting of S and G, $X_7$ is present or absent, and if present, is S, $X_8$ is selected from the group consisting of I and S, and $X_9$ is selected from the group consisting of S and G.

HC4 Consensus

CDR1 S$X_1$GMH (SEQ ID NO:128), wherein $X_1$ is selected from the group consisting of F and Y.

CDR2 VIS$X_1$DGS$X_2$KY$X_3X_4$DSVKG (SEQ ID NO:129), wherein $X_1$ is selected from the group consisting of F and Y, $X_2$ is selected from the group consisting of I and H, $X_3$ is selected from the group consisting of S and Y, and $X_4$ is selected from the group consisting of V and A.

CDR3 $X_1$R$X_2X_3X_4X_5X_6$S$X_7X_8$YY$X_9X_{10}X_{11}$YYG$X_{12}X_{13}$V (SEQ ID NO:130), wherein $X_1$ is selected from the group consisting of D and E, $X_2$ is selected from the group consisting of L and K, $X_3$ is selected from the group consisting of N and R, $X_4$ is selected from the group consisting of Y and V, $X_5$ is selected from the group consisting of Y and T, $X_6$ is selected from the group consisting of D and M, $X_7$ is selected from the group consisting of S and T, $X_8$ is selected from the group consisting of G and L, $X_9$ is selected from the group consisting of H and Y, $X_{10}$ is present or absent, and if present, is Y, $X_{11}$ is selected from the group consisting of K and F, $X_{12}$ is selected from the group consisting of M and L, and $X_{13}$ is selected from the group consisting of A and D.

HCA Consensus

CDR1 $X_1X_2X_3MX_4$ (SEQ ID NO:131), wherein $X_1$ is selected from the group consisting of N and S, $X_2$ is selected from the group consisting of A, Y and F, $X_3$ is selected from the group consisting of W, A and G, and $X_4$ is selected from the group consisting of S and H.

CDR2 $X_1IX_2X_3X_4X_5X_6GX_7X_8X_9X_{10}X_{11}X_{12}X_{13}X_{14}VKG$ (SEQ ID NO:132), wherein $X_1$ is selected from the group consisting of R, A and V, $X_2$ is selected from the group consisting of K, S and W, $X_3$ is selected from the group consisting of S, G, F and Y, $X_4$ is present or absent, and if present, is selected from the group consisting of K and T, $X_5$ is present or absent, and if present, is T, $X_6$ is selected from the group consisting of D and S, $X_7$ is selected from the group consisting of G and S, $X_8$ is selected from the group consisting of T, R, I, N and H, $X_9$ is selected from the group consisting of T and K, $X_{10}$ is selected from the group consisting of D and Y, $X_{11}$ is selected from the group consisting of Y and S, $X_{12}$ is selected from the group consisting of T, A and V, $X_{13}$ is selected from the group consisting of A and D, and $X_{14}$ is selected from the group consisting of P and S.

CDR3 $X_1X_2X_3X_4X_5X_6X_7X_8X_9X_{10}X_{11}X_{12}X_{13}X_{14}X_{15}X_{16}X_{17}GX_{18}X_{19}V$ (SEQ ID NO:133), wherein $X_1$ is selected from the group consisting of D, A and E, $X_2$ is selected from the group consisting of R, Q and G, $X_3$ is selected from the group consisting of T, R, L, G and K, $X_4$ is selected from the group consisting of G, E, N, I and R, $X_5$ is selected from the group consisting of Y, V and A, $X_6$ is selected from the group consisting of S, G, Y, A and T, $X_7$ is selected from the group consisting of I, P, D, A and M, $X_8$ is present or absent, and if present, is selected from the group consisting of S and Y, $X_9$ is present or absent, and if present, is selected from the group consisting of W, S and T, $X_{10}$ is selected from the group consisting of S, G and L, $X_{11}$ is selected from the group consisting of S, G, L and Y, $X_{12}$ is present or absent, and if present, is selected from the group consisting of W and Y, $X_{13}$ is selected from the group consisting of Y and H, $X_{14}$ is present or absent, and if present, is selected from the group consisting of Y and D, $X_{15}$ is selected from the group consisting of Y, K and F, $X_{16}$ is present or absent, and if present, is Y, $X_{17}$ is present or absent, and if present, is Y, $X_{18}$ is selected from the group consisting of M and L, and $X_{19}$ is selected from the group consisting of D and A.

HCB Consensus

CDR1 $X_1X_2X_3X_4X_5$ (SEQ ID NO:134), wherein $X_1$ is selected from the group consisting of N, G, D, S and A, $X_2$ is selected from the group consisting of A, F and Y, $X_3$ is selected from the group consisting of W, Y, A and G, $X_4$ is selected from the group consisting of M and L, and $X_5$ is selected from the group consisting of S and H.

CDR2 $X_1IX_2X_3X_4X_5X_6X_7X_8X_9X_{10}X_{11}X_{12}X_{13}X_{14}X_{15}X_{16}X_{17}G$ (SEQ ID NO:135), wherein $X_1$ is selected from the group consisting of R, W, A, V, S and F, $X_2$ is selected from the group consisting of K, N, S, W and R, $X_3$ is selected from the group consisting of S, P, G, F and Y, $X_4$ is present or absent, and if present, is selected from the group consisting of K, T and R, $X_5$ is present or absent, and if present, is selected from the group consisting of T and A, $X_6$ is selected from the group consisting of D, N, H, S and Y, $X_7$ is selected from the group consisting of G and S, $X_8$ is selected from the group consisting of T, G, R, I, N, H and Y, $X_9$ is selected from the group consisting of T, K, R and P, $X_{10}$ is selected from the group consisting of D, N, Y and E, $X_{11}$ is selected from the group consisting of Y and S, $X_{12}$ is selected from the group consisting of T, A and V, $X_{13}$ is selected from the group consisting of A, Q and D, $X_{14}$ is selected from the group consisting of P, K and S, $X_{15}$ is selected from the group consisting of V and F, and $X_{16}$ is selected from the group consisting of K and Q.

CDR3 $X_1X_2X_3X_4X_5SX_6X_7X_8X_9X_{10}X_{11}X_{12}X_{13}X_{14}X_{15}X_{16}GX_{17}X_{18}V$ (SEQ ID NO:136), wherein $X_1$ is selected from the group consisting of D, G, A and E, $X_2$ is selected from the group consisting of R, G and Q, $X_3$ is selected from the group consisting of T, M, Y, R, L, G and K, $X_4$ is selected from the group consisting of G, S, E, N, I and R, $X_5$ is selected from the group consisting of Y, I, G, V and A, $X_6$ is selected from the group consisting of S, I, Y, G, A and T, $X_7$ is selected from the group consisting of I, M, A, P and D, $X_8$ is present or absent, and if present, is selected from the group consisting of S, L and Y, $X_9$ is present or absent, and if present, is selected from the group consisting of W, R, S and T, $X_{10}$ is selected from the group consisting of S, G and L, $X_{11}$ is selected from the group consisting of S, V, L, G and Y, $X_{12}$ is present or absent, and if present, is selected from the group consisting of F, Y and W, $X_{13}$ is selected from the group consisting of Y, P, S and H, $X_{14}$ is present or absent, and if present, is selected from the group consisting of Y, P, D and H, $X_{15}$ is selected from the group consisting of Y, K and F, $X_{16}$ is present or absent, and if present, is Y, $X_{17}$ is present or absent, and if present, is Y, and $X_{18}$ is selected from the group consisting of M and L.

In some cases the antigen binding protein comprises at least one heavy chain CDR1, CDR2, or CDR3 having one of the above consensus sequences. In some cases, the antigen binding protein comprises at least one light chain CDR1, CDR2, or CDR3 having one of the above consensus sequences. In other cases, the antigen binding protein comprises at least two heavy chain CDRs according to the above consensus sequences, and/or at least two light chain CDRs according to the above consensus sequences. In still other cases, the antigen binding protein comprises at least three heavy chain CDRs according to the above consensus sequences, and/or at least three light chain CDRs according to the above consensus sequences.

Exemplary Antigen Binding Proteins

According to one aspect, provided is an isolated antigen-binding protein that binds CGRP R comprising (A) one or more heavy chain complementary determining regions (CDRHs) selected from the group consisting of: (i) a CDRH1 selected from the group consisting of SEQ ID NO:73, 76, 79, 82, 85, 88, 92, 97, and 100; (ii) a CDRH2 selected from the group consisting of SEQ ID NO:74, 77, 80, 83, 86, 89, 91, 93, 95, 98, 101, and 129; (iii) a CDRH3 selected from the group consisting of SEQ ID NO:75, 78, 81, 84, 87, 90, 96, 99, 102, and 123; and (iv) a CDRH of (i), (ii) and (iii) that contains one or more, e.g., one, two, three, four or more amino acid substitutions, deletions or insertions of no more than five, four, three, four, two or one amino acids; (B) one or more light chain complementary determining regions (CDRLs) selected from the group consisting of: (i) a CDRL1 selected from the group consisting of SEQ ID NO:42, 45, 48, 51, 54, 57, 62, 65, 66, and 69; (ii) a CDRL2 selected from the group consisting of SEQ ID NO:43, 46, 49, 52, 55, 58, 61, 63, 67, and 70; (iii) a CDRL3 selected from the group consisting of SEQ ID NO:44, 47, 50, 53, 56, 59, 64, 68, 71, and 72; and (iv) a CDRL of (i), (ii) and (iii) that contains one or more, e.g., one, two, three, four or more amino acid substitutions, deletions or insertions of no more than five, four, three, four, two or one amino acids; or (C) one or more heavy chain CDRHs of (A) and one or more light chain CDRLs of (B).

In yet another embodiment, the isolated antigen-binding protein may comprise (A) a CDRH selected from the group consisting of (i) a CDRH1 selected from the group consisting of SEQ ID NO:73, 76, 79, 82, 85, 88, 92, 97, and 100; (ii) a CDRH2 selected from the group consisting of SEQ ID NO:74, 77, 80, 83, 86, 89, 91, 93, 95, 98, 101, and 129; and (iii) a CDRH3 selected from the group consisting of SEQ ID NO:75, 78, 81, 84, 87, 90, 96, 99, 102, and 123; (B) a CDRL selected from the group consisting of (i) a CDRL1 selected from the group consisting of SEQ ID NO:42, 45, 48, 51, 54, 57, 62, 65, 66, and 69; (ii) a CDRL2 selected from the group consisting of SEQ ID NO:43, 46, 49, 52, 55, 58, 61, 63, 67, and 70; and (iii) a CDRL3 selected from the group consisting of SEQ ID NO:44, 47, 50, 53, 56, 59, 64, 68, 71, and 72; or (C) one or more heavy chain CDRHs of (A) and one or more light chain CDRLs of (B). In one embodiment, the isolated antigen-binding protein may include (A) a CDRH1 of SEQ ID NO:73, 76, 79, 82, 85, 88, 92, 97, and 100, a CDRH2 of SEQ ID NO:74, 77, 80, 83, 86, 89, 91, 93, 95, 98, 101, and 129, and a CDRH3 of SEQ ID NO:75, 78, 81, 84, 87, 90, 96, 99, 102, and 123, and (B) a CDRL1 of SEQ ID NO:42, 45, 48, 51, 54, 57, 62, 65, 66, and 69, a CDRL2 of SEQ ID NO:43, 46, 49, 52, 55, 58, 61, 63, 67, and 70, and a CDRL3 of SEQ ID NO:44, 47, 50, 53, 56, 59, 64, 68, 71, and 72.

In another embodiment, the heavy chain variable region ($V_H$) has at least 70%, 75%, 80%, 85%, 90%, 95%, 97% or 99% sequence identity with an amino acid sequence selected from the group consisting of SEQ ID NO:158-170, and/or the $V_L$ has at least 70%, 75%, 80%, 85%, 90%, 95%, 97% or 99% sequence identity with an amino acid sequence selected from the group consisting of SEQ ID NO:137-153. In a further embodiment, the $V_H$ is selected from the group consisting of SEQ ID NO: 158-170, and/or the $V_L$ is selected from the group consisting of SEQ ID NO: 137-153.

In another aspect, also provided is an isolated antigen binding protein that specifically binds to an epitope formed of amino acid residues from both the CRLR and RAMP1 components of the CGRP R.

In yet another embodiment, the isolated antigen binding protein described hereinabove comprises a first amino acid sequence comprising at least one of the CDRH consensus sequences disclosed herein, and a second amino acid sequence comprising at least one of the CDRL consensus sequences disclosed herein. In one aspect, the first amino acid sequence comprises at least two of the CDRH consensus sequences, and/or the second amino acid sequence comprises at least two of the CDRL consensus sequences.

In certain embodiments, the first and the second amino acid sequence are covalently bonded to each other.

In a further embodiment, the first amino acid sequence of the isolated antigen-binding protein includes the CDRH3 of SEQ ID NO:75, 78, 81, 84, 87, 90, 96, 99, 102, and 123, CDRH2 of SEQ ID NO:74, 77, 80, 83, 86, 89, 91, 93, 95, 98, 101, and 129, and CDRH1 of SEQ ID NO:73, 76, 79, 82, 85, 88, 92, 97, and 100, and/or the second amino acid sequence of the isolated antigen binding protein comprises the CDRL3 of SEQ ID NO:44, 47, 50, 53, 56, 59, 64, 68, 71, and 72, CDRL2 of SEQ ID NO:43, 46, 49, 52, 55, 58, 61, 63, 67, and 70, and CDRL1 of SEQ ID NO:42, 45, 48, 51, 54, 57, 62, 65, 66, and 69.

In a further embodiment, the antigen binding protein comprises at least two CDRH sequences of heavy chain sequences H1, H2, H3, H4, H5, H6, H7, H8, H9, H10, H11, H12, or H13, as shown in Table 5A. In again a further embodiment, the antigen binding protein comprises at least two CDRL sequences of light chain sequences L1, L2, L3, L4, L5, L6, L7, L8, L9, L10, L11, L12, L13, L14, L15, L16, or L17, as shown in Table 5B. In again a further embodiment, the antigen binding protein comprises at least two CDRH sequences of heavy chain sequences H1, H2, H3, H4, H5, H6, H7, H8, H9, H10, H11, H12, or H13, as shown in Table 5A, and at least two CDRLs of light chain sequences L1, L2, L3, L4, L5, L6, L7, L8, L9, L10, L11, L12, L13, L14, L15, L16, or L17, as shown in Table 5B.

In again another embodiment, the antigen binding protein comprises the CDRH1, CDRH2, and CDRH3 sequences of heavy chain sequences H1, H2, H3, H4, H5, H6, H7, H8, H9, H10, H11, H12, or H13, as shown in Table 5A. In yet another embodiment, the antigen binding protein comprises the CDRL1, CDRL2, and CDRL3 sequences of light chain sequences L1, L2, L3, L4, L5, L6, L7, L8, L9, L10, L11, L12, L13, L14, L15, L16, or L17, as shown in Table 5B.

In yet another embodiment, the antigen binding protein comprises all six CDRs of L1 and H1, or L2 and H2, or L3 and H3, or L4 and H4, or L5 and H5, or L6 and H1, or L7 and H6, or L8 and H5, or L9 and H1, or L10 and H7, or L11 and H8, or L12 and H9, or L12 and H10, or L13 and H5, or L14 and H11, or L15 and H12, or L16 and H13, or L17 and H13, as shown in Tables 5A and 5B.

TABLE 5A

Exemplary Heavy Chain Amino Acid Sequence Regions

| Reference | Full Heavy Chain Group | Full Heavy Chain SEQ ID NO | Heavy Chain Variable Region Group | Heavy Chain Variable Region SEQ ID NO | CDRH1 SEQ ID NO | CDRH2 SEQ ID NO | CDRH3 SEQ ID NO |
|---|---|---|---|---|---|---|---|
| 1E11 | H1 | 29 | $V_H1$ | 158 | 73 | 74 | 75 |
| 1H7 | H2 | 30 | $V_H2$ | 159 | 76 | 77 | 78 |
| 2E7 | H3 | 31 | $V_H3$ | 160 | 79 | 80 | 81 |
| 3B6 | H4 | 32 | $V_H4$ | 161 | 82 | 83 | 84 |
| 3C8 | H5 | 33 | $V_H5$ | 162 | 85 | 86 | 87 |
| 4E4 | H1 | 29 | $V_H1$ | 158 | 73 | 74 | 75 |
| 4H6 | H6 | 34 | $V_H6$ | 163 | 88 | 89 | 90 |
| 5F5 | H5 | 33 | $V_H5$ | 162 | 85 | 86 | 87 |
| 9D4 | H1 | 29 | $V_H1$ | 158 | 73 | 74 | 75 |
| 9F5 | H7 | 35 | $V_H7$ | 164 | 76 | 91 | 78 |
| 10E4 | H8 | 36 | $V_H8$ | 165 | 92 | 93 | 94 |
| 11D11 | H9 | 37 | $V_H9$ | 166 | 76 | 95 | 78 |
| 11H9 | H10 | 38 | $V_H10$ | 167 | 76 | 95 | 78 |
| 12E8 | H5 | 33 | $V_H5$ | 162 | 85 | 86 | 87 |
| 12G8 | H11 | 39 | $V_H11$ | 168 | 73 | 74 | 96 |
| 13H2 | H12 | 40 | $V_H12$ | 169 | 97 | 98 | 99 |
| 32H7 | H13 | 41 | $V_H13$ | 170 | 100 | 101 | 102 |

TABLE 5A-continued

Exemplary Heavy Chain Amino Acid Sequence Regions

| Reference | Full Heavy Chain Group | Full Heavy Chain SEQ ID NO | Heavy Chain Variable Region Group | Heavy Chain Variable Region SEQ ID NO | CDRH1 SEQ ID NO | CDRH2 SEQ ID NO | CDRH3 SEQ ID NO |
|---|---|---|---|---|---|---|---|
| 32H7 CS | H13 | 41 | $V_H13$ | 170 | 100 | 101 | 102 |
| 32H8 | | | $V_H14$ | 171 | | | |
| 33B5 | | | $V_H15$ | 172 | | | |
| 33E4 | | | $V_H16$ | 173 | | | |
| 34E3 | | | $V_H17$ | 174 | | | |

TABLE 5B

Exemplary Light Chain Amino Acid Sequence Regions

| Reference | Full Light Chain Group | Full Light Chain SEQ ID NO | Light Chain Variable Region Group | Light Chain Variable Region SEQ ID NO | CDRL1 SEQ ID NO | CDRL2 SEQ ID NO | CDRL3 SEQ ID NO |
|---|---|---|---|---|---|---|---|
| 1E11 | L1 | 12 | $V_L1$ | 137 | 42 | 43 | 44 |
| 1H7 | L2 | 13 | $V_L2$ | 138 | 45 | 46 | 47 |
| 2E7 | L3 | 14 | $V_L3$ | 139 | 48 | 49 | 50 |
| 3B6 | L4 | 15 | $V_L4$ | 140 | 51 | 52 | 53 |
| 3C8 | L5 | 16 | $V_L5$ | 141 | 54 | 55 | 56 |
| 4E4 | L6 | 17 | $V_L6$ | 142 | 42 | 43 | 44 |
| 4H6 | L7 | 18 | $V_L7$ | 143 | 57 | 58 | 59 |
| 5F5 | L8 | 19 | $V_L8$ | 144 | 60 | 55 | 56 |
| 9D4 | L9 | 20 | $V_L9$ | 145 | 42 | 43 | 44 |
| 9F5 | L10 | 21 | $V_L10$ | 146 | 45 | 61 | 47 |
| 10E4 | L11 | 22 | $V_L11$ | 147 | 62 | 63 | 64 |
| 11D11 | L12 | 23 | $V_L12$ | 148 | 45 | 61 | 47 |
| 11H9 | L12 | 23 | $V_L12$ | 148 | 45 | 61 | 47 |
| 12E8 | L13 | 24 | $V_L13$ | 149 | 65 | 55 | 56 |
| 12G8 | L14 | 25 | $V_L14$ | 150 | 42 | 43 | 44 |
| 13H2 | L15 | 26 | $V_L15$ | 151 | 66 | 67 | 68 |
| 32H7 | L16 | 27 | $V_L16$ | 152 | 69 | 70 | 71 |
| 32H7 CS | L17 | 28 | $V_L17$ | 153 | 69 | 70 | 72 |
| 32H8 | | | $V_L18$ | 154 | | | |
| 33B5 | | | $V_L19$ | 155 | | | |
| 33E4 | | | $V_L20$ | 156 | | | |
| 34E3 | | | $V_L21$ | 157 | | | |

In one aspect, the isolated antigen-binding proteins provided herein can be a monoclonal antibody, a polyclonal antibody, a recombinant antibody, a human antibody, a humanized antibody, a chimeric antibody, a multispecific antibody, or an antibody antigen binding fragment thereof.

In another embodiment, the antibody fragment of the isolated antigen-binding proteins provided herein can be a Fab fragment, a Fab' fragment, an F(ab')$_2$ fragment, an Fv fragment, a diabody, or a single chain antibody molecule.

In a further embodiment, the isolated antigen binding protein provided herein is a human antibody and can be of the IgG1-, IgG2- IgG3- or IgG4-type.

In another embodiment, the antigen binding protein consists of a just a light or a heavy chain polypeptide as set forth in Tables 5A-5B. In some embodiments, the antigen binding protein consists just of a light chain variable or heavy chain variable domain such as those listed in Tables 5A-5B. Such antigen binding proteins can be pegylated with one or more PEG molecules.

In yet another aspect, the isolated antigen-binding protein provided herein can be coupled to a labeling group and can compete for binding to the extracellular portion of human CGRP R with an antigen binding protein of one of the isolated antigen-binding proteins provided herein. In one embodiment, the isolated antigen binding protein provided herein can reduce monocyte chemotaxis, inhibit monocyte migration into tumors or inhibit accumulation and function of tumor associated macrophage in a tumor when administered to a patient.

As will be appreciated by those in the art, for any antigen binding protein with more than one CDR from the depicted sequences, any combination of CDRs independently selected from the depicted sequences is useful. Thus, antigen binding proteins with one, two, three, four, five or six of independently selected CDRs can be generated. However, as will be appreciated by those in the art, specific embodiments generally utilize combinations of CDRs that are non-repetitive, e.g., antigen binding proteins are generally not made with two CDRH2 regions, etc.

Some of the antigen binding proteins provided are discussed in more detail below.

Antigen Binding Proteins and Binding Epitopes and Binding Domains

When an antigen binding protein is said to bind an epitope, such as one or both components of CGRP R, or the extracellular domain of CGRP R, for example, what is meant is that the antigen binding protein specifically binds to a specified portion of CGRP R, which may be on CRLR, RAMP1, or span portions of both CRLR and RAMP1. In cases where the antigen binding protein binds only CRLR (and not RAMP1), the antigen binding protein would not be expected to selectively bind CGRP R because CRLR is shared, inter alia, with AM1 and AM1 receptors. Similarly, in cases where the antigen binding protein binds only RAMP1 (and not CRLR), the antigen binding protein would not be expected to selectively bind CGRP R because RAMP1 is shared, inter alia, with AMY1 receptor. In cases where the antigen binding protein interacts with both CRLR and RAMP1, the antigen binding protein is expected to bind residues or sequences of residues, or regions in both CRLR and RAMP1. In none of the foregoing embodiments is an antigen binding protein expected to contact every residue within CRLR or RAMP1. Similarly, not every amino acid substitution or deletion within CRLR, RAMP1 or the extracellular domains thereof is expected to significantly affect binding affinity.

Methods detailed, e.g., in Example 10, maybe used to assess what regions of multimeric receptors, such as CGRP R, may be involved in binding to selected antigen binding proteins.

Competing Antigen Binding Proteins

In another aspect, antigen binding proteins are provided that compete with one of the exemplified, or "reference" antibodies or functional fragments binding to the epitope described above for specific binding to CGRP R. Such antigen binding proteins may also bind to the same epitope as one of the herein exemplified antigen binding proteins, or an overlapping epitope. Antigen binding proteins and fragments that compete with or bind to the same epitope as the exemplified or reference antigen binding proteins are expected to show similar functional properties. The exemplified antigen binding proteins and fragments include those with the heavy and light chains, variable region domains $V_L1$-$V_L17$ and $V_H1$-$V_H13$, and CDRs included in Tables 2A, 2B, 3, 4A, 4B, 5A and 5B. Thus, as a specific example, the antigen binding proteins that are provided include those that compete with an antibody having: (a) all 6 of the CDRs listed for an antibody listed in Tables 5A and 5B; (b) a $V_H$ and a $V_L$ selected from $V_L1$-$V_L17$ and $V_H1$-$V_H13$ and listed for an antibody listed in Tables 5A and 5B; or (c) two light chains and two heavy chains as specified for an antibody listed in Tables 5A and 5B. Other examples of suitable reference antibodies include those that have a heavy chain variable region having a sequence corresponding to any of the sequences identified as SEQ ID NO:158-170 and a light chain variable region having a sequence corresponding to any of the sequences identified as SEQ ID NO:137-153.

Binding competition may be assessed, for example, using a binning assays, such as the Biacore assay described in Example 7, below. In that example, 19 antibodies described herein were tested against each of six "reference" antibodies—five neutralizing antibodies (11D11, 3B6, 4H6, 12G8, and 9F5) and one non-neutralizing antibody (34E3). The assay results, shown in Table 13, indicate that all of the tested neutralizing antibodies (1E11, 1H7, 2E7, 3B6, 3C8, 4E4, 4H6, 5F5, 9D4, 9F5, 10E4, 11D11, 11H9, 12E8, 12G8, 13H2 and 32H7) bind to essentially the same region of CGRP R, which is distinct from the region of CGRP R that is bound by the non-neutralizing antibodies tested (32H8, 33B5, 33E4 and 34E3). Based on these data, any of the neutralizing antibodies would make exemplary reference antigen binding proteins in a competition assay, particularly any of the neutralizing antibodies that were immobilized in the assay described in Example 7—11D11, 3B6, 4H6, 12G8, and 9F5.

Monoclonal Antibodies

The antigen binding proteins that are provided include monoclonal antibodies that bind to CGRP R. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6. An exemplary method of preparing monoclonal antibodies is described in Example 2, below.

In some instances, a hybridoma cell line is produced by immunizing an animal (e.g., a transgenic animal having human immunoglobulin sequences) with a CGRP R immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds CGRP R (e.g., as described in Examples 1-3, below). Such hybridoma cell lines, and anti-CGRP R monoclonal antibodies produced by them, are aspects of the present application.

Monoclonal antibodies secreted by a hybridoma cell line can be purified using any technique known in the art. Hybridomas or mAbs may be further screened to identify mAbs with particular properties, such as the ability to bind cells expressing CGRP, ability to block or interfere the binding of the CGRP ligand or $CGRP_{8-37}$ peptide, or the ability to functionally block the receptor, e.g., using a cAMP assay, e.g., as described below.

Chimeric and Humanized Antibodies

Chimeric and humanized antibodies based upon the foregoing sequences are also provided. Monoclonal antibodies for use as therapeutic agents may be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, *Proc. Natl. Acad. Sci. USA* 81:6851-6855, which are hereby incorporated by reference. CDR grafting is described, for example, in U.S. Pat. Nos. 6,180,370, 5,693,762, 5,693,761, 5,585,089, and U.S. Pat. No. 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089, and 5,693,762; Jones et al., 1986, *Nature* 321:522-525; Riechmann et al., 1988, *Nature* 332: 323-27; Verhoeyen et al., 1988, *Science* 239:1534-1536), In one aspect, the CDRs of the light and heavy chain variable regions of the antibodies provided herein (see, Table 4) are grafted to framework regions (FRs) from antibodies from the same, or a different, phylogenetic species. For example, the CDRs of the heavy and light chain variable regions $V_H1$, $V_H2$, $V_H3$, $V_H4$, $V_H5$, $V_H6$, $V_H7$, $V_H8$, $V_H9$, $V_H10$, $V_H11$, $V_H12$, and $V_H13$, and/or $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, and $V_L17$ can be grafted to consensus human FRs. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of anti-CGRP R antibody are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In certain embodiments, constant regions from species other than human can be used along with the human variable region(s) to produce hybrid antibodies.

Fully Human Antibodies

Fully human antibodies are also provided. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, Nature 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, *Nature* 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, *Intern. Rev. Immunol.* 13: 65-93; Harding and Lonberg, 1995, *Ann. N.Y. Acad. Sci.* 764:536-546). The preparation of HuMab mice is described in detail in Taylor et al., 1992, *Nucleic Acids Research* 20:6287-6295; Chen et al., 1993, *International Immunology* 5:647-656; Tuaillon et al., 1994, *J. Immunol.* 152:2912-2920; Lonberg et al., 1994, *Nature* 368: 856-859; Lonberg, 1994, *Handbook of Exp. Pharmacology* 113:49-101; Taylor et al., 1994, *International Immunology* 6:579-591; Lonberg and Huszar, 1995, *Intern. Rev. Immunol.* 13:65-93; Harding and Lonberg, 1995, *Ann. N.Y Acad. Sci.* 764:536-546; Fishwild et al., 1996, *Nature Biotechnology* 14:845-851; the foregoing references are hereby incorporated by reference in their entirety for all purposes. See, further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., 1997, *Nature Genetics* 15:146-156, which are hereby incorporated by reference. For example, the HCo7 and HCo12 transgenic mice strains can be used to generate anti-CGRP R antibodies. Further details regarding the production of human antibodies using transgenic mice are provided in the examples below.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., 1991, *J. Mol. Biol.* 227:381; and Marks et al., 1991, *J. Mol. Biol.* 222:581). Phage display techniques mimic immune selection through the display of antibody repertoires on the surface of filamentous bacteriophage, and subsequent selection of phage by their binding to an antigen of choice. One such technique is described in PCT Publication No. WO 99/10494 (hereby incorporated by reference), which describes the isolation of high affinity and functional agonistic antibodies for MPL- and msk-receptors using such an approach.

Bispecific or Bifunctional Antigen Binding Proteins

The antigen binding proteins that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553.

Various Other Forms

Some of the antigen binding proteins that are provided are variant forms of the antigen binding proteins disclosed above (e.g., those having the sequences listed in Tables 2-5). For instance, some of the antigen binding proteins have one or more conservative amino acid substitutions in one or more of the heavy or light chains, variable regions or CDRs listed in Tables 2-5.

Naturally-occurring amino acids may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (–0.4); threonine (–0.7); serine (–0.8); tryptophan (–0.9); tyrosine (–1.3); proline (–1.6); histidine (–3.2); glutamate (–3.5); glutamine (–3.5); aspartate (–3.5); asparagine (–3.5); lysine (–3.9); and arginine (–4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within ±1 are included, and in other aspects, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (–0.4); proline (–0.5±1); alanine (–0.5); histidine (–0.5); cysteine (–1.0); methionine (–1.3); valine (–1.5); leucine (–1.8); isoleucine (–1.8); tyrosine (–2.3); phenylalanine (–2.5) and tryptophan (–3.4). In making changes based upon similar hydrophilicity values, in certain embodiments, the substitution of amino acids whose hydrophilicity values are within ±2 is included, in other embodiments, those which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in Table 6.

TABLE 6

Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |

TABLE 6-continued

Conservative Amino Acid Substitutions

| Original Residue | Exemplary Substitutions |
|---|---|
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for CGRP R neutralizing activity, (see examples below) thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See, Moult, 1996, *Curr. Op. in Biotech.* 7:422-427; Chou et al., 1974, *Biochem.* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% can have similar structural topologies. The recent growth of the protein structural database (PDB) has provided enhanced predictability of secondary structure, including the potential number of folds within a polypeptide's or protein's structure. See, Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See, Holm, 1999, supra; and Brenner, 1997, supra).

In some embodiments, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antigen binding protein). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105, which are each incorporated herein by reference.

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to CGRP R. For example, one or more of the CDRs listed in Tables 4 and 5 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., CGRP R or epitope thereof).

Mimetics (e.g., "peptide mimetics" or "peptidomimetics") based upon the variable region domains and CDRs that are described herein are also provided. These analogs can be peptides, non-peptides or combinations of peptide and non-peptide regions. Fauchere, 1986, *Adv. Drug Res.* 15:29; Veber and Freidinger, 1985, *TINS p.* 392; and Evans et al., 1987, *J. Med. Chem.* 30:1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antibody displaying a desired biological activity, such as here the ability to specifically bind CGRP R, but have one or more peptide linkages optionally replaced by a linkage selected from: —CH$_2$NH—, —CH$_2$S—, —CH$_2$—CH$_2$—, —CH—CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used in certain embodiments to generate more stable proteins. In addition, constrained peptides comprising a consensus sequence or a substantially identical consensus sequence variation may be generated by methods known in the art (Rizo and Gierasch, 1992, *Ann. Rev. Biochem.* 61:387), incorporated herein by reference), for example, by adding internal cysteine residues capable of forming intramolecular disulfide bridges which cyclize the peptide.

Derivatives of the antigen binding proteins that are described herein are also provided. The derivatized antigen binding proteins can comprise any molecule or substance that imparts a desired property to the antibody or fragment, such as increased half-life in a particular use. The derivatized antigen binding protein can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antigen binding protein for a particular use (e.g., administration to a subject, such as a human subject, or other in vivo or in vitro uses). Examples of molecules that can be used to derivatize an antigen binding protein include albumin (e.g., human serum albumin) and polyethylene glycol (PEG). Albumin-linked and PEGylated derivatives of antigen binding proteins can be prepared using techniques well known in the art. Certain antigen binding proteins include a pegylated single chain polypeptide as described herein. In one embodiment, the antigen binding protein is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of CGRP R binding proteins with other proteins or polypeptides, such as by expression of recombinant fusion proteins comprising heterologous polypeptides fused to the N-terminus or C-terminus of a CGRP R binding protein. For example, the conjugated peptide may be a heterologous signal (or leader) polypeptide, e.g., the yeast alpha-factor leader, or a peptide such as an epitope tag. CGRP antigen binding protein-containing fusion proteins can comprise peptides added to facilitate purification or identification of the CGRP R binding protein (e.g., poly-His). A CGRP R binding protein also can be linked to the FLAG peptide as described in Hopp et al., 1988, *Bio/Technology* 6:1204; and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more CGRP R binding proteins may be employed as CGRP R antagonists. Oligomers may be in the form of covalently-linked or non-covalently-linked dimers, trimers, or higher oligomers. Oligomers comprising two or more CGRP R binding proteins are contemplated for use, with one example being a homodimer. Other oligomers include heterodimers, homotrimers, heterotrimers, homotetramers, heterotetramers, etc.

One embodiment is directed to oligomers comprising multiple CGRP R-binding polypeptides joined via covalent or non-covalent interactions between peptide moieties fused to the CGRP R binding proteins. Such peptides may be peptide linkers (spacers), or peptides that have the property of promoting oligomerization. Leucine zippers and certain polypeptides derived from antibodies are among the peptides that can promote oligomerization of CGRP R binding proteins attached thereto, as described in more detail below.

In particular embodiments, the oligomers comprise from two to four CGRP R binding proteins. The CGRP R binding protein moieties of the oligomer may be in any of the forms described above, e.g., variants or fragments. Preferably, the oligomers comprise CGRP R binding proteins that have CGRP R binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11.

One embodiment is directed to a dimer comprising two fusion proteins created by fusing a CGRP R binding protein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 and U.S. Pat. Nos. 5,426,048 and 5,262,522, is a single chain polypeptide extending from the N-terminal hinge region to the native C-terminus of the Fc region of a human IgG1 antibody. Another useful Fc polypeptide is the Fc mutein described in U.S. Pat. No. 5,457,035, and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of a CGRP R binding protein such as disclosed herein may be substituted for the variable portion of an antibody heavy and/or light chain.

Alternatively, the oligomer is a fusion protein comprising multiple CGRP R binding proteins, with or without peptide linkers (spacer peptides). Among the suitable peptide linkers are those described in U.S. Pat. Nos. 4,751,180 and 4,935,233.

Another method for preparing oligomeric CGRP R binding protein derivatives involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-278. In one approach, recombinant fusion proteins comprising a CGRP R binding protein fragment or derivative fused to a leucine zipper peptide are expressed in suitable host cells, and the soluble oligomeric CGRP R binding protein fragments or derivatives that form are recovered from the culture supernatant.

In certain embodiments, the antigen binding protein has a $K_D$ (equilibrium binding affinity) of less than 1 pM, 10 pM, 100 pM, 1 nM, 2 nM, 5 nM, 10 nM, 25 nM or 50 nM.

Another aspect provides an antigen-binding protein having a half-life of at least one day in vitro or in vivo (e.g., when administered to a human subject). In one embodiment, the antigen binding protein has a half-life of at least three days. In another embodiment, the antibody or portion thereof has a half-life of four days or longer. In another embodiment, the antibody or portion thereof has a half-life of eight days or longer. In another embodiment, the antibody or antigen-binding portion thereof is derivatized or modified such that it has a longer half-life as compared to the underivatized or unmodified antibody. In another embodiment, the antigen binding protein contains point mutations to increase serum half life, such as described in WO 00/09560, published Feb. 24, 2000, incorporated by reference.

Glycosylation

The antigen-binding protein may have a glycosylation pattern that is different or altered from that found in the native species. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev, Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118: 131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Hence, aspects include glycosylation variants of the antigen binding proteins wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region.

Labels and Effector Groups

In some embodiments, the antigen-binding comprises one or more labels. The term "labeling group" or "label" means any detectable label. Examples of suitable labeling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used as is seen fit.

The term "effector group" means any group coupled to an antigen binding protein that acts as a cytotoxic agent. Examples for suitable effector groups are radioisotopes or radionuclides (e.g. $^{3}H$, $^{14}C$, $^{15}N$, $^{35}S$, $^{90}Y$, $^{99}Tc$, $^{111}In$, $^{125}I$, $^{131}I$). Other suitable groups include toxins, therapeutic groups, or chemotherapeutic groups. Examples of suitable groups include calicheamicin, auristatins, geldanamycin and maytansine. In some embodiments, the effector group is coupled to the antigen binding protein via spacer arms of various lengths to reduce potential steric hindrance.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in MOLECULAR PROBES HANDBOOK by Richard P. Haugland, hereby expressly incorporated by reference.

Suitable proteinaceous fluorescent labels also include, but are not limited to, green fluorescent protein, including a *Renilla, Ptilosarcus*, or *Aequorea* species of GFP (Chalfie et al., 1994, *Science* 263:802-805), EGFP (Clontech Labs., Inc., Genbank Accession Number U55762), blue fluorescent protein (BFP, Quantum Biotechnologies, Inc., Quebec, Canada; Stauber, 1998, *Biotechniques* 24:462-471; Heim et al., 1996, *Curr. Biol.* 6:178-182), enhanced yellow fluorescent protein (EYFP, Clontech Labs., Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558).

Nucleic Acid Sequences Encoding CGRP Antigen Binding Proteins

Nucleic acids that encode for the antigen binding proteins described herein, or portions thereof, are also provided, including nucleic acids encoding one or both chains of an antibody, or a fragment, derivative, mutein, or variant thereof, polynucleotides encoding heavy chain variable regions or only CDRs, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Table 7 shows exemplary nucleic acid sequences encoding an IgG2 heavy chain constant region, a kappa light chain constant region and a lambda hCL-1 light chain constant region. Any variable region provided herein may be attached to these constant regions to form complete heavy and light chain sequences. However, it should be understood that these constant regions sequences are provided as specific examples only—one of skill in the art may employ other constant regions, including IgG1 heavy chain constant region, IgG3 or IgG4 heavy chain constant regions, any of the seven lambda light chain constant regions, including hCL-1, hCL-2, hCL-3 and hCL-7; constant regions that have been modified for improved stability, expression, manufacturability or other desired characteristics, and the like. In some embodiments, the variable region sequences are joined to other constant region sequences that are known in the art. Exemplary nucleic acid sequences encoding heavy and light chain variable regions are provided in Table 8.

TABLE 7

Exemplary Heavy And Light Chain Constant Region Nucleic Acid Sequences

| Type | Nucleic Acid Sequence/SEQ ID NO. |
|---|---|
| IgG2 heavy chain | gctagcaccaagggcccatcggtcttccccctggcgccc tgctccaggagcacctccgagagcacagcggccctgggc tgcctggtcaaggactacttccccgaaccggtgacggtg tcgtggaactcaggcgctctgaccagcggcgtgcacacc ttcccagctgtcctacagtcctcaggactctactccctc agcagcgtggtgaccgtgccctccagcaacttcggcacc cagacctacacctgcaacgtagatcacaagcccagcaac accaaggtggacaagacagttgagcgcaaatgttgtgtc gagtgcccaccgtgcccagcaccacctgtggcaggaccg tcagtcttcctcttccccccaaaacccaaggacaccctc atgatctcccggacccctgaggtcacgtgcgtggtggtg gacgtgagccacgaagacccccgaggtccagttcaactgg tacgtggacggcgtggaggtgcataatgccaagacaaag ccacgggaggagcagttcaacagcacgttccgtgtggtc agcgtcctcaccgttgtgcaccaggactggctgaacggc aaggagtacaagtgcaaggtctccaacaaaggcctccca gcccccatcgagaaaaccatctccaaaaccaaagggcag ccccgagaaccacaggtgtacaccctgcccccatcccgg gaggagatgaccaagaaccaggtcagcctgacctgcctg gtcaaaggcttctaccccagcgacatcgccgtggagtgg gagagcaatgggcagccggagaacaactacaagaccaca cctcccatgctggactccgacggctccttcttcctctac agcaagctcaccgtggacaagagcaggtggcagcagggg aacgtcttctcatgctccgtgatgcatgaggctctgcac aaccactacacgcagaagagcctctccctgtctccgggt aaatga [SEQ ID NO: 259] |
| IgG2 kappa light chain | cgtacggtggctgcaccatctgtcttcatcttcccgcca tctgatgagcagttgaaatctggaactgcctctgttgtg tgcctgctgaataacttctatcccagagaggccaaagta cagtggaaggtggataacgccctccaatcgggtaactcc caggagagtgtcacagagcaggacagcaaggacagcacc tacagcctcagcagcaccctgacgctgagcaaagcagac tacgagaaacacaaagtctacgcctgcgaagtcacccat caggggcctgagctcgcccgtcacaaagagcttcaacagg ggagagtgttag [SEQ ID NO: 260] |
| IgG2 lambda hCL-1 light chain | ggtcagcccaaggccaacccactgtcactctgttcccg ccctcctctgaggagcttcaagccaacaaggccacacta gtgtgtctgatcagtgacttctacccgggagctgtgaca gtggcctggaaggcagatggcagccccgtcaaggcggga gtggagaccaccaaaccctccaaacagagcaacaacaag tacgcggccagcagctacctgagcctgacgcccgagcag tggaagtcccacagaagctacagctgccaggtcacgcat gaagggagcaccgtggagaagacagtggcccctacagaa tgttcatag [SEQ ID NO: 261] |

Table 8 shows exemplary nucleic acid sequences encoding heavy chain and light chain variable regions, in which the various CDRL1, CDRL2 and CDRL3, or CDRH1, CDRH2 and CDRH3, sequences are embedded.

TABLE 8

Exemplary Light and Heavy Chain Variable Region Nucleic Acid Sequences

| Reference | SEQ ID NO. | Nucleic Acid Sequence |
|---|---|---|
| 2E7 V$_L$ | 175 | gacatccagatgacccagtctccatcctc cctgtctgcatctgtaggagacagagtca ccatcacttgccgggcaagtcagggcatt agaaatgatttaggctggtttcagcagaa accagggaaagcccctaagcgcctgatct atgctgcatccagtttgcaaagtggggtc ccatcaaggttcagcggcagtggatctgg gacagaattcactctcacaatcagcagcc tgcagcctgaagatttagcaacttattac tgtctacagtataatatttacccgtggac gttcggccaagggaccaaggtggaaatca aa |
| 13H2 V$_L$ | 176 | gacatccagatgacccagtctccatcctc cctgtctgcatctgtaggagacagagtca ccatcacttgccgggcaagtcagggcatt agaaaggattaggctggtatcagcagaa accagggaaagcccctaagcgcctgatct atggagcatccagtttgcaaagtggggtc ccatcaaggttcagcggcagtggatctgg gacagaattcactctcacaatcagcagcc tgcagcctgaagattttgcaacttattac tgtctacagtataatagtttcccgtggac gttcggccaagggaccaaggtggaaatca aa |
| 33B5 V$_L$ | 177 | aggtgcagctggtgcagtctggggctgag gtgaagaagtctggggcctcagtgaaggt ctcctgcaaggcttctggatacaccttca ccggctactatatgcactgggtgcgacag gcccctggacaagggcttgagtggatggg atggatcaaccctaacagtggtggcacaa actatgcacagaagtttcagggcagggtc accatgaccagggacacgtccatcagcac agcctacatggagctgagcaggctgagat ctgacgacacggccgtgtattactgtgcg agaaatgagtatagcagtgcctggccctt ggggtattggggccagggaaccctggtca ccgtctctagt |
| 4H6 V$_L$ | 178 | gatattgtgatgactcagtctccactctc cctgcccgtcacccctggagagccggcct ccatctcctgcaggtctagtcagagcctc ctgcatagttttgggtacaactatttgga ttggtacctgcagaagccagggcagtctc cacagctcctgatctatttgggttctaat cgggcctccggggtccctgacaggttcag tggcagtggatcaggcacagattttacac tgaaaatcagcagagtggaggctgaggat gttggggtttattactgcatgcaagctct acaaactccattcactttcggccctggga ccaaagtggatatcaaa |
| 3C8 V$_L$ | 179 | gatattatactgcccagactccactttc tctgtccgtcacccctggacagccggcct ccatctcctgcaagtctagtcagagcctc ctgcacagtgctggaaagacctatttgta ttggtacctgcagaagccaggccagcctc cacagctcctgatctatgaagtttccaac cggttctctggagtgccagataggttcag tggcagcgggtcagggacagatttcacac tgaaaatcagccgggtggaggctgaggat gttgggatttattactgcatgcaaagttt tccgcttccgctcactttcggcggaggga ccaaggtggagatcaaa |
| 5F5 V$_L$ | 180 | gatattattctgacccagactccactttc tctgtccgtcacccctggacagccggcct ccatctcctgcaagtctagtcagagcctc ctgcacagtgatgaaagacctatttgta ttggtacctgcagaagcccggccagcctc cacagctcctgatctatgaagtttccaac cggttctctggagagccagataggttcag tggcagcgggtcagggacagatttcacac tgaaaatcagccgggtggaggctgaggat gttgggacttattattgcatgcaaagttt tccgcttccgctcactttcggcggaggga ccaaggtggagatcaaa |
| 12E8 V$_L$ | 181 | gatattacactgacccagactccactttc tctgtccgtctcccctggacagccggcct ccatctcctgcaagtctagtcagagcctc ctgcacagtgatggaaggaactatctgta |

TABLE 8-continued

Exemplary Light and Heavy Chain Variable Region Nucleic Acid Sequences

| Reference | SEQ ID NO. | Nucleic Acid Sequence |
|---|---|---|
| | | ttggtacctgcagaagccaggccagcctc cacagctcctgatctatgaagtgtccaac cggttctctggactgccagataggttcag tggcagcgggtcagggacagatttcacac tgaaaatcagccgggtggaggctgaggat gttgggatttattactgcatgcaaagttt tccgcttccgctcacttttcggcggaggga ccaaggtggagatcaaa |
| 32H7 $V_L$ | 182 | gaaattgtgttgacgcagtctccaggcac cctgtctttgtctctcaggggaaagagcca ccctctcctgcagggccagtcagagtgtt agcagcggctacttaacctggtaccagca gaaacctggccaggctcccaggctcctca tctatggtgcatccagcagggccactggc atcccagacaggttcagtggcagtgggtc tgggacagacttcactctcaccatcagca gactggagcctgaagattttgcagtgtat tactgtcagcagtatggtaactcactgtg caggtttggccaggggaccaagctggaga tcaaa |
| 32H7 CS $V_L$ | 183 | gaaattgtgttgacgcagtctccaggcac cctgtctttgtctctcaggggaaagagcca ccctctcctgcagggccagtcagagtgtt agcagcggctacttaacctggtaccagca gaaacctggccaggctcccagactcctca tctatggtgcatccagcagggccactggc atcccagacaggttcagtggcagtgggtc tgggacggacttcactctcaccatcagca gactggagcctgaagattttgcagtgtat tactgtcagcagtatggtaactcactgag caggtttggccaggggaccaagctggaga tcaaa |
| 33E4 $V_L$ | 184 | gaaatagtgatgacgcagtctccagccac cctgtctgtgtctccaggggaaagagcca ccctctcctgtagggccagtcagagtgtt cgcagcaatttagcctggtaccagcagaa acctggccaggctcccaggctcctcattc atgatgcatcccccaggaccgctggtatc ccagccaggttcagtggcagtggatctgg gacagaattcactctcaccatcaacagcc tgcagtctgaagattttgcagtttattac tgtcagcagtataattactggactccgat cacctttggccaagggacacgactggaga ttaaa |
| 32H8 $V_L$ | 185 | gacatcgtgatgacccagtctccagactc cctggctgtgtctctgggcgagagggcca ccatcaactgcaagtccagccagagtatt ttagacagctccaacaatgataactactt agcttggtaccagcagaaaccaggacagc ctcctaaactgctcatttactgggcatct acccgggaatccggggtccctgaccgatt cagtggcagcgggtctgggacagatttca ctctcaccatcagcagcctgcaggctgaa gatgtggcagtttattactgtcagcaata ttataatactccattcactttcggccctg ggaccaaagtggatatcaaa |
| 1E11 $V_L$ | 186 | cagtctgtgttgacgcagccgccctcagt gtctgaggcccaggacagaaggtcacca tctcctgctctggaagcagctccaacatt gggaataattatgtatcctggtaccagca gctcccaggaacagcccccaaactcctca tttatgacaataataagcgaccctcaggg attcctgaccgattctctggctccaagtc tggcacgtcagccaccctgggcatcaccg gactccagactggggacgaggccgattat tactgcgaacatgggatagccgcctgag tgctgtggttttcggcggagggaccaagc tgaccgtccta |
| 4E4 $V_L$ | 187 | cagtctgtgttgacgcagccgccctcagt gtctgcggccccaggacagaaggtcacca tctcctgctctggaagcagctccaacatt gggaataattatgtatcctggtaccagca gctcccaggaacagcccccaaactcctca tttatgacaataataagcgaccctcaggg attcctgaccgattctctggctccaagtc tggcacgtcaaccaccctgggcatcaccg gactccagactggggacgaggccgattat tactgcgaacatgggatagccgcctgag tgctgtggttttcggcggagggaccaagc tgaccgtccta |
| 9D4 $V_L$ | 188 | cagtctgtgttgacgcagccgccctcagt gtctgcggccccaggacagaaggtcacca tctcctgctctggaagcagctccaacatt gggaataattatgtatcctggtaccagca gttcccaggaacagcccccaaactcctca tttatgacaataataagcgaccctcaggg attcctgaccgattctctggctccaagtc tggcacgtcagccaccctgggcatcaccg gactccagactggggacgaggccgattat tactgcgaacatgggatagccgcctgag tgctgtggttttcggcggagggaccaagc tgaccgtccta |
| 12G8 $V_L$ | 189 | cagtctgtgttgacgcagccgccctcagt gtctgcggccccaggacagaaggtcacca tctcctgctctggaagcagctccaacatt gggaataattatgtatcctggtaccagca gctcccaggaacagcccccaaactcctca tttatgacaataataagcgaccctcaggg attcctgaccgattctctggctccaagtc tggcacgtcagccaccctgggcatcaccg gactccagactggggacgaggccgattat tactgcgaacatgggatagccgcctgag tgctgtggttttcggcggagggaccaagc tgaccgtccta |
| 34E3 $V_L$ | 190 | cagtctgtgttgacgcagccgccctcaat gtctgcggccccaggacagaaggtcacca tctcctgctctggaagcagctccaacatt gggaataattatgtatcctggtaccagca gctcccaggaacagcccccaaactcctca tttatgacaataataagcgaccctcaggg attcctgaccgattctctggctccaagtc tggcacgtcagccaccctgggcatcaccg gactccagactggggacgaggccaattac tgctgcgaacatgggatatcggcctgag tgtttgggtgttcggcggagggaccaaac tgaccgtccta |
| 10E4 $V_L$ | 191 | cagtctgtgctgactcagccaccctcagc gtctgggaccccgggcagagggtcacca tctcttgttctggaagcagttccaatatc ggaagtaatactgtgaactggtaccagca gctcccaggaacggcccccaaactcctca tctatactaataatcagcggccctcaggg gtccctgaccgattctctggctccaagtc tggcacctcagcctcctggccatcagtg gactccagtctgaggatgaggctgattt tactgtgcagcgggatgagagcctgaa tggtgtggtattcggcggagggaccaagc tgaccgtccta |
| 11D11 $V_L$ 11H9 $V_L$ | 192 | cagtctgtgctgactcagccaccctcagc gtctgggaccccgggcagagagtcacca tctcttgttctggaagcagctccaacatc ggcagtaattatgtatactggtaccagca gctcccaggaacggcccccaaactcctca tctttaggaataatcagcggccctcaggg gtccctgaccgcttctctggctccaagtc tggcacctcagcctcctggccatcagtg ggctccggtccgaggatgaggctgattat |

TABLE 8-continued

Exemplary Light and Heavy Chain
Variable Region Nucleic Acid Sequences

| Reference | SEQ ID NO. | Nucleic Acid Sequence |
|---|---|---|
| | | tactgtgcagcatgggatgacagcctgag tggttgggtgttcggcggagggaccaagc tgaccgtccta |
| 1H7 V_L | 193 | cagtctgtgctgactcagccaccctcagc gtctgggaccccccgggcagagagtcacca tctcttgttctggaagcagctccaacatc ggcagtaattatgtatactggtaccagca gctcccaggagcggcccccaaactcctca tctttaggagtaatcagcggccctcaggg gtccctgaccgattctctggctccaagtc tggcacctcagcctcctggccatcagtg ggctccggtccgaggatgaggctgattat tactgtgcagcatgggatgacagcctgag tggttgggtgttcggcggagggaccaagc tgaccgtccta |
| 9F5 V_L | 194 | cagtctgtgctgactcagtcaccctcagc gtctgggaccccccgggcagagagtcacca tctcttgttctggaagcagctccaacatc ggcagtaattatgtatactggtaccagca gctcccaggagcggcccccaaactcctca tccttaggaataatcagcggccctcaggg gtccctgaccgattctctggctccaagtc tggcacctcagcctcctgaccatcagtg ggctccggtccgaggatgaggctgactat tattgtgcagcatgggatgacagcctgag tggttgggtgttcggcggagggaccaagc tgaccgtccta |
| 3B6 V_L | 195 | tcttctgagctgactcaggaccctactgt gtctgtggccttgggacagacagtcaaaa tcacatgccaaggagacagcctcagaagt ttttatgcaagctggtaccagcagaagcc aggacaggcccctgtacttgtcttctatg gtaaaacaaccggcccctcaggatccca gaccgattctctggctccagctcaggaaa cacagcttccttgaccatcactggggctc aggcggaagatgaggctgactattattgt aattcccgggacagcagtgtttaccatct ggtactcggcggagggaccaagctgaccg tccta |
| 3B6 V_H | 196 | caggtgcagttggtgcagtctggggctga ggtgaagaagcctggggcctcagtgaagg tctcctgcaaggcttctggatacaccttc accggctactatatgcactgggtgcgaca ggcccctggacaagggcttgagtggatgg gatggatcaaccctaacagtggtggcaca aactatgcacagaagtttcagggcaggt caccatgaccagggacacgtccatcagca cagcctacatggagctgagcaggctgaga tctgacgacacggccgtgtatttctgtgc gagagatcaaatgagtattattatgcttc ggggagttttcccccttactattacggt atggacgtctggggccaagggaccacggt caccgtctctagt |
| 10E4 V_H | 197 | caggtgcagctggtgcagtctggggctga ggtgaagaagcctggggcctcagtgaagg tctcctgcaaggcttctggatacaccttc accgactactatatgtactgggtgcgaca ggcccctggacaagggcttgagtggatgg gatggatcagccctaatagtggtggcaca aactatgcccagaagtttcagggcagggt caccatgaccagggacacgtctatcagca cagcctacatggagctgaggctgaga tctgacgacacggccgtgtattactgtgt gagaggaggatatagtggctacgctgggc tctactcccactactacggtatggacgtc tggggccaagggaccacggtcaccgtctc tagt |
| 32H8 V_H | 198 | caggtgcagctggtgcagtctggggctga ggtgaagaagcctggggcctcagtgaagg tctcctgcaaggcttctggatacaccttc accgcctactatttacactgggtgcgaca ggcccctggacaagggcttgagtggatgg gatggatcaaccctcacagtggtggcaca aactatgcacagaagtttcagggcagggt caccatgaccagggacacgtccatcagca cagcctacatggagctgagcaggctgaga tctgacgacacggccgtgttctactgtgc gagaggaaggcagtggctgggctttgact actggggccagggaaccctggtcaccgtc tctagt |
| 33B5 V_H | 199 | gacatccagatgacccagtctccatcctc cctgtctgcatctgtaggagacagagtta ccattacttgccgggcaagtcagggcatt agaaatgatttaggctggtatcagcagaa accagggaaagcccctaagcgcctgatct atgttgcatccagtttgcaaagtggggtc ccatcaaggttcagcggcagtggatctgg gacagaattcactctcacaatcagcagcc tgcagcctgaagattttgcaacttattac tgtctacagtataacacttacccgctcac tttcggcggagggaccaaggtggagatca ag |
| 11D11 V_H | 200 | gaggtacagctggtggagtctggggagg cttggtaaagcctggggggtccctcagac tctcctgtgcagcctctggattcactttc ggtaacgcctggatgagctgggtccgcca ggctccaggaaggggctgagtggggttg gccgtattaaaagcaaaactgatggtggg acaacagactacgctgcacccgtgaaagg cagattcaccatctcaagagatgattcaa aaaacacgctgtatctgcaaatgaacagc ctgaaaaccgaggacacagccgtgtattt ctgtaccacagatcggacccgggtatagca tcagctggtctagttactactactactac ggtatggacgtctggggccaagggaccac ggtcaccgtctctagt |
| 9F5 V_H | 201 | gaggtgcagctggtggagtctggggagg cttggtaaagcctggggggtccctcagac tctcctgtgcagcctctggattcactttc agtaacgcctggatgagctgggtccgcca ggctccaggaaggggctgagtggggttg gccgtattaaaagcaaaactgatggtggg acaacagactacactgcacccgtgaaagg cagattcaccatctcaagagatgattcaa aaaacacgctgtatctgcaaatgaatagc ctgaaagccgaggacacagccgtgtatta ctgtaccacagatcggacccgggtatagca tcagctggtctagttactactactactac ggtatggacgtctggggccaagggaccac ggtcaccgtctctagt |
| 11H9 V_H | 202 | gaggtacagctggtggagtctggggagg cttggtaaagcctggggggtccctcagac tctcctgtgcagcctctggattcactttc ggtaacgcctggatgagctgggtccgcca ggctccaggaaggggctgagtggggttg gccgtattaaaagcaaaactgatggtggg acaacagactacgctgcacccgtgaaagg cagattcaccatctcaagagatgattcaa aaaacacgctgtatctgcaaatgaacagc ctgaaaaccgaggacacagccgtgtatta ctgtaccacagatcggacccgggtatagca tcagctggtctagttactactactactac ggtatggacgtctggggccaagggaccac ggtcaccgtctctagt |

TABLE 8-continued

Exemplary Light and Heavy Chain Variable Region Nucleic Acid Sequences

| Reference | SEQ ID NO. | Nucleic Acid Sequence |
|---|---|---|
| 1H7 V$_H$ | 203 | gaggtgcagctggtggagtctgggggagg cttggtaaagcctggggggtcccttagac tctcctgtgcagcctctggattcactttc agtaacgcctggatgagctgggtccgcca ggctccagggaaggggctggagtgggttg gccgtattaaaagcacaactgatggtggg acaacagactacgctgcacccgtgaaagg cagattcaccatctcaagagatgattcaa aaaacacgctgtatctgcaaatgaacagc ctgaaaaccgaggacacagccgtgtatta ctgtaccacagatcggaccggatatagca tcagctggtctagttactactactactac ggtatggacgtctggggccaagggaccac ggtcaccgtctctagt |
| 13H2 V$_H$ | 204 | gaggtgcagctggtggagtctgggggagg cctggtcaagcctggggggtccctgagac tctcctgtgcagcctctggatacacctc agtacctatagcatgaactgggtccgcca ggctccagggaaggggctggagtgggtct catccattagtagtagtagtagttacaga tattacgcagactcagtgaagggccgatt caccatctccagagacaacgccaagaact cactgtatctgcaaatgagtagcctgaga gccgaggacacggctgtgtattactgtgc gagagaaggggtgtctggcagttcgccgt atagcatcagctggtacgactactattac ggtatggacgtctggggccaagggaccac ggtcaccgtctctagt |
| 2E7 V$_H$ | 205 | gaggtgcagctattggagtctgggggagg cttggtacagcctggggagtccctgagac tctcctgtgcagcctctggggttcacctt agcagctatgccatgagctgggtccgcca ggctccagggaaggggctggagtgggtct cagctattagtggtagtggtggtcgcaca tactacgcagactccgtgaagggccggtt caccatctccagagacaattccaagaaca cgctgtatctgcaaatgaatagcctgaga gccgaggacacgccgtatattactgtgc gaaagatcaaagggaggtagggccgtata gcagtggctggtacgactactactacggt atggacgtctggggccaagggaccacggt caccgtctctagt |
| 3C8 V$_H$<br>12E8 V$_H$<br>5F5 V$_H$ | 206 | caggtgcagctggtggagtctgggggagg cgtggtccagcctggggaggtccctgagac tctcctgtgcagcctctggattcacttc agtagctatggcatgcactgggtccgcca ggctccaggcaaggggctggagtgggtgg cagttatttcatatgatggaagtcatgaa tcctatgcagactccgtgaagggccgatt caccatctccagagacatttccaagaaca cgctgtatctgcaaatgaacagcctgaga gctgaggacacggctgtgtatttctgtgc gagagagaggaaacgggttacgatgtcta cctatatactacttctactacggtatg gacgtctggggccaagggaccacggtcac cgtctctagt |
| 4E4 V$_H$<br>9D4 V$_H$<br>1E11 V$_H$ | 207 | caggtgcagctggtggaatctgggggagg cgtggtccagcctggggaggtccctgagac tctcctgtgcagcctctggattcacttc agtagctttggcatgcactgggtccgcca ggctccaggcaaggggctggagtgggtgg cagttatatcatttgatggaagtattaag tattctgtagactccgtgaagggccgatt caccatctccagagacaattccaagaaca cgctgtttctgcaaatgaacagcctgcga gccgaggacacggctgtgtattactgtgc |

TABLE 8-continued

Exemplary Light and Heavy Chain Variable Region Nucleic Acid Sequences

| Reference | SEQ ID NO. | Nucleic Acid Sequence |
|---|---|---|
| | | gagagatcggctcaattactatgatagta gtggttattatcactacaaatactacggt atggccgtctggggccaagggaccacggt caccgtctctagt |
| 12G8 V$_H$ | 208 | caggtgcagctggtggaatctgggggagg cgtggtccagcctggggaggtccctgagac tctcctgtgcagcctctggattcacctc agtagctttggcatgcattgggtccgcca ggctccaggcaaggggctggagtgggtgg cagttatatcatttgatggaagtattaag tactctgtagactccgtgaagggccgatt caccatctccagagacaattcaaagaaca cgctgtttctgcaaatgaacagcctgcga gccgaggacacggctgtgtattactgtgc gagagatcggctcaattactatgatagta gtggttattatcactacaaatactacggt ctggccgtctggggccaagggaccacggt caccgtctctagt |
| 4H6 V$_H$ | 209 | gaggtgcagctggtggagtctgggggagg cttggtaaagccaggggcggtccctgagac tctcctgtacagcttctggattcacctt ggtgattatgctatgagctggttccgcca ggctccaggcaaggggctggagtggatag gtttcattagaagcagagcttatggtggg acaccagaatacgccgtctgtgaaaagg cagattcaccatctcaagagatgattcca aaaccatcgcctatctgcaaatgaacagc ctgaaaaccgaggacacagccgtgtatttt ctgtgctagaggacggggtattgcagctc gttgggactactggggccagggaaccctg gtcaccgtctctagt |
| 32H7 V$_H$ | 210 | caggtgcagctggtggagtctgggggagg cgtggtccagcctggggaggtccctgagac tctcctgtgcagcgtctggattcacctc agtagctatggcatgcactgggtccgcca ggctccaggcaaggggctggagtgggtgg cagttatatggtatgatggaagtaataaa tactatgcagactccgtgaagggccgatt catcatctccagagataaatccaagaaca cgctgtatctgcaaatgaacagcctgaga gccgaggacacggctgtgtattactgtgc gagagcgggggggtatagcagcagctggcc tctactactactacggtatggacgtctgg ggccaagggaccacggtcaccgtctctag t |
| 33E4 V$_H$ | 211 | caggtgcagttacagcagtggggcgcagg actgttgaagccttcggagaccctgtccc tcagctgcgctgtctatggtgggtccttc ggtggttactactggagctggatccgcca gcccccaggaaggggctggagtggattg ggaaatcaatcatagtggaggcaccaag tacaacccgtccctcaagagtcgagtcac catatcagtagacacgtccaagaaccagt tctccctgaagctgagctctgtgaccgcC gcggacacggctgtgtatttctgtgcgag aggcgatgtagtaggtttctttgactatt ggggccagggaaccctggtcaccgtctct agt |

Table 9 shows the SEQ ID NOs of exemplary nucleic acid sequences encoding complete heavy and light chains, as well as heavy and light chain variable regions, of exemplary isolated antigen-binding proteins, specifically, hCGRP R binding proteins, disclosed herein.

TABLE 9

Exemplary HC, LC, $V_H$ and $V_L$ Nucleic Acid Sequence SEQ ID NOs

| Ref | Variable Light SEQ ID NO. | Variable Heavy SEQ ID NO. | Full Light SEQ ID NO. | Full Heavy SEQ ID NO |
|---|---|---|---|---|
| 2E7 | 175 | 205 | 226 | 244 |
| 13H2 | 176 | 204 | 239 | 257 |
| 4H6 | 178 | 209 | 230 | 248 |
| 3C8 | 179 | 206 | 228 | 246 |
| 5F5 | 180 | 206 | 231 | 249 |
| 12E8 | 181 | 206 | 237 | 255 |
| 1E11 | 186 | 207 | 224 | 242 |
| 4E4 | 187 | 207 | 229 | 247 |
| 9D4 | 188 | 207 | 232 | 250 |
| 12G8 | 189 | 208 | 238 | 256 |
| 10E4 | 191 | 197 | 234 | 252 |
| 11D11 | 192 | 200 | 235 | 253 |
| 11H9 | 192 | 202 | 236 | 254 |
| 1H7 | 193 | 203 | 225 | 243 |
| 9F5 | 194 | 201 | 233 | 251 |
| 3B6 | 195 | 196 | 227 | 245 |
| 32H7 | 182 | 210 | 240 | 258 |
| 32H7 CS | 183 | 210 | 241 | 258 |
| 32H8 | 185 | 198 | | |
| 33B5 | 177 | 199 | | |
| 33E4 | 184 | 211 | | |
| 34E3 | 190 | 212 | | |

Nucleic acids encoding certain antigen binding proteins, or portions thereof (e.g., full length antibody, heavy or light chain, variable domain, or CDRH1, CDRH2, CDRH3, CDRL1, CDRL2, or CDRL3) may be isolated from B-cells of mice that have been immunized with CGRP R or immunogenic components thereof, e.g., by immunizing with full-length CGRP R (comprising both CRLR and RAMP1), with the extracellular domain of CGRP R (comprising extracellular domains of CRLR and RAMP1), with whole cells expressing CGRP R, with membranes prepared from cells expressing CGRP R, with fusion proteins, e.g., Fc fusions, comprising CRLR, RAMP1 (or extracellular domains thereof) fused to Fc, and other methods known in the art, for example, as described in the Examples 1-3 herein. The nucleic acid may be isolated by conventional procedures such as polymerase chain reaction (PCR). Phage display is another example of a known technique whereby derivatives of antibodies and other antigen binding proteins may be prepared. In one approach, polypeptides that are components of an antigen binding protein of interest are expressed in any suitable recombinant expression system, and the expressed polypeptides are allowed to assemble to form antigen binding protein molecules.

The nucleic acids provided in Tables 7-9 are exemplary only. Due to the degeneracy of the genetic code, each of the polypeptide sequences listed in Tables 2-5 or otherwise depicted herein are also encoded by a large number of other nucleic acid sequences besides those provided. One of ordinary skill in the art will appreciate that the present application thus provides adequate written description and enablement for each degenerate nucleotide sequence encoding each antigen binding protein.

An aspect further provides nucleic acids that hybridize to other nucleic acids (e.g., nucleic acids comprising a nucleotide sequence listed in Table 7, Table 8, Table 9 and/or SEQ ID NOs:224-258) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other typically remain hybridized to each other.

The basic parameters affecting the choice of hybridization conditions and guidance for devising suitable conditions are set forth by, for example, Sambrook, Fritsch, and Maniatis (2001, Molecular Cloning: A Laboratory Manual, Cold Spring Harbor Laboratory Press, Cold Spring Harbor, N.Y., supra; and Current Protocols in Molecular Biology, 1995, Ausubel et al., eds., John Wiley & Sons, Inc., sections 2.10 and 6.3-6.4), and can be readily determined by those having ordinary skill in the art based on, e.g., the length and/or base composition of the nucleic acid.

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively changes the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody. In one embodiment, a nucleic acid encoding any antigen binding protein described herein can be mutated to alter the amino acid sequence using molecular biology techniques that are well-established in the art.

Another aspect provides nucleic acid molecules that are suitable for use as primers or hybridization probes for the detection of nucleic acid sequences. A nucleic acid molecule can comprise only a portion of a nucleic acid sequence encoding a full-length polypeptide, for example, a fragment that can be used as a probe or primer or a fragment encoding an active portion (e.g., a CGRP R binding portion) of a polypeptide.

Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Another aspect provides vectors comprising a nucleic acid encoding a polypeptide or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors can comprise a nucleic acid in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see, Voss et al., 1986, *Trends Biochem. Sci.* 11:287, Maniatis et al., 1987, *Science* 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see, id.). It will be appreciated by those skilled in the art that the design of the expression vector can depend on such factors as the choice of the host cell to be transformed, the level of expression of protein desired, etc. The expression vectors can be introduced into host cells to thereby produce proteins or peptides, including fusion proteins or peptides, encoded by nucleic acids as described herein.

Another aspect provides host cells into which a recombinant expression vector has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Preparing of Antigen Binding Proteins

Non-human antibodies that are provided can be, for example, derived from any antibody-producing animal, such as mouse, rat, rabbit, goat, donkey, or non-human primate (such as monkey (e.g., cynomolgus or rhesus monkey) or ape (e.g., chimpanzee)). Non-human antibodies can be used, for instance, in in vitro cell culture and cell-culture based applications, or any other application where an immune response to the antibody does not occur or is insignificant, can be prevented, is not a concern, or is desired. In certain embodiments, the antibodies may be produced by immunizing animals using methods known in the art, as described above and/or in Examples 1-3 below. The examples describe the generation of anti CGRP R antibodies using three different immunogen preparations (i) whole cells expressing full-length versions of two major components of CGRP R-RAMP1 and CRLR; (ii) membrane extracts from such cells; and (iii) soluble CGRP R obtained by co-expressing and purifying the N-terminal extracellular domains of CRLR and RAMP1. The antibodies may be polyclonal, monoclonal, or may be synthesized in host cells by expressing recombinant DNA. Fully human antibodies may be prepared as described above by immunizing transgenic animals containing human immunoglobulin loci or by selecting a phage display library that is expressing a repertoire of human antibodies.

The monoclonal antibodies (mAbs) can be produced by a variety of techniques, including conventional monoclonal antibody methodology, e.g., the standard somatic cell hybridization technique of Kohler and Milstein, 1975, *Nature* 256: 495. Alternatively, other techniques for producing monoclonal antibodies can be employed, for example, the viral or oncogenic transformation of B-lymphocytes. One suitable animal system for preparing hybridomas is the murine system, which is a very well established procedure. Immunization protocols and techniques for isolation of immunized splenocytes for fusion are known in the art and illustrative approaches are described in the Examples, below. For such procedures, B cells from immunized mice are typically fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse may be used. Fusion procedures for making hybridomas also are well known.

The single chain antibodies that are provided may be formed by linking heavy and light chain variable domain (Fv region) fragments via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. U.S.A.* 85:5879; Ward et al., 1989, *Nature* 334:544, de Graaf et al., 2002, *Methods Mol. Biol.* 178:379-387. Single chain antibodies derived from antibodies provided herein include, but are not limited to scFvs comprising the variable domain combinations of the heavy and light chain variable regions depicted in Table 3, or combinations of light and heavy chain variable domains which include CDRs depicted in Tables 4A and 4B.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, *Methods Mol. Biol.* 178:303-316.

Accordingly, the antibodies that are provided include those comprising, for example, the variable domain combinations described, supra., having a desired isotype (for example, IgA, IgG1, IgG2, IgG3, IgG4, IgE, and IgD) as well as Fab or F(ab')$_2$ fragments thereof. Moreover, if an IgG4 is desired, it may also be desired to introduce a point mutation (CPSCP->CPPCP) in the hinge region as described in Bloom et al., 1997, *Protein Science* 6:407, incorporated by reference herein) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, *BioTechnology* 10:779.

Conservative modifications may be made to the heavy and light chain variable regions described in Table 3, or the CDRs described in Tables 4A and 4B (and corresponding modifications to the encoding nucleic acids) to produce a CGRP R binding protein having certain desirable functional and biochemical characteristics. Methods for achieving such modifications are described above.

CGRP antigen binding proteins may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or antigen binding fragment thereof. Another useful fusion partner for the antigen binding proteins or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antigen binding proteins described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. See, Table 4, supra. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for human CGRP R or for modifying the binding affinity of other antigen-binding proteins described herein.

Methods of Expressing Antigen Binding Proteins

Expression systems and constructs in the form of plasmids, expression vectors, transcription or expression cassettes that comprise at least one polynucleotide as described above are also provided herein, as well host cells comprising such expression systems or constructs.

The antigen binding proteins provided herein may be prepared by any of a number of conventional techniques. For example, CGRP R antigen binding proteins may be produced by recombinant expression systems, using any technique known in the art. See, e.g., Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Antigen binding proteins can be expressed in hybridoma cell lines (e.g., in particular antibodies may be expressed in hybridomas) or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216; 4,912,040; 4,740,461; 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: one or more CDRs provided herein; a light chain constant region; a light chain variable region; a heavy chain constant region (e.g., $C_H1$, $C_H2$ and/or $C_H3$); and/or another scaffold portion of a CGRP R antigen binding protein. These nucleic acid sequences are inserted into an appropriate expression vector using standard ligation techniques. In one embodiment, the heavy or light chain constant region is appended to the C-terminus of the anti-CGRP R-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments include those described in Bianchi and McGrew, 2003, *Biotech. Biotechnol. Bioeng.* 84:439-44, which is hereby incorporated by reference. Additional suitable expression vectors are discussed, for example, in *Methods Enzymol.*, vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the CGRP R binding protein coding sequence; the oligonucleotide sequence encodes polyHis (such as hexa-His), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the CGRP R binding protein from the host cell. Affinity purification can be accomplished, for example, by column chromatography using antibodies against the tag as an affinity matrix. Optionally, the tag can subsequently be removed from the purified CGRP R binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein that binds to CGRP R. As a result, increased quantities of a polypeptide such as an antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding a CGRP R binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding heavy chain or light chain comprising a CGRP R binding protein by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thomsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene (Prinster et al., 1982, *Nature* 296:39-42); and prokaryotic promoters such as the beta-lactamase promoter (VIIIa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising a human CGRP R binding protein by higher eukaryotes. Enhancers are cis-acting elements of DNA, usually about 10-300 by in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising a CGRP R antigen binding sequence has been inserted into the proper site of the vector, the completed vector may be inserted into a suitable host cell for amplification and/or polypeptide expression. The transformation of an expression vector for an antigen-binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antigen binding proteins with CGRP R binding properties. In another embodiment, a cell line from the B cell lineage that does not make its own antibody but has a capacity to make and secrete a heterologous antibody can be selected.

Use of Human CGRP Antigen Binding Proteins for Diagnostic and Therapeutic Purposes Antigen binding proteins are useful for detecting CGRP R in biological samples and identification of cells or tissues that produce CGRP R. For instance, the CGRP R antigen binding proteins can be used in diagnostic assays, e.g., binding assays to detect and/or quantify CGRP R expressed in a tissue or cell. Antigen binding proteins that specifically bind to CGRP R can also be used in treatment of diseases related to CGRP R in a patient in need thereof. In addition, CGRP R antigen binding proteins can be used to inhibit CGRP R from forming a complex with its ligand CGRP, thereby modulating the biological activity of CGRP R in a cell or tissue. Examples of activities that can be modulated include, but are not limited to, inhibiting vasodialation and/or decrease neurogenic inflammation. Antigen binding proteins that bind to CGRP R thus can modulate and/or block interaction with other binding compounds and as such may have therapeutic use in ameliorating diseases related to CGRP R.

Indications

A disease or condition associated with human CGRP R includes any disease or condition whose onset in a patient is caused by, at least in part, the interaction of CGRP R with its ligand, CGRP. The severity of the disease or condition can also be increased or decreased by the interaction of CGRP R with CGRP. Examples of diseases and conditions that can be treated with the antigen binding proteins described herein include headaches, such as cluster headaches, migraine, including migraine headaches, chronic pain, type II diabetes mellitus, inflammation, e.g., neurogenic inflammation, cardiovascular disorders, and hemodynamic derangement associated with endotoxemia and sepsis.

In particular, antigen binding proteins described herein can be used to treat migraine, either as an acute treatment commencing after a migraine attack has commenced, and/or as a prophylactic treatment administered, e.g., daily, weekly, biweekly, monthly, bimonthly, biannually, etc.) to prevent or reduce the frequency and/or severity of symptoms, e.g., pain symptoms, associated with migraine attacks.

Diagnostic Methods

The antigen binding proteins described herein can be used for diagnostic purposes to detect, diagnose, or monitor diseases and/or conditions associated with CGRP R. Also provided are methods for the detection of the presence of CGRP R in a sample using classical immunohistological methods known to those of skill in the art (e.g., Tijssen, 1993, *Practice and Theory of Enzyme Immunoassays*, Vol 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105: 3087-3096). The detection of CGRP R can be performed in vivo or in vitro.

Diagnostic applications provided herein include use of the antigen binding proteins to detect expression of CGRP R and binding of the ligands to CGRP R. Examples of methods useful in the detection of the presence of CGRP R include immunoassays, such as the enzyme linked immunosorbent assay (ELISA) and the radioimmunoassay (RIA).

For diagnostic applications, the antigen binding protein typically will be labeled with a detectable labeling group. Suitable labeling groups include, but are not limited to, the following: radioisotopes or radionuclides (e.g. $^{3}$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used.

In another aspect, an antigen binding protein can be used to identify a cell or cells that express CGRP R. In a specific embodiment, the antigen binding protein is labeled with a labeling group and the binding of the labeled antigen binding protein to CGRP R is detected. In a further specific embodiment, the binding of the antigen binding protein to CGRP R detected in vivo. In a further specific embodiment, the CGRP R antigen binding protein is isolated and measured using techniques known in the art. See, for example, Harlow and Lane, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Another aspect provides for detecting the presence of a test molecule that competes for binding to CGRP R with the antigen binding proteins provided. An example of one such assay would involve detecting the amount of free antigen binding protein in a solution containing an amount of CGRP R in the presence or absence of the test molecule. An increase in the amount of free antigen binding protein (i.e., the antigen binding protein not bound to CGRP R) would indicate that the test molecule is capable of competing for CGRP R binding with the antigen binding protein. In one embodiment, the antigen binding protein is labeled with a labeling group. Alternatively, the test molecule is labeled and the amount of free test molecule is monitored in the presence and absence of an antigen binding protein.

Methods of Treatment: Pharmaceutical Formulations, Routes of Administration

Methods of using the antigen binding proteins are also provided. In some methods, an antigen binding protein is provided to a patient. The antigen binding protein inhibits binding of CGRP to human CGRP R.

Pharmaceutical compositions that comprise a therapeutically effective amount of one or a plurality of the antigen binding proteins and a pharmaceutically acceptable diluent, carrier, solubilizer, emulsifier, preservative, and/or adjuvant are also provided. In addition, methods of treating a patient, e.g., for migraine, by administering such pharmaceutical composition are included. The term "patient" includes human patients.

Acceptable formulation materials are nontoxic to recipients at the dosages and concentrations employed. In specific embodiments, pharmaceutical compositions comprising a therapeutically effective amount of human CGRP R antigen binding proteins are provided.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins disclosed. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute. In certain embodiments, human CGRP R antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the human CGRP R antigen binding protein may be formulated as a lyophilizate using appropriate excipients such as sucrose.

The pharmaceutical compositions can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions may be provided in the form of a pyrogen-free, parenterally acceptable aqueous solution comprising the desired human CGRP R binding protein in a pharmaceutically acceptable vehicle. A particularly suitable vehicle for parenteral injection is sterile distilled water in which the human CGRP R antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Certain pharmaceutical compositions are formulated for inhalation. In some embodiments, human CGRP R antigen binding proteins are formulated as a dry, inhalable powder. In specific embodiments, human CGRP R antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins. Some formulations can be administered orally. Human CGRP R antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the human CGRP R antigen binding protein. Diluents, flavorings, low melting point waxes, vegetable oils, lubricants, suspending agents, tablet disintegrating agents, and binders may also be employed.

Some pharmaceutical compositions comprise an effective quantity of one or a plurality of human CGRP R antigen binding proteins in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving human CGRP R antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 2:547-556), poly (2-hydroxyethyl-inethacrylate) (Langer et al., 1981, *J. Biomed. Mater. Res.* 15:167-277 and Langer, 1982, *Chem. Tech.* 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.* 82:3688-3692; European Patent Application Publication Nos. EP 036, 676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

In certain embodiments, cells expressing a recombinant antigen binding protein as disclosed herein is encapsulated for delivery (see, Invest. Opthalmol Vis Sci 43:3292-3298, 2002 and Proc. Natl. Acad. Sciences 103:3896-3901, 2006).

In certain formulations, an antigen binding protein has a concentration of at least 10 mg/ml, 20 mg/ml, 30 mg/ml, 40 mg/ml, 50 mg/ml, 60 mg/ml, 70 mg/ml, 80 mg/ml, 90 mg/ml, 100 mg/ml or 150 mg/ml. Some formulations contain a buffer, sucrose and polysorbate. An example of a formulation is one containing 50-100 mg/ml of antigen binding protein, 5-20 mM sodium acetate, 5-10% w/v sucrose, and 0.002-0.008% w/v polysorbate. Certain, formulations, for instance, contain 65-75 mg/ml of an antigen binding protein in 9-11 mM sodium acetate buffer, 8-10% w/v sucrose, and 0.005-0.006% w/v polysorbate. The pH of certain such formulations is in the range of 4.5-6. Other formulations have a pH of 5.0-5.5 (e.g., pH of 5.0, 5.2 or 5.4).

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. Kits for producing a single-dose administration unit are also provided. Certain kits contain a first container having a dried protein and a second container having an aqueous formulation. In certain embodiments, kits containing single and multi-chambered pre-filled syringes (e.g., liquid syringes and lyosyringes) are provided. The therapeutically effective amount of a human CGRP R antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the human CGRP R antigen binding protein is being used, the route of administration, and the size (body weight, body surface or organ size) and/or condition (the age and general health) of the patient. In certain embodiments, the clinician may titer the dosage and modify the route of administration to obtain the optimal therapeutic effect.

A typical dosage may range from about 1 μg/kg to up to about 30 mg/kg or more, depending on the factors mentioned above. In specific embodiments, the dosage may range from 10 μg/kg up to about 30 mg/kg, optionally from 0.1 mg/kg up to about 30 mg/kg, alternatively from 0.3 mg/kg up to about 20 mg/kg. In some applications, the dosage is from 0.5 mg/kg to 20 mg/kg. In some instances, an antigen binding protein is dosed at 0.3 mg/kg, 0.5 mg/kg, 1 mg/kg, 3 mg/kg, 10 mg/kg, or 20 mg/kg. The dosage schedule in some treatment regimes is at a dose of 0.3 mg/kg qW, 0.5 mg/kg qW, 1 mg/kg qW, 3 mg/kg qW, 10 mg/kg qW, or 20 mg/kg qW.

Dosing frequency will depend upon the pharmacokinetic parameters of the particular human CGRP R antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Appropriate dosages may be ascertained through use of appropriate dose-response data. In certain embodiments, the antigen binding proteins can be administered to patients throughout an extended time period. Chronic administration of an antigen binding protein minimizes the adverse immune or allergic response commonly associated with antigen binding proteins that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intraparenchymal), intracerebroventricular, intramuscular, intraocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use human CGRP R antigen binding protein pharmaceutical compositions ex vivo. In such instances, cells, tissues or organs that have been removed from the patient are exposed to human CGRP R antigen binding protein pharmaceutical compositions after which the cells, tissues and/or organs are subsequently implanted back into the patient.

In particular, human CGRP R antigen binding proteins can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semipermeable polymeric enclosures or membranes that allow the release of the protein product(s) but prevent the destruction of the cells by the patient's immune system or by other detrimental factors from the surrounding tissues.

The following examples, including the experiments conducted and the results achieved, are provided for illustrative purposes only and are not to be construed as limiting the scope of the appended claims.

EXAMPLE 1

Generation of CGRP Receptor as Antigens

A. Molecular Cloning of Human CRLR and RAMP1

Human CRLR cDNA (GenBank Accession No. U17473; SEQ ID NO:1) and RAMP1 cDNA (GenBank Accession No. AJ001014; SEQ ID NO:3) were cloned into the mammalian cell expression vectors pcDNA3.1-Zeo and pcDNA3.1-Hyg (Invitrogen, Carlsbad, Calif.), respectively, for transfections of HEK 293EBNA cells (Invitrogen) as described below. The hCRLR cDNA and hRAMP1 cDNA were also cloned into the pDSRα24 vector (Kim, H. Y. et al. J. Inv. Derm. Symp. Proc. (2007) 12: 48-49) for transfections of AM-1 CHO cells (U.S. Pat. No. 6,210,924).

B. Stably-Transfected Cell Lines

1. Stable Expression of Human CGRP R in 293EBNA Cells

HEK 293EBNA cells (available from ATCC or Invitrogen) were seeded at a density of $1.5 \times 10^6$ cells per 100 mm dish. After 24 hours, the cells were co-transfected with 6 µg linearized DNAs of huRAMP1/pcDNA3.1-Hyg and huCRLR/pcDNA3.1-Zeo with FuGene6 (Invitrogen, Carlsbad, Calif.) following instructions supplied by Invitrogen. After two days, the cells were trypsinized and subcultured into growth medium containing 400 µg/ml hygromycin+250 µg/ml zeocin. After two weeks, the resulting drug resistant colonies were trypsinized and combined into pools. The pools were subjected to four rounds of FACS sorting an Alexa 647-labeled CGRP$_{8-37}$peptide analog (described below). The highest 5% of expressing cells were collected at each round.

2. Stable Expression of Human CGRP R in AM-1 CHO Cells

AM-1 CHO cells (a serum-free growth media-adapted variant from the CHO DHFR-deficient cell line described in Urlaub and Chasin, *Proc. Natl. Acad. Sci.* 77, 4216 (1980), were seeded at $1.5 \times 10^6$ cells per 100 mm dish. After 24 hours, the cells were co-transfected with linearized 4 µg DNAs each of pDSRα24/huRAMP1 and pDSRα24/huCRLR with FuGene6 (Invitrogen, Carlsbad, Calif.) following instructions supplied by Invitrogen. The transfected cells were trypsinized 2 days after transfection and seeded into CHO DHFR selective growth medium containing 10% dialyzed FBS and without hypoxanthine/thymidine supplement. After 2 weeks, the resulting transfected colonies were trypsinized and pooled. The pools were subjected to FACS sorting analysis.

3. Stable Expression of Human Adrenomedullin (AM1) in HEK 293EBNA Cells

293EBNA cells were seeded in 100 mm dishes at $1.5 \times 10^6$ cells/dish in DMEM (high glucose)+5% FBS+1% MEM non-essential amino acids+1% sodium pyruvate. The following day the cells were co-transfected using FuGENE 6 transfection reagent (Roche) with pcDNA3.1/zeocin/huCRLR plus pcDNA3.1/hygromycin/huRAMP2. Both DNA constructs were linearized with FspI. After 48 hours the cells were subcultured into 100 mm dishes at 3 cell densities ($8 \times 10^5$, $3.2 \times 10^5$, and $8 \times 10^4$ cells/dish) in growth medium containing 200 µg/ml zeocin. The medium was changed twice weekly. After one week the plates were fed with medium containing 200 µg/ml hygromycin+200 µg/ml zeocin. After two weeks, 96 colonies were isolated with cloning rings. The remaining colonies were collected into a single pool culture. The clones and pools were assayed for their response to stimulation by receptor agonist or forskolin. Several clones showed a good response, and one was selected for use in subsequent experiments.

4. Stable Expression of Cyno CGRP R in HEK 293EBNA Cells

293EBNA cells were seeded in 100 mm dishes at $1.5 \times 10^6$ cells/dish in DMEM (high glucose)+5% FBS+1% MEM non-essential amino acids+1% sodium pyruvate. The following day the cells were co-transfected using FuGENE 6 with pcDNA3.1/zeocin/cynoCRLR plus pcDNA3.1/hygromycin/cynoRAMP1. Both constructs were linearized with FspI. After 48 hours the cells were subcultured into growth medium containing 200 µg/ml zeocin+400 µl/ml hygromycin at dilutions of 1:20, 1:40, 1:100, and 1:200. The medium was changed twice weekly. After two weeks, 96 transfected colonies were isolated using cloning rings. The clones were assayed for their response to stimulation by CGRP ligand. Several clones showed similar high levels of response and one was selected for use in subsequent experiments.

C. Isolation of High-expressing CGRP Receptor Cells

A CGRP$_{8-37}$peptide analog was synthesized (Midwest Bio-Tech Inc. Fishers, Ind.) with the sequence below:

Ac-WVTHRLAGLLSRSGGVVRCNFVPTDV
   GPFAF-$_{NH2}$ (SEQ ID NO:9)

The peptide was labeled with Alexa 647-NHS following the manufacturer's instructions (Molecular Probes, Inc. Cat A 2006). The Alexa 647-labeled CGRP$_{8-37}$ showed specific staining of CGRP receptor transfected cells and not the non-transfected parental cells and was used as the FACS reagent.

The huCGRP receptor-transfected 293EBNA and AM-1 CHO cell pools (generated as above) were sorted repeatedly up to four times pools using with Alexa 647-labeled CGRP$_{8-37}$ peptide. High expressing cells were collected at each sort, expanded and after the final sorting frozen into vials. The AM-1 CHO/huCGRP R cells were used for immunization as described below, and the 293EBNA/huCGRP R cells were used for titering mouse sera after immunization and in binding screens of the hybridoma supernatants.

D. Generation of Soluble CGRP Receptor

Soluble CGRP receptor polypeptides containing the N-terminal extracellular domains (ECDs) of human CRLR (SEQ ID NO:6) and human RAMP1 (SEQ ID NO:8) were generated by transiently co-transfecting 293 6E cells (Durocher, et al., *Nucleic Acids Res.* 30:E9 (2002)) with vectors containing the corresponding cDNAs (SEQ ID NO:5 or SEQ ID NO:7) as described below. Commonly used tags (polyHis, Flag, HA and/or Fc) were employed to facilitate secretion and/or subsequent purification.

A soluble heterodimeric CGRP R ECD fused to Fc was prepared by PCR cloning with the appropriate primers into the transient expression vector pTT5 (Durocher, et al., supra). The CRLR N-terminal ECD-Fc consisted of the N-terminal extracellular domain of CRLR (SEQ ID NO:6) fused to human IgG1 Fc. The RAMP1 ECD-Fc contains the extracellular domain of RAMP1 (SEQ ID NO:8) fused to human IgG1 Fc. In both cases, there was a linker consisting of five consecutive glycines between the ECD domain and Fc.

The soluble heterodimeric CGRP receptor was expressed by co-transfecting the two constructs as follows. 293-6E cells at $1\times10^6$ cells/ml in shake flasks were transfected with 0.5 mg/L DNA (hCRLR N-ter ECD-Fc/pTT5 and huRAMP1 ECD-Fc/pTT5) with 3 ml PEI/mg DNA in FreeStyle 293 media (Invitrogen). Cells were grown in suspension in FreeStyle 293 expression medium supplemented with 0.1% Pluronic F68 and 50 μg/ml Geneticin for 7 days and harvested for purification.

Purifications from conditioned media ("CM") were performed by buffering the CM with the addition of 50 mM Tris, 400 mM sodium citrate, and adjusting the pH to 8.5. The buffered CM was then passed over a Protein A affinity column equilibrated in 50 mM Tris, 400 mM sodium citrate and pH adjusted to pH 8.5. The Protein A column was washed with PBS and the Fc fusion protein eluted with 0.1 N HOAc. The eluted peak contained both CRLR and RAMP1 components when tested by western blot using individual antibodies specific to either CRLR or RAMP1. Further LC-MS and N-terminal sequencing confirmed the presence of both CRLR: RAMP1 heterodimer and CRLR:CRLR homodimer in approximately (2:3) ratio. This "soluble CGRP receptor" was shown to compete in Alexa647 labeled $CGRP_{8-37}$ binding to CGRP receptor expressing recombinant cells in the FMAT analysis, although it failed to bind CGRP ligand as determined using Biacore testing. The material was used as an immunogen as described in Example, despite, inter alia, its heterogeneity and lack of CGRP ligand binding.

E. Generation of Membrane Extracts from Recombinant CGRP Receptor Expressing Cells Membrane extracts were prepared from CGRP receptor expressing cells using a method described by Bossé, R. et al., (*Journal of Biomolecular Screening*, 3(4): 285-292 (1998)). Briefly, approximately 5 grams of cell paste were pelleted in 50 ml of PBS at 3,000 rpm for 10 min at 4° C. and re-suspended in 30 ml of cold lysis buffer (25 mM HEPES, pH 7.4, 3 mM $MgCl_2$ plus one Roche protease inhibitor cocktail tablet/50 mL). The lysate was homogenized with Glas-Col (Teflon-glass homogenizer) with ~20 strokes at 5,000 rpm and spun in a JA21 rotor at 20,000 rpm for 15 min at 4° C. This process was repeated once more and the final pellet was re-suspended in ~1-5 ml 'final pellet' buffer (25 mM HEPES, pH 7.4, 3 mM $MgCl_2$, 10% (w/v) sucrose plus one Roche protease inhibitor cocktail tablet/50 mL). The membrane extracts were sheared by passing through 16 G and 25 G needles 2-3 times. Total membrane protein concentration was determined with a Microplate BCA Protein Assay (Pierce).

EXAMPLE 2

Generation of Antibodies to CGRP Receptor

A. Immunization

Immunizations were conducted using the following forms of CGRP receptor antigens, prepared as described in Example 1:

(i) AM-1 CHO transfectants expressing full length human CRLR and RAMP1 at the cell surface, obtained by co-transfecting CHO cells with human full length CRLR cDNA (SEQ ID NO:1) encoding a polypeptide having the sequence SEQ ID NO:2, and RAMP1 cDNA (SEQ ID NO:3) encoding a polypeptide having the sequence SEQ ID NO:4

(ii) membrane extract from the cells described in (i) above; and (iii) soluble CGRP receptor obtained by co-expressing and purifying the N-terminal ECD of CRLR (SEQ ID NO:6) and the extracellular domain (ECD) of RAMP1 (SEQ ID NO:8) as described in Example 1.

XENOMOUSE animals were immunized with purified soluble CGRP receptor protein and purified CGRP R membranes prepared from AM-1 CHO cells stably expressing CGRP R in the same manner using doses of 10 μg/mouse and 150 μg/mouse respectively. CGRP membranes were prepared using methods described above.

Subsequent boosts were administered at doses of ten μg/mouse of soluble CGRP R or 75 μg of purified CGRP R membranes. XENOMOUSE animals were also immunized with CGRP receptor-expressing cells using doses of $3.4\times10^6$ CGRP R transfected cells/mouse and subsequent boosts were of $1.7\times10^6$ CGRP R transfected cells/mouse. Injection sites used were combinations of subcutaneous base-of-tail and intraperitoneal. Immunizations were performed in accordance with methods disclosed in U.S. Pat. No. 7,064,244, filed Feb. 19, 2002, the disclosure of which is hereby incorporated by reference. Adjuvants TiterMax Gold (Sigma; cat. #T2684), Alum (E.M. Sergent Pulp and Chemical Co., Clifton, N.J., cat. #1452-250) were prepared according to manufacturers' instructions and mixed in a 1:1 ratio of adjuvant emulsion to antigen solution.

Sera were collected 4-6 weeks after the first injection and specific titers were determined by FACs staining of recombinant CGRP receptor-expressing 293EBNA cells.

Mice were immunized with either cells/membranes expressing full length CGRP R cells or soluble CGRP R extracellular domain, with a range of 11-17 immunizations over a period of approximately one to three and one-half months. Mice with the highest sera titer were identified and prepared for hybridoma generation. The immunizations were performed in groups of multiple mice, typically ten. Popliteal and inguinal lymph nodes and spleen tissues were typically pooled from each group for generating fusions.

B. Preparation of Monoclonal Antibodies

Animals exhibiting suitable titers were identified, and lymphocytes were obtained from draining lymph nodes and, if necessary, pooled for each cohort. Lymphocytes were dissociated from lymphoid tissue in a suitable medium (for example, Dulbecco's Modified Eagle Medium; DMEM; obtainable from Invitrogen, Carlsbad, Calif.) to release the cells from the tissues, and suspended in DMEM. B cells were selected and/or expanded using a suitable method, and fused with suitable fusion partner, for example, nonsecretory myeloma P3X63Ag8.653 cells (American Type Culture Collection CRL 1580; Kearney et al, *J. Immunol.* 123, 1979, 1548-1550).

Lymphocytes were mixed with fusion partner cells at a ratio of 1:4. The cell mixture was gently pelleted by centrifugation at 400×g for 4 minutes, the supernatant decanted, and the cell mixture gently mixed by using a 1 ml pipette. Fusion was induced with PEG/DMSO (polyethylene glycol/dimethyl sulfoxide; obtained from Sigma-Aldrich, St. Louis Mo.; 1 ml per million of lymphocytes). PEG/DMSO was slowly added with gentle agitation over one minute followed, by one minute of mixing. IDMEM (DMEM without glutamine; 2 ml per million of B cells), was then added over 2 minutes with gentle agitation, followed by additional IDMEM (8 ml per million B-cells) which was added over 3 minutes.

The fused cells were gently pelleted (400×g 6 minutes) and resuspended in 20 ml Selection media (for example, DMEM containing Azaserine and Hypoxanthine [HA] and other supplemental materials as necessary) per million B-cells. Cells were incubated for 20-30 minutes at 37° C. and then resuspended in 200 ml Selection media and cultured for three to four days in T175 flasks prior to 96-well plating.

Cells were distributed into 96-well plates using standard techniques to maximize clonality of the resulting colonies. After several days of culture, the hybridoma supernatants were collected and subjected to screening assays as detailed in the examples below, including confirmation of binding to human CGRP receptor, identification of blocking antibodies by a ligand binding competition assay and evaluation of cross-reactivity with other receptors related to CGRP receptor (for example, human Adrenomedullin receptor). Positive cells were further selected and subjected to standard cloning and subcloning techniques. Clonal lines were expanded in vitro, and the secreted human antibodies obtained for analysis.

C. Sequence Analysis of Selected Monoclonal Antibodies

Selected subcloned monoclonal antibodies were sequenced using standard RT-PCR methods. Table 2A shows the amino acid sequences of the light chains of exemplary antibodies disclosed herein. Table 2B shows the amino acid sequences of the heavy chains of exemplary antibodies disclosed herein.

Amino acid sequences corresponding to CDR regions of sequenced antibodies were aligned and the alignments were used to group the clones by similarity.

Sequence alignments of light chain CDRs from clones having kappa light chains, and certain corresponding consensus sequences, are shown in FIGS. 3A and 3B.

Sequence alignments of light chain CDRs from clones having lambda light chains, and certain corresponding consensus sequences, are shown in FIG. 4.

Sequence alignments of heavy chain CDRs of exemplary antibodies disclosed herein, and certain corresponding consensus sequences, are shown in FIGS. 5A, 5B, 5C, 5D and 5E.

Certain consensus sequences of exemplary heavy chain CDRs disclosed herein are shown in FIG. 5F.

EXAMPLE 3

Identification of CGRP Receptor Specific Antibodies

A. Selection of CGRP Receptor Specific Binding Antibodies by FMAT

After 14 days of culture, hybridoma supernatants were screened for CGRP R-specific monoclonal antibodies by Fluorometric Microvolume Assay Technology (FMAT) (Applied Biosystems, Foster City, Calif.). The supernatants were screened against either the AM-1 CHO huCGRP R cells or recombinant HEK 293 cells that were transfected with human CGRP R and counter-screened against parental HEK293 cells (prepared as described in Example 1).

Briefly, the cells in Freestyle media (Invitrogen, Carlsbad, Calif.) were seeded into 384-well FMAT plates in a volume of 50 µL/well at a density of approximately 4000 cells/well for the stable transfectants, and at a density of approximately 16,000 cells/well for the parental cells, and cells were incubated overnight at 37° C. Then, 10 µL/well of supernatant was added and plates were incubated for approximately one hour at 4° C., after which 10 µL/well of anti-human IgG-Cy5 secondary antibody (Jackson Immunoresearch, West Grove, Pa.) was added at a concentration of 2.8 µg/ml (400 ng/ml final concentration). Plates were then incubated for one hour at 4° C., and fluorescence was read using an FMAT macroconfocal scanner (Applied Biosystems, Foster City, Calif.).

For counter screens, the parental AM-1 CHO cells or HEK 293 cells were seeded similarly and supernatants screened by FMAT on these cells in parallel to differentiate and eliminate hybridomas binding to cellular proteins, but not to the CGRP receptor.

B. Identification of Blocking Antibodies by Ligand Binding Competition Assay through FMAT A ligand binding competition method was developed to identify antibodies (in the hybridoma supernatants) that bind CGRP receptor and block CGRP ligand binding. 384-wells plates (Corning Costar, Cat:#3712) were prepared with 5,000 AM-1 huCGRP R Pool 2 cells and 20,000 untransfected CHO-S cells in each well. 20 µl of anti-CGRP R hybridoma supernatant were added to each well, and the plates were incubated for 1 hr at room temperature. 10 µl of 2.8 µg/ml Alexa647-CGRP$_{8-37}$ peptide were then added to each well and the plates were incubated for a further 3 hours at room temperature. The amount of Alexa647-CGRP$_{8-37}$ bound to the cells was assayed on a FMAT 8200 Cellular Detection System (Applied Biosystems). Output data were both a numerical FL1 value of signal intensity (higher FL1 values indicate higher signal intensity) and also an image of the cells.

The experiments included negative control hybridoma supernatants. The average FL1 value observed in these negative control experiments was adopted as the maximum possible signal for the assay. Experimental supernatants were compared to this maximum signal and a percent inhibition was calculated for each well (% Inhibition=(1−(FL1 of the anti-CGRP R hybridoma supernatant/Maximum FL1 signal)).

An overview of the data is shown in FIG. 6. In this experiment, 1092 anti-CGRP R supernatants were tested using the receptor ligand assay. The data were rank ordered using the average percent inhibition. Ninety supernatants had >25% average inhibition, 31 of these were >50% and 7 were >70% average inhibition.

An abbreviated data set is shown in Table 10, below. Sample ID Nos. 1-5 illustrate examples of anti-CGRP R hybridoma supernatants which inhibited the binding Alexa647-CGRP$_{8-37}$ peptide to CGRP receptor and Sample ID Nos 536-540 illustrate examples of anti-CGRP R hybridoma supernatants which did not inhibit the binding of the Alexa647-CGRP$_{8-37}$ peptide to the CGRP receptor.

TABLE 10

Exemplary data from FMAT ligand binding competition assay

| Sample ID | Expt. #1 | | | Expt. #2 | | |
|---|---|---|---|---|---|---|
| | FL1 | Image | % Inhibition | FL1 | Image | % Inhibition |
| 1 | 2264 | | 84% | 2585 | | 88% |
| 2 | 3007 | | 77% | 2804 | | 85% |
| 3 | 3460 | | 72% | 2929 | | 84% |
| 4 | 3650 | | 70% | 3294 | | 79% |
| 5 | 3764 | | 69% | 3246 | | 80% |
| 536 | 10412 | | 0% | 11142 | | −17% |
| 537 | 10413 | | 0% | 9388 | | 5% |
| 538 | 10414 | | 0% | 9420 | | 4% |
| 539 | 10415 | | 0% | 10943 | | −14% |
| 540 | 10415 | | 0% | 10561 | | −10% |

Based on the binding competition assays, approximately 30 supernatants were selected for further characterization.

EXAMPLE 4

Activity of CGRP Receptor Specific Blocking Monoclonal Antibodies in a cAMP Functional Assay A. CGRP Receptor Antibody Activity.

Selected CGRP receptor antibodies were screened in an in vitro CGRP receptor mediated cAMP assay to determine intrinsic potency. The in vitro cAMP assay employed a human neuroblastoma-derived cell line (SK-N-MC; Spengler, et al., (1973) In Vitro 8: 410) obtained from ATCC (ATCC Number HTB-10; "HTB-10 cells"). HTB-10 cells express CRLR and RAMP1, which form CGRP receptor (L. M. McLatchie et al, 1998). A 293EBNA cell line expressing recombinant cynomolgus CGRP R was generated as described in Example 1, and a rat L6 cell line expressing rat CGRP receptor was obtained from the ATCC(CRL-1458).

The LANCE cAMP assay kit (PerkinElmer, Boston, Mass.) was used in the screening. The assays were performed in white 96-well plates in a total volume of 60 µL. Briefly, on the day of the assay, the frozen HTB-10 cells were thawed at 37° C., cells were washed once with assay buffer and 12 µL of cell suspension containing 10000 cells mixed with Alexa-labeled anti-cAMP antibody was added into 96 half-area white plates. After adding 12 µL CGRP receptor antibody, the mixture was incubated for 30 min at room temperature. Then 12 µL CGRP receptor agonist human α-CGRP (1 nM final concentration) was added and further incubated for 15 min at room temperature. After human α-CGRP stimulation, 24 µL of detection mix was added and incubated for 60 minutes at room temperature and the plates were red on EnVision instrument (PerkinElmer, Boston, Mass.) at Em665 nM. Data were processed and analyzed by Prizm (GraphPad Software Inc.) or ActivityBase (IDBS).

Figure 7A:
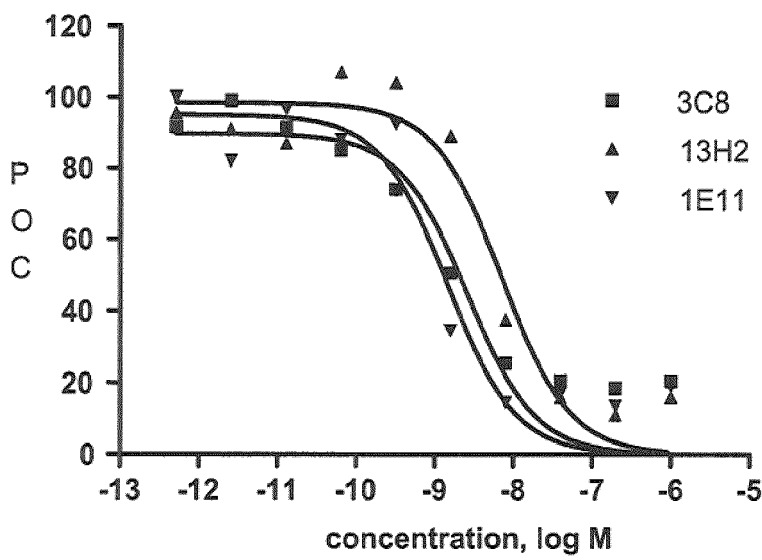
FIGS. 7A-D show exemplary cAMP assay IC50 data from cells expressing hCGRP receptor (FIG. 7A), hAM1 (FIG. 7B), hAM2 (FIG. 7C) and human amylin receptors (FIG. 7D) for three indicated anti-CGRP R mAbs.

FIG. 7A shows exemplary data obtained as described above using the hCGRP receptor-expressing cell line HTB-10 for three antibodies—3C8, 13H2 and 1E11. The data are plotted as percentage over control ("POC") as a function of antibody (3C8, 13H2 or 1E11) concentration, and are fitted with standard nonlinear regression curves to yield the IC50 values shown at the bottom of the figure.

B. Lack of Antibody Activity in Related Receptors.

Figure 7B:
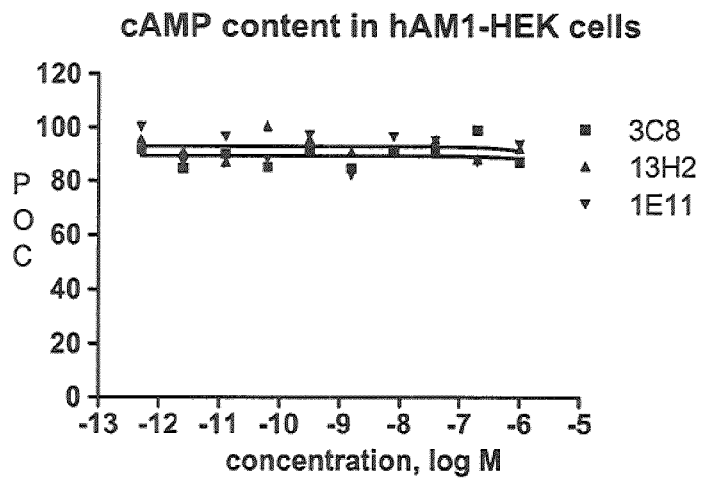
Figure 7C:
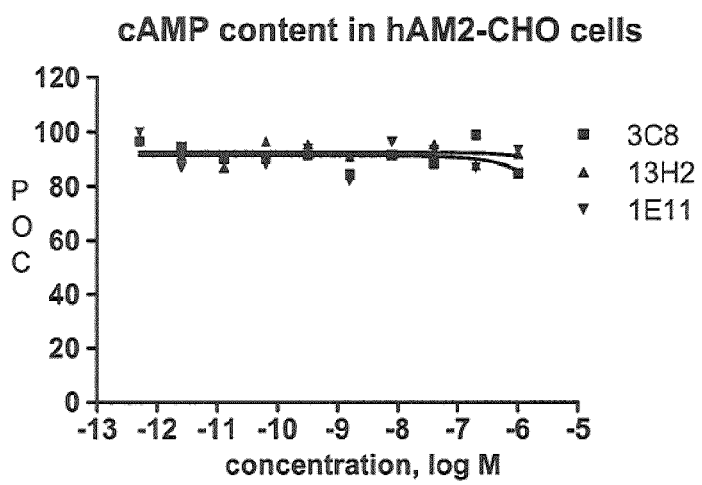
Figure 7D:
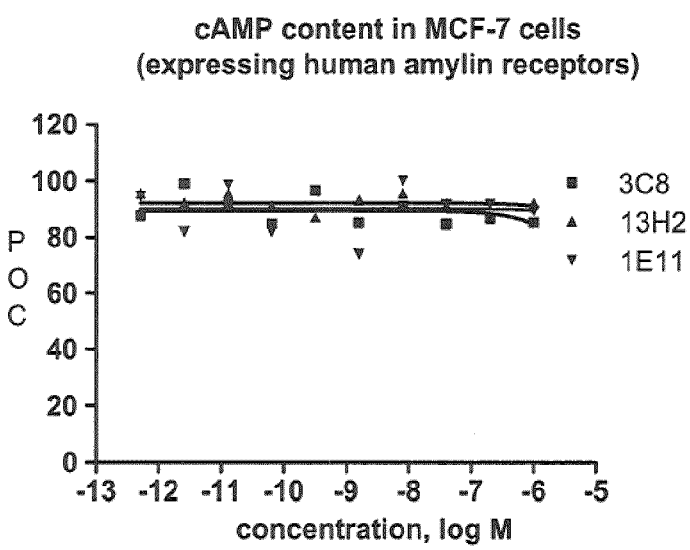

Cells expressing related receptors AM1 (HEK 293 cells expressing hCRLR+hRAMP2; D. R. Poyner, et al, Pharmacological review, 54:233-246, 2002), AM2 (CHO cells expressing hCRLR+hRAMP3; D. R. Poyner, et al, Pharmacological review, 54:233-246, 2002) or human amylin AMY1 receptor (MCF-7 cells hCTR+hRAMP1; Wen-Ji Chen, et al, Molecular pharmacology, 52: 1164-1175, 1997) were used to determine the selectivity of the tested antibodies. The AM1-expressing HEK 293 cell line was generated as described in Example 1, above. The AM2-expressing CHO cell line was purchased from EuroScreen (now PerkinElmer, Inc.); and the human amylin AMY1 receptor-expressing MCF-7 cell line (Zimmermann, et al, Journal of Endocrinology, 423-431, 1997), was obtained from the ATCC (HTB-22). Exemplary results, plotted as described above, are shown in FIGS. 7B (hAM1-HEK cells), 7C (hAM2-CHO cells) and 7D (hAMY-MCF-7 cells). Note that none of the tested antibodies had significant inhibitory activity against hAM1, hAM2 or hAMY1 receptors over the range tested.

Similar experiments were performed using recombinant HEK cells expressing cynomolgus CGRP receptors and rat L6 cells expressing rat CGRP receptor (ATCC). Data from these studies, as well as additional IC50 data obtained as described in part A of this Example, are shown in the "cAMP" columns in Table 11, below. Note that the IC50 values against the human and cyno CGRP receptors are in the nanomolar range, whereas activities against rat CGRP receptor, and human AM1, AM2 and AMY1 receptors, as well as MCF7 cells expressing calcitonin (data not shown) are all greater than 1 micromolar. The difference in IC50 between human CGRP receptor and human AM1, AM2, amylin and calcitonin receptors illustrates the high selectivity of the these antibodies for the CGRP receptor over related receptors formed in part of the same receptor components. IC50 obtained using human and cynomolgus CGRP receptors were similar, whereas the tested antibodies did not appear to cross-react with rat CGRP receptor.

TABLE 11

| | cAMP assay | | | | | | $^{125}I$ assay |
|---|---|---|---|---|---|---|---|
| Clone | hCGRP R IC50 (nM) | Cyno CGRP R IC50 (nM) | Rat CGRP R IC50 (nM) | hAmylin 1 IC50 (nM) | hAM1 IC50 (nM) | hAM2 IC50 (nM) | Human CGRP Ki (nM) |
| 01E11.2 | 1.77 | 2.79 | >1000 | >1000 | >1000 | >1000 | 0.030 |
| 01H7.2 | 3.27 | 4.74 | >1000 | >1000 | >1000 | >1000 | 0.079 |
| 02A10.1 | 11.81 | 17.6 | >1000 | >1000 | >1000 | >1000 | 0.291 |
| 02E7.2 | 6.30 | 5.51 | >1000 | >1000 | >1000 | >1000 | 0.117 |

TABLE 11-continued

| | cAMP assay | | | | | | 125I assay |
|---|---|---|---|---|---|---|---|
| Clone | hCGRP R IC50 (nM) | Cyno CGRP R IC50 (nM) | Rat CGRP R IC50 (nM) | hAmylin 1 IC50 (nM) | hAM1 IC50 (nM) | hAM2 IC50 (nM) | Human CGRP Ki (nM) |
| 03A5.1 | 9.89 | 28.9 | >1000 | >1000 | >1000 | >1000 | 0.093 |
| 03B6.2 | 2.74 | 2.22 | >1000 | >1000 | >1000 | >1000 | 0.033 |
| 03C8.2 | 6.66 | 5.32 | >1000 | >1000 | >1000 | >1000 | 0.044 |
| 03H8.2 | 10.84 | 10.6 | >1000 | >1000 | >1000 | >1000 | 0.111 |
| 04E4.2 | 2.38 | 3.52 | >1000 | >1000 | >1000 | >1000 | 0.015 |
| 04H6.1 | 3.78 | 5.59 | >1000 | >1000 | >1000 | >1000 | 0.052 |
| 05F5.1 | 4.79 | 4.78 | >1000 | >1000 | >1000 | >1000 | 0.147 |
| 07B2.1 | 8.96 | 27.7 | >1000 | >1000 | >1000 | >1000 | 0.116 |
| 07B3.1 | 10.2 | 14.1 | >1000 | >1000 | >1000 | >1000 | 0.127 |
| 07F1.1 | 8.92 | 10.5 | >1000 | >1000 | >1000 | >1000 | 0.140 |
| 08B11.2 | 10.7 | 17.0 | >1000 | >1000 | >1000 | >1000 | 0.118 |
| 09D4.2 | 1.40 | 2.46 | >1000 | >1000 | >1000 | >1000 | 0.023 |
| 09F5.2 | 3.06 | 4.44 | >1000 | >1000 | >1000 | >1000 | 0.043 |
| 10E4.2 | 3.08 | 3.23 | >1000 | >1000 | >1000 | >1000 | 0.100 |
| 11A9.1 | 16.1 | 47.8 | >1000 | >1000 | >1000 | >1000 | 0.157 |
| 11D11.1 | 4.93 | 3.85 | >1000 | >1000 | >1000 | >1000 | 0.044 |
| 11H9.1 | 4.56 | 5.07 | >1000 | >1000 | >1000 | >1000 | 0.057 |
| 12E8.2 | 2.93 | 4.13 | >1000 | >1000 | >1000 | >1000 | 0.097 |
| 12G8.2 | 2.14 | 2.74 | >1000 | >1000 | >1000 | >1000 | 0.017 |
| 13D6.2 | 8.23 | 11.8 | >1000 | >1000 | >1000 | >1000 | 0.055 |
| 13E2.2 | 18.3 | 49.2 | >1000 | >1000 | >1000 | >1000 | 0.128 |
| 13H2.2 | 1.95 | 8.41 | >1000 | >1000 | >1000 | >1000 | 0.033 |
| 32H7.1G | | 1.93 | | >1000 | >1000 | >1000 | |

EXAMPLE 5

Radioligand CGRP Binding Assay for Ki Determination Receptor Blocking Antibodies $^{125}$I-labeled CGRP (Amersham Biosciences, Piscataway, N.J.) and cell membranes from HTB-10 cells (PerkinElmer Inc., Waltham, Mass.) were used for radioligand binding experiment in the presence of various concentrations of the test antibodies to determine the corresponding Ki values. The CGRP binding assay was set up at room temperature in 96-well plates containing: 110 μl binding buffer (20 mM Tris-HCl, pH7.5, 5.0 mM MgSO4, 0.2% BSA (Sigma), 1 tablet of Complete™/50 ml buffer (a protease inhibitor)); 20 μl test compound (10×); 20 μl $^{125}$I-hαCGRP (Amersham Biosciences; 10×); and 50 μl human neuroblastoma cell (HTB-10) membrane suspension (10 μg per well, PerkinElmer). The plates were incubated at room temperature for 2 hours with shaking at 60 rpm, and then the contents of each well were filtered over 0.5% polyethyleneimine (PEI)-treated (for at least one hour) GF/C 96-well filter plates. The GF/C filter plates were washed six times with ice-cold 50 mM Tris, pH 7.5 and dried in an oven at 55° C. for 1 hour. The bottoms of the GF/C plates were then sealed. 40 μl Microscint™ 20 was added to each well, the tops of the GF/C plates were sealed with TopSeal™-A (a press-on adhesive sealing film), and the GF/C plates were counted with TopCount NXT (Packard). The data were analyzed using Prizm (GraphPad Software Inc.)

Figure 8:
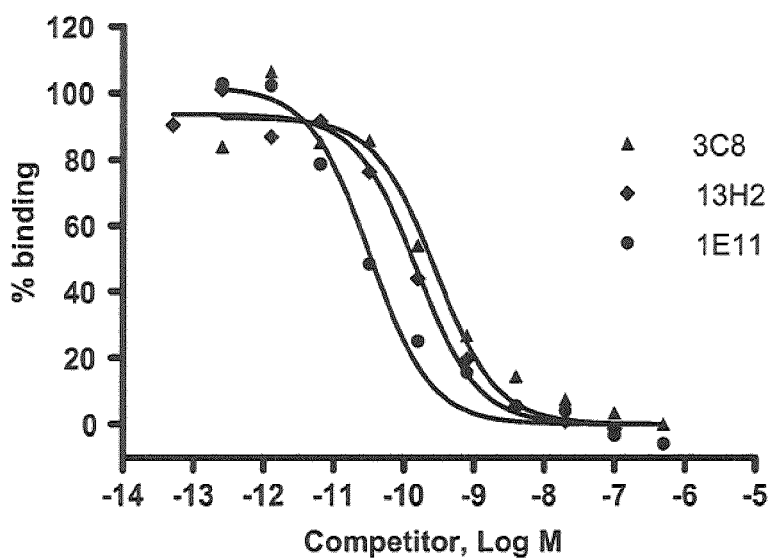
FIG. 8 shows an example of $^{125}$I-CGRP binding data such as may be used to determine the Ki of mAbs to human CGRP receptor.

Exemplary data and Ki values obtained using antibodies 3C8, 12H2 and 1E11 are shown in FIG. 8.

The right-most column in Table 11, above, lists the Ki values of the indicated mAbs in the radiolabeled $^{125}$I-CGRP competition binding assay to HTB-10 cell membranes. The data demonstrate that the CGRP receptor antibodies were highly competitive (all sub-nanomolar range) against CGRP binding.

EXAMPLE 6

FACS Binding Assay for Kd Determination of CGRP Receptor Blocking Antibodies

The affinities of anti-CGRP R mAbs for CGRP receptors expressed on cells were determined using a FACS method. Briefly, AM-1 CHO huCGRP R-expressing cells, prepared as described above, were plated in 96-well plates at densities of 16,000 or 160,000 cells per well in DMEM medium containing 10% FBS, NEAA, PS, L Glut, NaPyr and 0.05% sodium azide. CGRP receptor antibodies were titrated in the same medium from 50 nM to 1 μM and incubated with cells. After an overnight incubation at 4° C. in a total volume of 120 μl, on a plate shaker, the cells were washed 2× with PBS+2% FBS, centrifuging and discarding supernatant each time. 100 μl/well of G anti-Hu Fc Cy5 (5 μg/mL; Jackson ImmunoResearch Laboratories Inc., West Grove, Pa., USA) containing 7AAD (5 μl/well) was then added and incubated at 4° C. for 40 min. The cells were washed 2× with PBS+2% FBS, centrifuging and discarding the supernatant each time. 100 μl PBS+2% FBS buffer was then added and analyzed by FACS to determined the binding geomean. The Kd was calculated using KinExA software by taking the negative geomean at each antibody concentration as the amount of free Ab present Rathanaswami, et al., *Biochemical and Biophysical Research Communications* 334 (2005) 1004-1013. The data obtained at the two different cell concentrations were analyzed by n-curve analysis to determine the Kd and the 95% confidence interval as described in Rathanaswami, et al., *Biochemical and Biophysical Research Communications* 334 (2005) 1004-1013.

Exemplary data with corresponding curve fits are shown in FIG. 10 for antibody 12G8.2. The data of eight blocking antibodies generated in support of the present disclosure are shown in Table 12. One of the antibodies (3B6) was analyzed on two different days. The ratio of 0.9 obtained for the experiment with 16K cells indicates that the antigen concentration is predicted as 0.9× the Kd and hence the curve obtained by this experiment is a Kd controlled curve. It can be appreciated that the Kd values obtained in this manner were in the low single-digit nanomolar range for all tested antibodies.

TABLE 12

| | N curve analysis | | | | |
|---|---|---|---|---|---|
| | Kd (nM) | Kd Low (nM) | Kd High (nM) | % error | Ratio 16K |
| 1H7 | 1.9 | 1.5 | 3 | 3.8 | 0.001 |
| 2E7 | 1.5 | 0.7 | 3.4 | 6.3 | 0.19 |
| 3B6 (a) | 1.7 | 1.1 | 2.7 | 5.3 | 0.060 |
| 3B6 (b) | 2.0 | 1.6 | 2.6 | 3.2 | 0.21 |
| 4E4 | 1.3 | 0.9 | 2.05 | 3.9 | 0.16 |
| 4H6 | 2.4 | 1.78 | 4.35 | 3.8 | 0.070 |
| 9D4 | 2.5 | 1.8 | 4.39 | 4.3 | 0.060 |
| 12E8 | 2.3 | 1.58 | 3.36 | 3.7 | 0.55 |
| 12G8 | 1.4 | 0.92 | 2.21 | 3.6 | 0.94 |

EXAMPLE 7

Binning of CGRP Receptor Blocking Antibodies by Bicore Binding Competition

Biacore analyses (Karlsson, R. et al., *Methods; A Companion to Methods in Enzymology*, 6: 99-110 (1994) were carried out as follows. Immobilization of anti-CGRP receptor antibodies to the CM5 sensor chip surface was performed according to manufacturer's instructions, using a continuous flow of 10 mM HEPES, 0.15M NaCl, 3.4 mM EDTA, 0.005% P-20, pH 7.4 (HBS-EP buffer). Carboxyl groups on the sensor chip surfaces were activated by injecting 60 µL of a mixture containing 0.2 M N-ethyl-N' (dimethylaminopropyl)carbodiimide (EDC) and 0.05 M N-hydroxysuccinimide (NHS). Specific surfaces were obtained by injecting 180 µl of anti-CGRP receptor antibody diluted in 10 mM acetate, pH 4.0 at a concentration of 30 µg/mL. Excess reactive groups on the surfaces were deactivated by injecting 60 µL of 1 M ethanolamine. Final immobilized levels for the individual antibodies were as follows:

| Antibody | Resonance Units (RU) |
|---|---|
| 11D11 | ~5,900 |
| 3B6 | ~7,200 |
| 4H6 | ~8,000 |
| 12G8 | ~7,800 |
| 9F5 | ~6,600 |
| 34E3 | ~3,700 |

A blank, mock-coupled reference surface was also prepared on the sensor chip. Soluble huCGRP receptor at a concentration of 100 nM was captured on sensor chips having one of the six immobilized antibodies referenced above (11D11, 3B6, 4H6, 12G8, 9F5 or 34E3). Each of the 20 test anti-CGRP R antibodies was then injected over the captured huCGRP receptor. If the injected antibody recognized a distinct epitope relative to that recognized by the immobilized antibody, a second binding event would be observed. If the antibodies recognize the same or very similar epitopes, only the binding of the huCGRP receptor would be observed.

Figure 9A:
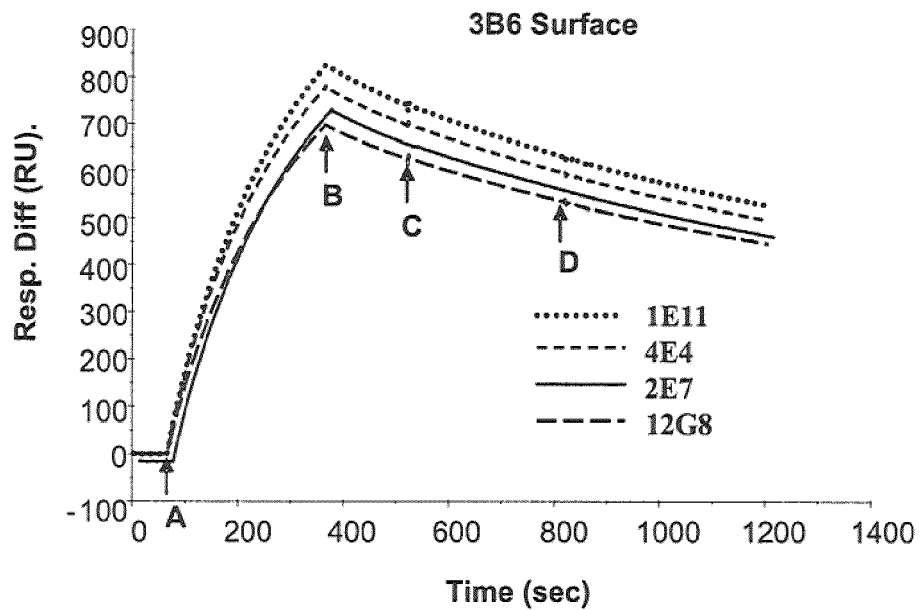
FIGS. 9A-D show Biacore competition data for selected antibodies disclosed herein.

Exemplary data obtained using a sensor chip coated with immobilized antibody 3B6 are shown in FIG. 9A. The four traces are data obtained using antibodies 1E11, 4E4, 2E7 and 12G8 in the injected solution. Events during the experiment are represented by letters, with "A" corresponding to injection of huCGRP R-Fc, "B" corresponding to end of the huCGRP R-Fc injection, "C" corresponding to injection of second mAb, and "D" corresponding to end second mAb injection and start of the buffer wash. Note that there is no indication of any binding signal from any of the injected antibody on the immobilized antibody surface, indicating that the four injected antibodies apparently recognize the same or very similar epitope(s) as the immobilized antibody. Essentially the same results were observed with all tested blocking antibodies washed over each the five immobilized neutralizing antibody surfaces, indicating that all tested anti-huCGRP receptor blocking antibodies recognize the same or very similar and strongly overlapping epitope(s).

Figure 9B:
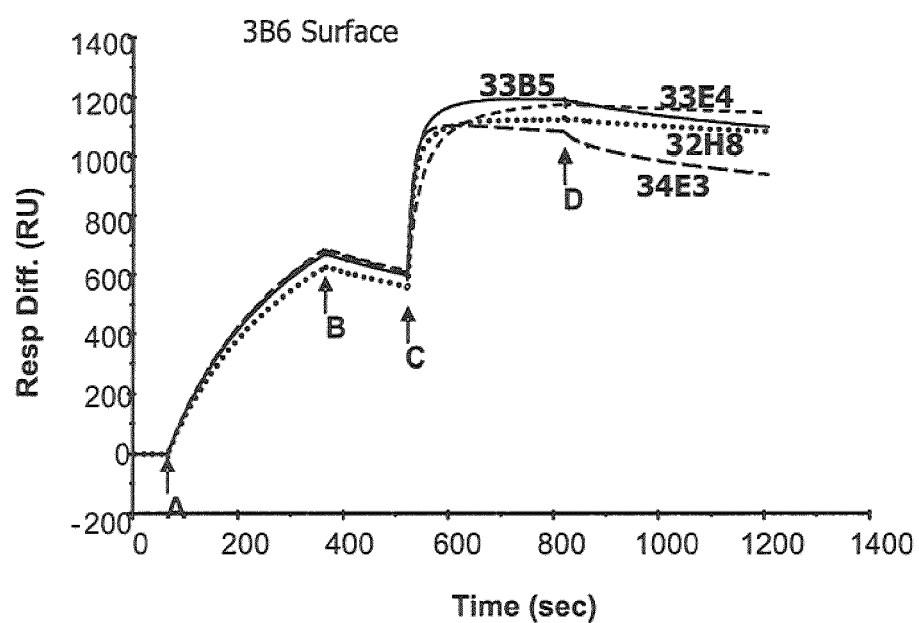
Figure 9C:
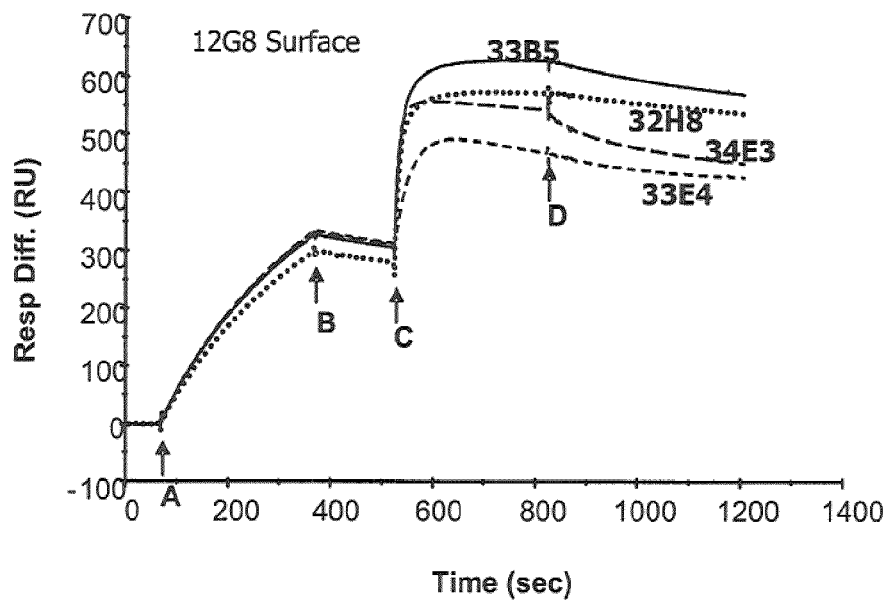
Figure 9D:
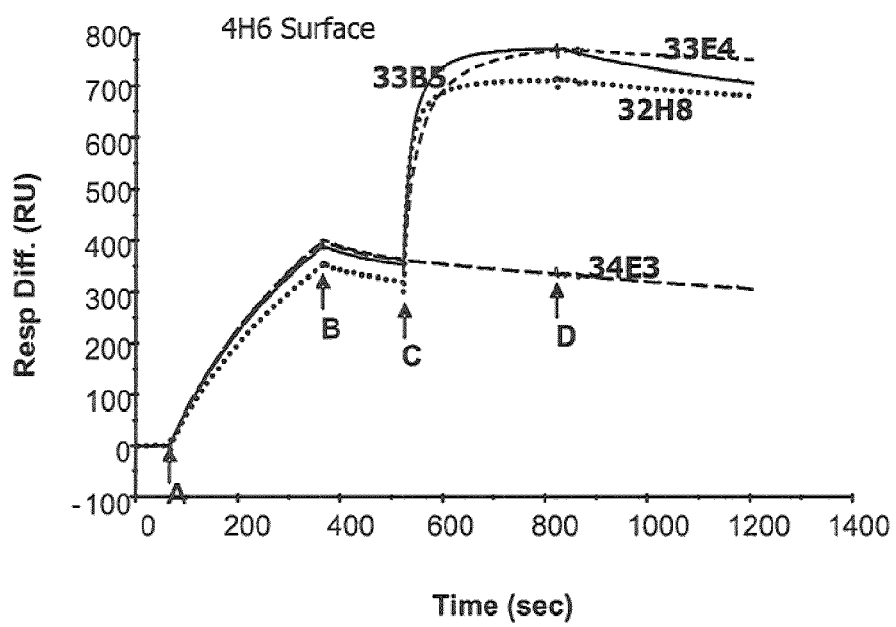

In contrast, as shown in part in FIGS. 9B, 9C and 9D, the four tested non-blocking, CGRP receptor specific antibodies 32H8, 33B5, 33E4 and 34E3 failed to compete with 11D11 (data not shown), 3B6 (FIG. 9B), 12G8 (FIG. 9C) and 9F5 (data not shown) although 34E3 was able to compete with 4H6 (FIG. 9D) and weakly with 32H7 (data not shown). 32H8 failed to compete with 3B6, 4H6, 12G8, 9F5 or the non-blocking antibody 34E3, but 33B5 and 33E4 could compete with the non-blocking antibody 34E3. The data for all blocking and non-blocking antibodies are summarized in Table 13, below. "NB" indicates no binding; "+" indicates significant binding; and "Weak" indicates weak binding.

TABLE 13

| | Immobilized Antibodies | | | | | |
|---|---|---|---|---|---|---|
| Ab in Solution | 11D11 | 3B6 | 4H6 | 12G8 | 9F5 | 34E3 |
| 1E11 | NB | NB | NB | NB | NB | + |
| 1H7 | NB | NB | NB | NB | NB | + |
| 2E7 | NB | NB | NB | NB | NB | + |
| 3B6 | NB | NB | NB | NB | NB | + |
| 3C8 | NB | NB | NB | NB | NB | + |
| 4E4 | NB | NB | NB | NB | NB | + |
| 4H6 | NB | NB | NB | NB | NB | NB |
| 5F5 | NB | NB | NB | NB | NB | + |
| 9D4 | NB | NB | NB | NB | NB | + |
| 9F5 | NB | NB | NB | NB | NB | + |
| 10E4 | NB | NB | NB | NB | NB | + |
| 11D11 | NB | NB | NB | NB | NB | + |
| 11H9 | NB | NB | NB | NB | NB | + |
| 12E8 | NB | NB | NB | NB | NB | + |
| 12G8 | NB | NB | NB | NB | NB | + |
| 13H2 | NB | NB | NB | NB | NB | + |
| 32H7 | NB | NB | NB | NB | NB | Weak |
| 32H8 | + | + | + | + | + | + |
| 33B5 | + | + | + | + | + | NB |
| 33E4 | + | + | + | + | + | NB |

As can be appreciated from the data, all the tested blocking or neutralizing antibodies bind to the same region as the five immobilized blocking antibodies; i.e., all of the tested neutralizing antibodies bind the same region of the CGRP R molecule. On the other hand, the non-blocking antibodies did not generally compete with the immobilized blocking antibodies, indicating that the non-blocking antibodies primarily bind a different region of CGRP R.

EXAMPLE 8

Binding of CGRP Receptor Antibodies to Soluble CGRP Receptor in Western Blot

Three representative CGRP receptor blocking antibodies were tested using Western blots for binding to a soluble CGRP receptor-muFc fusion protein.

100 ng of purified CGRP R-muFc (produced and purified as described above for the CGRP R-huFc except the mouse Fc was used and the linker between RAMP1 or CRLR ECD and muFc was changed to "GGGGGVDGGGGGV" (SEQ ID NO:213)) was diluted in PBS with PAGE sample buffer with (reduced) or without (non-reduced) beta-mercaptoethanol (βME) at 13.3% concentration. The sample containing βME was then boiled for 4 min. Reduced and non-reduced samples were loaded onto separate 4-20% Tris-glycine gels (Invitrogen) with alternating lanes of CGRP R-Fc protein and molecular weight markers (Invitrogen). Gels were electroblotted onto 0.2 µm nitrocellulose filters (Invitrogen). The blots were washed with Tris-buffered saline +1% Tween 20 (TBST) and then blocked with TBST+5% powered dry milk for 30 min. The blots were cut into strips along the molecular weight marker lanes. One strip each with reduced and non-reduced CGRP R-muFc were incubated with purified huCGRP R antibodies 4E4, 9F5, or 3B6 (1:500 dilution in TBST+5% milk), goat anti-huRAMP1 N-20 (1:500; Santa Cruz Biotechnology, Inc), rabbit anti-mouse IgG-Fc-HRP (1:10,000) (Pierce), or goat anti-human IgG-Fc-HRP (1:10,000) (Pierce). Blots were incubated with the antibodies for one hour followed by 3×10 min washes with TBST+1% milk. The blots treated with the huCGRP R antibodies were then incubated with goat anti-mouse IgG-Fc-HRP (1:10,000 in TBST+1% milk) and the blots treated with anti-huRAMP1 (N-20 anti-RAMP1 goat polyclonal antibody, Santa Cruz Biotech, CA) were incubated with rabbit anti-goat IgG-Fc-HRP (1:10,000) for 20 min. Blots were washed 3×15 min with TBST. The huCGRP R and anti-huRAMP1 antibody blots were treated with Pierce Supersignal West Pico Detection reagent, and the anti-mouse and anti-human IgG-Fc-HRP blots were treated with Pierce standard Detection Reagent (1 min.). Blots were then exposed with Kodak Biomax MS X-ray film.

All of the three CGRP receptor antibodies, 4E4, 9F5 and 3B6 were able to detect the soluble CGRP R-muFc (containing RAMP1-ECD and CRLR ECD) under non-reduced condition but not under reduced condition indicating that the binding epitope of these CGRP R antibodies was conformational and sensitive to the disulfide linkages (3 pairs in RAMP1-ECD and 3 pairs in CRLR N-ter ECD). In contrast, the commercial anti-RAMP1 antibody N-20 (Santa Cruz Biotech) bound RAMP 1 under both reduced and no reduced conditions indicating that the binding site for N-20 antibody was primarily linear and not sensitive to disulfide linkages.

EXAMPLE 9

Binding of CGRP Receptor Blocking Antibodies to Chimeric Receptors

CGRP receptors formed of either native RAMP1 with chimeric CRLR, or native CRLR with chimeric RAMP1, were used to identify CGRP receptor sequences involved in antibody binding. Since all of the human CGRP receptor blocking antibodies tested failed to show functional activity to the rat CGRP receptor, the chimeric components contained regions of rat sequence in a human sequence background. The following chimeras were generated for binding analysis by FACS:

RAMP1 chimera#1 (Q28 to A34); SEQ ID NO:217

Amino acid residues Q28 to A34 in the human RAMP1 were replaced with the corresponding sequences from rat RAMP1. This stretch included five amino acid residues that are different between human and rat RAMP1.

RAMP1 chimera#2 (Q43 to E53); SEQ ID NO:218

Amino acid residues Q43 to E53 in the human RAMP1 were replaced with the corresponding sequences from rat RAMP1. This stretch included six amino acid residues that are different between human and rat RAMP1.

RAMP1 chimera#3 (R67 to E78); SEQ ID NO:219

Amino acid residues R67 to E78 in the human RAMP1 were replaced with the corresponding sequences from rat RAMP1. This stretch included seven amino acid residues that are different between human and rat RAMP1.

CRLR chimera#1 (L24 to Q33); SEQ ID NO:223

Amino acid residues L24 to Q33 in the human CRLR were replaced with the corresponding sequences from rat CRLR. This stretch included eight amino acid residues that are different between human and rat CRLR.

FIG. 11 shows an alignment of RAMP1 amino acid sequences from cynomolgus monkey (SEQ ID NO:215), human (SEQ ID NO:4), rat (SEQ ID NO:214) and rhesus monkey (SEQ ID NO:216), together with sequences of RAMP1 chimera #1 (SEQ ID NO:217), chimera #2 (SEQ ID NO:218) and chimera #3 (SEQ ID NO:219). FIGS. 12A and 12B show an alignment of CRLR amino acid sequences from human (SEQ ID NO:2), cynomolgus monkey (SEQ ID NO:221), rhesus monkey (SEQ ID NO:222), rat (SEQ ID NO:220) and, as well as the amino acid sequence of CRLR chimera #1 (SEQ ID NO:223).

293-6E cells were transiently transfected with CGRP R chimera DNA constructs (CRLR wt+RAMP1 Q28-A34; CRLR wt+RAMP1 Q43-E53; CRLR wt+RAMP1 R67-E78; CRLR L24-Q33+RAMP wt; CRLR wt+RAMP1 wt; pTT5 vector control). Cells were harvested after 72 hr, washed with PBS+0.5% BSA, and counted. Each transfected cell line was resuspended at a dilution of $5 \times 10^5$ cells per 100 µl PBS/BSA. 100 µl of cell suspension was aliquot per well in a 96-well round-bottom plate (Falcon). The cells were pelleted at 1200 rpm for 5 min. The supernatant was removed and replaced with 100 µl containing 0.5 µg purified huCGRP R antibodies 1H7, 2E7, 3B6, 9F5, 4H6, 12G8, 3C8, 10E4, 11D11, 32H8, or 33B5. Control wells were treated with anti-DNP huIgG2 (0.5 µg), Alexa647-CGRP peptide (0.5 µg), or PBS/BSA alone. Cells were incubated on ice for 1 hr. and then washed twice with PBS/BSA. The cells were resuspended in 100 µl/well PBS/BSA containing anti-hug-Fc-FITC (0.5 µg) (except for Alexa647-CGRP treated cells). Cells were incubated on ice in the dark for 1 hr. and then washed twice with PBS/BSA. Cells were resuspended in 200 µl PBS/BSA and analyzed using a FACS Calibur.

Ten representative blocking antibodies (3B6, 9F5, 4H6, 12G8, 3C8, 10E4, 32H7, 4E4, 11D11 and 1H7) and two non-blocking antibody (32H8 and 33B5) were tested. Representative data (9F5 antibody) are shown in FIGS. 13A, 13B and 13C. FIG. 13A shows binding to the wild-type CGRP receptor; FIG. 13B show binding to CGRP receptors containing the CRLR L24-Q33 chimera, and FIG. 13C show binding to CGRP receptors containing the RAMP1 Q28-A34 chimera. The FACS analysis showed that all 12 antibodies bind wild type human CGRP receptor control as expected. All 12 antibodies showed significantly reduced binding to any of the three RAMP1 chimera RAMP1 (Q28-A34), (Q43-E53) and (R67-E78). This could result from (1) the expression level of the chimera receptor was much lower, (2) the RAMP1 chimera impaired the folding with human CRLR and altered the conformation of the receptor complex, and/or (3) these three selected regions on RAMP1 are directly involved in the binding of these antibodies to CGRP receptor.

When the FACS tracing were gated to include only the very small "expressing" cell populations, the non-blocking antibodies 33B5 and 32H8 appeared to consistently bind less well (lower Geo Means) to the RAMP1 Q43-E53 chimera as compared to the blocking antibodies, suggesting binding to the RAMP1 Q43-E53 region may be more important for the non-blocking antibodies. On the other hand, 33B5 and 32H8 consistently bound better to the RAMP1 R67-E78 chimera than the blocking antibodies, suggesting the RAMP1 R67-E78 sequence may be more important for the blocking antibodies.

All CGRP receptor antibodies tested bound reasonably well to the CRLR chimera (L24-Q33), suggesting this site is not essential for binding of blocking antibodies.

In summary, the data show that three discontinuous regions on RAMP1—(Q28-A34), (Q43-E53) and (R67-E78)—could be involved in CGRP receptor antibody binding, with (R67-E78) more important to the blocking antibodies. The N-terminal sequences (L24-Q33) of CRLR did not appear to be critically involved in binding for the CGRP receptor antibodies as analyzed by this method. This approach does not rule out additional binding sites that share identical or similar sequences between human and rat CGRP receptors which were not targeted in the analysis.

EXAMPLE 10

Identification of Human CGRP R Epitopes for Anti-CGRP R Neutralizing Antibodies by Protease Protection Assay The CRLR portion in the mature form of the CRLR-Fc fusion molecule (with signal peptide removed; disclosed herein as SEQ ID NO:10) contains 116 amino acids (preceding the glycine linker) and has three large loop structures created by formation of three disulfide bonds. The three disulfide bonds in CRLR are Cys1 at sequence position 26 (all CRLR sequence positions listed in this paragraph are with respect to the mature sequence presented as SEQ ID NO:10) linked to Cys3 at sequence position 52 (referred to as CRLR C1-C3), Cys2 at sequence position 43 linked to Cys5 at sequence position 83 (referred to as CRLR C2-C5), Cys4 at sequence position 66 linked to Cys6 at sequence position 105 (referred to as CRLR C4-C6). RAMP1 portion in mature form of RAMP1-Fc fusion molecule contains 91 amino acids (SEQ ID NO:11) preceding the glycine linker, which also forms three intramolecular disulfide bonds. The three disulfide bonds in RAMP1 are Cys1 at sequence position 1 (all RAMP1 sequence positions listed in this paragraph are with respect to the mature sequence presented as SEQ ID NO:11) linked to Cys5 at sequence position 56 (referred to as RAMP1 C1-C5), Cys2 at sequence position 14 linked to Cys4 at sequence position 46 (referred to as RAMP1 C2-C4), Cys3 at sequence position 31 linked to Cys6 at sequence position 78 (referred to as RAMP1 C3-C6).

Regions of the human CGRP receptor protein bound by anti-CGRP neutralizing monoclonal antibodies were identified by fragmenting h CGRP R into peptides with specific proteases, and determining the sequence of the resulting h CGRP R peptides (i.e., both disulfide- and non-disulfide-containing peptide fragments for CRLR and RAMP1 portions). A protease protection assay was then performed to determine the proteolytic digestion of hCGRP R in the presence of binding monoclonal antibodies. The general principle of this assay is that binding of a mAb to CGRP R can result in protection of certain specific protease cleavage sites and this information can be used to determine the region or portion of CGRP R where the mAb binds to.

Briefly, the peptide digests were subjected to HPLC peptide mapping; the individual peaks were collected, and the peptides identified and mapped by on-line electrospray ionization LC-MS (ESI-LC-MS) analyses and/or by N-terminal sequencing. All HPLC analyses for these studies were performed using a narrow bore reverse-phase C18 column (2.1 mm i.d.×15 cm length; Zorbax 300SB, 5 µm, Agilent Technologies) for off-line analysis and using a capillary reverse phase C18 column (0.5 mm i.d.×25 cm Vydac C18 MS, 5 µm; The Separation Group) for LC-MS. HPLC peptide mapping was performed with a linear gradient from 0.05% trifluoroacetic acid (mobile phase A) to 90% acetonitrile in 0.05% trifluoroacetic acid. Columns were developed over 90 minutes at a flow rate of 0.25 ml/min for narrow bore HPLC for off-line or on-line LC-MS analyses, and 0.018 ml/min for capillary HPLC for on-line LC-MS analyses.

Mature form human CGRP R was digested with AspN (which cleaves after aspartic acid and some glutamic acid residues at the amino end) by incubating about 100 µg of CGRP R at 1.0 mg/ml in 0.1M sodium phosphate (pH 6.5) for 20 hrs at 37° C. with 2 µg of AspN.

Figure 14:
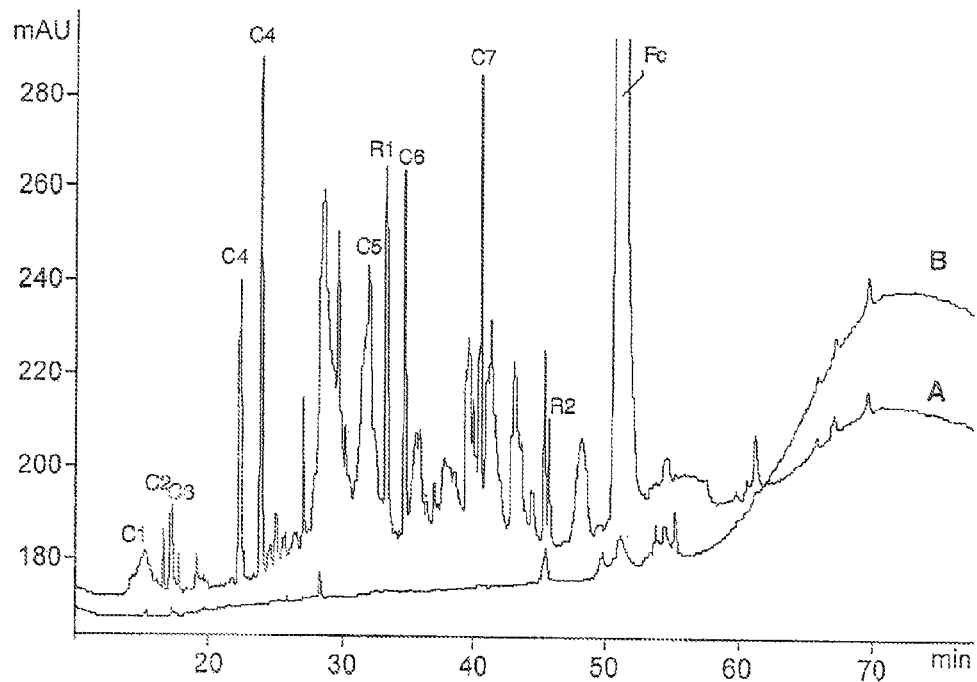
FIG. 14 shows peptide maps derived from AspN digestions of CGRP R alone (chromatogram A) and from digestion of a control sample containing CGRP R monoclonal antibody 12G8 (chromatogram B).

HPLC chromatography of the AspN digests generated a peptide profile as shown in FIG. 14 (each sample 30 µg injected), chromatogram labeled A for CGRP R alone (concentration 1 mg/ml), while a control digestion with a similar amount of CGRP R neutralizing antibody, clone 12G8, shows that the antibody is essentially resistant to AspN endoproteinase (chromatogram labeled B; CGRP R:antibody ratio, 100:2; 100:7; 100:20, weight by weight, respectively). Sequence analyses were conducted by on-line LC-MS/MS and by Edman sequencing on the peptide peaks recovered from HPLC. On-line ESI LC-MS analyses of the peptide digest were performed to determine the precise mass and sequence of the peptides that were separated by HPLC. The identities of several peptides present in the peptide peaks from the AspN digestion were thus determined (indicated as numbered peaks in FIG. 14). Table 14, below, shows the locations of these peptide sequences in the corresponding component (CRLR or RAMP1) of the hCGRP R. A capital letter C followed by a number or X represents a peptide identified as a CRLR peptide; a capital letter R followed by a number or X is a RAMP1 peptide and "Fc" represents the large, undigested Fc fragment released from the CRLR-Fc and RAMP1-Fc fusion molecules.

TABLE 14

CRLR and RAMP1 peptides identified by peptide mapping of CGRP R AspN digestion

| Peptide | Sequence location | Disulfide (#) | Intact mass | Origin |
|---|---|---|---|---|
| C1 | E111-V122 | 0 | 1059 | CRLR |
| C2 | D33-A38 | 0 | 670 | CRLR |
| C3 | D55-M63 | 0 | 880 | CRLR |
| C4 | D68-Q71 | 0 | 571 | CRLR |
| C5 | D55-P67/D86-H110 | | n.d. | CRLR |
| C6 | D8-Y24 | 0 | 1938 | CRLR |
| C7 | E25-Q32/D48-N54 | 1 | 1933 | CRLR |
| C-X | | 3 | n.d. | CRLR |
| R1 | D32-A44 | 0 | 1622 | RAMP1 |
| R2 | E12-V20/D45-A51 | 1 | 1939 | RAMP1 |
| R-X | C1-R86 | 3 | 10049 | RAMP1 |
| Fc | | | 20500 | RAMP1/CRLR |

Figure 15:
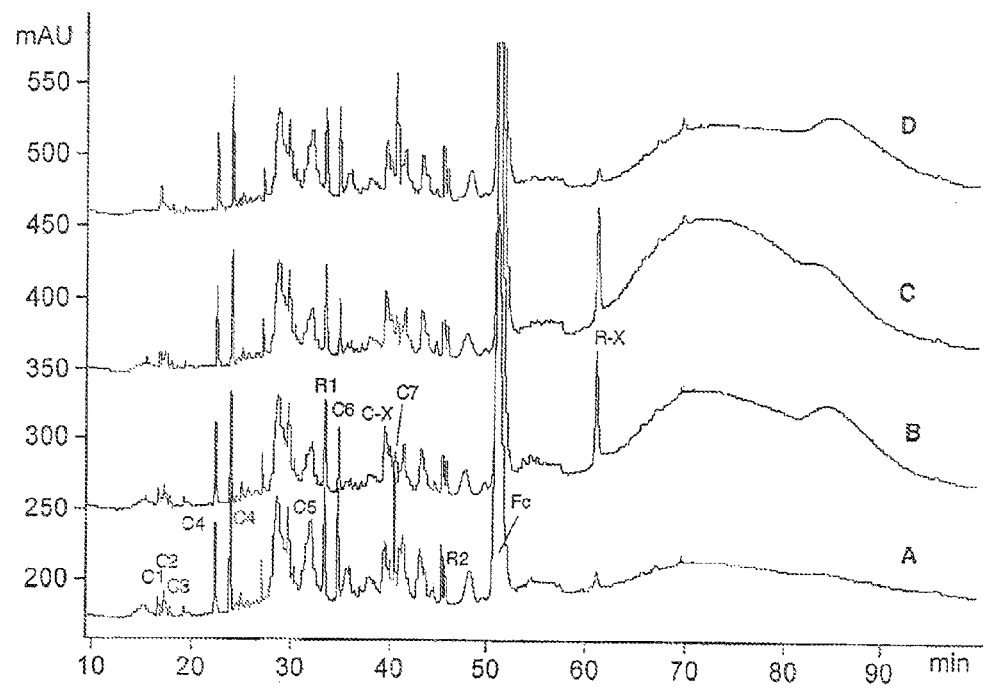
FIG. 15 shows AspN digestions of CGRP R in the presence of different concentrations of CGRP R neutralizing antibody.

FIG. 15 shows a comparison of an AspN digestion experiment (each sample 30 µg injected) with CGRP R alone (chromatogram labeled A) with one performed in the presence of neutralizing antibody 12G8 (chromatogram labeled B). The weight ratio of CGRP R:antibody was 1:1. Several peaks (C5, C6, and C7) show a decreased in peak height in chromatogram B relative to chromatogram A, while two other peaks (C-X and R-X) show an increase in peak height in chromatogram B relative to chromatogram A. A similar peptide map pattern was also observed if a different neutralizing anti-CGRP R antibody (10E4, 3B6, 3C8 or 4E4) at a similar quantity was present in the digestion sample as seen in the chromatogram labeled C. Both C6 and C7 are disulfide linked peptides which cover a major portion of the CRLR molecule while C5 is a CRLR non-disulfide containing peptide residing at the N-terminal end of the molecule and is penultimate to the C7 disulfide peptide. Peak C-X contains three CRLR disulfide bonds with multiple sequences, indicating at least two to three peptides are linked together by disulfide bonds. The fact that peak C-X has increased peak height in a CGRP R digest in the presence of CGRP neutralizing antibody indicates that the antibody has protected CGRP R from AspN digestion at several cleavage sites related to Glu25 and Asp55. The antibody does not appear to have a significant protective effect on Asp33 and Asp72 as peak intensity for peptides C2 and C4 did not decrease at all. Therefore the antibody appears to bind to a region of CRLR which includes the CRLR C1-C3 and CRLR C4-C6 disulfide region together with the loop region between Cys53 and Cys66.

The AspN mapping of hCGRP R also identified a RAMP1 disulfide peptide (R2) and a RAMP1 non-disulfide peptide (R1) (see Table 14 and FIG. 14). In the presence of any of the above-mentioned neutralizing antibodies (12G8, 10E4, 4E4, 3B6 or 3C8), peptide R-X was recovered at a significantly higher peak intensity than what was obtained from the digestion with no antibody in the sample. Mass and sequence analyses showed that R-x contains a single polypeptide chain corresponding to the RAMP1 sequence between Cys1 and Arg86. These experiments indicate that CGRP R neutralizing antibody can protect a significant region of RAMP1 from AspN proteolytic digestion.

To assess whether the protective effect of CGRP R AspN proteolysis is specific to CGRP R-neutralizing (blocking) antibodies (as compared with anti-CGRP R non-neutralizing antibodies), an AspN digestion of CGRP R was performed in the presence of an unrelated control monoclonal antibody which does not neutralize CGRP R activity. The results are shown in FIG. 15 in chromatogram D. The non-neutralizing antibody does not show any significant blocking effect on CGRP R AspN proteolysis; indeed, the peptide map profile (chromatogram D) is nearly indistinguishable in the relevant aspects to the profile derived from digestion of CGRP R alone (chromatogram A).

Figure 16:
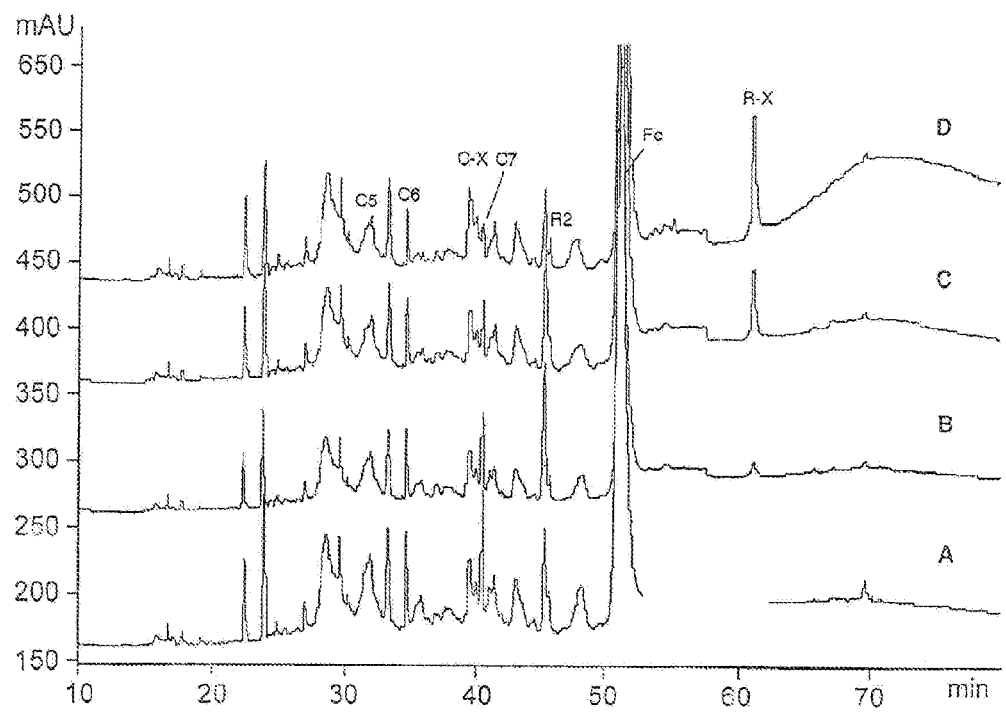
FIG. 16 shows AspN digestions of CGRP R in the presence of different concentration of CGRP R neutralizing antibody, 4E4.
Figure 17:
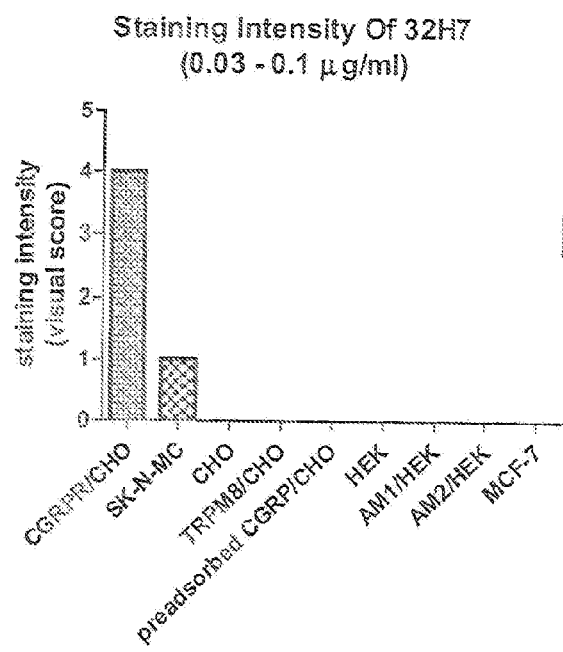
FIG. 17 shows immunohistochemistry staining intensity of cells expressing various receptor components with antibody 32H7.

The proteolysis protection effect was dependent on the concentration added to the digestion sample. As seen in FIG. 16, a fixed CGRP R quantity in the sample (100 μg) with variable amounts of anti-CGRP R neutralizing antibody 4E4 (CGRP R:antibody ratio in micrograms, 100:2; 100:7; 100:20, weight by weight, respectively) was performed for Aspen proteolysis. The protection profile can be observed and the protection is antibody concentration-dependent.

Taken together, these data demonstrate that blocking or neutralizing anti-CGRP R antibodies disclosed herein can block CGRP R (on both CRLR and RAMP1 components) from AspN proteolysis, suggesting that the blocking antibodies bind to both CRLR and RAMP1 when these antibodies bind to the CGRP receptor. Further, the protection effect is antibody-concentration dependent. These results also indicate that CGRP R neutralizing antibodies bind to common regions on human CGRP R which are close the Asp N cleavage sites.

EXAMPLE 11

Commercially-Available Anti-RAMP1 and Anti-CRLR Antibodies in a cAMP Functional Assay Commercially-available antibodies directed against one or the other components (RAMP1 or CRLR) of the human CGRP receptor were screened in the CGRP receptor mediated cAMP assay using HTB-10 cells as described in Example 4, above, to determine whether the antibodies had biological activity. The data are presented in Table 15, below. The antibodies had either no detectable ("ND"), very weak ("VW") or weak ("W") biological activity over a concentration range where the exemplary antibodies disclosed herein had strong biological activity.

TABLE 15

Commercially-available antibody activity

| Name | Source | Antigen or epitope | Vendor | HTB-10 activity |
| --- | --- | --- | --- | --- |
| CRLR antibody (ab13164) | Rabbit polyclonal Ab | N-terminal ECD of hCRLR | Abcam Inc., Cambridge, MA | ND |
| CALCRL antibody | Rabbit polyclonal Ab | N-terminal ECD of hCRLR | GenWay Biotech, Inc., San Diego, CA | ND |
| CRLR (N-18) | Goat polyclonal Ab | epitope mapping near N-terminus of hCRLR | Santa Cruz Biotech | VW |
| CRLR (H-42) | Rabbit polyclonal Ab | aa23-64 of hCRLR | Santa Cruz Biotech | ND |
| CALCRL Antibody (A01) | Mouse polyclonal Ab | aa23-133 of hCRLR | Novus Biologicals, Inc. | VW |
| RAMP1 (N-20) | Goat polyclonal Ab | epitope mapping at N-terminus of hCRLR | Santa Cruz Biotech | ND |
| RAMP1 Antibody (M01) | Mouse polyclonal Ab | aa27-118 of hRAMP1 | Novus Biologicals, Inc., Littleton, CO | W |

TABLE 15-continued

Commercially-available antibody activity

| Name | Source | Antigen or epitope | Vendor | HTB-10 activity |
|---|---|---|---|---|
| RAMP1 Antibody (1F1) | Mouse monoclonal Ab | aa27-118 of hRAMP1 | Novus Biologicals, Inc. | ND |
| RAMP1 antibody (ab67151) | Mouse polyclonal Ab | full-length of hRAMP1 | Abcam, Inc. | W |
| RAMP1 (FL-148) | Rabbit polyclonal Ab | full length hRAMP1 | Santa Cruz Biotech, Santa Cruz, CA | ND |

EXAMPLE 12

Immunohistochemistry Staining of Cells Expressing Different Receptor Components $2-4\times10^6$ cells were injected per colla plug (Integra Life-Sciences Co., Plainsboro, N.J.). Colla plugs were embedded in OCT medium (Sakura Finetek Inc., Torrance, Calif.), frozen at −20° C. and cut into 20 µm sections using a cryostat. Sections were fixed with 4% paraformaldehyde for 1 hour at room temperature (RT) and subsequently washed in phosphate-buffered saline (PBS). Endogenous peroxidase was blocked with 3% $H_2O_2$/PBS for 15 min and sections were incubated in blocking solution (PBS with 3% normal goat serum (Vector Labs, Burlingame, Calif.) and 0.3% triton X-100) for 1 hour. Subsequently, sections were incubated in human anti-CGRP receptor primary antibody (32H7, 0.03-0.1 µg/ml) at 4° C. over night, washed in PBS and incubated in secondary antibody (biotinylated goat anti-human IgG Fc fragment, 1:800, Jackson Immunoresearch, West Grove, Pa.) in 1% normal goat serum/PBS for 1 hour at RT. Immunoreactivity was amplified using the Vector Elite Kit according to the manufacturer's instructions (Vector Labs, Burlingame, Calif.) and staining was developed using 3,3'-diaminobenzidine-nickel as chromogen (Sigma-Aldrich, St. Louis, Mo.). Sections were cleared with xylene and cover slipped with Permount (Fisher Chemicals, Fair Lawn, N.J.). Immunoreactivity was analyzed using a Nikon E-800 microscope and associated software (Nikon, Melville, N.Y.).

Data from cells expressing different receptor components (as identified below) using antibody 32H7 as described above revealed pronounced staining of CHO cells expressing recombinant human CGRP receptor (CRLR+RAMP1; "CHO/CGRP R cells") and weaker staining of SK-N-MC cells that endogenously express CGRP receptors (due to much lower receptor density). No staining was observed in the parent CHO cell line, CHO cells expressing an unrelated recombinant protein (TRPM8), CHO/CGRP R cells after pre-absorption with the corresponding 32H7 antigen, CHO cells expressing recombinant human adrenomedullin receptor 2 (CRLR+RAMP3), MCF-7 cells endogenously expressing amylin receptors, HEK cells expressing recombinant human adrenomedullin receptor 1 (CRLR+RAMP2), or the parent HEK cells. The data from these experiments are summarized in Table 16, below.

TABLE 16

Immunohistochemical staining intensity of indicated cells

| Cell line | Staining intensity (visual score) |
|---|---|
| CGRP/CHO | 4+ |
| SK-N-MC | 1+ |
| CHO | 0 |
| TRPM8/CHO | 0 |
| CGRP/CHO preadsorbed | 0 |
| AM2/CHO | 0 |
| MCF-7 | 0 |
| AM1/HEK | 0 |
| HEK | 0 |

All patents and other publications identified are expressly incorporated herein by reference for the purpose of describing and disclosing, for example, the methodologies described in such publications that might be used in connection with the subject matter disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An isolated antibody or antigen-binding fragment thereof, wherein said antibody or antigen-binding fragment thereof specifically binds the human CGRP receptor and comprises a CDRH1 having the sequence of SEQ ID NO:73, a CDRH2 having the sequence of SEQ ID NO:74, a CDRH3 having the sequence of SEQ ID NO:75, a CDRL1 having the sequence of SEQ ID NO:42, a CDRL2 having the sequence of SEQ ID NO:43, and a CDRL3 having the sequence of SEQ ID NO:44.

2. The isolated antibody or antigen-binding fragment thereof of claim 1, wherein the isolated antibody is a monoclonal antibody selected from the group consisting of a fully human antibody and a chimeric antibody.

3. The isolated antibody or antigen-binding fragment thereof of claim 1, wherein the antibody is a monoclonal IgG1 or monoclonal IgG2 antibody.

4. The isolated antibody or antigen-binding fragment thereof of claim 1, wherein the isolated antibody or antigen-binding fragment thereof specifically binds to human CGRP receptor with a $K_D \leq 100$ nM.

5. The isolated antibody or antigen-binding fragment thereof of claim 4, wherein the isolated antibody or antigen-binding fragment thereof specifically binds to human CGRP receptor with a $K_D \leq 10$ nM as determined using a FACS binding assay.

6. The isolated antibody or antigen-binding fragment thereof of claim 1, wherein said antibody or antigen-binding fragment thereof comprises (i) a heavy chain variable region ($V_H$) sequence that has at least 95% sequence identity with SEQ ID NO:158, and (ii) a light chain variable region ($V_L$) sequence that has at least 95% sequence identity with SEQ ID NO:142.

7. The isolated antibody or antigen-binding fragment thereof of claim 1 wherein the isolated antibody or antigen-binding fragment thereof is selected from the group consisting of a monoclonal antibody, a Fab fragment, an Fab' fragment, an F(ab')$_2$ fragment, an Fv fragment, a diabody, and a single chain antibody.

8. The isolated antibody or antigen-binding fragment thereof of claim 7, wherein the isolated antibody or antigen-binding fragment thereof is a monoclonal antibody selected from the group consisting of a fully human antibody and a chimeric antibody.

9. The isolated antibody or antigen-binding fragment thereof of claim 8, wherein the monoclonal antibody is an IgG1-, IgG2-, IgG3-, or IgG4-type antibody.

10. The isolated antibody or antigen-binding fragment thereof of claim 9, wherein the monoclonal antibody is an IgG1 or IgG2 antibody.

11. The isolated antibody or antigen-binding fragment thereof of claim 6, wherein the isolated antibody is a monoclonal antibody selected from the group consisting of a fully human antibody and a chimeric antibody.

12. The isolated antibody or antigen-binding fragment thereof of claim 6, wherein the antibody is a monoclonal IgG1 or monoclonal IgG2 antibody.

13. An isolated antibody that specifically binds the human CGRP receptor and comprises a heavy chain variable region ($V_H$) comprising the sequence of SEQ ID NO:158, and a light chain variable region ($V_L$) comprising the sequence of SEQ ID NO:142.

14. An isolated antibody that specifically binds the human CGRP receptor and comprises a heavy chain comprising the sequence of SEQ ID NO:29, and a light chain comprising the sequence of SEQ ID NO:17.

15. A pharmaceutical composition comprising an antibody or antigen-binding fragment thereof of claim 1 and a pharmaceutically acceptable excipient.

* * * * *